US008895002B2

(12) United States Patent
Lin et al.

(10) Patent No.: US 8,895,002 B2
(45) Date of Patent: Nov. 25, 2014

(54) HEMOJUVELIN FUSION PROTEINS AND USES THEREOF

(75) Inventors: Herbert Y. Lin, Watertown, MA (US); Jodie Babitt, Newton Highlands, MA (US); Clifford J. Woolf, Newton, MA (US); Tarek A. Samad, Guilford, CT (US)

(73) Assignee: The General Hospital Corporation, Boston, MA (US)

( * ) Notice: Subject to any disclaimer, the term of this patent is extended or adjusted under 35 U.S.C. 154(b) by 1412 days.

(21) Appl. No.: 12/595,423

(22) PCT Filed: Apr. 9, 2008

(86) PCT No.: PCT/US2008/059753
§ 371 (c)(1),
(2), (4) Date: Mar. 14, 2012

(87) PCT Pub. No.: WO2008/124768
PCT Pub. Date: Oct. 16, 2008

(65) Prior Publication Data

US 2012/0164140 A1 Jun. 28, 2012

Related U.S. Application Data

(60) Provisional application No. 60/922,459, filed on Apr. 9, 2007.

(51) Int. Cl.

| | |
|---|---|
| ***A61K 38/18*** | (2006.01) |
| ***C07K 14/475*** | (2006.01) |
| ***C12N 15/62*** | (2006.01) |
| ***C12N 15/63*** | (2006.01) |
| ***C07H 21/04*** | (2006.01) |
| ***C07K 14/71*** | (2006.01) |

(52) U.S. Cl.
CPC ............. *C07K 14/71* (2013.01); *C07K 2319/30* (2013.01); *C07K 2319/40* (2013.01)
USPC .................... 424/134.1; 435/69.7; 435/252.3; 435/320.1; 435/325; 536/23.1; 536/23.4; 514/1.1; 514/5.4; 514/7.6; 530/300; 530/350

(58) Field of Classification Search
None
See application file for complete search history.

(56) References Cited

U.S. PATENT DOCUMENTS

| | | | |
|---|---|---|---|
| 5,571,714 | A | 11/1996 | Dasch et al. |
| 5,719,120 | A | 2/1998 | Letarte et al. |
| 5,830,847 | A | 11/1998 | Letarte et al. |
| 6,015,693 | A | 1/2000 | Letarte et al. |
| 6,800,455 | B2 | 10/2004 | Stanton et al. |
| 6,943,241 | B2 | 9/2005 | Isogai et al. |
| 7,511,018 | B2 | 3/2009 | Goldberg et al. |
| 7,534,764 | B2 | 5/2009 | Ganz et al. |
| 2004/0014141 | A1 | 1/2004 | Woolf et al. |
| 2004/0102376 | A1 | 5/2004 | Mueller et al. |
| 2004/0248249 | A1 | 12/2004 | Tran et al. |
| 2006/0035263 | A1 | 2/2006 | Woolf et al. |
| 2006/0063208 | A1 | 3/2006 | Woolf et al. |
| 2007/0231863 | A1 | 10/2007 | Woolf et al. |
| 2007/0259816 | A1 | 11/2007 | Woolf et al. |

FOREIGN PATENT DOCUMENTS

| | | | |
|---|---|---|---|
| CN | 1284380 | | 2/2001 |
| EP | 1130094 | A2 | 9/2001 |
| WO | WO9424314 | | 10/1994 |
| WO | WO9512608 | | 5/1995 |
| WO | WO0154708 | A1 | 8/2001 |
| WO | WO02051438 | A2 | 7/2002 |
| WO | 02/098444 | A2 | 12/2002 |
| WO | WO03004615 | A2 | 1/2003 |
| WO | 03/089608 | A2 | 10/2003 |
| WO | WO03089608 | A2 | 10/2003 |
| WO | 2004/003150 | A2 | 1/2004 |
| WO | 2004/004750 | A2 | 1/2004 |
| WO | 2004003150 | | 1/2004 |
| WO | WO2004004750 | A2 | 1/2004 |
| WO | 2004/016606 | A2 | 2/2004 |
| WO | 2005/028517 | A2 | 3/2005 |
| WO | WO2005028517 | A2 | 3/2005 |
| WO | 2006088972 | | 8/2006 |

OTHER PUBLICATIONS

Anderson, D.J. "Cellular and molecular biology of neural crest cell lineage determination." Trends Genet., 13:276-280 (1997).
Anderson, D.J. "Lineages and transcription factors in the specification of vertebrate primary sensory neurons." Curr. Opin. Neurobiol., 9:517-524 (1999).
Augsburger, A., et al. "BMPs as Mediators of Roof Plate Repulsion of Commissural Neurons." Neuron., 24:127-141 (1999).
Babitt, J.L., et al. "Repulsive Guidance Molecule (RGMa), a DRAGON Homologue, Is a Bone Morphogenetic Protein Co-receptor." J. Biol. Chem., 280:29820-29827 (2005).
Balemans, W., et al. "Extracellular Regulation of BMP Signaling in Vertebrates: A Cocktail of Modulators." Dev. Biol., 250:231-250 (2002).
Bell, E., et al. "Dynamic Domains of Gene Expression in the Early Avian Forebrain." Dev. Biol., 236:76-88 (2001).
Benson, D., et al. "Molecules, Maps and Synapse Specificity." Nat. Rev. Neurosci., 2:899-909 (2001).
Bork, P., et al. "Go hunting in sequence databases but watch out for the traps." Trends in Genetics, 12(10):425-427 (1996).
Bork, Peer. "Powers and Pitfalls in Sequence Analysis: the 70% Hurdle." Genome Res., 10:398-400 (2000).
Brenner, S.E. "Errors in genome annotation." Trends in Genetics, 15(4):132-133 (1999).

(Continued)

*Primary Examiner* — Christine J Saoud
*Assistant Examiner* — Jon M Lockard
(74) *Attorney, Agent, or Firm* — Lathrop & Gage LLP

(57) ABSTRACT

The present invention provides a hemojuvelin (HJV) fusion protein (e.g., a human HJV.Fc) protein, polynucleotides and vectors encoding such proteins, and methods for making such proteins. Also provided are methods for treating iron-related disorders which include administration of a HJV fusion protein to a patient in need thereof.

38 Claims, 37 Drawing Sheets

(56) References Cited

OTHER PUBLICATIONS

Brinks, et al. "The Repulsive Guidance Molecule RGMa Is Involved in the Formation of Afferent Connections in the Dentate Gyrus." J. Neurosci., 24(15):3862-3869 (2004).
Brose, K., et al. "Slit Proteins Bind Robo Receptors and Have an Evolutionarily Conserved Role in Repulsive Axon Guidance." Cell, 96:795-806 (1999).
Brose, K., et al. "Slit proteins: key regulators of axon guidance, axonal branching, and cell migration." Curr. Opin. Neurobiol., 10:95-102 (2000).
Brown, C.B., et al. "Requirement of Type II TGF-Beta Receptor for Endocardial Cell Transformation in the Heart." Science, 283:2080-2082 (1999).
Camus, L.M., et al. "Molecular Evolution of Hemojuvelin and the Repulsive Guidance Molecule Family." J. Mol. Evol., 65:68-81 (2007).
Chappuis-Flament, S., et al. "Multiple cadherin extracellular repeats mediate homophilic binding and adhesion." J. Cell Biol., 154(1):231-243 (2001).
Chen, Z-F., et al. "The Paired Homeodomain Protein DRG11 Is Required for the Projection of Cutaneous Sensory Afferent Fibers to the Dorsal Spinal Cord." Neuron, 31:59-73 (2001).
Cheng, H-J., et al., "Plexin-a3 mediates semaphorin signaling and regulates the development of hippocampal axonal projections." Neuron 32:249-263 (2001).
Cheng, S.K., et al. "EGF-CFC proteins are essential coreceptors for the TGF-beta signals Vg1 and GDF1." Genes Dev., 17:31-36 (2003).
Cross, S.H., et al. "Purification of CpG islands using a methylated DNA binding column." Nat. Genet. 6:236-244 (1994).
Cross, S.H., et al. "Isolation of CpG islands from large genomic clones." Nucleic Acids Res. 27:2099-2107 (1999).
De Angelis, M., et al. "The acid-stress response in *Lactobacillus sanfranciscensis* CB1." Microbiol., 147:1863-1873 (2001).
del Re, E., et al. "In the Absence of Type III Receptor, the Transforming Growth Factor (TGF)-Beta Type II-B Receptor Requires the Type I Receptor to Bind TGF-Beta2." J. Biol. Chem., 279(21):22765-22772 (2004).
Dennler, S., et al. "Direct binding of Smad3 and Smad4 to critical TGFBeta-inducible elements in the promoter of human plasminogen activator inhibitor-type 1 gene." EMBO J., 17(11):3091-3100 (1998).
Doerks, T., et al. "Protein annotation: detective work for function prediction." Trends Gen., 14(6):248-250 (1998).
Emahazion, T., et al. "SNP association studies in Alzheimer's disease highlight problems for complex disease analysis." Trends Gen., 17:407-413 (2001).
Enomoto, H., et al. "RET signaling is essential for migration, axonal growth and axon guidance of developing sympathetic neurons." Development, 128:3963-3974 (2001).
European Application No. 06735151.0, Examination Report, dated Nov. 12, 2008.
European Application No. 10196139.9, European Search Report, dated May 10, 2011.
European Application No. 10196139.9, Extended European Search Report, dated May 18, 2011.
Feng, L.-X., et al. "Generation and in Vitro Differentiation of a Spermatogonial Cell Line." Science, 297:392-395 (2002).
Filip, S., et al. "Issues in stem cell plasticity." J. Cell. Mol. Med.,8(4):572-577 (2004).
Frisen, J., et al. "Ephrin-A5 (AL-1/RAGS) Is Essential for Proper Retinal Axon Guidance and Topographic Mapping in the Mammalian Visual System." Neuron, 20:235-243 (1998).
Gray, P.C., et al. "Cripto forms a complex with activin and type II activin receptors and can block activin signaling." PNAS, 100(9):5193-5198 (2003).
Groppe, J., et al. "Structural basis of BMP signalling inhibition by the cystine knot protein Noggin." Nature, 420 (12):636-642 (2002).
Hao, J.C., et al. "*C. elegans* Slit Acts in Midline, Dorsal-Ventral, and Anterior-Posterior Guidance via the SAX-3/Robo Receptor." Neuron, 32:25-38 (2001).
Hirschhorn, J.C., et al. "A comprehensive review of genetic association studies." Gen. Med., 4(2):45-61 (2002).
Hollnagel, A., et al. "Id Genes Are Direct Targets of Bone Morphogenetic Protein Induction in Embryonic Stem Cells." J. Biol. Chem., 274(28):19838-19845 (1999).
Hoodless, P.A., et al. "MADR1, a MAD-Related Protein That Functions in BMP2 Signaling Pathways." Cell, 85:489-500 (1996).
Hsu, D. R., et al. "The Xenopus Dorsalizing Factor Gremlin Identifies a Novel Family of Secreted Proteins that Antagonize BMP Activities." Molecular Cell, 1:673-683 (1998).
Hu, et al. "Plexin B Mediates Axon Guidance in *Drosophila* by Simultaneously Inhibiting Active Rac and Enhancing RhoA Signaling." Neuron, 32:39-51 (2001).
Ioannidis, J., et al. "Replication validity of genetic association studies." Nature Gen., 1(29):306-309, (2001).
Jessell, T.M., et al. "Development the decade of the developing brain." Current Opin. Neurobio., 10:599-611 (2000).
Jessell, Thomas M. "Neuronal Specification in the Spinal Cord: Inductive Signals and Transcriptional Codes." Nat. Rev. Genetics, 1:20-29 (2000).
Keutmann, H.T., et al. "The Role of Follistatin Domains in Follistatin Biological Action." Mol. Endocrinol., 18(1):228-240 (2004).
Klahr, Saulo. "The bone morphogenetic proteins (BMPs). Their role in renal fibrosis and renal function." J. Nephrol., 16-179-185 (2003).
Korchynskyi, O., et al. "Identification and Functional Characterization of Distinct Critically Important Bone Morphogenetic Protein-specific Response Elements in the Id1 Promoter." J. Biol. Chem., 277(7):4883-4891 (2002).
Lin, L., et al. "Competitive regulation of hepcidin mRNAby soluble and cell-associated hemojuvelin." Blood, 106:2884-2889 (2005).
Liu, B.P., et al. "Semaphorin-mediated axonal guidance via Rho-related G proteins." Curr. Opin. Cell Bio., 13:619-626 (2001).
Lo, L., et al. "Specification of Neurotransmitter Identity by Phox2 Proteins in Neural Crest Stem Cells." Neuron, 22:693-705 (1999).
Babitt, Jodie L., et al. "Bone morphogenetic protein signaling by hemojuvelin regulates hepcidin expression". Nature Genetics, 38(5):531-539 (2006).
Babitt, Jodie L., et al. "Modulation of bone morphogenetic protein signaling in vivo regulates systemic iron balance". The Journal of Clinical Investigation, 117(7):1933-1939 (2007).
International Search Report, International Application No. PCT/US2008/059753, International Searching Authority, European Patent Office, Sep. 1, 2008.
Mueller, B.K., "RGM, A Repulsive Guidance Molecule, is Involved in Retinal Axon Guidance In Vitro." Biological Basis of Schizophrenic Disorders, Taniguchi Symposia on Brain Sciences, 20:215-229 (1997).
Weinstein et al., "Inappropriate expression of Hepcidin is associated with iron refractory anemia: implications for the anemia of chronic disease", Blood (2002), 100(10): 3776-3781.
Nemeth et al., "Hepcidin is decreased in TRF2 hemochromatosis", Blood (2005), 105(4): 1803-1806.
Database WPI Week 2001 Thomson Scientific (2001), AN 2001-317422 & CN 1284380A, Inst Hematology Chinese Acad Medical Sci.
Roetto et al., "Mutant antimicrobial peptide Hepcidin is associated with severe juvenile hemochromatosis", Nature Genetics (2003), 33(1):21-22.
Krijt et al., "Expression of Rgmc, the murine ortholog of hemojuvelin gene, is modulated by development and inflammation, but not by iron status or Erythropoietin", Blood (2004), 104(13).
European Examination Report, Application No. EP 06735151.0, Mail Date: Apr. 16, 2010.
Lopez-Casillas, F., et al. "Betaglycan Presents Ligand to the TGFP-Beta Signaling Receptor." Cell, 73:1435-1444 (1993).
Lopez-Rovira, T., et al. "Direct Binding of Smad1 and Smad4 to Two Distinct Motifs Mediates Bone Morphogenetic Protein-specific Transcriptional Activation of Id1 Gene." J. Biol. Chem., 277(5):3176-3185 (2002).
Lu, M.M., et al. "The Bone Morphogenic Protein Antagonist Gremlin Regulates Proximal-Distal Patterning of the Lung." Dev. Dyn., 222(4):667-680 (2001).

(56) References Cited

OTHER PUBLICATIONS

Lucentini, J. "Gene Association Studies Typically Wrong." The Scientist, p. 20 (Dec. 20, 2004).
Lundquist, E.A., et al. "Three *C. elegans* Rac proteins and several alternative Rac regulators control axon guidance, cell migration and apoptotic cell phagocytosis." Development, 128:4475-4488 (2001).
Macias-Silva, M., et al. "MADR2 Is a Substrate of the TGFb Receptor and Its Phosphorylation Is Required for Nuclear Accumulation and Signaling." Cell, 87:1215-1224 (1996).
Martinez, A.R., et al. "Hepatic and extrahepatic expression of the new iron regulatory protein hemojuvelin." Haematologica, 89:1441-1445 (2004).
Massague, J. "TGF-Beta Signal Transduction." Annu. Rev. Biochem., 67:753-791 (1998).
Massague, J. "Controlling TGF-b signaling." Genes & Dev., 14:627-644 (2000).
Massague, J. "How Cells Read TGF-Beta Signals." Mol. Cell Biol., 200(1):169-178 (2000).
Matsunaga, E., et al. "RGM and its receptor neogenin regulate neuronal survival." Nat. Cell Biol. 6:749-755 (2004).
McMahon, J.A., et al. "Noggin-mediated antagonism of BMP signaling is required for growth and patterning of the neural tube and?somite." Genes Dev., 12:1438-1452 (1998).
Mikayama, T., et al. "Molecular cloning and functional expression of a cDNA encoding glycosylation-inhibiting factor." Proc. Natl. Acad. Sci. USA, 90:10056-10060 (1993).
Monnier, P.P., et al. "RGM is a repulsive guidance molecule for retinal axons." Nature, 419:392-395 (2002).
Muller, B.K., et al. "Chromophore-assisted laser inactivation of a repulsive axonal guidance molecule." Current Biology, 6(11):1497-1502 (1996).
NCBI Accession No. CAB98207.1, hypothetical protein [*Homo sapiens*] [online] [Retrieved on Apr. 11, 2012]. Retrieved from http://www.ncbi.nih.gov/protein/CAB98207.
NCBI Accession No. Q95XN8: UniProtKB/Swiss-Prot, Hypothetical protein [online] [Retrieved on Apr. 11, 2012]. Retrieved from http://www.ncbi.nih.gov/protein/Q95XN8.
Ngo, J.T., et al. "Computational complexity, protein structure prediction, and the Levinthal paradox", The Protein Folding Problem and Tertiary Structure Prediction. Merz and Le Grand (Eds.), Birkhauser Pub., Boston, MA, pp. 492-495 (1994).
Niederkofler, V., et al. "Repulsive Guidance Molecule (RGM) Gene Function Is Required for Neural Tube Closure But Not Retinal Topography in the Mouse Visual System." J. Neurosci., 24(4):808-818 (2004).
Nishi, Y., et al. "Establishment and Characterization of a Steroidogenic Human Granulosa-Like Tumor Cell Line, KGN, That Expresses Functional Follicle-Stimulating Hormone Receptor." Endocrinology, 142:437-445 (2001).
Ogura, T., et al. "Evidence for two distinct retinoic acid response pathways for HOXB1 gene regulation." Proc. Natl. Acad. Sci. USA, 92:392-396 (1995).
Oldekamp, J., et al. "Expression pattern of the repulsive guidance molecules RGM A, B and C during mouse development." Gene Expression Patterns, 4:283-288 (2004).
Onichtchouk, D., et al. "Silencing of TGF-b signalling by the pseudoreceptor BAMBI." Nature, 401:480-485 (1999).
Papanikolaou, G., et al. "Mutations in HFE2 cause iron overload in chromosome 1q-linked juvenile hemochromatosis." Nature Genetics, 36:77-82 (2004).
International App. No. PCT/US/2008/059753, International Preliminary Report on Patentability, issued by The International Bureau of WIPO, Oct. 13, 2009.
Puglisi, R., et al. "Regulatory role of BMP2 and BMP7 in spermatogonia and Sertoli cell proliferation in the immature mouse." European Journal of Endocrinology, 151:511-520 (2004).
Rajagopalan, S., et al. "Neogenin mediates the action of repulsive guidance molecule." Nature Cell Biol., 6:756-762 (2004).
Saito, T., et al. "Identification by Differential RT-PCR of a Novel Paired Homeodomain Protein Specifically Expressed in Sensory Neurons and a Subset of Their CNS Targets." Mol. and Cell. Neuroscience, 6:280-292 (1995).
Samad, T., et al. "DRAGON: A Member of the Repulsive Guidance Molecule-Related Family of Neuronal- and Muscle-Expressed Membrane Proteins Is Regulated by DRG11 and Has Neuronal Adhesive Properties." J. Neurosci., 24:2027-2036 (2004).
Samad, T., et al. "DRAGON, a Bone Morphogenetic Protein Co-receptor." J. Bio. Chem., 280(14):14122-14129 (2005).
Schmidtmer, J. "Isolation and expression pattern of three mouse homologues of chick Rgm." Gene Expression Patterns, 4:105-110 (2004).
Shen, M. M., et al. "The EGF-CFC gene family in vertebrate development." Trends Genet., 16:303-309 (2000).
Skolnick, J., et al. "From genes to protein structure and function: novel applications of computational approaches in the genomic era." Trends in Biotech., 18(1):34-39, (2000).
Smith, T.F., et al. "The challenges of genome sequence annotation or The devil is in the details." Nature Biotech., 15:122-1223 (1997).
Storm, E.E., et al. "Joint patterning defects caused by single and double mutations in members of the bone morphogenetic protein (BMP) family." Development, 122:3969-3979 (1996).
Supplementary European Search Report, European Patent Application No. 03728442, European Patent Office, issued on Mar. 17, 2006.
Watanabe, T., et al. "Isolation of Estrogen-Responsive Genes with a CpG Island Library." Mol. Cell Biol., 18:442-449 (1998).
Wells, James A. "Additivity of Mutational Effects in Proteins." Biochemistry, 29(37):8509-8517, (1990).
Wiater, E., et al. "Inhibin Is an Antagonist of Bone Morphogenetic Protein Signaling." J. Biol. Chem., 278 (10):7934-7941 (2003).
Xia, Y., et al. "Overexpression of Follistatin-Like 3 in Gonads Causes Defects in Gonadal Development and Function in Transgenic Mice." Mol. Endocrinol., 18:979-994 (2004).
Xia, Y., et al. "Localization and Action of Dragon (Repulsive Guidance Molecule b), a Novel Bone Morphogenetic Protein Coreceptor, throughout the Reproductive Axis." Endocrinology, 146:3614-3621 (2005).
Xia, Y., et al. "Repulsive Guidance Molecule RGMa Alters Utilization of Bone Morphogenetic Protein (BMP) Type II Receptors by BMP2 and BMP4." J. Biol. Chem., 282(25):18129-18140 (2007).
Yamaguchi, Y., et al. "Negative regulation of transforming growth factor-beta by the proteoglycan decorin." Nature, 346:281-284 (1990).
Zheng, A-S., et al. "Interaction of Hemojuvelin with Neogenin Results in Iron Accumulation in Human Embryonic Kidney 293 Cells." J. Biol. Chem., 280(40):33885-33894 (2005).

```
human  -321  GCTCATCAAACTGCTTAACCGCTGAAGCAAAAGGGGGAACTTTTTCCCGATCAGCAG--
Chimp  -321  GCTCATCAAACTGCTTAACCGCTGAAGCAAAAGGGGGAACTTTTTCCCGATCAGCAG--
dog    -334  GCTCATCGACCTGTTCGACTCTTGGGGCAAAGGAGGGACTTTATTTTCCGCCGTCAACA
Rat    -292  AGTCACCAATCAA-----TGTTTAGGGTAAAAGAGGGGGATTTTTCTGAGAGCCATGG--
mouse  -306  ACTCACCAATCCAATCACTGTTTAGGGGAAAGAAGGGGAATTTTTCTGAGAGCCACAG--
              *** * * *          *   * ***   ***   *** *        *

human  -263  AATGACATCGTGATGGGGAAAGGGCTCCCCAGATGGCTGGTGAG----------CAGTGT
Chimp  -263  AATGACATCGTGATGGGGAAAGGGCTCCCCAGATGGCTGGCGAG----------CAGTGT
dog    -274  GATGATGCCATGTCAGGGAAAGTGTTTCCCAGGTGGCTGGCTAGAGGCGTGTGTCTGTGT
Rat    -239  --------------------GGTGACATCACAGGTGGCTGGCTGG----------AGGCTT
mouse  -248  --------------------TGTGACATCACAGGTGGCTGGCTGC----------AGGCTT
                                                   * *** *******          *  *

human  -213  GTGTCTGTGACCCCGTCTGCCCCACCCCCTGAACACACCTCTGCCGGCTGAGGGTGACAC
Chimp  -213  GTGTCTGTGACCCCGTCTGCCCCACCCCCTGAACACACCTCTGCCGGCTGAGGGTGACAC
dog    -214  GTGTCTGTGGCCCCGTCTGCCCCACCCCCTGGACACACCTCTGCTGGCTAAGGGTGACAT
Rat    -208  GTTGTCCATGGC---TCTGCCCCACCTTCTGAATGCACCTCTGCTGGCTGACAGTGACAT
mouse  -217  GTGTCCCTGGTTCTGTCTGCCCCACCCTCTGGATGCACCTCTGCTGGCTGTAGGTGACAC
             **              ***********  *** *  ********* ****    ******

human  -153  AACCCTGTTCCCTGTCGCTCTGTTCCCCGCTTATCTCTCCCGCCTTTTCGGCGCCCACCACC
Chimp  -153  AACCCTGTTCCCTGTCGCTCTGTTCCCCGCTTATCTCTCCCGCCTTTTCGGCGCCCACCACC
dog    -154  AACACTGTTCCCTGTCACTCTGTTCCCCGCTTATCTC--CCGTCTTGTCGGCGCCCACCACC
Rat    -151  AACCCTGTCCCCTGTCACTCTGTTCCCCGCTTATCTCTCCCGCCTGTTTGGCGCCCACTATC
mouse  -157  AACCCTGTCCCCTGTCACT--GTTCCCCGCTTATCTCTCCCGCCTGTTTGGCGCCCACTATT
             *** **** ******* **  ***************  *** **  * ******** *

human   -93  TTCTTGGAAATGAGACAGAGCAAAGGGGAGGGGGCTCAG-ACCA-----CCGCCTCCCCT
Chimp   -93  TTCTTGGAAATGAGACAGAGCAAAGGGGAGGGGGCTCAG-ACCA-----CCGCCTCCCCT
dog     -94  TTCTTGGAAATGAGTTAGGACAAAGGGGAGGGGGCTCAGCACCC-----CCGCCTCCCCC
Rat     -91  TTCTTGGAAATGAGTCAGGGCAAAAGGGAGGGGGCTCAGGTGA---------CCCTCCTCC
mouse   -99  TTCTTGGAAATGAGTCAGAGCAAAATGGGGGTGGGTGAGGCGCAGGTGACCCTCCCCTAC
             **************  **  ****  ** ** ** * **                * **

                       TATA                       +1
human   -39  GGCAGGCCCCATAAAAGCGACTGTCACTCGGTCCCAGACACCAGAGCAAGCTCAAGACCC
Chimp   -39  GGCAGGCCCCATAAAAGCGACTGTCACTCGGTCCCAGACACCAGAGCAAGCTCAAGACCC
dog     -39  AGAAGGACCCATAAAAGCAACCGAATCGGGGCCCCAGACACCACAGCAAGTCTGAAACCT
Rat     -39  CACTGGTCCCATAAAAAGGACTGGGACTGGCTCCTAGACACCAGCT-------CAAGTCC
mouse   -39  CACTAGTCCCATAAAAAGGACTGGGACTGGCTCCTAGACAGCCACCACA----CAAGTCC
                  * *********   ** *   *  *  ** ***** *               *   *

human   +22  AGCAGTGGGACAGCCAGACAGACGGCACGATGGCACTGAGCTCCCAGATCTGGGCCGCTT
Chimp   +22  AGCAGTGGGACAGCCAGACAGACGGCACGATGGCACTGAGCTCCCAGATCTGGGCCGCTT
dog     +22  GACAGCAGGACAGCCAGACGGACGGCACAATGGCCCTGAGCACGCGGATCCAGGCTGCCT
Rat     +15  TTGGACTACACTGCAGGACAGAAGGCAAGATGGCACTAAGCACTCGGATCCAGGCTGCCT
mouse   +18  TTAGACTGCACAGCAGAACAGAAGGCATGATGGCACTCAGCACTCGGACCCAGGCTGCCT
                       ** **   ** ** ****  ***** ** *** * * ** *  *** ** *
```

FIG. 12

Human HJV.Fc fusion (HJV 33-399) with extracellular signal sequence and FLAG tag in place of N-terminal sequence and GPI anchoring domain removed (SEQ ID NO:1)

MSALLIILALVGAAVADYKDHDGDYKDHDIDYKDDDDKLAAAHSQCKILRCNAEYVSSTLSLRGGGSSGALRGGGGGGRGG
GVGSGGLCRALRSYALCTRRTARTCRGDLAFHSAVHGIEDLMIQHNCSRQGPTAPPPPRGPALPGAGSGLPAPDPCDYEG
RFSRLHGRPPGFLHCASFGDPHVRSFHHHFHTCRVQGAWPLLDNDFLFVQATSSPMALGANATATRKLTIIFKNMQECID
QKVYQAEVDNLPVAFEDGSINGGDRPGGSSLSIQTANPGNHVEIQAAYIGTTIIIRQTAGQLSFSIKVAEDVAMAFSAEQ
DLQLCVGGCPPSQRLSRSERNRRGAITIDTARRLCKEGLPVEDAYFHSCVFDVLISGDPNFTVAAQAALEDARAFLPDLE
KLHLFPSLELVPRGSGDPIEGRGGGGGDPKSCDKPHTCPLCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPIEKTISKAKGQPREPQV
YTLPPSRDELTKNQVSLTCLVKGFYPSDIAVEWESNGQPENNYKATPPVLDSDGSFFLYSKLTVDKSRWQQGNVFSCSVM
HEALHNHYTQKSLSLSPGK

*FIG. 21A*

Human HJV isoform A (SEQ ID NO:2)

```
  1 mgepgqspsp rsshgsppt1 stltlllllc ghahsqckil rcnaeyvsst lslrgggssg
 61 alrggggggr gggvgsgglc ralrsyalct rrtartcrgd lafhsavhgi edlmiqhncs
121 rqgptapppp rgpalpgags glpapdpcdy egrfsrlhgr ppgflhcasf gdphvrsfhh
181 hfhtcrvqga wplldndflf vqatsspmal ganatatrkl tiifknmqec idqkvyqaev
241 dnlpvafedg singgdrpgg sslsiqtanp gnhveiqaay igttiiirqt agqlsfsikv
301 aedvamafsa eqdlqlcvgg cppsqrlsrs ernrrgaiti dtarrlckeg lpvedayfhs
361 cvfdvlisgd pnftvaaqaa ledaraflpd leklhlfpsd agvplssatl lapllsglfv
421 lwlciq
```

*FIG. 21B*

Human HJV isoform B (SEQ ID NO:3)

```
  1 miqhncsrqg ptapppprgp alpgagsglp apdpcdyegr fsrlhgrppg flhcasfgdp
 61 hvrsfhhhfh tcrvqgawpl ldndflfvqa tsspmalgan atatrkltii fknmqecidq
121 kvyqaevdnl pvafedgsin ggdrpggssl siqtanpgnh veiqaayigt tiiirqtagq
181 lsfsikvaed vamafsaeqd lqlcvggcpp sqrlsrsern rrgaitidta rrlckeglpv
241 edayfhscvf dvlisgdpnf tvaaqaaled araflpdlek lhlfpsdagv plssatllap
301 llsglfvlwl ciq
```

*FIG. 21C*

Human HJV isoform C (SEQ ID NO:4)

```
  1 mqecidqkvy qaevdnlpva fedgsinggd rpggsslsiq tanpgnhvei qaayigttii
 61 irqtagqlsf sikvaedvam afsaeqdlql cvggcppsqr lsrsernrrg aitidtarrl
121 ckeglpveda yfhscvfdvl isgdpnftva aqaaledara flpdleklhl fpsdagvpls
181 satllaplls glfvlwlciq
```

FIG. 21D

Mouse HJV (SEQ ID NO:5)

```
  1 mqecidqkvy qaevdnlpaa fedgsinggd rpggsslsiq tanlgshvei raayigttii
 61 irqtagqlsf sirvaedvar afsaeqdlql cvggcppsqr lsrsernrrg aiaidtarrl
121 ckeglpveda yfqscvfdvs vsgdpnftva actalddarv fltdlenlhl fpsdagppls
181 paiclvplls alfvlwlcfs k
```

FIG. 21E

Human Fc (SEQ ID NO:6)

LELVPRGSGDPIEGRGGGGGDPKSCDKPHTCPLCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYTLPPSRDELTKN
QVSLTCLVKGFYPSDIAVEWESNGQPENNYKATPPVLDSDGSFFLYSKLTVDKSRWQQGNVFSCSVMHEALHNHYTQKSLSLS
PGK

FIG. 21F

HJV-D172A.Fc - Noncleavable form of the HJV.Fc protein (SEQ ID NO:7)

MSALLILALVGAAVADYKDHDGDYKDHDIDYKDDDDKLAAAHSQCKILRCNAEYVSSTLSLRGGGSSGALRGGGGGGRGGGVG
SGGLCRALRSYALCTRRTARTCRGDLAFHSAVHGIEDLMIQHNCSRQGPTAPPPPRGPALPGAGSGLPAPDPCDYEGRFSRLH
GRPPGFLHCASFGAPHVRSFHHHFHTCRVQGAWPLLDNDFLFVQATSSPMALGANATATRKLTIIFKNMQECIDQKVYQAEVD
NLPVAFEDGSINGGDRPGGSSLSIQTANPGNHVEIQAAYIGTTIIIRQTAGQLSFSIKVAEDVAMAFSAEQDLQLCVGGCPPS
QRLSRSERNRRGAITIDTARRLCKEGLPVEDAYFHSCVFDVLISGDPNFTVAAQAALEDARAFLPDLEKLHLFPSLELVPRGS
GDPIEGRGGGGGDPKSCDKPHTCPLCPAPELLGGPSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKTISKAKGQPREPQVYTLPPSRDELTKNQVSLTCLV
KGFYPSDIAVEWESNGQPENNYKATPPVLDSDGSFFLYSKLTVDKSRWQQGNVFSCSVMHEALHNHYTQKSLSLSPGK

FIG. 21G

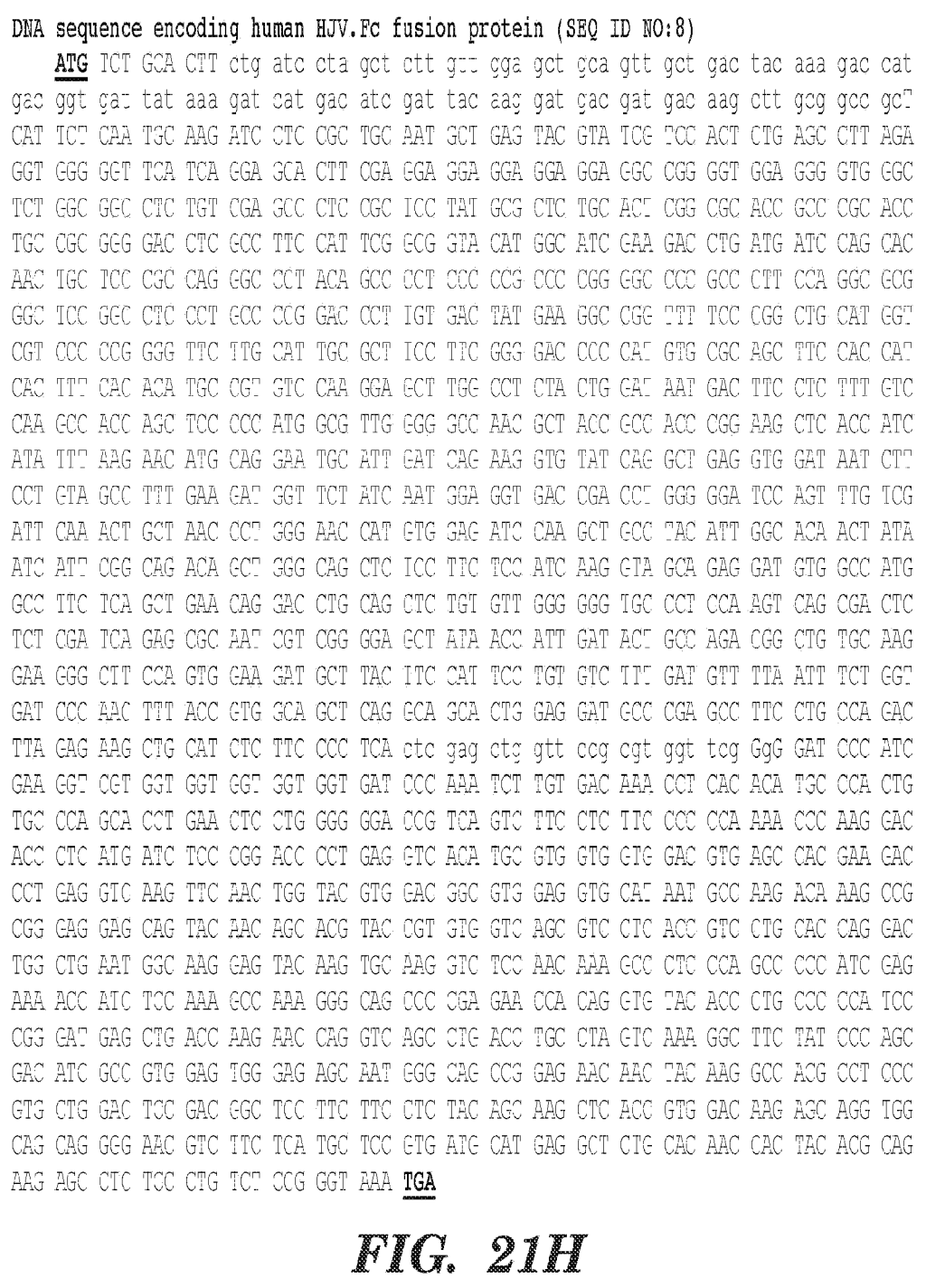

DNA sequence encoding human HJV.Fc fusion protein (SEQ ID NO:8)

ATG TCT GCA CTT ctg atc cta gct ctt gtt gga gct gca gtt gct gac tac aaa gac cat
gac ggt gat tat aaa gat cat gac atc gat tac aag gat gac gat gac aag ctt gcg gcc gcT
CAT TCT CAA TGC AAG ATC CTC CGC TGC AAT GCT GAG TAC GTA TCG TCC ACT CTG AGC CTT AGA
GGT GGG GGT TCA TCA GGA GCA CTT CGA GGA GGA GGA GGA GGA GGC CGG GGT GGA GGG GTG GGC
TCT GGC GGC CTC TGT CGA GCC CTC CGC TCC TAT GCG CTC TGC ACT CGG CGC ACC GCC CGC ACC
TGC CGC GGG GAC CTC GCC TTC CAT TCG GCG GTA CAT GGC ATC GAA GAC CTG ATG ATC CAG CAC
AAC TGC TCC CGC CAG GGC CCT ACA GCC CCT CCC CCG CCC CGG GGC CCC GCC CTT CCA GGC GCG
GGC TCC GGC CTC CCT GCC CCG GAC CCT TGT GAC TAT GAA GGC CGG TTT TCC CGG CTG CAT GGT
CGT CCC CCG GGG TTC TTG CAT TGC GCT TCC TTC GGG GAC CCC CAT GTG CGC AGC TTC CAC CAT
CAC TTT CAC ACA TGC CGT GTC CAA GGA GCT TGG CCT CTA CTG GAT AAT GAC TTC CTC TTT GTC
CAA GCC ACC AGC TCC CCC ATG GCG TTG GGG GCC AAC GCT ACC GCC ACC CGG AAG CTC ACC ATC
ATA TTT AAG AAC ATG CAG GAA TGC ATT GAT CAG AAG GTG TAT CAG GCT GAG GTG GAT AAT CTT
CCT GTA GCC TTT GAA GAT GGT TCT ATC AAT GGA GGT GAC CGA CCT GGG GGA TCC AGT TTG TCG
ATT CAA ACT GCT AAC CCT GGG AAC CAT GTG GAG ATC CAA GCT GCC TAC ATT GGC ACA ACT ATA
ATC ATT CGG CAG ACA GCT GGG CAG CTC TCC TTC TCC ATC AAG GTA GCA GAG GAT GTG GCC ATG
GCC TTC TCA GCT GAA CAG GAC CTG CAG CTC TGT GTT GGG GGG TGC CCT CCA AGT CAG CGA CTC
TCT CGA TCA GAG CGC AAT CGT CGG GGA GCT ATA ACC ATT GAT ACT GCC AGA CGG CTG TGC AAG
GAA GGG CTT CCA GTG GAA GAT GCT TAC TTC CAT TCC TGT GTC TTT GAT GTT TTA ATT TCT GGT
GAT CCC AAC TTT ACC GTG GCA GCT CAG GCA GCA CTG GAG GAT GCC CGA GCC TTC CTG CCA GAC
TTA GAG AAG CTG CAT CTC TTC CCC TCA ctc gag ctg gtt ccg cgt ggt tcg GgG GAT CCC ATC
GAA GGT CGT GGT GGT GGT GGT GGT GAT CCC AAA TCT TGT GAC AAA CCT CAC ACA TGC CCA CTG
TGC CCA GCA CCT GAA CTC CTG GGG GGA CCG TCA GTC TTC CTC TTC CCC CCA AAA CCC AAG GAC
ACC CTC ATG ATC TCC CGG ACC CCT GAG GTC ACA TGC GTG GTG GTG GAC GTG AGC CAC GAA GAC
CCT GAG GTC AAG TTC AAC TGG TAC GTG GAC GGC GTG GAG GTG CAT AAT GCC AAG ACA AAG CCG
CGG GAG GAG CAG TAC AAC AGC ACG TAC CGT GTG GTC AGC GTC CTC ACC GTC CTG CAC CAG GAC
TGG CTG AAT GGC AAG GAG TAC AAG TGC AAG GTC TCC AAC AAA GCC CTC CCA GCC CCC ATC GAG
AAA ACC ATC TCC AAA GCC AAA GGG CAG CCC CGA GAA CCA CAG GTG TAC ACC CTG CCC CCA TCC
CGG GAT GAG CTG ACC AAG AAC CAG GTC AGC CTG ACC TGC CTA GTC AAA GGC TTC TAT CCC AGC
GAC ATC GCC GTG GAG TGG GAG AGC AAT GGG CAG CCG GAG AAC AAC TAC AAG GCC ACG CCT CCC
GTG CTG GAC TCC GAC GGC TCC TTC TTC CTC TAC AGC AAG CTC ACC GTG GAC AAG AGC AGG TGG
CAG CAG GGG AAC GTC TTC TCA TGC TCC GTG ATG CAT GAG GCT CTG CAC AAC CAC TAC ACG CAG
AAG AGC CTC TCC CTG TCT CCG GGT AAA TGA

*FIG. 21H*

DNA sequence encoding human HJV-D172A.Fc fusion protein (SEQ ID NO:9)

ATG TCT GCA CTT ctg atc cta gct ctt gtt cga gct gca gtt gct gac tac aaa gac cat
gac ggt gat tat aaa gat cat gac atc gat tac aag gat gac gat gac aag ctt gcg gcc gcT
CAT TCT CAA TGC AAG ATC CTC CGC TGC AAT GCT GAG TAC GTA TCG TCC ACT CTG AGC CTT AGA
GGT GGG GGT TCA TCA GGA GCA CTT CGA GGA GGA GGA GGA GGA GGC CGG GGT GGA GGG GTG GGC
TCT GGC GGC CTC TGT CGA GCC CTC CGC TCC TAT GCG CTC TGC ACT CGG CGC ACC GCC CGC ACC
TGC CGC GGG GAC CTC GCC TTC CAT TCG GCG GTA CAT GGC ATC GAA GAC CTG ATG ATC CAG CAC
AAC TGC TCC CGC CAG GGC CCT ACA GCC CCT CCC CCG CCC CGG GGC CCC GCC CTT CCA GGC GCG
GGC TCC GGC CTC CCT GCC CCG GAC CCT TGT GAC TAT GAA GGC CGG TTT TCC CGG CTG CAT GGT
CGT CCC CCG GGG TTC TTG CAT TGC GCT TCC TTC GGG GCC CCC CAT GTG CGC AGC TTC CAC CAT
CAC TTT CAC ACA TGC CGT GTC CAA GGA GCT TGG CCT CTA CTG GAT AAT GAC TTC CTC TTT GTC
CAA GCC ACC AGC TCC CCC ATG GCG TTG GGG GCC AAC GCT ACC GCC ACC CGG AAG CTC ACC ATC
ATA TTT AAG AAC ATG CAG GAA TGC ATT GAT CAG AAG GTG TAT CAG GCT GAG GTG GAT AAT CTT
CCT GTA GCC TTT GAA GAT GGT TCT ATC AAT GGA GGT GAC CGA CCT GGG GGA TCC AGT TTG TCG
ATT CAA ACT GCT AAC CCT GGG AAC CAT GTG GAG ATC CAA GCT GCC TAC ATT GGC ACA ACT ATA
ATC ATT CGG CAG ACA GCT GGG CAG CTC TCC TTC TCC ATC AAG GTA GCA GAG GAT GTG GCC ATG
GCC TTC TCA GCT GAA CAG GAC CTG CAG CTC TGT GTT GGG GGG TGC CCT CCA AGT CAG CGA CTC
TCT CGA TCA GAG CGC AAT CGT CGG GGA GCT ATA ACC ATT GAT ACT GCC AGA CGG CTG TGC AAG
GAA GGG CTT CCA GTG GAA GAT GCT TAC TTC CAT TCC TGT GTC TTT GAT GTT TTA ATT TCT GGT
GAT CCC AAC TTT ACC GTG GCA GCT CAG GCA GCA CTG GAG GAT GCC CGA GCC TTC CTG CCA GAC
TTA GAG AAG CTG CAT CTC TTC CCC TCA ctc gag ctg gtt ccg cgt ggt tcg GgG GAT CCC ATC
GAA GGT CGT GGT GGT GGT GGT GGT GAT CCC AAA TCT TGT GAC AAA CCT CAC ACA TGC CCA CTG
TGC CCA GCA CCT GAA CTC CTG GGG GGA CCG TCA GTC TTC CTC TTC CCC CCA AAA CCC AAG GAC
ACC CTC ATG ATC TCC CGG ACC CCT GAG GTC ACA TGC GTG GTG GTG GAC GTG AGC CAC GAA GAC
CCT GAG GTC AAG TTC AAC TGG TAC GTG GAC GGC GTG GAG GTG CAT AAT GCC AAG ACA AAG CCG
CGG GAG GAG CAG TAC AAC AGC ACG TAC CGT GTG GTC AGC GTC CTC ACC GTC CTG CAC CAG GAC
TGG CTG AAT GGC AAG GAG TAC AAG TGC AAG GTC TCC AAC AAA GCC CTC CCA GCC CCC ATC GAG
AAA ACC ATC TCC AAA GCC AAA GGG CAG CCC CGA GAA CCA CAG GTG TAC ACC CTG CCC CCA TCC
CGG GAT GAG CTG ACC AAG AAC CAG GTC AGC CTG ACC TGC CTA GTC AAA GGC TTC TAT CCC AGC
GAC ATC GCC GTG GAG TGG GAG AGC AAT GGG CAG CCG GAG AAC AAC TAC AAG GCC ACG CCT CCC
GTG CTG GAC TCC GAC GGC TCC TTC TTC CTC TAC AGC AAG CTC ACC GTG GAC AAG AGC AGG TGG
CAG CAG GGG AAC GTC TTC TCA TGC TCC GTG ATG CAT GAG GCT CTG CAC AAC CAC TAC ACG CAG
AAG AGC CTC TCC CTG TCT CCG GGT AAA TGA

*FIG. 21I*

Optimized human HJV-Fc fusion with extracellular signal sequence and GPI anchoring domain removed (SEQ ID NO:10)

MSALLILALVGAAVAHSQCKILRCNAEYVSSTLSLRGGGSSGALRGGGGGGRGGGVGSGGLC
RALRSYALCTRRTARTCRGDLAFHSAVHGIEDLMIQHNCSRQGPTAPPPPRGPALPGAGSGL
PAPDPCDYEGRFSRLHGRPPGFLHCASFGDPHVRSFHHHFHTCRVQGAWPLLDNDFLFVQAT
SSPMALGANATATRKLTIIFKNMQECIDQKVYQAEVDNLPVAFEDGSINGGDRPGGSSLSIQ
TANPGNHVEIQAAYIGTTIIIRQTAGQLSFSIKVAEDVAMAFSAEQDLQLCVGGCPPSQRLS
RSERNRRGAITIDTARRLCKEGLPVEDAYFHSCVFDVLISGDPNFTVAAQAALEDARAFLPD
LEKLHLFPKSCDKTHTCPPCPAPELLGGPSVFLFPPKPKDTLMISRTPEVTCVVVDVSHEDP
EVKFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK

*FIG. 21J*

Codon-optimized DNA sequence encoding human HJV.Fc fusion protein (SEQ ID NO:11). BamHI/HindIII linker sites are underlined; Kozak sequence in lower case; Start codon in bold; EcoRI/NotI linker sites are underlined; Stop Codon in bold GGATCCAAGCTTgccgccATGAGCGCCCTGCTTATTCTGGCCCTGGTTGGAGCAGCCGTGGC
TCATAGCCAGTGCAAGATCCTGCGATGCAATGCCGAGTACGTGTCTTCCACCCTCAGTCTCA
GAGGCGGGGGAGTTCCGGCGCACTGCGCGGGGGAGGTGGAGGTGGCCGCGGAGGCGGAGTG
GGATCTGGGGGACTGTGCCGAGCTTTGCGGAGTTACGCTCTGTGCACAAGACGCACCGCCAG
GACCTGCAGGGGAGACCTGGCATTCCACAGCGCAGTGCACGGCATTGAAGACTTGATGATTC
AGCATAATTGTAGTAGACAAGGCCCTACCGCTCCCCCCCCTCCCAGGGGCCCCGCTTTGCCT
GGGGCAGGTTCCGGACTGCCCGCCCCAGATCCTTGTGACTACGAGGGGCGGTTCAGCCGACT
CCATGGAAGGCCCCCAGGCTTCCTGCACTGCGCAAGTTTTGGCGATCCACACGTCAGGTCAT
TTCACCACCACTTTCATACCTGTCGTGTCCAGGGCGCATGGCCTCTGCTGGACAACGACTTC
CTCTTCGTCCAAGCAACAAGTTCACCTATGGCTCTGGGGGCAAATGCTACTGCCACCCGAAA
ACTTACCATTATCTTTAAGAATATGCAAGAATGTATCGATCAGAAGGTCTACCAGGCCGAAG
TTGACAACCTGCCCGTGGCTTTCGAGGATGGTTCAATCAACGGAGGGGACCGGCCTGGAGGC
TCCAGTCTGAGCATCCAGACCGCCAATCCTGGAAATCACGTGGAGATCCAGGCTGCCTACAT
CGGCACAACAATCATAATTAGGCAGACCGCTGGCCAGCTGAGCTTCTCCATCAAGGTCGCCG
AAGACGTGGCCATGGCTTTCTCTGCCGAACAGGACCTCCAGCTTTGCGTGGGTGGTTGTCCA
CCCTCCCAGCGCCTTTCTCGATCCGAACGCAATAGGCGAGGCGCAATCACTATCGACACTGC
TCGCAGATTGTGCAAAGAGGGCCTGCCTGTGGAGGATGCATACTTCCATTCTTGTGTGTTCG
ACGTCCTGATAAGCGGAGACCCAAATTTCACAGTGGCTGCTCAGGCCGCACTGGAGGATGCC
AGGGCCTTTTTGCCCGATCTGGAAAAGTTGCATCTGTTCCCAAAATCCTGTGACAAGACTCA
TACCTGTCCACCGTGTCCCGCCCCCGAACTCTTGGGCGGGCCTTCTGTGTTCCTCTTCCCAC
CCAAACCAAAAGACACACTGATGATCTCCAGGACCCCTGAAGTGACTTGCGTCGTGGTTGAC
GTGTCTCATGAAGACCCCGAGGTGAAGTTCAACTGGTACGTCGATGGAGTGGAGGTTCATAA
CGCCAAGACAAAACCAAGGGAGGAACAATACAACTCTACATACAGGGTGGTCAGTGTGCTGA
CTGTGCTGCACCAGGACTGGCTCAACGGCAAAGAGTACAAATGCAAGGTGTCTAACAAGGCA
CTTCCTGCTCCAATTGAAAAAACCATCTCCAAGGCTAAGGGGCAGCCAAGGGAACCACAGGT
GTATACTCTTCCTCCTTCTCGCGACGAACTGACTAAAAATCAGGTGTCATTGACCTGTCTGG
TGAAGGGCTTTTACCCCTCCGATATAGCTGTGGAGTGGGAGAGCAACGGGCAGCCCGAGAAC
AATTATAAAACCACACCACCTGTCCTCGACAGTGATGGATCATTTTTCCTCTACAGTAAGCT
GACCGTGGATAAATCTAGGTGGCAGCAGGGGAACGTGTTTTCTTGCTCCGTGATGCACGAGG
CCCTTCACAACCATTACACACAGAAGAGCCTGAGCCTGTCCCCAGGAAAGTGAGAATTCGCG
GCCGC

*FIG. 21K*

```
DRAGON :  MGVRAAPSCAAAPAAAGAEQSRRPGLWPPSPPPPLLLLLLSLGLLHAGDCQQPTQCRIQ : 60
DL-2   :  ---------MQPPRERLVVTGRAGWMGMGRGAGRSALGLWPTLAFLLCSFPAAISPCKIL : 51
DL-1   :  -----------------------MGQSPSPRSPHGSPPTLSTLTLLLLLCGQAHSQCKIL : 37

DRAGON :  KCITDFVALTAHL----------NSAADGFDS-EFCKALRAYAGCTQRTSKACRGNLVYH : 109
DL-2   :  KCNSEFWSATSSG----------SHAPASDDVPEFCAALRTYALCTRRTARTCRGDLAYH : 101
DL-1   :  KCNAEYVSSTLHLRGGGSPDTPRGGGRGGLASGGLCRALRSYALCTRRTARTCRGDLAFH : 97

DRAGON :  SAVLGISDLMSQRNCSKDGPTSSTNPEVTHDPCNYHSHGG------VREHGGGDQRPPNY : 163
DL-2   :  SAVHGIEDLMSQHNCSKDGPTSQPRVRTLPPAGDSQERSDSPEICHYEKSFHKHSAAPNY : 161
DL-1   :  SAVHGIEDLMIQHNCSRQGPTAPPPARGPALPGAGPAPLTPDPCDYEARFSRLHGRAPGF : 157

DRAGON :  LFCGLFGDPHLRTFKDHFQTCKVEGAWPLIDNNYLSVQVTNVPVVPGSSATATNKVTIIF : 223
DL-2   :  THCGLFGDPHLRTFTDHFQTCKVQGAWPLIDNNYLNVQVTNTPVLPGSAATATSKLTIIF : 221
DL-1   :  LHCASFGDPHVRSFHNQFHTCRVQGAWPLLDNDFLFVQATSSPVSSGANATTIRKVTIIF : 217

DRAGON :  KAQHECTDQKVYQAVTDDLPAAFVDGTTSGGDGD-VKSLHIVEKESGRYVEMHARYIGTT : 282
DL-2   :  KNFQECVDQKVYQAEMDELPSAFADGSKNGGDKHGANSLKITEKVSGQHVEIQAKYIGTT : 281
DL-1   :  KNMQECIDQKVYQAEVDNLPAAFEDGSINGGDRPGGSSLSIQTANLGSHVEIRAAYIGTT : 277

DRAGON :  VFVRQLGRYLTLAIRMPEDLAMSYEE--SQDLQLCVNGCPMSECIDDGQGQVSAILGHSL : 340
DL-2   :  IVVRQVGRYLTFAVRMPEEVVNAVEDRDSQGLYLCLRGCPLNQQIDFQAFRANAESPRRP : 341
DL-1   :  IIIRQTAGQLSFSIRVAEDVARAFSA--EQDLQLCVGGCPPSQRLSRSERNR-------- : 327

DRAGON :  PHTTSVQAWPG-YTLETASTQCHEKMPVKDIYFQSCVFDLLTTGDANFTAAAHSALEDVE : 399
DL-2   :  AAASPSPVVPETFPYETAVAKCKEKLPVEDLYYQACVFDLLTTGDVNFTLAAYYALEDGK : 401
DL-1   :  ---------RGAIAIDTARRLCKEGLPVEDAYFQSCVFDVSVSGDPNFTVAAQTALDDAR : 378

DRAGON :  ALHPRKERWHIFP------------SSCGGCRDLPVGLGLTCLILIMFL------- : 436
DL-2   :  MLHSNKDKLHLFERTRELPGAVAAAAAATTFPLAPQILLGTIPLLVLLPVLW--- : 454
DL-1   :  IFLTDLENLHLFP--------------SDAGPPLSPAICLVPLLSALFVLWLCFSK : 420
```

*FIG. 23*

```
Human Hjv  1    MGEPGQSPSPRSSHGSPPTLSTLTLLLLLCGHAHSQCKILRCNAEYVSST
Mouse RGMc 1    ---MGQSPSPRSPHGSPPTLSTLTLLLLLCGQAHSQCKILRCNAEYVSST
Consensus  1    mge GQSPSPRS HGSPPTLSTLTLLLLLCG AHSQCKILRCNAEYVSST
                                                 ↑  *     *

Human Hjv  51   LSLRGGGSSGALRGGGGGGRGGGVGSGGLCRALRSYALCTRRTARTCRGD
Mouse RGMc 48   LSLRGGGSPDTPRGGGRG----GLASGGLCRALRSYALCTRRTARTCRGD
Consensus  51   LSLRGGGS    RGGG GgrggGvgSGGLCRALRSYALCTRRTARTCRGD
                                             *        *       *

Human Hjv  101  LAFHSAVHGIEDLMIQHNCSRQGPTAPPPPRGPALPGAGSGLPAPDPCDY
Mouse RGMc 94   LAFHSAVHGIEDLMIQHNCSRQGPTAPPPARGPALPGAGPAPLTPDPCDY
Consensus  101  LAFHSAVHGIEDLMIQHNCSRQGPTAPPP RGPALPGAG g   PDPCDY
                                  *

Human Hjv  151  EGRFSRLHGRPPGFLHCASFGDPHVRSFHHHFHTCRVQGAWPLLDNDFLF
Mouse RGMc 144  EARFSRLHGRAPGFLHCASFGDPHVRSFHNQFHTCRVQGAWPLLDNDFLF
Consensus  151  EgRFSRLHGR PGFLHCASFGDPHVRSFH  FHTCRVQGAWPLLDNDFLF
                                *    ↑            *

Human Hjv  201  VQATSSPMALGANATATRKLTIIFKNMQECIDQKVYQAEVDNLPVAFEDG
Mouse RGMc 194  VQATSSPVSSGANATTIRKITIIFKNMQECIDQKVYQAEVDNLPAAFEDG
Consensus  201  VQATSSPm  GANAT  RKlTIIFKNMQECIDQKVYQAEVDNLP AFEDG
                                             *

Human Hjv  251  SINGGDRPGGSSLSIQTANPGNHVEIQAAYIGTTIIIRQTAGQLSFSIKV
Mouse RGMc 244  SINGGDRPGGSSLSIQTANLGSHVEIRAAYIGTTIIIRQTAGQLSFSIRV
Consensus  251  SINGGDRPGGSSLSIQTAN G HVEI AAYIGTTIIIRQTAGQLSFSIkV

Human Hjv  301  AEDVAMAFSAEQDLQLCVGGCPPSQRLSRSERNRRGAITIDTARRLCKEG
Mouse RGMc 294  AEDVARAFSAEQDLQLCVGGCPPSQRLSRSERNRRGAIAIDTARRLCKEG
Consensus  301  AEDVA AFSAEQDLQLCVGGCPPSQRLSRSERNRRGAI IDTARRLCKEG
                                    *                           *

Human Hjv  351  LPVEDAYFHSCVFDVLISGDPNFTVAAQAALEDARAFLPDLEKLHLFPSD
Mouse RGMc 344  LPVEDAYFQSCVFDVSVSGDPNFTVAAQTALDDARIFLTDLENLHLFPSD
Consensus  351  LPVEDAYF SCVFDV iSGDPNFTVAAQ ALeDAR FL DLE LHLFPSD
                         *                                      ↑

Human Hjv  401  AGVPLSSATLLAPLLSGLFVLWLCIQ-
Mouse RGMc 394  AGPPLSPAICLVPLLSALFVLWLCFSK
Consensus  401  AG PLS A  L PLLSgLFVLWLC  k
```

*FIG. 24*

```
___Region 1 36-50_  _________________Region 2 51-79____________

QCKILRCNAE YVSSTLSLRG GGSSGALRGG GGGGRGGGVG SGGLCRALRS
eeeeeebeee bbebbbebee eeeeeeeeee eeebeeeeee eeebbebbeb
 f f  sf                                         s ssf

________Region 3 80-125_____________________________ ___________

YALCTRRTAR TCRGDLAFHS AVHGIEDLMI QHNCSRQGPT APPPPRGPAL
bbebeeeeee ebeeebbbbb bbbbbeebbb eeebeeeeee eeeeeeeeee
s  s   f     fff   ss     s f     fsf  fff

________Region 4 126-166_________________ ______________________

PGAGSGLPAP DPCDYEGRFS RLHGRPPGFL HCASFGDPHV RSFHHHFHTC
eeeeeeeeee ebbeeeeebe eeeeeeeebb bbbbbebeeb ebbeeebeeb
f             s                   s   sfsff  f s      fs

_________________________Region 5 167-256______________________

RVQGAWPLLD NDFLFVQATS SPMALGANAT ATRKLTIIFK NMQECIDQKV
eeeebbbbbe eebbbbebee eeeeeebebe beeebbbbbe ebeebbeeeb
 f fs sssf f     sfsff  f        f   f f s          s  f

___________________________ __________________________________

YQAEVDNLPV AFEDGSINGG DRPGGSSLSI QTANPGNHVE IQAAYIGTTI
beeeeeeebeb bbeeeeeeee eeeeeebbeb beeeeeeebb bbbebbbbbb
s f     sf      fff    f                 f    s s     s

_____________Region 6 257-327__________________________ _________

IIRQTAGQLS FSIKVAEDVA MAFSAEQDLQ LCVGGCPPSQ RLSRSERNRR
bbeebbebbb bbbebbeebb ebbeeeeebe bbbeebeeee ebeeeeeeee
  f  s    s  s f s               f ss  fsf

__________________Region 7 328-400_____________________________

GAITIDTARR LCKEGLPVED AYFHSCVFDV LISGDPNFTV AAQAALEDAR
eebebeebee ebeeebebee bbbebbbbbb bbeeebebbb bbbbbbeebe
        s     s         f      ssss    fff f    s   s  f

__________________

AFLPDLEKLH LFPSD
ebbeeeeebe beeee
```

FIG. 25

HEMOJUVELIN FUSION PROTEINS AND USES THEREOF

CROSS REFERENCED APPLICATIONS

This application is a national stage application under 35 U.S.C. 371 of International Application No. PCT/US2008/059753, filed on Apr. 9, 2008, which claims benefit under 35 U.S.C. 119(e) of U.S. Provisional Patent Application Ser. No. 60/922,459 filed on Apr. 9, 2007, the contents of which are incorporated by reference in their entireties.

STATEMENT AS TO FEDERALLY FUNDED RESEARCH

This invention was made with the United States Government support under Grant numbers F32 DK-068997, RO1 DK-69533, RO1 DK-71837, T32 HL07623, K08 DK-075846, and RO1 DK-053813 awarded by National Institutes of Health (NIH). The Government of the United States has certain rights in the invention.

FIELD OF THE INVENTION

The present invention is directed towards a soluble form of hemojuvelin (HJV), particularly HJV fusion proteins for the use in compositions and methods for regulation of iron metabolism.

REFERENCE TO A "SEQUENCE LISTING"

The sequence listing material in the text file entitled "12595423_Seq_List_New.txt" (112,388 bytes), which was created on Jul. 29, 2010, is herein incorporated by reference in its entirety.

BACKGROUND OF THE INVENTION

In general, the invention relates to hemojuvelin fusion proteins and uses of such proteins.

Iron homeostasis is vitally important. Iron is required for many biological reactions and processes, including oxygen transport by hemoglobin, yet excessive iron can be toxic. To maintain proper serum levels, a complex system of iron transport and storage involving organisms employ iron storage protein ferritin, the iron transporter transferrin, and the transferrin receptor. When feedback controlling this system is disrupted, either insufficient iron (anemia) or iron overload (hemochromatosis) can result. Mutations in HFE2, the gene coding for hemojuvelin, have been previously been identified to cause iron overload in chromosome 1q-linked juvenile hemochromatosis.

Hemojuvelin was identified as a member of the Repulsive Guidance Molecule (RGM) family of proteins, which include DRAGON and RGMa. The proteins were initially identified as being responsive to the transcription factor DRG11 (see, e.g., U.S. Patent Application Publication No. 2004/0014141, which is incorporated herein by reference) and their ability to promote neural adhesion and survival.

SUMMARY OF THE INVENTION

The present invention relates to methods and compositions comprising a soluble form of HJV. In some embodiments the soluble form of HJV is HJV fused to a stabilizing polypeptide, such as for example, but not limited to fusion with a Fc polypeptide or fragment thereof.

As disclosed herein, the inventors have discovered a novel therapeutic, HJV.Fc, useful in the treatment of conditions involving hepcidin regulation (e.g., iron-related disorders such as those described herein). HJV.Fc increases ferroportin expression, mobilizes splenic iron stores, and increases serum iron levels in vivo. The inventors also show herein that BMP-2 administration increases hepcidin expression and decreases serum iron levels in vivo.

Accordingly, one aspect of the present invention provides HJV fusion proteins (for example, HJV.Fc), pharmaceutical compositions containing such proteins, polynucleotides encoding such proteins, and methods for treating HJV-related disorders such as iron-related disorders including iron overload and anemia of chronic disease (e.g., those described herein). These data also support a role for modulators of the BMP signaling pathway in treating diseases of iron overload and anemia of chronic disease.

Accordingly, in a first aspect the invention provides a fusion protein including a hemojuvelin (HJV) fragment or full length HJV protein, where the fragment has at least 85% (e.g., at least 90%, 95%, or 99%, or 100%) amino acid sequence identity to a functional portion of the HJV protein (e.g., the human HJV protein); and a first fusion partner, such as IgG1 Fc, e.g., human or mouse IgG1 Fc, covalently bonded to the HJV fragment. The first fusion partner may be covalently bonded to the N-terminus or to the C-terminus of the HJV protein fragment. The HJV fragment may be a soluble fragment of the full length HJV, may lack the C-terminal GPI anchoring domain, or may lack the N-terminal signal sequence (e.g., lacks both the C-terminal GPI anchoring domain and the N-terminal signal sequence). The HJV sequence may be based on any naturally occurring HJV isoform. The fusion protein may further include a second fusion partner (e.g., in place of the N-terminal signal sequence). The fusion protein may have an amino acid sequence with at least 85% (e.g., at least 90%, 95% or 99%, or 100%) identity to the sequence of SEQ ID NO:1. The fusion protein may have enhanced proteolytic stability (e.g., a mutation at a position corresponding to amino acid 172 such as an aspartic acid to alanine point mutation of isoform A of the human HJV sequence). The fusion protein with enhanced proteolytic stability may have an amino acid sequence with at least 85% (e.g., at least 90%, 95%, or 99%) sequence identity to SEQ ID NO:7. The HJV fragment must be a functional fragment. As used herein, the fragment must display at least 30% agonist or antagonist biological activity of the wild-type HJV as determined in any in vitro or in vivo test, such as the assays as used herein and in the Examples. The biological activity in one embodiment is related to iron regulation. The fragment must be at least 6 amino acids, in another embodiment, the fragment must be at least 7 or at least 10, or at least 14, or at least 18, or at least 25, or at least 30, or at least 50, or at least 70 amino acids, or more than 70 amino acids in length. The fusion protein may be produced recombinantly, may be isolated, or may be substantially pure.

In another aspect, the invention provides a pharmaceutical composition including the fusion protein of the first aspect and a pharmaceutically acceptable carrier.

In another aspect, the invention also provides a method for producing the fusion protein of the invention including introducing into a cell with a vector including a sequence encoding the fusion protein operably linked to a promoter; and culturing the cell under conditions where the protein is expressed. The method may further include purifying the protein.

The invention also provides a polynucleotide encoding the fusion protein of the first aspect, a vector including the polynucleotide, and a host cell containing the vector. The vector may be suitable for expressing the fusion protein in a eukaryotic (e.g., mammalian, yeast, insect) cell or in prokaryotic cell (e.g., *E. coli*). The host cell may be any host cell described herein.

The invention also features a method for treating a patient having a hepcidin- or an HJV-related disorder such as iron-related disorder. The method includes administering to the patient the fusion protein of the first aspect in an amount effective to treat the patient. The iron-related disorder may be any of those described herein, e.g., hereditary hemochromatosis, porphyria cutanea tarda, hereditary spherocytosis, hyprochromic anemia, hysererythropoietic anemia (CDAI), faciogenital dysplasia (FGDY), Aarskog syndrome, atransferrinemia, sideroblastic anemia (SA), pyridoxine-responsive sidero-blastic anemia, and a hemoglobinopathy, thalassemia, sickle cell, anemia of chronic disease, iron deficiency anemia, functional iron deficiency, or microcytic anemia. A "fusion protein" is meant a polypeptide sequence formed from two or more (e.g., three, four, or five) heterologous joined sequences. The HJV fusion protein may be administered by any route or an any dosage described herein.

Accordingly, one aspect of the present invention relates to a fusion protein comprising: (a) a hemojuvelin (HJV) polypeptide or fragment thereof, wherein the fragment has at least 95% amino acid sequence identity to a portion of the HJV protein and is at least 6 amino acids; and (b) a first fusion partner which is conjugated to said HJV polypeptide or fragment thereof. In some embodiments, the first fusion partner is fused to the N-terminus or to the C-terminus of the HJV protein fragment. In some embodiments, the first fusion partner is IgG1 Fc, such as human IgG1 Fc.

In some embodiments, a HJV fragment useful in the HJV fusion protein as disclosed herein is a soluble fragment. In another embodiment, a HJV fragment is a functional HJV fragment. In some embodiments, a HJV fragment can lack the C-terminal GPI anchoring domain, or alternatively, a HJV fragment can lack the N-terminal signal sequence, or alternatively, a HJV fragment can lack both the C-terminal GPI anchoring domain and the N-terminal signal sequence.

In some embodiments, a HJV fusion protein as disclosed herein can further comprise a second fusion partner. In some embodiments, the HJV protein or fragment thereof is conjugated to the first fusion partner by way of a covalent bond, such as a peptide bond, although the HJV protein and fusion partner can be conjugated together by any means commonly known by persons of ordinary skill in the art.

In some embodiments, a HJV fusion protein as disclosed herein comprises a HJV fragment which lacks the N-terminal signal sequence. In some embodiments, the HJV protein useful in the HJV fusion protein as disclosed herein is a human HJV protein, such as a human HJV protein which corresponds to amino acid SEQ ID NO: 2, or 3 or 4, or functional variants or functional derivatives thereof, as those terms are defined herein. In alternative embodiments, a human HJV protein useful in the HJV fusion protein as disclosed herein is not SEQ ID NO: 62, 63 or 64 (which refer to SEQ ID NOs 7, 10 and 30 of U.S. Pat. No. 7,319,138, respectively).

In some embodiments, a HJV protein useful in the HJV fusion protein as disclosed herein has enhanced proteolytic stability, for example where the enhanced proteolytic stability is conferred by a sequence alteration at the amino acid corresponding to amino acid 172 of isoform A of human HJV (SEQ ID NO: 2).

Further embodiments relate to a HJV fusion protein which comprises, or alternatively consists essentially of an amino acid sequence with at least 95% identity to the sequence of SEQ ID NO: 10, or a functional derivative or functional variant thereof. In another embodiment, a HJV fusion protein can have an amino acid sequence which comprises, or alternatively consists essentially of the sequence of SEQ ID NO: 10, or a functional derivative or functional variant thereof.

In an alternative embodiment, a HJV fusion protein can comprise an amino acid sequence with at least 95% identity to the sequence of SEQ ID NO:7, or in a further embodiment, the HJV fusion protein can have an amino acid sequence comprising, or alternatively consisting essentially of the sequence of SEQ ID NO:7.

In an alternative embodiment, a HJV fusion protein can comprise an amino acid sequence with at least 95% identity to the sequence of SEQ ID NO:1. In another embodiment, the HJV fusion protein can have an amino acid sequence comprising, or alternatively consisting essentially of the sequence of SEQ ID NO:1.

Another aspect of the present invention relates to the use of the HJV fusion protein as disclosed herein for the treatment or prevention of a HJV-related disorder, such as for example an iron-related disorder. Iron related disorders are well known by persons of ordinary skill in the art, for example but are not limited to; hereditary hemochromatosis, porphyria cutanea tarda, hereditary spherocytosis, hyprochromic anemia, hysererythropoietic anemia (CDAI), faciogenital dysplasia (FGDY), Aarskog syndrome, atransferrinemia, sideroblastic anemia (SA), pyridoxine-responsive sidero-blastic anemia, and a hemoglobinopathy, thalassemia, sickle cell, anemia of chronic disease, iron deficiency anemia, functional iron deficiency, and microcytic anemia.

Another aspect of the present invention relates to a pharmaceutical composition comprising the HJV fusion protein as disclosed herein and a pharmaceutically acceptable carrier.

Another aspect of the present invention relates to a method for producing a HJV fusion protein as disclosed herein, comprising (a) introducing into a cell with a vector comprising a sequence encoding the fusion protein operably linked to a promoter; and (b) culturing the cell under conditions where said protein is expressed. In some embodiments, the method for producing the HJV fusion protein as disclosed herein further comprises a step of purifying the protein of step (b) by any method commonly known by one of ordinary skill in the art.

Another aspect of the present invention relates to a polynucleotide encoding the HJV fusion protein as disclosed herein, wherein the polynucleotide encodes both a HJV polypeptide or fragment thereof which has at least 85% amino acid sequence identity to a portion of the HJV protein; and a first fusion partner.

Another aspect of the present invention relates to a vector comprising the polynucleotide as discussed herein. In some embodiments, the vector is a viral vector, such as for example but not limited to an adenoviral vector, a poxvirus vector and a lentiviral vector. In some embodiments, the vector can comprise a nucleic acid sequence which encodes a HJV polypeptide or fragment thereof which has at least 95% amino acid sequence identity to a portion of the HJV protein; and a first fusion partner, wherein the nucleic acid sequence is operatively linked to tissue- or cell-type specific promoter, such as but no limited to muscle- or liver specific promoters, such as those disclosed herein and other muscle and/or liver promoters which are commonly known by persons of ordinary skill in the art.

Another aspect of the present invention relates to a pharmaceutical composition comprising a vector which comprises the nucleic acid encoding the HJV fusion protein as disclosed herein and, optionally, a pharmaceutically acceptable carrier.

Another aspect of the present invention relates to a host cell comprising the vector as disclosed herein, where the vector comprises the nucleic acid encoding the HJV fusion protein as disclosed herein.

Another aspect of the present invention relates to a method for treating or preventing a patient having an HJV-related disorder comprising administering to a patient the HJV fusion protein as disclosed herein in an amount effective to treat said patient. In some embodiments, a HJV-related disorder which can be treated by the methods as disclosed herein is an iron-related disorder, such as but not limited to; hereditary hemochromatosis, porphyria cutanea tarda, hereditary spherocytosis, hyprochromic anemia, hysererythropoietic anemia (CDAI), faciogenital dysplasia (FGDY), Aarskog syndrome, atransferrinemia, sideroblastic anemia (SA), pyridoxine-responsive sidero-blastic anemia, and a hemoglobinopathy, thalassemia, sickle cell, anemia of chronic disease, iron deficiency anemia, functional iron deficiency, and microcytic anemia.

BRIEF DESCRIPTION OF THE DRAWINGS

FIGS. 3A and 3B show HepG2 cells were transfected with a BMP-responsive firefly luciferase reporter (BRE-Luc) and a control *Renilla* luciferase vector (pRL-TK) alone (bars 1-2, 5-6) or with 40 ng/ml cDNA encoding murine hemojuvelin (Hjv) (bars 3-4). Transfected cells were treated in the absence (bars 1-4) or presence of 25 ng/ml BMP-2 (bars 5-6) for 16 hours, without (bars 1, 3, 5) or with 1 μg/ml noggin (FIG. 3A, bars 2, 4, 6) or 20 μg/ml neutralizing antibody against BMP-2 and BMP-4 (FIG. 3B, αBMP2/4, bars 2, 4, 6) for 48 hours followed by measurement of luciferase activity. Relative luciferase activity was calculated as the ratio of firefly to *Renilla* luciferase values to control for transfection efficiency and is expressed as fold increase compared with unstimulated cells transfected with reporter alone. Results are reported as the mean+/−standard deviation (n=2 to 6 in each group; * $P<0.05$ for treatment with noggin or αBMP2/4 compared to no treatment in each group: a, bar 2 compared to 1 P=0.0009, bar 4 compared to 3 P=0.03, bar 6 compared to 5 P=0.0006; b, bar 2 compared to 1 P=0.003, bar 4 compared to 3 P=0.007, bar 6 compared to 5 P=0.00008). FIG. 3C shows results from reverse transcription PCR which was performed on total RNA from HepG2 cells using primers for BMP2 or BMP4 as indicated (lanes 3-4). Purified plasma cDNAs encoding BMP-2 or BMP-4 were used as positive controls (+, lane 1), and reactions without template were used as negative controls (−, lane 2).

FIG. 4A shows a Western blot of purified HJV.Fc fusion protein with a rabbit polyclonal antibody generated against a C-terminal peptide of hemojuvelin upstream (at amino acid 399) of its GPI anchor (α-HJV, left panel) or anti-human Fc antibody (α-Fc, right panel). Bands at ~75 kDa and ~60 kDa correspond to the predicted size of the Fc portion of human immunoglobulin fused to full length hemojuvelin and hemojuvelin which has been cleaved at a previously described proteolytic cleavage site between aspartic acid and proline residues at amino acid 165 (Niederkofler et al. J. Neurosci. 24, 808-818, 2004; Lin et al. Blood 106, 2884-2889, 2005; Zhang et al. J. Biol. Chem. 280, 33885-33894, 2005). A lower band at ~40-45 kDa may represent another cleavage form. FIGS. 4B and 4C show $^{125}$I-BMP-2 (FIG. 4B) or $^{125}$I-BMP-4 (FIG. 4C) was incubated overnight alone (Control) or in combination with 60 ng Hjv.Fc, in the absence (Binding) or presence of excess unlabeled BMP-2, -4, -7, or TGF-β1, followed by incubation on protein A coated plates and determination of bound radioactivity using a standard γ counter. Results are reported as the mean+/−standard deviation (n=2 to 3 in each group; * $P<0.05$ compared to Control: b, bar 2 P=0.0003; c, bar 2 P=0.0004; ** $P<0.05$ compared to Binding: b, bar 3 P=0.002, bar 4 P=0.011; c, bar 3 P=0.000005, bar 4 P=0.0005).

FIG. 6A shows HepG2 cells were transfected with BRE-Luc and pRL-TK alone (bars 1, 5-7), or in combination with 40 ng/ml HJV (bars 2-4), without (bars 2, 5) or with co-transfection with 200 ng/ml cDNA encoding dominant negative BMP type I receptor ALK3 (ALK3 DN, bars 3, 6) or ALK6 (ALK6 DN, bars 4, 7). Transfected cells were incubated in the absence (bars 1-4) or presence of 25 ng/ml BMP-2 (bars 5-7). Cell lysates were analyzed for luciferase activity as in FIG. 3. Results are reported as the mean+/−standard deviation (n=2 to 3 in each group; * $P<0.05$ compared to cells transfected with Hjv alone (bar 2): bar 3 compared to 2 P=0.0000006, bar 4 compared to 2 P=0.0003). FIG. 6B shows that HEK293 cells which were transfected with cDNA encoding FLAG-tagged human hemojuvelin (FLAG-HJV) (lanes 2-3, 5-6) and/or HAtagged ALK6 (ALK6-HA) (lanes 1, 3, 4, 6). Transfected cells were incubated in the absence (lanes 1-3) or presence of BMP-2 (lanes 4-6) followed by crosslinking with DSS. Cell lysates were immunoprecipitated with anti-HA antibody (α-HA), and immunoprecipitates were analyzed by Western blot with anti-FLAG antibody (α-FLAG) to demonstrate the formation of a complex between FLAG-HJV and ALK6-HA in the presence of BMP-2 (lane 6). As a control to confirm protein expression, Western blot of total cell lysates was performed with α-FLAG and α-HA.

FIG. 8A shows a protein blot of cell lysates from CHO cells transfected with cDNA encoding empty vector ('mock'), wild-type mouse hemojuvelin (Hjv) or mutant mouse hemojuvelin G313V (G313V-Hjv) with antihemojuvelin antibody (α-HJV). Blots were stripped and reprobed with anti-β-actin antibody (α-β-actin) as a loading control. FIGS. 8B-8D show cells transfected with BRE-Luc, pRL-TK in the presence of increasing amounts of Hjv or G313V-Hjv. HepG2 (FIG. 8B), or Hep3B cells (FIG. 8C, 8D) were transfected with BRE-Luc, pRL-TK and increasing amounts of Hjv or G313V-Hjv (b, 0.04-400 ng ml-1) or, alternatively, cDNA encoding Flag-tagged wild-type human hemojuvelin (Flag-HJV) or Flag-tagged mutant human hemojuvelin G99V (Flag-G99V-HJV) (c, 2-200 ng ml-1; d, 20-800 ng ml-1). Cell lysates were analyzed for luciferase activity as in FIG. 1 (FIGS. 8B, 8C) or by protein blot with α-HJV (FIG. 8D). Blots were stripped and reprobed with α-β-actin as a loading control. (b,c) Results are expressed as mean±s.d. n=2 in each group. * $P<0.05$ (Flag-HJV versus control in FIG. 8C).  $P<0.05$ (G313V-Hjv versus Hjv in b, and Flag-G99V-HJV versus Flag-HJV in c). Exact P-values are shown above points in FIG. 8C. In FIG. 8**B, P-values are 0.0016, 0.0039, 0.058 and 0.0008 for open circles 4-7, respectively.

FIGS. 10A and 10B show Hep3B cells which were transfected with an empty vector (control) or increasing amounts of cDNA encoding Flag-HJV (FIG. 10A) or 40 ng $ml^{-1}$ Flag-HJV or Flag-G99V-HJV (FIG. 10B). Total RNA was isolated and real-time quantification of hepcidin mRNA transcripts was performed using a two-step RT-PCR. Quantitative real-time PCR for β-actin was performed in parallel as an internal control. Samples were analyzed in triplicate and are reported as the ratio of mean values for hepcidin to ββ-actin. FIGS. 10C and 10D show a firefly luciferase reporter driven by 2.7 kb of the proximal hepcidin promoter which was cotransfected into Hep3B cells with pRL-TK to control for transfection efficiency, either alone or with increasing concentrations of Flag-HJV or Flag-G99V-HJV (2-20 ng $ml^{-1}$; FIG. 10C) or alternatively Hjv or G313V-Hjv (2-200 ng $ml^{-1}$; d). Relative luciferase activity was calculated as in FIGS. 2A and 2B. Results are reported as mean±s.d. n=3 in each group. * $P<0.05$ (Flag-HJV versus control in a-c and Hjv versus control in FIG. 10D).  $P<0.05$ (Flag-G99V-HJV versus Flag-HJV or G313V-Hjv versus Hjv in FIG. 10B-10D). Exact P-values are shown above points and bars. In FIG. 10**D, P=0.004 and 0.05 for circles 3 and 4, respectively.

FIGS. 11A-11C show HepG2 cells (11A, 11C) or Hep3B cells (11B) were incubated in the absence or presence of 1 mg $ml^{-1}$ noggin for 48 h, 50 ng $ml^{-1}$ BMP-2 for 16 h (FIG. 11A, 11B) or 50 ng $ml^{-1}$ BMP-2 for 0-16 h (FIG. 11C). Quantitative real-time PCR for hepcidin and β-actin were performed as described in FIG. 5. FIG. 11D shows cells which were transfected with the hepcidin promoter luciferase construct and pRL-TK were incubated in the absence or presence of increasing concentrations of BMP-2 (6-150 ng $ml^{-1}$) for 16 h. Relative luciferase activity was calculated as in FIG. 1. Results are reported as mean±s.d. n=2 to 4 in each group. * $P<0.05$ compared with control.

FIG. 12 shows that the proximal hepcidin promoter is conserved among mammals and contains putative BMP-responsive elements. Genome sequences were retrieved from the UCSC Genome Bioinformatics Group website (world wide web site: "genome-dot-ucsc-dot-edu") following a BLAT Search on each of the genome assemblies using human hepcidin cDNA (GenBank accession number NM_021175) as the query. Shown is the aligned sequence of the proximal hepcidin promoter in human (SEQ ID NO: 51), chimp (SEQ ID NO: 52), dog (SEQ ID NO: 53), rat (SEQ ID NO: 54), and mouse (SEQ ID NO: 55). Putative common mediator Smad4 binding elements (Shi & Massague, Cell 113, 685-700, 2003; Korchynskyi & ten Dijke. J. Biol. Chem. 277, 4883-4891, 2002; Dennler et al. EMBO J. 17, 3091-3100, 1998) are shown in black. Putative BMP receptor-activated Smad binding elements (Korchynskyi & ten Dijke, J. Biol. Chem. 277, 4883-4891, 2002; Henningfeld et al. J. Biol. Chem. 275, 21827-21835, 2000; Ishida et al. J. Biol. Chem. 275, 6075-6079, 2000) are shown in gray. Putative TATA box, transcription initiation start site (+1) and translation initiation codon (Courselaud et al. J. Biol. Chem. 277, 41163-41170, 2002) are indicated in bold.

FIGS. 14A-14C show Hep3B cells which were transfected with the hepcidin promoter luciferase construct and pRL-TK were incubated either (i) alone, or (ii) in the presence of 30 ng $ml^{-1}$ BMP-2 alone (as shown by a "+"), or (iii) in the presence of 30 ng $ml^{-1}$ BMP-2 after cotransfection with increasing concentrations (i.e. 2 or 20 or 200 ng/ml) of cDNA encoding Flag-HJV, Flag-G99V-HJV, Hjv or G313V-Hjv as indicated. Relative luciferase activity was determined as in FIGS. 2A and 2B. Values are mean±s.d. n=2-4 in each group. * P<0.05 for Flag-HJV versus control in a-c;  P<0.05 for Flag-G99V-HJV versus Flag-HJV in FIGS. 14B and G313V-Hjv versus Hjv in 14C. In FIG. 14A, bar 4 P=0.0008, bar 5 P=0.0001; FIG. 14B, square 3 P=0.0004, square 4 P=0.00006; circle 3 P=0.003, circle 4 P=0.0004; FIG. 14C, square 4 P=0.007, circle 4 P=0.007. FIG. 14**D shows primary hepatocytes isolated from $Hfe2^{+/+}$ or $Hfe2^{-/-}$ mice which were incubated in the absence (control) or presence of 10 ng $ml^{-1}$ BMP-2 for 12 h, followed by RNA blot analysis for hepcidin mRNA. Expression was quantified using a phosphorimager and normalized to β-actin as a loading control. Ratios of hepcidin to β-actin mRNA are shown as a multiple of values for control hepatocytes. Values are mean±s.d. n=3 in each group. * P<0.05 for BMP-2-stimulated hepatocytes versus control; ** P<0.05 for $Hfe2^{-/-}$ versus $Hfe2^{+/+}$. For $Hfe2^{+/+}$, P=0.001 compared with control, and for $Hfe2^{-/-}$, P=0.003 compared with control and P=0.01 compared with $Hfe2^{+/+}$.

FIG. 15A shows Hep3B cells which were transfected with a hepcidin promoter firefly luciferase reporter and a control *Renilla* luciferase vector (pRL-TK). Transfected cells were incubated either alone (Control) or with 50 ng/ml BMP or GDF ligands, 5 ng/ml TGF-β ligands, or 30 ng/ml Activin A as indicated. Cell lysates were analyzed for luciferase activity. Relative luciferase activity was calculated as the ratio of firefly to *Renilla* luciferase values to control for transfection efficiency, and is expressed as the fold increase compared with Control. Results are reported as the mean+/−standard deviation (n=2 to 3 in each group). FIG. 15B shows Hep3B cells which were treated with BMP, GDF, TGF-β, or Activin A ligands as in A. Total RNA was analyzed by quantitative real-time RT-PCR for hepcidin mRNA expression and β-actin mRNA expression. Samples were analyzed in triplicate, and are reported as the ratio of mean values for hepcidin to β-actin.

FIG. 16A shows total mRNA which was isolated from livers and analyzed by quantitative real-time RTPCR for hepcidin mRNA expression relative to GAPDH mRNA expression as an internal control. FIG. 16B shows serum iron which was measured by colorimetric assay. FIGS. 16A and 16B show the results reported as the mean+/−standard deviation, * P<0.05 for BMP-2 treated mice compared with Control.

FIG. 17A shows a western blot of purified soluble HJV.Fc fusion protein with anti-hemojuvelin antibody (α-HJV) and anti-Fc antibody (α-Fc). FIGS. 17B and 17C show HepG2 cells which were incubated alone (Control) or with 25 μg/ml HJV.Fc alone, 25 ng/ml BMP-2 alone, or a combination of HJV.Fc and BMP-2 as indicated. Total RNA was isolated and quantitative real-time PCR (RT-PCR) for hepcidin mRNA relative to β-actin mRNA was performed as in FIG. 15. Results are reported as the mean+/−standard deviation (n=3 in each group, * P<0 05 for HJV.Fc compared with Control in FIG. 17B, or for HJV.Fc plus BMP-2 compared with BMP-2 alone in FIG. 17C). FIG. 17D shows Hep3B cells which were transfected with the hepcidin promoter luciferase construct and pRL-TK. Transfected cells were incubated alone or with 5 ng/ml BMP-9, 50 ng/ml BMP-5, or 25 ng/ml BMP-2, -4, -6, or -7 ligands, either alone or in combination with 0.2 to 25 μg/ml HJV.Fc as indicated followed by measurement of relative luciferase activity as in FIG. 15. Results are reported as the mean+/−standard deviation of the percent decrease in relative luciferase activity for cells treated with BMP ligands in combination with HJV.Fc compared with cells treated with the respective BMP ligands alone (n=2 in each group).

FIG. 18A show the expression of endogenous BMP ligands in HepG2 cells as measured by RT-PCR. PCR of purified plasmid cDNAs expressing BMP ligands were used as positive controls (Control). FIGS. 18B and 18C show HepG2 cells which were transfected with BMP ligand siRNA's or a Control scrambled siRNA as indicated. Total RNA was analyzed for BMP ligand expression (FIG. 18B) or hepcidin expression (FIG. 18C) relative to β-actin expression by real-time quantitative RT-PCR. Results are reported as the mean+/−standard deviation of the percent decrease in the ratio of hepcidin or BMP ligand to β-actin 35 for cells treated with various BMP siRNAs compared with cells treated with Control siRNA; n=3 to 6 per group; * P<0.05.

FIG. 19A shows liver lysates which were analyzed for phosphorylated Smad1/5/8 expression by Western blot. Blots were stripped and re-probed for total Smad1 expression and β-actin expression as loading controls. Chemiluminescence was quantitated by IP Lab Spectrum software for phosphorylated Smad1/5/8 relative to total Smad1 expression. FIG. 19B shows total mRNA which was isolated from livers and analyzed by quantitative real-time PCR for hepcidin mRNA expression relative to GAPDH mRNA expression as an internal control. FIG. 19C shows spleen membrane preparations which were analyzed for ferroportin expression by Western blot. Blots were stripped and re-probed for β-actin expression as a loading control. FIGS. 19D and 19E show the measurement and levels of serum iron and transferrin saturation. FIGS. 19F and 19G shows the quantitation of liver (FIG. 19F) and spleen (FIG. 19G) tissue iron content. Results are expressed as mean+/−standard deviation, n=3 mice per group, * P<0.05 for HJV.Fc treated mice compared with Control mice.

FIG. 21 shows the sequences of an exemplary HJV.Fc fusion protein. FIG. 21A shows Human HJV.Fc fusion (HJV 33-399) with extracellular signal sequence and FLAG tag in place of N-terminal sequence and GPI anchoring domain removed (SEQ ID NO:1). FIGS. 21B-21D shows three human HJV isoforms (SEQ ID NOS:2-4), with FIG. 21B showing Human HJV isoform A (SEQ ID NO:2), FIG. 21C showing Human HJV isoform B (SEQ ID NO:3); FIG. 21D showing Human HJV isoform C (SEQ ID NO:4). FIG. 21E shows mouse HJV (SEQ ID NO:5). FIG. 21F shows the human Fc sequence (SEQ ID NO:6), and FIG. 21G shows an exemplary HJV.Fc fusion protein with enhanced proteolytic stability (HJV-D172A.Fc) which is a non-cleavable form of the HJV.Fc protein (SEQ ID NO:7). FIGS. 21H and 21I shows nucleic acid sequences corresponding to the HJV.Fc (SEQ ID NO:8) and HJV-D172A.Fc fusion proteins (SEQ ID NO:9), with FIG. 21H showing the DNA sequence encoding human HJV.Fc fusion protein (SEQ ID NO:8) and FIG. 21I showing DNA sequence encoding human HJV-D172A.Fc fusion protein (SEQ ID NO:9). FIG. 21J shows the amino acid sequence of codon optimized human HJV-Fc fusion, with extracellular signal sequence and the GPI anchoring domain removed (SEQ ID NO:10), and FIG. 21K shows codon-optimized DNA sequence encoding human HJV.Fc fusion protein (SEQ ID NO:11). In FIG. 21K, the exemplary DNA linkers are shown, a -BamHI/HindIII-linker site at the 5' end and a -EcoRI/NotI-linker site at the 3' (shown sites are underlined); with the Kozak sequence in lower case, the start ATG codon in bold; and the TGA Stop Codon in bold.

FIG. 22A shows serum iron and FIG. 22B shows transferrin saturation. Results are expressed as mean+/−standard deviation, n=3 mice per group, * $P<0.05$ for HJV.Fc treated mice compared with Control mice.

FIG. 23 shows the amino acid sequence alignment and comparison of mouse HJV (DL-2) with other mouse homologue members of the RGM family. Amino acid sequence alignment of mouse HJV (mDL-2) (SEQ ID NO: 56), and mouse DRAGON (mRGMb) (SEQ ID NO: 57) and mouse DL-1 (mDL-1, mRGMa) (SEQ ID NO: 58) are shown, with the conserved amino acids residues shown in black boxes.

FIG. 24 shows the amino acid sequence alignment and comparison of part of the amino acid sequence of human HJV (SEQ ID NO: 59) and mouse RGMc (SEQ ID NO: 60). Human HJV is 88% identical and 92% similar to mouse RGMc, with conserved amino acids shown in black boxes. Both have a predicted signal peptide cleavage site (gray arrow), three consensus sequences for N-linked glycosylation (solid line), and twelve cys residues conserved in HJV and all of the mouse RGM family of proteins (asterisk). Both HJV and RGMc have one predicted acid sensitive autocatalytic cleavage site (black arrow) and a predicted GPI-linked site (white arrow). An anti-peptide antibody can be generated to the sequence denoted by a dashed line (FIG. 24 is reproduced from Zhang et al, 2005; JBC).

FIG. 25 shows a prediction of residue conservation and location based on ConSeq. Sequence shown in human HJV (which is based on GenBank Accession No Q6ZVN8 (SEQ ID NO:61) with the signal and propeptides removed. Protein regions, as defined in the text, are shown above the sequence. Residues that are more conserved are shown in increasingly darker background with white text; more variable sequences are shown in black text. Below the sequence, "e" indicates a residue predicted to be exposed (surface) and "b" indicates a buried residue. "s" and "f" represent ConSeq's prediction of residues of "structural" or "functional" importance. (FIG. 25 is reproduced from Camus et al, J Mol Evol, 2007; 65:68-81).

DETAILED DESCRIPTION OF THE PRESENT INVENTION

Figure 1:
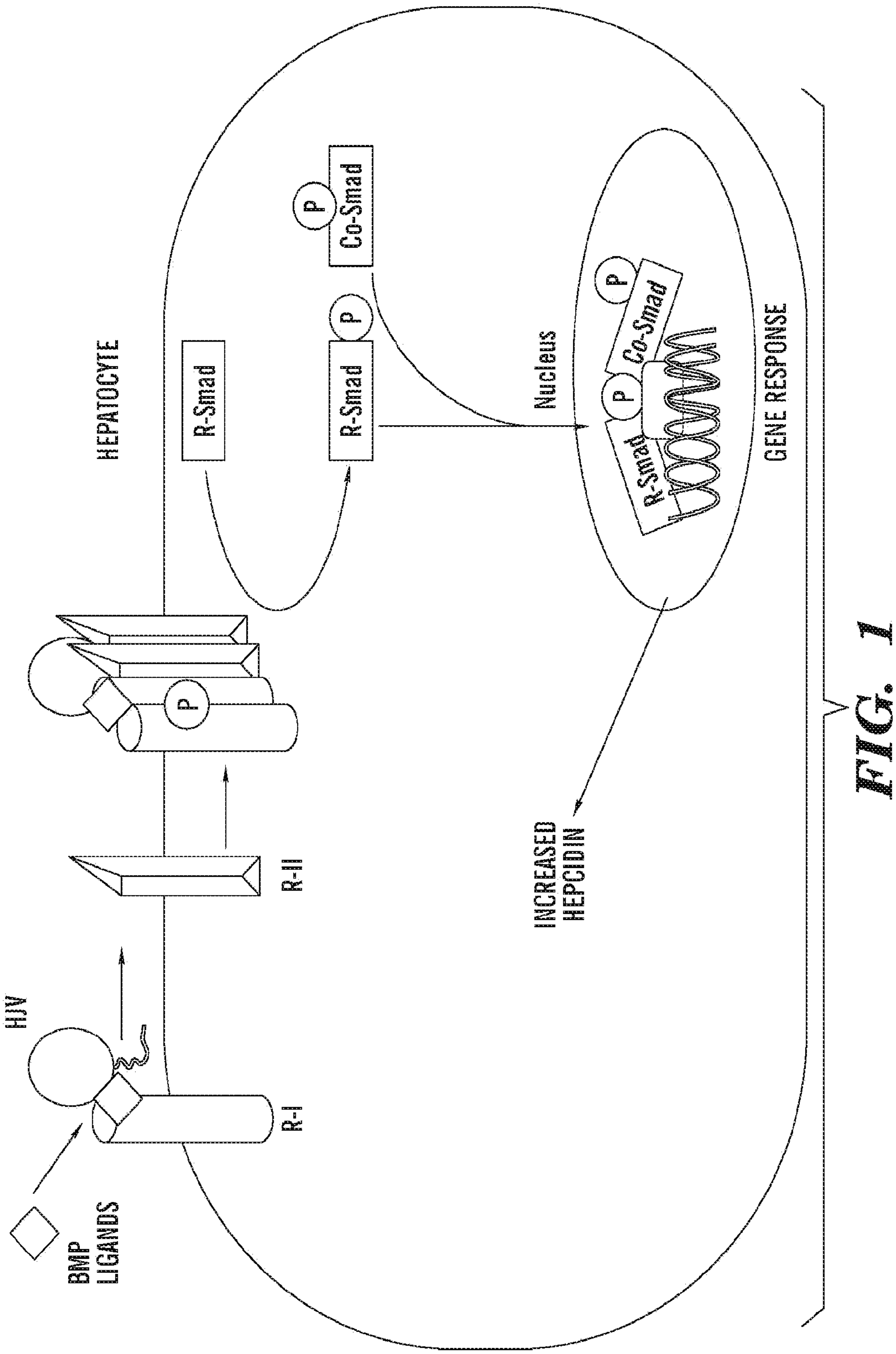
FIG. 1 is a schematic diagram depicting the role of hemojuvelin (HJV) in the BMP signaling pathway and hepcidin regulation. HJV interacts with BMP ligands and BMP type I (R-I) and type II receptors (R-II) to generate an active signaling complex. Upon formation of the complex, type II receptors phosphorylate type I receptors, which then phosphorylate receptor-activated Smad1, Smad5, and Smad8 (R-Smad). Phosphorylated R-Smads form a complex with common mediator Smad4 (Co-Smad), and the Smad complex translocates to the nucleus, where it increases transcription of hepcidin mRNA.

The inventors have identified a novel therapeutic, HJV.Fc, useful in the treatment of conditions involving hepcidin regulation (e.g., iron-related disorders such as those described herein). Accordingly the present invention provides HJV fusion proteins (e.g., HJV.Fc), pharmaceutical compositions containing such proteins, polynucleotides encoding such proteins, and methods for treating HJV-related disorders such as iron-related disorders (e.g., those described herein).

One aspect of the present invention relates to a soluble form of HJV. In some embodiments, such a soluble form of HJV is where polypeptides of full length HJV, or a fragment of HJV are fused to a second peptide, for example a IgG1 Fc or fragment thereof, and is referred to as "HJV.Fc" herein. In some embodiments, the HJV which is fused to a second polypeptide (i.e. the first fusion partner) can be a fragment of HJV, such as HJV lacking the C-terminal GPI domain and/or the N-terminal signal sequence or alternatively, the HJV can be a functional derivative of HJV or a functional variant of HJV, as these terms are defined herein. In some embodiments, the HJV proteins useful for fusion to a first fusion partner can be any isoform of HJV, for example HJV proteins corresponding to SEQ ID NOS: 2, 3, 4 or 5, respectively, or functional fragments or functional derivatives or a functional variants of HJV polypeptides corresponding to SEQ ID NOs: 2 to 5.

Additionally, a fusion partner bound to HJV, or functional fragments, derivatives or variants thereof can be an IgG1 Fc fragment, such as the Fc fragment corresponding to SEQ ID NO: 6 or functional fragments or derivatives or variants thereof. In alternative embodiments, the first fusion partner can be any polypeptide sequence that increases the stability of the HJV polypeptide or functional derivative, functional fragment or functional variant thereof. For example, fusion of HJV polypeptides to a serum protein, e.g., serum albumin, can increase the circulating half-life of a HJV polypeptide.

In some embodiments, an example of a HJV.Fc as disclosed herein corresponds to SEQ ID NO:7 or a functional variant or functional derivative thereof, where SEQ ID NO:7 is the amino acid sequence for human HJV.Fc with a non-cleavable variant of HJV without the GPI anchoring domain fused to a Fc fragment.

In another embodiment, a HJV.Fc as disclosed herein corresponds to SEQ ID NO:10 or a functional variant or functional derivative thereof, where SEQ ID NO:10 is the amino acid sequence for human HJV.Fc where HJV without the GPI anchoring domain, has been codon-optimized for optimal expression in mammalian cells is fused to a Fc fragment.

In another embodiment, a HJV.Fc as disclosed herein corresponds to SEQ ID NO:1 or a functional variant or functional derivative thereof, where SEQ ID NO:1 is the amino acid sequence for human HJV.Fc with HJV comprising an extracellular signal sequence and FLAG tag, but with the GPI anchoring domain removed.

In one embodiment, the HJV fusion polypeptide comprises a human HJV polypeptide and a first fusion partner. In one embodiment, the HJV fusion polypeptide consists essentially of a human HJV polypeptide and a first fusion partner. In one embodiment, the HJV fusion polypeptide consists of a human HJV polypeptide and a first fusion partner.

In another embodiment, the HJV fusion polypeptide comprises human HJV polypeptide which comprises, or alternatively, consists of a polypeptide having the sequence of SEQ ID NO: 2 or 3, or 4, or a functional fragment thereof, or a HJV functional fragment of SEQ ID NO: 7 or 10. In another embodiment, the nucleic acid construct comprises a polypeptide encoded by the sequence corresponding to SEQ ID NO: 8, 9 or 11.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

By "human Fc" is meant a polypeptide with an amino acid sequence at least about 50%, or at least about 60%, or at least about 70%, or at least about 80%, or at least about 90%, or at least about 95%, or at least about 96%, or at least about 97%, or at least about 98%, or at least about 99% identical to the sequence of SEQ ID NO:6 (FIG. 21).

By a "polynucleotide encoding human Fc" is meant a polynucleotide that encodes a polypeptide sequence having at least about 50%, or at least about 60%, or at least about 70%, or at least about 80%, or at least about 90%, or at least about 95%, or at least about 96%, or at least about 97%, or at least about 98%, or at least about 99% identity to the sequence of SEQ ID NO:6 (FIG. 21).

By "hemojuvelin" or "HJV" is meant a polypeptide having an amino acid sequence at least about 60%, or at least about 70%, or at least about 80%, or at least about 90%, or at least about 95%, or at least about 96%, or at least about 97%, or at least about 98%, or at least about 99% identical to any of SEQ ID NOs: 2 to 5 (FIG. 21).

By a "polynucleotide encoding hemojuvelin" is meant a polynucleotide encoding a polypeptide having at least about 60%, or at least about 70%, or at least about 80%, or at least about 90%, or at least about 95%, or at least about 96%, or at least about 97%, or at least about 98%, or at least about 99% sequence identity to any of the amino acid sequences corresponding to SEQ ID NOs: 2 to 5 (FIG. 21).

The term "wild type" refers to the naturally-occurring polynucleotide sequence encoding a protein, or a portion thereof, or protein sequence, or portion thereof, respectively, as it normally exists in vivo. Accordingly, as disclosed herein, the wild type amino acid sequence for the human HJV protein corresponds to SEQ ID NOs: 2, 3 and 4, which refer to human HJV isoforms A, B and C respectively.

The term "soluble HJV polypeptide" as used herein refers to a HJV polypeptide that does not comprise at least part of, or all of, the amino acids which allow it to functionally bind to the membrane. An example of a soluble HJV polypeptide is a HJV with the removal of the GPI anchor.

The term "mutant" refers to any change in the genetic material of an organism, in particular a change (i.e., deletion, substitution, addition, or alteration) in a wild-type polynucleotide sequence or any change in a wild-type protein sequence. The term "variant" is used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent). The term mutation is used interchangeably herein with polymorphism in this application.

The terms "polypeptide" and "protein" are used interchangeably to refer to a polymer of amino acid residues, and are not limited to a minimum length. Peptides, oligopeptides, dimers, multimers, and the like, are also composed of linearly arranged amino acids linked by peptide bonds, and whether produced biologically, recombinantly, or synthetically and whether composed of naturally occurring or non-naturally occurring amino acids, are included within this definition. Both full-length proteins and fragments thereof are encompassed by the definition. The terms also include co-translational (e.g., signal peptide cleavage) and post-translational modifications of the polypeptide, such as, for example, disulfide-bond formation, glycosylation, acetylation, phosphorylation, proteolytic cleavage (e.g., cleavage by furins or metalloproteases), and the like. Furthermore, for purposes of the present invention, a "polypeptide" refers to a protein that includes modifications, such as deletions, additions, and substitutions (generally conservative in nature as would be known to a person in the art), to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods. Polypeptides or proteins are composed of linearly arranged amino acids linked by peptide bonds, but in contrast to peptides, has a well-defined conformation. Proteins, as opposed to peptides, generally consist of chains of 50 or more amino acids. For the purposes of the present invention, the term "peptide" as used herein typically refers to a sequence of amino acids of made up of a single chain of D- or L-amino acids or a mixture of D- and L-amino acids joined by peptide bonds. Generally, peptides contain at least two amino acid residues and are less than about 50 amino acids in length.

The incorporation of non-natural amino acids, including synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides. In some embodiments, the HJV.Fc are comprised of D- or L-amino acid residues, as use of naturally occurring L-amino acid residues has the advantage that any break-down products should be relatively non-toxic to the cell or organism.

In yet a further embodiment, the HJV proteins or fragments or derivatives thereof can be a retro-inverso peptides. A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous α-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., Int J Pept Protein Res. 24(6): 553-6 (1984); Verdini, A. and Viscomi, G. C., J. Chem. Soc. Perkin Trans. 1:697-701 (1985); and U.S. Pat. No. 6,261,569, which are incorporated herein in their entirety by reference. Processes for the solid-phase synthesis of partial retro-inverso peptide analogues have been described (EP 97994-B) which is also incorporated herein in its entirety by reference.

The terms "homology", "identity" and "similarity" refer to the degree of sequence similarity between two peptides or between two optimally aligned nucleic acid molecules. Homology and identity can each be determined by comparing a position in each sequence which can be aligned for purposes of comparison. For example, it is based upon using a standard homology software in the default position, such as BLAST, version 2.2.14. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectfully. A sequence which is "unrelated" or "non-homologous" shares less than 40% identity, though preferably less than 25% identity with the sequences as disclosed herein.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G. U. or I) or residue occurs in both sequences to yield the number of matched positions, dividing the number of matched positions by the total number of positions in the comparison window (i.e., the window size), and multiplying the result by 100 to yield the percentage of sequence identity.

The terms "substantial identity" as used herein denotes a characteristic of a polynucleotide or amino acid sequence, wherein the polynucleotide or amino acid comprises a sequence that has at least 85% sequence identity, preferably at least 90% to 95% sequence identity, more usually at least 99% sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which can include deletions or additions which total 20 percent or less of the reference sequence over the comparison window. The reference sequence can be a subset of a larger sequence. The term "similarity", when used to describe a polypeptide, is determined by comparing the amino acid sequence and the conserved amino acid substitutes of one polypeptide to the sequence of a second polypeptide.

As used herein, the terms "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see herein) are identical, with appropriate nucleotide insertions or deletions or amino-acid insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. Determination of homologs of the genes or peptides of the present invention can be easily ascertained by the skilled artisan.

The term "substantially homologous" refers to sequences that are at least 90%, at least 95% identical, at least 96%, identical at least 97% identical, at least 98% identical or at least 99% identical. Homologous sequences can be the same functional gene in different species. Determination of homologs of the genes or peptides of the present invention can be easily ascertained by the skilled artisan.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference amino acid sequence if the smallest sum probability in a comparison of the test amino acid to the reference amino acid is less than about 0.1, more typically less than about 0.01, and most typically less than about 0.001.

The term "variant" as used herein refers to a peptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally occurring amino acid of similar character either in relation to polarity, side chain functionality or size. Substitutions encompassed by the present invention may also be "non conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide). A "variant" of a HJV polypeptide, for example SEQ ID NOs: 2, 3 or 4 is meant to refer to a molecule substantially similar in structure and function, i.e. where the function is the ability to increase serum iron levels in vivo and/or decrease or inhibit hepcidin expression.

For example, a variant of an HJV peptide can contain a mutation or modification that differs from a reference amino acid in SEQ ID NOs: 2, 3, 4 or 5. In some embodiments, a variant of SEQ ID NOs: 2, 3, 4 or 5 is a fragment of SEQ ID NOs: 2, 3, 4 or 5 as disclosed herein. In some embodiments, a variant can be a different isoform of SEQ ID NOs: 2, 3, 4 or 5 or can comprise different isomer amino acids. Variants can be naturally-occurring, synthetic, recombinant, or chemically modified polynucleotides or polypeptides isolated or generated using methods well known in the art. Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the BBB). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In some embodiments, individual substitutions, deletions or additions that alter, add or delete a single amino acid or a small percentage of amino acids can also be considered "conservative substitutions" is the change does not reduce the activity of the peptide (i.e. the ability of an HJV peptide variant to increase serum iron in vivo). Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al, J. Theor. Biol. 119 (1986); 205-218 and S. French and B. Robson, J. Mol. Evol. 19 (1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants. A variant of a HJV peptide, for example a variant of SEQ ID NOs:2, 3, 4 or 5 is meant to refer to any molecule substantially similar in structure and function to either the entire molecule of SEQ ID NOs:2, 3, 4 or 5, or to a fragment thereof.

The term "derivative" as used herein refers to peptides which have been chemically modified, for example but not limited to by techniques such as ubiquitination, labeling, pegylation (derivatization with polyethylene glycol) or addition of other molecules. A molecule also a "derivative" of another molecule when it contains additional chemical moieties not normally a part of the molecule. Such moieties can improve the molecule's solubility, absorption, biological half life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

The term "functional" when used in conjunction with "derivative" or "variant" refers to a molecule such as a protein which possess a biological activity (either functional or structural) that is substantially similar to a biological activity of the entity or molecule its is a functional derivative or functional variant thereof. The term functional derivative is intended to include the fragments, analogues or chemical derivatives of a molecule.

A molecule is said to be "substantially similar" to another molecule if both molecules have substantially similar structures or if both molecules possess a similar biological activity, for example if both molecules are able to increase serum iron in vivo and/or decrease or inhibit hepcidin expression. Thus, provided that two molecules possess a similar activity, (i.e. a variant of an HJV peptide which can increase serum iron concentration in vivo similar to that of the HJV peptide which corresponds to SEQ ID NOs: 2, 3, 4 or 5 when fused to Fc) are considered variants and are encompassed for use as disclosed herein, even if the structure of one of the molecules not found in the other, or if the sequence of amino acid residues is not identical. Thus, provided that two molecules possess a similar biological activity, they are considered variants as that term is used herein even if the structure of one of the molecules not found in the other, or if the sequence of amino acid residues is not identical.

As used herein, the term "nonconservative" refers to substituting an amino acid residue for a different amino acid residue that has different chemical properties. The nonconservative substitutions include, but are not limited to aspartic acid (D) being replaced with glycine (G); asparagine (N) being replaced with lysine (K); or alanine (A) being replaced with arginine (R).

The term "insertions" or "deletions" are typically in the range of about 1 to 5 amino acids. The variation allowed can be experimentally determined by producing the peptide synthetically while systematically making insertions, deletions, or substitutions of nucleotides in the sequence using recombinant DNA techniques.

The term "substitution" when referring to a peptide, refers to a change in an amino acid for a different entity, for example another amino acid or amino-acid moiety. Substitutions can be conservative or non-conservative substitutions.

The term "substantially similar", when used to define a soluble form of HJV, such as a HJV fusion protein comprising a functional variant of HJV or a functional derivative of HJV as compared to the HJV protein encoded by SEQ ID NOs: 2-5, means that a particular subject sequence, for example, a HJV fragment or HJV variant or HJV derivative sequence, varies from the sequence of the natural (or wild-type) HJV protein (i.e. HJV encoded by SEQ ID NOs: 2, 3, 4 to 5), by one or more substitutions, deletions, or additions, although the net effect of which is to retain at least some of the biological activity found in the native natural HJV protein. As such, nucleic acid and amino acid sequences having lesser degrees of similarity but comparable biological activity to HJV are considered to be equivalents. In determining polynucleotide sequences, all subject polynucleotide sequences capable of encoding substantially similar amino acid sequences are considered to be substantially similar to a reference polynucleotide sequence, regardless of differences in codon sequence. A nucleotide sequence is "substantially similar" to a specific nucleic acid sequence of SEQ ID NOs:2 to 5 as disclosed herein if: (a) the nucleotide sequence is hybridizes to the coding regions of the natural HJV, or (b) the nucleotide sequence is capable of hybridization to nucleotide sequence of HJV encoded by SEQ ID NO:2 to 5 under moderately stringent conditions and has biological activity similar to the native human HJV protein; or (c) the nucleotide sequences which are degenerative as a result of the genetic code to the nucleotide sequences defined in (a) or (b). Substantially similar proteins will typically be greater than about 80% similar to the corresponding sequence of the native protein.

Figure 22A:
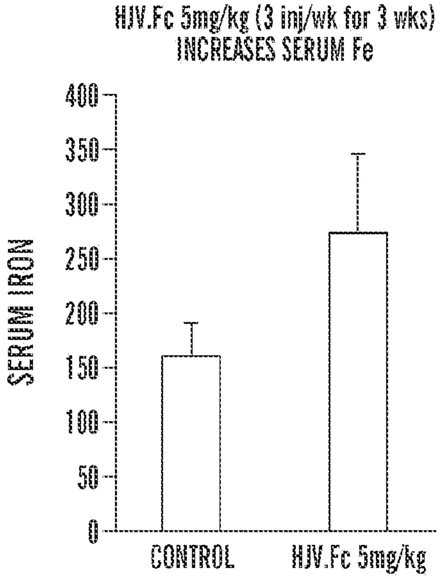
FIGS. 22A-22B shows that a lower dose of soluble human HJV.Fc administration increases serum iron. 12956/SvEvTac mice received an intraperitoneal injection of 5 mg/kg HJV.Fc or normal saline (Control) three times weekly for three weeks.
Figure 22B:
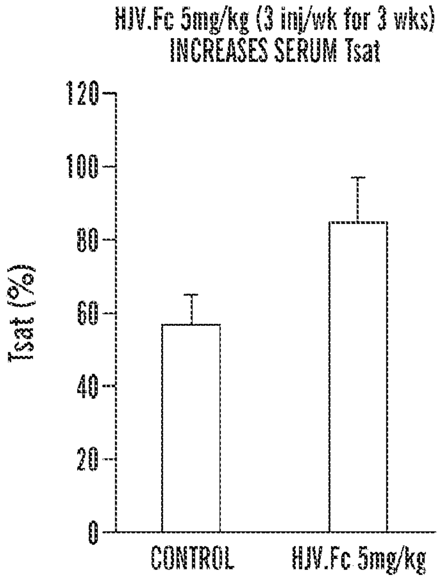

The term "fragment" of a peptide or molecule as used herein refers to any contiguous polypeptide subset of the molecule. Fragments of an HJV peptide, for example functional fragments of SEQ ID NOs: 2, 3, 4 or 5 useful in the methods as disclosed herein have at least 30% of agonist or antagonist activity as that of SEQ ID NOs: 2, 3, 4 or 5. Stated another way, a fragment of an HJV polypeptide is a fragment of any of SEQ ID NOs: 2, 3, 4 or 5 which, when fused to Fc can result in at least 30% of the same activity as compared to SEQ ID NOs: 1, 7 or 10 to increase serum iron concentration and/or increase transferrin saturation when administered in a soluble form to a mouse in vivo (as disclosed in the Examples and FIGS. 19 and 22 herein) and/or results in at least 30% of the activity as compared with SEQ ID NOs: 1, 7 or 10 to decrease basal hepcidin expression in HepG cells in vitro or decrease BMP-mediated induction of hepcidin expression using the BRE-luciferase in vitro assay as disclosed herein in the Examples and in FIGS. 17A-17D. It can also include fragments that decrease the wild type activity of one property by at least 30%. Fragments as used herein are soluble (i.e. not membrane bound), and typically bound to a first fusion partner, however, they do not need to be fused to a fusion protein if the soluble HJV fragment is stable. A "fragment" can be at least about 6, at least about 9, at least about 15, at least about 20, at least about 30, least about 40, at least about 50, at least about 100, at least about 250, at least about 500 nucleic or amino acids, and all integers in between. Exemplary fragments include C-terminal truncations, N-terminal truncations, or truncations of both C- and N-terminals (e.g., deletions of, for example, at least 1, at least 2, at least 3, at least 4, at least 5, at least 8, at least 10, at least 15, at least 20, at least 25, at least 40, at least 50, at least 75, at least 100 or more amino acids deleted from the N-termini, the C-termini, or both). One of ordinary skill in the art can create such fragments by simple deletion analysis. Such a fragment of SEQ ID NOs: 2 to 5 can be, for example, 1, 2, 3, 4, 5, 6, 7, 8, 9 or 10 amino acids or more than 10 amino acids, such as 15, 30, 50, 100 or more than 100 amino acids deleted from the N-terminal and/or C-terminal of SEQ ID NOs: 2 to 5, respectively. Persons of ordinary skill in the art can easily identify the minimal peptide fragment of SEQ ID NOs: 2 to 5 useful in the fusion proteins and methods as disclosed herein, by sequentially deleting N- and/or C-terminal amino acids from SEQ ID NOs: 2 to 5 and assessing the function of the resulting peptide fragment fused to a Fc fragment. One can create functional fragments with multiple smaller fragments. These can be attached by bridging peptide linkers. One can readily select linkers to maintain wild type conformation. One of ordinary skill in the art can easily assess the function of the HJV-fragment.Fc fusion protein to increase serum iron concentration and/or increase transferrin saturation when administered to a mouse in vivo (as disclosed in the Examples and FIGS. 19 and 22 herein) as compared to HJV-Fc corresponding to SEQ ID NOs: 1, 7 or 10 as disclosed herein. Using such an in vivo assay, if the HJV-fragment.Fc protein has at least 30% of the biological activity of the HJV-Fc corresponding to SEQ ID NOs: 1, 7 or 10 as disclosed herein, then the HJV-fragment portion of the HJV-fragment.Fc protein is considered a valid HJV-fragment and can used in fusion proteins and methods as disclosed herein. Alternatively, one of ordinary skill in the art can easily assess the function of the HJV-fragment.Fc fusion protein by assessing its ability to decrease basal hepcidin expression in HepG cells in vitro as compared to HJV-Fc corresponding to SEQ ID NO: 1, 7 or 10 as disclosed herein, or to determine the ability of the HJV-fragment.Fc protein to decrease BMP-mediated induction of hepcidin expression using the BRE-luciferase in vitro assay as disclosed herein in the Examples and in FIGS. 17A-17D. Using such an in vitro assay, if the HJV-fragment.Fc protein has at least 30% of the biological activity of the HJV-Fc corresponding to SEQ ID NO: 1, 7 or 10 as disclosed herein, then the HJV-fragment portion of the HJV-fragment.Fc protein is considered a valid HJV-fragment and can used in fusion proteins and methods as disclosed herein. In some embodiments, a fragment of SEQ ID NOS: 2 to 5 can be less than 200, or less than 150 or less than 100, or less than 50, or less than 20 amino acids of SEQ ID NOS: 2, 3, 4 or 5. In some embodiments, a fragment of SEQ ID NOS: 2, 3, 4 or 5 is less than 100 peptides in length. However, as stated above, the fragment must be at least 6 amino acids, at least about 9, at least about 15, at least about 20, at least about 30, at least about 40, at least about 50, at least about 100, at least about 250, at least about 500 nucleic acids or amino acids, or any integers in between.

An "analog" of a molecule such as HJV peptide, for example SEQ ID NOs: 2 to 5 refers to a molecule similar in function to either the entire molecule or to a fragment thereof. The term "analog" is also intended to include allelic, species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are, for example but not limited to; acedisubstituted amino acids, N-alkyl amino acids, lactic acid, 4-hydroxyproline, γ-carboxyglutamate, ϵ-N,N,N-trimethyllysine, ϵ-N-acetyllysine, O-phosphoserine, N-acetylserine, N-formylmethionine, 3-methylhistidine, 5-hydroxylysine, σ-N-methylarginine. Fragments and analogs can be screened for prophylactic or therapeutic efficacy in transgenic animal models as described below.

By "covalently bonded" is meant joined either directly or indirectly (e.g., through a linker) by a covalent chemical bond.

The term "fusion protein" as used herein refers to a recombinant protein of two or more proteins. Fusion proteins can be produced, for example, by a nucleic acid sequence encoding one protein is joined to the nucleic acid encoding another protein such that they constitute a single open-reading frame that can be translated in the cells into a single polypeptide harboring all the intended proteins. The order of arrangement of the proteins can vary. As a non-limiting example, the nucleic acid sequence encoding the HJV fusion protein is derived from the nucleotide sequence of encoding a HJV protein or a functional derivative fragment or variant thereof, fused in frame to an end, either the 5' or the 3' end, of a gene encoding a first fusion partner, such as a IgG1 Fc fragment. In this manner, on expression of the gene, the HJV protein or a functional derivative fragment or variant thereof is functionally expressed and fused to the N-terminal or C-terminal end of the IgG1 Fc. In certain embodiments, modification of the polypeptide probe is such that the functionality of the HJV protein or a functional derivative fragment or variant thereof remains substantially unaffected in terms of its biological activity by fusion to the first fusion partner, such as IgG1 Fc.

The terms "subject" and "individual" and "patient" are used interchangeably herein, and refer to an animal, for example a human or non-human animal (e.g., a mammal), to whom treatment, including prophylactic treatment, with a pharmaceutical composition as disclosed herein, is provided.

The term "subject" as used herein refers to human and non-human animals. The term "non-human animals" and "non-human mammals" are used interchangeably herein and includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

"Treating" a disease or condition in a subject or "treating" a patient having a disease or condition refers to subjecting the individual to a pharmaceutical treatment, e.g., the administration of a drug, such that at least one symptom of the disease or condition is decreased, stabilized, or prevented.

By "specifically binds" or "specific binding" is meant a compound or antibody that recognizes and binds a desired polypeptide but that does not substantially recognize and bind other molecules in a sample, for example, a biological sample, which naturally includes a polypeptide of the invention.

By "substantially pure" or is meant a nucleic acid, polypeptide, or other molecule that has been separated from the components that naturally accompany it. Typically, a polypeptide is substantially pure when it is at least about 60%, or at least about 70%, at least about 80%, at least about 90%, at least about 95%, or even at least about 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

By a "decrease" or "inhibition" used in the context of the level of expression or activity of a gene refers to a reduction in protein or nucleic acid level or activity in a cell, a cell extract, or a cell supernatant. For example, such a decrease may be due to reduced RNA stability, transcription, or translation, increased protein degradation, or RNA interference. Preferably, this decrease is at least about 5%, at least about 10%, at least about 25%, at least about 50%, at least about 75%, at least about 80%, or even at least about 90% of the level of expression or activity under control conditions.

By an "increase" in the expression or activity of a gene or protein is meant a positive change in protein or nucleic acid level or activity in a cell, a cell extract, or a cell supernatant. For example, such a increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

By "enhanced proteolytic stability" is meant a reduction of in the rate or extent of proteolysis of a peptide sequence by at least about 2%, at least about 5%, at least about 10%, at least about 20%, at least about 30%, at least about 40%, at least about 50%, at least about 60%, at least about 70%, at least about 80%, at least about 85%, at least about 90%, at least about 95%, at least about 98%, or at least about 99% as compared to a control sequence under the same conditions (e.g., in vivo or in an in vitro system such as in a cell or cell lysate). A peptide with enhanced proteolytic stability may contain any modification, for example, insertions, deletions, or point mutations which reduce or eliminate a site subject to proteolytic cleavage at a particular site. Sites of proteolytic cleavage may be identified based on known target sequences or using computer software (e.g., software described by Gasteiger et al., *Protein Identification and Analysis Tools on the ExPASy Server*. In John M. Walker, ed. *The Proteomics Protocols Handbook*, Humana Press (2005)). Alternatively, proteolytic sites can be determined experimentally, for example, by Western blot for the protein following expression or incubation in a cellular system or cellular lysate, followed by sequencing of the identified fragments to determine cleavage sites.

The term "recombinant" as used herein to describe a nucleic acid molecule, means a polynucleotide of genomic, cDNA, viral, semisynthetic, and/or synthetic origin, which, by virtue of its origin or manipulation, is not associated with all or a portion of the polynucleotide with which it is associated in nature. The term recombinant as used with respect to a protein or polypeptide, means a polypeptide produced by expression of a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "vectors" refers to a nucleic acid molecule capable of transporting another nucleic acid to which it has been linked; a plasmid is a species of the genus encompassed by "vector". The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA loops which, in their vector form are not bound to the chromosome, and typically comprise entities for stable or transient expression or the encoded DNA. Other expression vectors can be used in the methods as disclosed herein for example, but are not limited to, plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self replicating extrachromosomal vectors or vectors which integrates into a host genome. Preferred vectors are those capable of autonomous replication and/or expression of nucleic acids to which they are linked. Vectors capable of directing the expression of genes to which they are operatively linked are referred to herein as "expression vectors".

The term "viral vectors" refers to the use of viruses, or virus-associated vectors as carriers of a nucleic acid construct into a cell. Constructs may be integrated and packaged into non-replicating, defective viral genomes like Adenovirus, Adeno-associated virus (AAV), or Herpes simplex virus (HSV) or others, including reteroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, e.g EPV and EBV vectors.

By "iron-related disorder" is meant any disease or condition where iron levels are altered (e.g., increased or decreased) from the levels typically found in healthy individuals. Specific conditions are described herein. Conditions associated with iron overload include both primary and secondary iron overload diseases, syndromes or disorders, including, but not limited to, hereditary hemochromatosis, porphyria cutanea tarda, hereditary spherocytosis, hyprochromic anemia, hysererythropoietic anemia (CDAI), faciogenital dysplasia (FGDY), Aarskog syndrome, atransferrinemia, sideroblastic anemia (SA), pyridoxine-responsive sidero-blastic anemia, and hemoglobinopathies such as thalassemia and sickle cell. Some studies have suggested an association between iron metabolism disorders, such as thalassemia and hemochromatosis, and a number of disease states, such as type II (non-insulin dependent) diabetes mellitus and atherosclerosis (Matthews et al., J. Surg. Res., 1997, 73: 35-40; Tuomainen et al, Diabetes Care, 1997, 20: 426-428).

Conditions associated with iron deficiency include anemia of chronic disease, iron deficiency anemias, functional iron deficiency, and microcytic anemia. The term "anemia of chronic disease" refers to any anemia that develops as a result of, for example, extended infection, inflammation, and neoplastic disorders. The anemia which develops is often characterized by a shortened red blood cell life span and sequestration of iron in macrophages, which results in a decrease in the amount of iron available to make new red blood cells. Conditions associated with anemia of chronic disease include, but are not limited to, chronic bacterial endocarditis, osteomyelitis, rheumatic fever, ulcerative colitis, and neoplastic disorders. Further conditions include other diseases and disorders associated with infection, inflammation, and neoplasms, including, for example, inflammatory infections (e.g., pulmonary abscess, tuberculosis), inflammatory noninfectious disorders (e.g., rheumatoid arthritis, systemic lupus erythrematosus, Crohn's disease, hepatitis, inflammatory bowel disease), and various cancers, tumors, and malignancies (e.g., carcinoma, sarcoma, lymphoma). Iron deficiency anemia may result from conditions such as pregnancy, menstruation, infancy and childhood, and blood loss due to injury.

Iron metabolism plays a role in a number of other diseases states, including cardiovascular disease, Alzheimer's disease, Parkinson's disease, and certain types of colo-rectal cancers (see, for example, Tuomainen et al., Circulation, 1997, 97: 1461-1466; McCord, Circulation, 1991, 83: 1112-1114; Sullivan, J. Clin. Epidemiol., 1996, 49: 1345-1352; Smith et al., Proc. Nat. Acad. Sci. USA, 1997, 94: 9866-9868; Riederer et al, J. Neurochem., 1989, 512: 515-520; Knekt et al., Int. J. Cancer, 1994, 56: 379-382).

The articles "a" and "an" are used herein to refer to one or to more than one (i.e., to at least one) of the grammatical object of the article. By way of example, "an element" means one element or more than one element.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following examples, but the scope of the invention should not be limited thereto.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Other features and advantages of the invention will be apparent from the following Detailed Description, the drawings, and the claims.

I. General a. Hemojuvelin

Hemojuvelin (also known as RGMc, HFE2) is a member of the Repulsive Guidance Molecule (RGM) family, including RGMa and DRAGON (also known as RGMb) (Papanikolaou et al., 2004. Nat. Genet. 36:77-82, Monnier et al., 2002. Nature. 419:392-395; Samad et al., 2004. J. Neurosci. 24:2027-2036). The inventors have recently demonstrated that like RGMa and DRAGON (Samad et al., 2005. J. Biol. Chem. 280:14122-14129; Babitt et al., 2005. J. Biol. Chem. 280:29820-29827), hemojuvelin functions as a BMP co-receptor that binds directly to BMP-2 and BMP-4 and enhances cellular responses to BMP, but not TGF-β, ligands. Furthermore, BMP-2 positively regulates hepcidin expression (Truksa et al., 2006. Proc. Natl. Acad. Sci. USA. 103:10289-10293), and hemojuvelin increases hepcidin induction in response to BMP-2.

Like RGM family members RGMa and DRAGON, the inventors show that hemojuvelin is a coreceptor that enhances BMP signaling via the classical BMP pathway involving BMP ligands, BMP receptors, and BMP receptor-activated Smads. The RGM family is the first documented family of BMP coreceptors. Although over 40 TGF-β superfamily ligands have been described, only five type I receptors and seven type II receptors have been identified. Coreceptors therefore have an important regulatory role for many TGF-β superfamily members to help generate specificity and a tight spatiotemporal coordination of these signals. The inventors believe RGM family members increase the sensitivity of cells in which they are expressed to low levels of BMP ligand (Samad et al., J. Biol. Chem. 280, 14122-14129 (2005); Babitt et al., J. Biol. Chem. 280, 29820-29827 (2005); Shi et al., Cell 113, 685-700 (2003)).

Hemojuvelin protein is expressed in the liver, where hepcidin is produced (Krause et al., FEBS Lett. 480, 147-150 (2000); Park et al., J. Biol. Chem. 276, 7806-7810 (2001); Pigeon et al., J. Biol. Chem. 276, 7811-7819 (2001)). Hepcidin levels are depressed in patients with HFE2 mutations and $Hfe2^{-/-}$ mice, suggesting that hemojuvelin is a positive regulator of hepcidin expression (Papanikolaou et al., Nat. Genet. 36, 77-82 (2004); Huang et al., J. Clin. Invest. 115, 2187-2191 (2005); Niederkofler et al., J. Clin. Invest. 115, 2180-2186 (2005)). $Hfe2^{-/-}$ mice also have markedly elevated intestinal and tissue macrophage ferroportin expression, presumably owing to low hepcidin levels. Here, direct experimental evidence that hemojuvelin positively regulates hepcidin expression in liver cells is provided and that hemojuvelin mutants associated with juvenile hemochromatosis have an impaired ability to upregulate hepcidin (Papanikolaou et al., Nat. Genet. 36, 77-82 (2004); Lanzara et al., Blood 103, 4317-4321 (2004); Lee et al., Blood 103, 4669-4671 (2004)). These hemojuvelin mutants also show impaired BMP signaling in liver cells compared with wild-type hemojuvelin. This demonstrates that hemojuvelin's ability to function as a BMP coreceptor may be integral for its role in regulating hepcidin expression and thereby systemic iron homeostasis.

Hemojuvelin expression in the liver is not uniform, as demonstrated in Hfe2 mutant mice expressing lacZ from the Hfe2 locus. In these mice, lacZ activity is restricted to hepatocytes surrounding portal tracts but is not present in other hepatocytes or in other cell types that comprise 30-40% of the liver, including Kupffer cells, stellate cells and sinusoidal endothelial cells (Niederkofler et al., J. Clin. Invest. 115, 2180-2186 (2005); Alpini et al., Hepatology 20, 494-514 (1994)). Rgma and Rgmb mRNA have also been detected in the rodent liver by RNA blot (Babitt et al., J. Biol. Chem. 280, 29820-29827 (2005)). It is possible that the cell type distribution of other RGM family members within the liver is different from hemojuvelin. For example, in the CNS, Rgma and Rgmb mRNA are expressed predominantly in nonoverlapping areas and seem to have different physiologic roles (Samad et al., J. Neurosci. 24, 2027-2036 (2004); Niederkofler et al., J. Neurosci. 24, 808-818 (2004); Monnier et al., Nature 419, 392-395 (2002); Rajagopalan et al. Nat. Cell Biol. 6, 756-762 (2004); Matsunaga et al., Nat. Cell Biol. 6, 749-755 (2004)). Alternatively, it is possible that hemojuvelin, but not other RGM family members, may interact with other molecules involved in regulating hepcidin expression and iron metabolism.

Hemojuvelin is also highly expressed in skeletal and cardiac muscle (Papanikolaou et al., Nat. Genet. 36, 77-82 (2004); Samad et al., J. Neurosci. 24, 2027-2036 (2004); Niederkofler et al., J. Neurosci. 24, 808-818 (2004); Rodriguez et al., Haematologica 89, 1441-1445 (2004)). Recent data suggest that human sera contains soluble hemojuvelin and that soluble hemojuvelin can inhibit the expression of hepcidin mRNA (Lin et al., Blood 106, 2884-2889 (2005)). Hemojuvelin in muscle may serve as a source of soluble hemojuvelin to regulate hepcidin expression (Lin et al., Blood 106, 2884-2889 (2005); Zhang et al., J. Biol. Chem. 280, 33885-33894 (2005)). Thus, whereas cell-surface hemojuvelin in the liver acts as a BMP coreceptor to enhance cellular responses to BMP ligands and increase hepcidin expression, soluble hemojuvelin may bind and sequester BMP ligands to inhibit both BMP signaling and hepcidin expression. Both soluble DRAGON.Fc24 and RGMa.Fc fusion proteins inhibit the biological activity of BMP ligands (data not shown). Hemojuvelin may also have a role in intracellular iron homeostasis, as overexpression of hemojuvelin and neogenin in vitro increases intracellular iron accumulation.

The inventors demonstrate herein that hemojuvelin is a novel BMP coreceptor whose enhancement of BMP signaling is important in regulating hepcidin expression and iron metabolism. Therapeutic strategies targeting the BMP signaling pathway may therefore have a role in treating disorders of iron homeostasis, such as hemochromatosis and anemia of chronic disease.

Recently, mutations in the gene encoding hemojuvelin were identified as the leading cause of juvenile hemochromatosis, resulting in a phenotype indistinguishable from hemochromatosis due to HAMP mutations. Humans with HFE2 mutations and $Hfe2^{-/-}$ mice have low hepcidin levels, and siRNA inhibition of HFE2 decreases hepcidin expression in vitro, suggesting that hemojuvelin positively regulates hepcidin expression. A member of the RGM family, hemojuvelin shares 50-60% amino acid identity and key structural features with RGMa and DRAGON(RGMb), including an N-terminal signal sequence, proteolytic cleavage site, partial von Willebrand factor type D domain and glycophosphatidylinositol (GPI) anchor.

Hemojuvelin mutants associated with juvenile hemochromatosis have impaired BMP signaling ability, and hepatocytes from $Hfe2^{-/-}$ mice demonstrate blunted hepcidin induction in response to BMP-2 (described herein and in Babitt et al., 2006. Nat. Genet. 38:531-539). This suggests that the mechanism for iron overload in patients with hemojuvelin mutations is due to decreased BMP signaling in the liver leading to decreased hepcidin expression.

b. BMP/TGF-β Superfamily

BMPs represent a large subfamily of the transforming growth factor β (TGF-β) superfamily of ligands, which share a common model of signal transduction (Shi et al., Cell 113, 685-700 (2003)). Signaling is initiated when ligand binds to complexes of two type I and two type II serine/threonine kinase receptors. Constitutively active type II receptors phosphorylate type I receptors, which phosphorylate Smad proteins. The BMP subfamily signals via one set of receptor-activated Smads (Smad1, Smad5 and Smad8), whereas the TGF-β subfamily signals via another set (Smad2 and Smad3). Phosphorylated receptor-activated Smads form heteromeric complexes with common mediator Smad4, and the Smad complexes translocate to the nucleus where they modulate gene transcription. Regulation of this pathway occurs at multiple levels in order to generate specificity and to finely tune these signals. One key regulatory mechanism is the promotion or inhibition of ligand binding by coreceptors. RGM family members RGMa and DRAGON are the first described coreceptors for the BMP subfamily. Both RGMa and DRAGON bind selectively to BMP-2 and BMP-4 ligands, interact with BMP receptors and enhance cellular responses to BMP ligands (Samad et al., J. Biol. Chem. 280, 14122-14129 (2005); Babitt et al., J. Biol. Chem. 280, 29820-29827 (2005); Shi et al., Cell 113, 685-700 (2003)).

BMPs have diverse roles in many physiologic and pathologic processes, including cell proliferation, differentiation and apoptosis (Hogan et al, Genes Dev. 10, 1580-1594 (1996); Zhao et al., Genesis 35, 43-56 (2003); Balemans et al., Dev. Biol. 250, 231-250 (2002)). Recently, a link between TGF-β superfamily signaling and iron metabolism was discovered: mice with a liver-specific conditional knockout of Smad4 were found to have reduced hepatic hepcidin expression and total body iron overload (Wang et al., Cell Metab. 2, 399-409 (2005)). Here, the inventors show that hemojuvelin is a BMP coreceptor and that by enhancing BMP signaling, hemojuvelin has a role in systemic iron metabolism through regulation of hepcidin expression.

Members of the BMP/TGF-β superfamily, which include BMPs, TGF-βs, growth and differentiation factors (GDFs), and Activins, initiate an intracellular signaling cascade by binding to a complex of type I and type II serine threonine kinase receptors (Shi et al., 2003. Cell. 113, 685-700). The activated receptor complex phosphorylates intracellular Smad proteins, which then complex with common-mediator Smad4. Smad complexes translocate to the nucleus where they modulate gene transcription. In general, BMPs and GDFs signal via one set of Smad proteins (1, 5, and 8), while TGF-βs and Activins signal via another set (Smad2 and Smad3).

A link between BMP/TGF-β signaling, hepcidin expression and iron metabolism in vivo is supported by the recent description of a mouse with a liver-specific conditional knockout of Smad4, encoding the common downstream mediator for all TGF-β superfamily ligands. These mice have reduced hepatic hepcidin expression and total body iron overload (Wang et al., Cell Metab. 2, 399-409 (2005)). Here, the inventors show that BMP-2 positively regulates hepcidin expression at the transcriptional level. the inventors also demonstrate that hemojuvelin enhances hepcidin induction in response to BMP-2 and that $Hfe2^{-/-}$ hepatocytes show a significantly reduced induction of hepcidin expression in response to BMP-2. Furthermore, livers of $Hfe2^{-/-}$ mice have reduced levels of phosphorylated Smad1/5/8, indicating that the absence of hemojuvelin results in lower hepatic BMP signaling in vivo. The inventors therefore propose that hemojuvelin-mediated BMP signaling is an important mechanism for regulating hepcidin expression and iron homeostasis (FIG. 1). Loss of hemojuvelin function leads to decreased BMP signaling in liver cells, which then decreases hepcidin expression. Impaired regulation by hepcidin leads to ferroportin overactivity, thereby resulting in increased intestinal iron absorption, increased macrophage iron release, elevated serum iron, and abnormal tissue iron deposition.

$Hfe2^{-/-}$ hepatocytes do maintain some induction of hepcidin expression in response to exogenous BMP-2. The inventors believe that under normal physiologic conditions, the liver expresses a low endogenous level of BMP ligand and that hemojuvelin serves to sensitize the cells to this low level of BMP ligand. Under these conditions, hemojuvelin is required to generate sufficient intracellular BMP signals to produce hepcidin. Under conditions of exposure to high levels of exogenous BMP ligands, the large excess of BMP ligand can bypass the requirement for hemojuvelin to generate sufficient intracellular BMP signals via BMP type I and type II receptors to stimulate hepcidin production.

Many BMP and TGF-β superfamily ligands are expressed endogenously in the adult liver (De Bleser et al., J. Hepatol. 26, 886-893 (1997); Kingsley et al., Trends Genet. 10, 16-21 (1994); Knittel et al., Exp. Cell Res. 232, 263-269 (1997); Miller et al., J. Biol. Chem. 275, 17937-17945 (2000)). As disclosed herein, the inventors findings demonstrate that hemojuvelin binds preferentially to BMP-2 and, to a lesser extent, BMP-4, but further work will be needed to definitively determine the endogenous BMP/TGF-β superfamily ligand(s) through which hemojuvelin regulates hepatic hepcidin expression in vivo. Both BMP-4 and TGF-β1 can increase hepatic hepcidin mRNA expression in vitro (Wang et al., Cell Metab. 2, 399-409 (2005)). However, data suggest that the TGF-β subfamily might be less critical than the BMP subfamily for positively regulating hepcidin expression in vivo, as livers of TGF-β receptor-activated $Smad3^{-/-}$ mice do not show any evidence of iron overload (Wang et al. Cell Metab. 2, 399-409 (2005)), and transgenic hepatic expression of a dominant-negative TGF-β type II receptor in mice does not result in any obvious liver abnormalities (Kanzler et al., Oncogene 20, 5015-5024 (2001)).

In addition to the BMP/TGF-β superfamily signaling pathway and iron status, inflammatory mediators also modulate hepcidin expression (Pigeon et al., J. Biol. Chem. 276, 7811-7819 (2001); Nicolas et al., J. Clin. Invest. 110, 1037-1044 (2002); Lee et al., Proc. Natl. Acad. Sci. USA 102, 1906-1910 (2005); Nemeth et al., Blood 101, 2461-2463 (2003); Nemeth et al., J. Clin. Invest. 113, 1271-1276 (2004)). Mice lacking hemojuvelin robustly upregulate hepcidin expression in response to lipopolysaccharide or interleukin-6 (IL-6; Niederkofler et al., J. Clin. Invest. 115, 2180-2186 (2005)). Further, suppression of hemojuvelin expression with small interfering RNA (siRNA) in Hep3B cells does not affect IL-6 induction of hepcidin expression. As disclosed herein, these data suggest that inflammatory mediators act independently of hemojuvelin to regulate hepcidin. Mice with a liver-specific knockout of Smad4 demonstrate attenuated induction of hepcidin expression in response to IL-6 (Wang et al. Cell Metab. 2, 399-409 (2005)). Additionally, soluble hemojuvelin inhibits induction of hepcidin mRNA expression by IL-6. Inflammatory stimuli have also been noted to decrease transcription of Hfe2 mRNA in wild-type mice. Thus there is a complex interplay between the inflammatory pathway, the BMP/TGF-β signaling pathway, and hemojuvelin (Niederkofler et al., J. Clin. Invest. 115, 2180-2186 (2005); Lin et al., Blood 106, 2884-2889 (2005); Wang et al., Cell Metab. 2, 399-409 (2005); Krijt et al., Blood 104, 4308-4310 (2004)).

Further evidence supporting a role for BMP signaling in regulating hepcidin expression and iron metabolism in vivo comes from mice with a conditional liver-specific knockout of Smad4. These mice have low hepcidin levels and develop iron overload. In that study, both BMP-4 and TGF-β1 induce hepcidin expression in liver cells in vitro (Wang et al., 2005. Cell Metab. 2:399-409). Hepcidin induction by BMP-9 has also been described (Truksa et al., 2006. Proc. Natl. Acad. Sci. USA. 103:10289-10293). Indeed, many superfamily members are endogenously expressed in the liver, including BMP-2, BMP-4, BMP-5, BMP-6, BMP-9, and all 3 TGF-β ligands (De Bleser et al., 1997. J. Hepatol. 26:886-893; Kingsley, 1994. Trends Genet. 10:16-21; Knittel et al., 1997. Exp. Cell Res. 232:263-269; Su et al., 2002. Proc. Natl. Acad. Sci. USA. 99:4465-4470; Miller et al., 2000. J. Biol. Chem. 275: 17937-17945 and data not shown). Data showing that hemojuvelin is a BMP co-receptor, but involved in not TGF-β signaling, suggests that members of the BMP subfamily are more important than members of the TGF-β subfamily for regulating iron metabolism in vivo. Here, the inventors show that many members of the TGF-β superfamily can induce hepcidin mRNA expression in vitro. However, a subset of BMP ligands, including BMP-2, BMP-4, BMP-5, BMP-6, BMP-7, and BMP-9 are much more potent inducers of hepcidin expression than other ligands tested, including all three TGF-β ligands. Three-fold induction of hepcidin expression by TGF-β1 is consistent with prior findings (Wang et al., 2005. Cell Metab. 2:399-409); however, BMP-4 and BMP-9 were much more potent inducers of hepcidin expression compared with prior studies (Wang et al., 2005. Cell Metab. 2:399-409; Truksa et al., 2006. Proc. Natl. Acad. Sci. USA. 103:10289-10293). This may be related to differences in ligand concentration (2 to 5-fold higher in our study) or differences in cell lines. Although BMP-9 is expressed in the liver (Miller et al., 2000. J. Biol. Chem. 275:17937-17945) and robustly increased hepcidin mRNA expression in vitro, HJV.Fc was unable to inhibit BMP-9 activation of the hepcidin promoter. HJV.Fc also has a reduced ability to inhibit BMP-7 as compared with BMP-2, -4, -5, and -6 ligands. The ability of HJV.Fc to inhibit hepcidin expression and increase serum iron in vivo indicates that BMP-2, BMP-4, BMP-5, and/or BMP-6 are good candidates for endogenous regulators of hepcidin expression, while BMP-9, BMP-7, and TGF-β ligands may be less important endogenous regulators of hepcidin.

Inhibition of hepatic BMP signaling may be the predominant mechanism by which HJV.Fc inhibits hepcidin expression and regulates systemic iron balance in vivo. Indeed, inhibition of endogenous BMP signaling in HepG2 cells using BMP siRNAs had a similar effect on decreasing hepcidin expression as treatment with HJV.Fc. Further, loss of TGF-β/BMP superfamily signaling in the liver is sufficient to reduce hepcidin expression and generate iron overload, as shown in mice with a liver-specific conditional knockout of Smad4 (Wang et al., 2005. Cell Metab. 2:399-409). However, HJV has been shown to bind to the receptor neogenin, a member of the Deleted in Colon Cancer (DCC) receptor group, which has been reported to have a role in diverse functions including cell survival, axonal guidance, and cellular iron uptake (Zhang et al., 2005. J. Biol. Chem. 280:33885-33894). Treatment with HJV.Fc in our study did not appear to have any other adverse effects on mice. Indeed, regulation of hepcidin expression and iron metabolism appears to be the principal role for TGF-β/BMP superfamily signaling in the adult liver in vivo, since iron overload was the predominant phenotype of liver-specific conditional Smad4 knockout mice (Wang et al., 2005. Cell Metab. 2:399-409).

c. Iron Homeostatis

Iron homeostasis is tightly regulated to provide this critical element for growth and survival while preventing the toxicity of iron excess. Plasma iron levels are maintained by intestinal absorption, reticuloendothelial cell recycling and mobilization of hepatocyte stores. Circulating iron is loaded onto serum transferrin and delivered primarily to the bone marrow for erythropoiesis. Sloughing of enterocytes and blood loss are the only significant means for removing excess iron from the body; the remaining iron is stored primarily in hepatocytes and macrophages (Hentze et al., Cell 117, 285-297 (2004)).

As there is no known regulated mechanism for iron excretion, systemic iron homeostasis is maintained by tight regulation of intestinal iron absorption and macrophage and hepatocyte iron release. Although the mechanism for this remains to be fully elucidated, hepcidin seems to have a key role. A soluble protein secreted by the liver (Krause et al., FEBS Lett. 480, 147-150 (2000); Park et al., J. Biol. Chem. 276, 7806-7810 (2001); Pigeon et al., J. Biol. Chem. 276, 7811-7819 (2001)), hepcidin promotes internalization and degradation of ferroportin, an iron exporter located on the surface of enterocytes, macrophages and hepatocytes (Nemeth et al., Science 306, 2090-2093 (2004)). Hepcidin thereby decreases both intestinal iron absorption and macrophage iron release. Mice lacking hepcidin expression and humans with mutations in the hepcidin gene (HAMP) have been found to develop severe iron overload at an early age, thus defining the first discovered cause of juvenile hemochromatosis (Nicolas et al., Proc. Natl. Acad. Sci. USA 98, 8780-8785 (2001); Roetto et al., Nat. Genet. 33, 21-22 (2003)). Data suggest that hepcidin expression is enhanced by iron overload and inflammation (Pigeon et al., J. Biol. Chem. 276, 7811-7819 (2001); Nicolas et al., J. Clin. Invest. 110, 1037-1044 (2002); Lee et al., Proc. Natl. Acad. Sci. USA 102, 1906-1910 (2005); Nemeth et al., Blood 101, 2461-2463 (2003); Nemeth et al., J. Clin. Invest. 113, 1271-1276 (2004)), whereas it is inhibited by anemia and hypoxia. This is consistent with a compensatory role for hepcidin to limit intestinal absorption during iron overload and to increase iron availability when needed for erythropoiesis.

Hepcidin deficiency is the common pathogenic mechanism for both juvenile and adult forms of the genetic iron overload disorder hereditary hemochromatosis, due to mutations in HAMP, HFE2, TFR2, and HFE (Pietrangelo, 2006. Biochim Biophys Acta. 1763:700-710; Roetto et al., 2003. Nat. Genet. 33:21-22; Papanikolaou et al., 2004. Nat. Genet. 36:77-82; Huang et al., 2005. J. Clin. Invest. 115:2187-2191; Niederkofle et al., 2005. J. Clin. Invest. 115:2180-2186; Ahmad et al., 2002. Blood Cells Mol. Dis. 29:361-366; Bridle et al., 2003. Lancet. 361:669-673; Muckenthaler et al., 2003. Nat. Genet. 34:102-107; Nicolas et al., 2003. Nat. Genet. 34:97-101; Kawabata et al., 2005. Blood. 105:376-381; Nemeth et al., 2005. Blood. 105:1803-1806). As described below, hemojuvelin acts as a co-receptor for BMP signaling and that BMP-2 signaling induces hepcidin expression in vitro. As shown herein, BMP-2 administration in mice increases hepcidin expression and reduces serum iron levels in vivo. The modest induction of hepcidin expression in response to BMP-2 in vivo compared to the in vitro data is likely multifactorial. First, the mice were maintained on a standard diet, where dietary iron is replete, basal hepcidin levels are generally high, and hepcidin induction by well-established regulators such as iron and LPS have been reported to be absent or less robust compared with mice maintained on an iron-deficient diet (Nemeth et al., 2004. J. Clin. Invest. 113:1271-1276). Indeed, the degree of hepcidin induction by BMP-2 in our study was similar to the 1.8-fold induction reported after LPS administration in mice fed on a standard diet (Roy et al., 2004. Nat. Genet. 36:481-485). BMPs typically act in an autocrine or paracrine fashion in vivo, while intravenously administered BMP-2 is rapidly eliminated from the systemic circulation ($t_{1/2}$=16 minutes) (See Summary of Safety and Effectiveness data for INFUSE# Bone Graft, Wyeth Pharmaceuticals, Inc, which is available at http://www.fda.gov/cdrh/PDF4/p000054b.pdf). Thus, the systemically administered BMP-2 dose may not be efficiently delivered to the liver. Nevertheless, the decrease in serum iron suggests that the BMP-2-induced increase in hepcidin expression was physiologically relevant, and the inventors believe reflects decreased iron export from reticuloendothelial cells and duodenal enterocytes due to hepcidin-induced internalization and degradation of ferroportin. Although systemic BMP-2 treatment may be impractical due to high cost and rapid elimination from the systemic circulation, therapies which enhance hepatic BMP signaling may provide alternative treatment strategies for managing iron overload in patients with hereditary hemochromatosis.

d. Anemia

Anemia of chronic disease, also known as anemia of inflammation, is prevalent in patients with many systemic diseases including autoimmune disorders, malignancy, and chronic kidney disease (Weiss et al., 2005. N. Engl. J. Med. 352:1011-1023). In these patients, intestinal iron absorption is impaired and iron remains sequestered in reticuloendothelial cells, leading to hypoferremia and anemia (Weiss et al., 2005. N. Engl. J. Med. 352:1011-1023). Research over the last several years implicates hepcidin excess in the pathogenesis of this disease (Weiss et al., 2005. N. Engl. J. Med. 352:1011-1023; Pigeon et al., 2001. J. Biol. Chem. 276:7811-7819; Nicolas et al., 2002. J. Clin. Invest. 110:1037-1044, Nemeth et al., 2004. J. Clin. Invest. 113:1271-1276, Nemeth et al., 2003. Blood. 101:2461-2463, Lee et al., 2005. Proc. Natl. Acad. Sci. USA. 102:1906-1910). A key regulator of systemic iron homeostasis (Hentze et al., 2004. Cell. 117: 285-297), hepcidin is secreted by the liver (Pigeon et al., 2001. J. Biol. Chem. 276:7811-7819; Krause et al., 2000. FEBS Lett. 480:147-150; Park et al., 2001. J. Biol. Chem. 276:7806-7810) and induces internalization and degradation of the iron exporter ferroportin in absorptive enterocytes and reticuloendothelial cells, thereby inhibiting iron absorption from the intestine and iron release from reticuloendothelial cell stores (Nemeth et al., 2004. Science. 306:2090-2093). Hepcidin expression is inhibited by anemia and hypoxia, thus increasing iron availability when needed for erythropoiesis (Nicolas et al., 2002. J. Clin. Invest. 110:1037-1044). Conversely, hepcidin expression is induced by iron loading, thus providing a feedback mechanism to limit further iron absorption (Pigeon et al., 2001. J. Biol. Chem. 276:7811-7819; Nicolas et al., 2002. J. Clin. Invest. 110:1037-1044; Nemeth et al., 2004. J. Clin. Invest. 113:1271-1276). Hepcidin expression is also induced by inflammatory cytokines, and this is thought to be the mechanism underlying the impaired intestinal iron absorption, reticuloendothelial cell iron sequestration, and hypoferremia characteristic of anemia of chronic disease (Weiss et al., 2005. N. Engl. J. Med. 352:1011-1023; Pigeon et al., 2001. J. Biol. Chem. 276:7811-7819; Nicolas et al., 2002. J. Clin. Invest. 110:1037-1044; Nemeth et al., 2004. J. Clin. Invest. 113:1271-1276; Nemeth et al., 2003. Blood. 101:2461-2463; Lee et al., 2005. Proc. Natl. Acad. Sci. USA. 102:1906-1910).

While hepcidin excess has a role in anemia of chronic disease, inadequate hepcidin expression appears to be a common pathogenic mechanism for the iron overload disorder hereditary hemochromatosis, due to mutations in the genes encoding hepcidin (HAMP), hemojuvelin (HFE2), HFE, or Transferrin receptor 2 (TFR2). In patients and animal models with iron overload due to mutations in these genes, hepcidin levels are low, thereby leading to ferroportin overactivity, increased intestinal iron absorption, increased reticuloendothelial cell iron release, elevated serum iron levels, and abnormal tissue iron deposition (Pietrangelo, 2006. Biochim Biophys Acta. 1763:700-710; Roetto et al., 2003. Nat. Genet. 33:21-22; Papanikolaou et al., 2004. Nat. Genet. 36:77-82; Huang et al., 2005. J. Clin. Invest. 115:2187-2191; Niederkofle et al., 2005. J. Clin. Invest. 115:2180-2186; Ahmad et al., 2002. Blood Cells Mol. Dis. 29:361-366; Bridle et al., 2003. Lancet. 361:669-673; Muckenthaler et al., 2003. Nat. Genet. 34:102-107; Nicolas et al., 2003. Nat. Genet. 34:97-101; Kawabata et al., 2005. Blood. 105:376-381; Nemeth et al., 2005. Blood. 105:1803-1806). Evidence suggests that hemojuvelin functions as a coreceptor for bone morphogenetic protein (BMP) signaling, and that BMP/TGF-β superfamily signaling has a role in regulating hepcidin expression and systemic iron balance (Wang et al., 2005. Cell Metab. 2:399-409; Truksa et al., 2006. Proc. Natl. Acad. Sci. USA. 103:10289-10293).

Anemia of chronic disease is associated with hypoferremia and reticuloendothelial cell iron sequestration. Inflammatory cytokines are potent inducers of hepcidin expression, and hepcidin excess may play a key role in the pathogenesis of anemia in these patients (Weiss et al., 2005. N. Engl. J. Med. 352:1011-1023; Pigeon et al., 2001. J. Biol. Chem. 276:7811-7819; Nicolas et al., 2002. J. Clin. Invest. 110:1037-1044; Nemeth et al., 2004. J. Clin. Invest. 113:1271-1276; Nemeth et al., 2003. Blood. 101:2461-2463; Lee et al., 2005. Proc. Natl. Acad. Sci. USA. 102:1906-1910). Presumably, inhibitors of hepcidin expression would allow for increased availability of iron from the diet and increased mobilization of iron from the spleen, thereby improving red blood cell production and ameliorating anemia. The data presented herein provide in vivo evidence that soluble HJV.Fc inhibits BMP signaling in the liver, inhibits hepcidin expression, increases ferroportin protein expression, decreases splenic iron stores, and increase serum iron levels. As described in detail below, HJV.Fc is thus a potential new treatment for anemia associated with hepcidin excess.

e. Other Mediators of Hepcidin Expression

Inflammatory mediators such as IL-6 may regulate hepcidin expression through STAT3 (Wrighting et al., 2006. Blood. 108:3204-3209; Verga Falzacappa et al., 2007. Blood. 109: 353-358; Pietrangelo et al., 2007. Gastroenterology. 132:294-300). Mice with a liver specific conditional knockout of Smad4 demonstrate attenuated hepcidin induction in response to IL-6 (Wang et al., 2005. Cell Metab. 2:399-409). This demonstrates that BMP/TGF-β superfamily signaling is necessary for hepcidin excess in inflammatory states, and that inhibition of BMP signaling with HJV.Fc attenuates this hepcidin excess. As shown below, HJV.Fc inhibits hepcidin induction in response to the inflammatory cytokine IL-6, consistent with prior reports for recombinant soluble hemojuvelin (Lin et al., 2005. Blood. 106:2884-2889). Taken together, HJV.Fc, or other inhibitors of BMP signaling, can provide treatments for anemia of chronic disease caused by inflammation.

II. HJV Polypeptides, Derivative and Fragments

Human hemojuvelin (HJV) has five predicted spliced transcripts encoding three different proteins of 426, 313 and 200 amino acids (corresponding to SEQ ID NOs: 2, 3, and 4 respectively). HJV is also commonly known in the art by the following alternative names; JH, HFE2A, RGMc, HJV, and HFE2. HJV possess multiple protein domains, including a hydrophobic N-terminal signal peptide, a conserved RGD triamino motif, a partial von Willbrandt factor D motif, and a C-terminal glycoylphosphatidylinisotol (GPI) membrane anchor domain (Papanikolaou et al, 2004; Nat Genetics, 36; 77-82). HJV shares considerable sequence identity to other RGM family members (see FIG. 23 and Papanikolaou et al, 2004; Nat Genetics, 36; 77-82), and human HJV is the orthologue to rRGMc (see FIG. 24). HJV can undergo autocleavage at a conserved Asp-Pro bond (residues 172-173 in human HJV), resulting in two fragments held together by a disulfide bond (Zhang et al, 2005; JBC, 280; 338885-94; Lin et al, 2005; blood, 106; 2884-89).

Phylogenetic analysis of HJV homologue sequences indicates a pattern of conserved residues (see Carnus et al, J Mol Evol, 2007; 65; 68-81, which is incorporated in its entirety herein by reference). Analysis of the full length human HJV indicates 7 regions (regions 1-7), a N-terminal Signal peptide (residues 1-35), and a propeptide (residues 401-426) (see FIG. 4 in Carnus et al, J Mol Evol, 2007; 65; 68-81). Regions 1, 3 and 5 have been identified as conserved regions, which correspond to amino acids 35-50 (region 1), 80-125 (region 3) and 167-267 (region 5) on human HJV. Residues for Region 1-7 classification are based on human HJV sequence GenBank Accession No. Q6ZVN8 (SEQ ID NO: 61).

Region 1 (residues 35-50) of HJV is a N-terminal conserved region of about 15 amino acids long comprising two conserved cysteine residues. Region 2 (residues 51-79) of HJV is variable but comprises a number of glycine residues for enhanced stability and several helical regions as well as structural flexibility (Carnus et al, J Mol Evol, 2007; 65; 68-81). Region 3 (residues 80-125) of HJV is a conserved region comprising a RGM motif (residues 98-100) which is predicted to be on the surface of the protein and may play a role in cell attachment or recognition signal for certain ligands or signal transduction, possibly in iron homeostasis (Collin et al, 2006; Biol Res, 39; 25-37).

Region 4 (residues 126-166) is a variable region except for a short CXY motif beginning at 148, with conserved residues 165 and 166 being conserved as either LH, TH or LF among different species HJV homologues. Region 5 (residues 167-256) is a conserved region comprising three cysteine residues and other structural motifs and a potential glycosylation site and a partial van Willebrand D motif (VWD: 167-310). This region also contains highly conserved mutations, such as F170 and D172E, which are associated with iron overload (De Gobbi et al, 2002, Br J Haematol 117:973-979), which are near the FGDPHL motif and the G250V mutation which leads to iron overload (De Gobbi et al, 2002, Br J Haematol 117:973-979). Region 6 (residues 257-256), comprises predicted β-sheets and two conserved cysteines, as well as known mutations in human HJV, C282Y (Feder et al., 1998, Proc Natl Acc Sci, USA, 95; 1472-77) and G320V, which is in a conserved motif, LCVXGCP (Rivard et al, 2003; Eur J Hum Genet 11; 585-589).

In one embodiment, a HJV fusion polypeptide useful in the compositions and methods as disclosed herein comprises a human HJV polypeptide and a first fusion partner. In one embodiment, the HJV fusion polypeptide consists essentially of a human HJV polypeptide and a first fusion partner. In one embodiment, the HJV fusion polypeptide consists of a human HJV polypeptide and a first fusion partner.

In another embodiment, the HJV fusion polypeptide comprises human HJV polypeptide which comprises, or alternatively, consists of a polypeptide having the sequence of SEQ ID NO: 2 or 3, or 4, or a functional fragment thereof, or a HJV functional fragment of SEQ ID NO: 7 or 10. In another embodiment, the nucleic acid construct comprises a polypeptide encoded by the sequence corresponding to SEQ ID NO: 8, 9 or 11.

Applicants envision the potential use of all described isoforms and homologs of HJV can be used in HJV fusion polypeptides of the present invention, with suitable modifications when necessary for activity. In addition, truncated polypeptides which comprise partial fragments of the full HJV polypeptides, and which retain the ability to promote increase in serum iron and/or transferrin saturation can also be useful for the present invention. Fragments of HJV as the term is used herein, refers to a truncated product (from either the C-terminus or N-terminus) which has no other sequence modifications (e.g. internal deletions or point mutations.) In particular, functional fragments of HJV sequences, which retain the ability to increase iron serum and/or transferrin saturation of HJV demonstrated in the Examples herein (referred to herein as HJV fragment), are suitable for use in the present invention. Such fragments may for example, be polypeptide fragments of HJV encoded by one or more exons of the HJV gene (GeneID: 148738, RefSeq ID: NM__145277, SEQ ID NO: 38 (HJV isoform b), or one or more protein regions identified in Gen Bank Accession Number, 148738, in various combinations. The identification of a partial HJV polypeptide as a functional fragment of HJV, or functional variant of HJV can readily be determined, for example, using the assays as described herein and in the Examples.

The fusion proteins of the present invention encompasses use of full length HJV or a HJV fragment and a fusion partner, e.g., an HJV.Fc fusion. The HJV fusion portion of the protein may include a soluble form of the HJV protein (e.g., lacking the GPI anchoring domain) or may be any functional fragment of HJV (e.g., a fragment capable of regulating hepcidin or acting as BMP co-receptor). The fragment may have at least 1, 2, 3, 5, 8, 10, 15, 20, 25, 50, 75, 100 amino acids deleted from the N-terminus, the C-terminus, or both, but the fragment be at least 6 amino acids as discussed above. In the fusion protein shown in SEQ ID NO:1, for example, the HJV fusion protein can include amino acids 33-399 of the full human HJV length protein. In other embodiments, the fusion protein may include a portion of the 33-399 HJV sequence that is a functional fragment of HJV (e.g., with 1, 2, 3, 5, 8, about 10, or about at least 15, or about at least 20, or about at least 25, or about at least 50, or about at least 75, or about at least 100 amino acids deleted from the N-terminus, the C-terminus, or both). The N-terminal signal sequence may be deleted, or alternatively replaced with another signal sequence (e.g., one that targets the protein to the nucleus or extracellularly). The HJV portion of the fusion protein may be at least about 75%, or about at least 80%, or about at least 85%, or about at least 90%, or about at least 95%, or about at least 99%, or about 100% identical to at least a portion of the full length HJV protein (e.g., the human protein).

In some embodiments, HJV fragments useful in a HJV fusion protein as disclosed herein include HJV fragments comprising structural and functional amino acids residues. In some embodiments, a HJV fragment as disclosed herein can be for example, but are not limited to, fragments which consist essentially of amino acids between residue about 70 to about residue 125 (fragment a), or about residue 167 to about residue 256 (fragment b), or about residue 167 to about residue 327 (fragment c), or about residue 257 to about residue 327 (fragment d), or about residue 257 to about residue 400 (fragment d). Residues are based on human HJV sequence GenBank Accession No. Q6ZVN8 (SEQ ID NO: 61). Alternatively, other fragments can be designed as so desired taking into account the structural and functional domains of human HJV protein as demonstrated in FIG. 25.

As disclosed herein, a functional fragment as defined by the terms herein, can be generated and assessed by on one of ordinary skill in the art by simple deletion analysis. Such a fragment of SEQ ID NOS:2 to 5 can be, for example, 1, 2, 3, 4, 5, 6, 7, 8, 9 or 10 amino acids or more than 10 amino acids, such as 15, 30, 50, 100 or more than 100 amino acids deleted from the N-terminal and/or C-terminal of SEQ ID NO: 2 to 5, respectively. Persons of ordinary skill in the art can easily identify the minimal peptide fragment of SEQ ID NO:2 to 5 useful in a HJV fusion protein by the methods as disclosed herein, by sequentially deleting N- and/or C-terminal amino acids from SEQ ID NO: 2 to 5 and assessing the function of the resulting peptide fragment fused to a Fc fragment. One of ordinary skill in the art can easily assess the function of the HJV-fragment.Fc fusion protein to increase serum iron concentration and/or increase transferrin saturation when administered to a mouse in vivo (as disclosed in the Examples and FIGS. 19 and 22 herein) as compared to HJV-Fc corresponding to SEQ ID NO: 1, 7 or 10 as disclosed herein. Using such an in vivo assay, if the HJV-fragment.Fc protein has at least 30% of the biological activity of the HJV-Fc corresponding to SEQ ID NO: 1, 7 or 10 as disclosed herein, then the HJV-fragment portion of the HJV-fragment.Fc protein is considered a valid HJV-fragment and can used in fusion proteins and methods as disclosed herein. Alternatively, one of ordinary skill in the art can easily assess the function of the HJV-fragment.Fc fusion protein by assessing its ability to decrease basal hepcidin expression in HepG cells in vitro as compared to HJV-Fc corresponding to SEQ ID NO: 1, 7 or 10 as disclosed herein, or to determine the ability of the HJV-fragment.Fc protein to decrease BMP-mediated induction of hepcidin expression using the BRE-luciferase in vitro assay as disclosed herein in the Examples and in FIGS. 17A-17D. Using such an in vitro assay, if the HJV-fragment.Fc protein has at least 30% of the biological activity of the HJV-Fc corresponding to SEQ ID NO: 1, 7 or 10 as disclosed herein, then the HJV-fragment portion of the HJV-fragment.Fc protein is considered a valid HJV-fragment and can used in fusion proteins and methods as disclosed herein. In some embodiments, a fragment of SEQ ID NOs: 2 to 5 can be less than 200, or less than 150 or less than 100, or less than 50, or less than 20 amino acids of SEQ ID NOs: 2, 3, 4 or 5. In some embodiments, a fragment of SEQ ID NOs: 2, 3, 4 or 5 is less than 100 peptides in length.

The present invention also features an HJV protein (to be fused with a first fusion partner) which has been engineered (e.g., with sequence changes such as insertions, deletions, and point mutations, or a combination thereof) to reduce proteolytic cleavage of the protein. Such proteins may exhibit enhanced half-life in vivo and allow for either reduced size of dosing or frequency of administration to generate a desired therapeutic effect. Such proteins may also exhibit increased efficacy as compared to a fusion containing the corresponding wild type HJV sequences, such as SEQ ID NO: 1, 2, 3, 4, or 5. One example of such a HJV polypeptide sequence is the HJV-D17A polypeptide, such as amino acids 1-407 of SEQ ID NO:7. In one embodiment, the HJV polypeptide which is fused to the first fusion protein are not HJV polypeptides of SEQ ID NO: 7, 10 or 30 in U.S. Pat. No. 7,319,138 (which correspond to SEQ ID NO: 62, 63 and 64 respectively herein).

As discussed above, a HJV protein or functional fragment thereof useful in a HJV fusion protein can correspond to a human HJV isoform A (SEQ ID NO: 2) or a functional fragment or functional variant or functional derivative thereof, where SEQ ID NO:2 is as follows:

```
  1 mgepgqspsp rsshgspptl stltllllllc ghahsqckil rcnaeyvsst lslrgggssg
 61 alrggggggr gggvgsgglc ralrsyalct rrtartcrgd lafhsavhgi edlmiqhncs
121 rqgptapppp rgpalpgags glpapdpcdy egrfsrlhgr ppgflhcasf gdphvrsfhh
181 hfhtcrvqga wplldndflf vqatsspmal ganatatrkl tiifknmqec idqkvyqaev
241 dnlpvafedg singgdrpgg sslsiqtanp gnhveigaay igttiiirqt agqlsfsikv
301 aedvamafsa eqdlqlcvgg cppsqrlsrs ernrrgaiti dtarrlckeg lpvedayfhs
361 cvfdvlisgd pnftvaaqaa ledaraflpd leklhlfpsd agvplssatl lapllsglfv
421 lwlciq
```

In another embodiment, a HJV protein or functional fragment thereof useful in a HJV fusion protein can correspond to a human HJV isoform B (SEQ ID NO: 3) or a functional fragment or functional variant or functional derivative thereof, where SEQ ID NO:3 is as follows:

```
  1 miqhncsrqg ptappprgp alpgagsglp apdpcdyegr fsrlhgrppg flhcasfgdp
 61 hvrsfhhhfh tcrvggawpl ldndflfvqa tsspmalgan atatrkltii fknmgecidq
121 kvyqaevdnl pvafedgsin ggdrpggssl siqtanpgnh veiqaayigt tiiirqtagq
181 lsfsikvaed vamafsaeqd lqlcvggcpp sqrlsrsern rrgaitidta rrlckeglpv
241 edayfhscvf dvlisgdpnf tvaaqaaled araflpdlek lhlfpsdagv plssatllap
301 llsglfvlwl ciq
```

In another embodiment, a HJV protein or functional fragment thereof useful in a HJV fusion protein can correspond to a human HJV isoform C (SEQ ID NO: 4) or a functional fragment or functional variant or functional derivative thereof, where SEQ ID NO:4 is as follows:

```
  1 mgecidqkvy qaevdnlpva fedgsinggd rpggsslsiq tanpgnhvei qaayigttii
 61 irqtagglsf sikvaedvam afsaeqdlql cvggcppsqr lsrsernrrg aitidtarrl
121 ckeglpveda yfhscvfdvl isgdpnftva agaaledara flpdleklhl fpsdagvpls
181 satllaplls glfvlwlciq
```

In another embodiment, a HJV protein or functional fragment thereof useful in a HJV fusion protein can correspond to a mouse HJV homologue (SEQ ID NO: 5) or a functional fragment or functional variant or functional derivative thereof, where SEQ ID NO:5 is as follows:

```
  1 mqecidqkvy qaevdnlpaa fedgsinggd rpggsslsiq tanlgshvei raayigttii
 61 irqtagqlsf sirvaedvar afsaeqdlql cvggcppsqr lsrsernrrg aiaidtarrl
121 ckeglpveda yfqscvfdvs vsgdpnftva aqtalddary fltdlenlhl fpsdagppls
181 paiclvplls alfvlwlcfs k
```

In one embodiment, a HJV fusion protein useful in the methods and compositions as disclosed herein can correspond to a human HJV protein fused to a Fc fragment, such as SEQ ID NO: 1, or alternatively where HJV is a functional fragment of HJV protein. Accordingly, in one embodiment, a HJV fusion protein useful in the methods and compositions as disclosed herein comprises SEQ ID NO: 1 or functional variants or functional derivatives thereof, where SEQ ID NO:1 is as follows:

```
MSALLILALVGAAVADYKDHDGDYKDHDIDYKDDDDKLAAAHSQCKILRCNAEYVSSTLSLRGG

GSSGALRGGGGGGRGGGVGSGGLCRALRSYALCTRRTARTCRGDLAFHSAVHGIEDLMIQHNCS

RQGPTAPPPPRGPALPGAGSGLPAPDPCDYEGRFSRLHGRPPGFLHCASFGDPHVRSFHHHFHT

CRVQGAWPLLDNDFLFVQATSSPMALGANATATRKLTIIFKNMQECIDQKVYQAEVDNLPVAFE

DGSINGGDRPGGSSLSIQTANPGNHVEIQAAYIGTTIIIRQTAGQLSFSIKVAEDVAMAFSAEQ

DLQLCVGGCPPSQRLSRSERNRRGAITIDTARRLCKEGLPVEDAYFHSCVFDVLISGDPNFTVA

AQAALEDARAFLPDLEKLHLFPSLELVPRGSGDPIEGRGGGGGDPKSCDKPHTCPLCPAPELLG

GPSVFLFPPKPKDTLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTLPPSRDELTKNQVS

LTCLVKGFYPSDIAVEWESNGQPENNYKATPPVLDSDGSFFLYSKLTVDKSRWQQGNVFSCSVM

HEALHNHYTQKSLSLSPGK
```

In one embodiment, a HJV fusion protein useful in the methods and compositions as disclosed herein can correspond to a human HJV protein which is a non cleavable form which is fused to a Fc fragment, such as SEQ ID NO: 7, or alternatively where HJV is a functional fragment of a non-cleavable form of a HJV protein. Accordingly, in one embodiment, a HJV fusion protein useful in the methods and compositions as disclosed herein comprises SEQ ID NO: 7 or functional variants or functional derivatives thereof, where SEQ ID NO:7 is as follows:

```
MSALLILALVGAAVADYKDHDGDYKDHDIDYKDDDDKLAAAHSQCKILRCNAEYVSSTLSLRGGG

SSGALRGGGGGGRGGGVGSGGLCRALRSYALCTRRTARTCRGDLAFHSAVHGIEDLMIQHNCSR

QGPTAPPPPRGPALPGAGSGLPAPDPCDYEGRFSRLHGRPPGFLHCASFGAPHVRSFHHHFHTC

RVQGAWPLLDNDFLFVQATSSPMALGANATATRKLTIIFKNMQECIDQKVYQAEVDNLPVAFED

GSINGGDRPGGSSLSIQTANPGNHVEIQAAYIGTTIIIRQTAGQLSFSIKVAEDVAMAFSAEQD

LQLCVGGCPPSQRLSRSERNRRGAITIDTARRLCKEGLPVEDAYFHSCVFDVLISGDPNFTVAA

QAALEDARAFLPDLEKLHLFPSLELVPRGSGDPIEGRGGGGGDPKSCDKPHTCPLCPAPELLGG

PSVFLFPPKPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTLPPSRDELTKNQVSL

TCLVKGFYPSDIAVEWESNGQPENNYKATPPVLDSDGSFFLYSKLTVDKSRWQQGNVFSCSVMH

EALHNHYTQKSLSLSPGK
```

In one embodiment, a HJV fusion protein useful in the methods and compositions as disclosed herein can correspond to a human HJV fusion protein comprising SEQ ID NO: 10 which is encoded by a polynucleotide which has been codon optimized, for example by polynucleotide SEQ ID NO:11 One can use the HJV protein in SEQ ID NO: 10 which has had the extracellular signal sequence and GPI anchoring domain removed. Accordingly, in one embodiment, a HJV fusion protein useful in the methods and compositions as disclosed herein comprises SEQ ID NO: 10 or functional variants or functional derivatives thereof, where SEQ ID NO:10 is as follows:

MSALLILALVGAAVAHSQCKILRCNAEYVSSTLSLRGGGSSGALRGGGGGGRGGGVGSGGLCRAL

RSYALCTRRTARTCRGDLAFHSAVHGIEDLMIQHNCSRQGPTAPPPPRGPALPGAGSGLPAPDPC

DYEGRFSRLHGRPPGFLHCASFGDPHVRSFHHHFHTCRVQGAWPLLDNDFLFVQATSSPMALGAN

ATATRKLTIIFKNMQECIDQKVYQAEVDNLPVAFEDGSINGGDRPGGSSLSIQTANPGNHVEIQA

AYIGTTIIIRQTAGQLSFSIKVAEDVAMAFSAEQDLQLCVGGCPPSQRLSRSERNRRGAITIDTA

RRLCKEGLPVEDAYFHSCVFDVLISGDPNFTVAAQAALEDARAFLPDLEKLHLFPKSCDKTHTCP

PCPAPELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRWQQGNV

FSCSVMHEALHNHYTQKSLSLSPGK

It will be appreciated that the HJV polypeptides useful for the HJV fusion proteins as disclosed herein often contain amino acids other than the 20 amino acids commonly referred to as the 20 naturally occurring amino acids, and many amino acids, including the terminal amino acids, can be modified either by natural processes such as glycosylation and other post-translational modifications, or by chemical modification techniques which are well known in the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which can be present in polypeptides of the present invention are, to name an illustrative few, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, 1. E. Creighton, Proteins-Structure and Molecular Properties, 2nd Ed., W.H. Freeman and Company, New York, 1993. Many detailed reviews are available on this subject, such as, for example, those provided by Wold, F., in Posttranslational Covalent Modification of Proteins, B. C. Johnson, Ed., Academic Press, New York, pp 1-12, 1983; Sifter et al., Meth. Enzymol. 182: 626-646, 1990 and Rattan et al., Protein Synthesis: Posttranslational Modifications and Aging, Ann. N.Y. Acad. Sci. 663: 48-62, 1992.

It will also be appreciated, as is well known and as noted above, that peptides and polypeptides are not always entirely linear. For instance, polypeptides can be branched as a result of ubiquitination, and they can be circular, with or without branching, generally as a result of posttranslational events, including natural processing events and events brought about by human manipulation which do not occur naturally. Circular, branched and branched circular polypeptides can be synthesized by non translational natural processes and by entirely synthetic methods.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and; synthetic polypeptides and such modifications can be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylation host, generally a eukaryotic cell. Insect cells often carry out the same posttranslational glycosylation as mammalian cells and, for this reason, insect cell expression systems have been developed to efficiently express mammalian proteins having native patterns of glycosylation, inter alia. Similar considerations apply to other modifications.

It will be appreciated that the same type of modification can be present to the same or varying degree at several sites in a given polypeptide. Also, a given peptide or polypeptide can contain many types of modifications.

In some embodiments, N-methyl and hydroxy-amino acids can be substituted for conventional amino acids in solid phase peptide synthesis. However, production of polymers with reduced peptide bonds requires synthesis of the dimmer of amino acids containing the reduced peptide bond. Such dimers are incorporated into polymers using standard solid phase synthesis procedures. Other synthesis procedures are well known in the art.

III. HJV Fusion Proteins and Protein Conjugation

In some embodiments, a HJV polypeptide (i.e. SEQ ID NOs: 2 to 5 or fragments, derivatives or variants thereof) are conjugated to a first fusion partner (i.e. IgG1 Fc). The conjugation can be a non-covalent or covalent interaction, for example, by means of chemical crosslinkage or conjugation.

As disclosed herein, the inventors have developed HJV-D172A.Fc (SEQ ID NO:7), an HJV.Fc fusion which exhibits reduced proteolytic cleavage as compared to the fusion protein including the corresponding wild type sequence (SEQ ID NO:1). The inventors have also developed a HJV.Fc (SEQ ID NO:10) which has been codon-optimized for expression in mammalian cells, an HJV.Fc fusion protein which exhibits the nucleotide bases more common to mammalian cell than bacterial cells as compared to the corresponding wildtype sequence (SEQ ID NO:1).

In some embodiments, the polynucleotides encoding any of the fusion proteins (e.g., SEQ ID NOS: 8, 9 and 11) may be produced using any molecular biological techniques known in the art (e.g., those described herein).

In one embodiment, a HJV fusion protein useful in the methods and compositions as disclosed herein can correspond to a human HJV fusion protein which is encoded by a polynucleotide which has been codon optimized such as the polynucleotide sequence of SEQ ID NO: 11. The polynucleotide of SEQ ID NO:11 is codon-optimized for protein expression in mammalian cells and encodes for a HJV fusion protein where the HJV protein has had the extracellular signal sequence and GPI anchoring domain removed. Accordingly, in one embodiment, a polynucleotide useful for encoding and producing a HJV fusion protein for use in the methods and compositions as disclosed herein comprises SEQ ID NO: 11 or analogues, variants or derivatives thereof, where SEQ ID NO:11 is as follows:

*GGATCCAAGCTT*gccgccATGAGCGCCCTGCTTATTCTGGCCCTGGTTGGAGCAGCCGT

GGCTCATAGCCAGTGCAAGATCCTGCGATGCAATGCCGAGTACGTGTCTTCCACCCTCA

GTCTCAGAGGCGGGGGGAGTTCCGGCGCACTGCGCGGGGGAGGTGGAGGTGGCCGCGGA

GGCGGAGTGGGATCTGGGGGACTGTGCCGAGCTTTGCGGAGTTACGCTCTGTGCACAAG

ACGCACCGCCAGGACCTGCAGGGGAGACCTGGCATTCCACAGCGCAGTGCACGGCATTG

AAGACTTGATGATTCAGCATAATTGTAGTAGACAAGGCCCTACCGCTCCCCCCCCTCCC

AGGGGCCCCGCTTTGCCTGGGGCAGGTTCCGGACTGCCCGCCCCAGATCCTTGTGACTA

CGAGGGGCGGTTCAGCCGACTCCATGGAAGGCCCCCAGGCTTCCTGCACTGCGCAAGTT

TTGGCGATCCACACGTCAGGTCATTTCACCACCACTTTCATACCTGTCGTGTCCAGGGC

GCATGGCCTCTGCTGGACAACGACTTCCTCTTCGTCCAAGCAACAAGTTCACCTATGGC

TCTGGGGGCAAATGCTACTGCCACCCGAAAACTTACCATTATCTTTAAGAATATGCAAG

AATGTATCGATCAGAAGGTCTACCAGGCCGAAGTTGACAACCTGCCCGTGGCTTTCGAG

GATGGTTCAATCAACGGAGGGGACCGGCCTGGAGGCTCCAGTCTGAGCATCCAGACCGC

CAATCCTGGAAATCACGTGGAGATCCAGGCTGCCTACATCGGCACAACAATCATAATTA

GGCAGACCGCTGGCCAGCTGAGCTTCTCCATCAAGGTCGCCGAAGACGTGGCCATGGCT

TTCTCTGCCGAACAGGACCTCCAGCTTTGCGTGGGTGGTTGTCCACCCTCCCAGCGCCT

TTCTCGATCCGAACGCAATAGGCGAGGCGCAATCACTATCGACACTGCTCGCAGATTGT

GCAAAGAGGGCCTGCCTGTGGAGGATGCATACTTCCATTCTTGTGTGTTCGACGTCCTG

ATAAGCGGAGACCCAAATTTCACAGTGGCTGCTCAGGCCGCACTGGAGGATGCCAGGGC

CTTTTTGCCCGATCTGGAAAAGTTGCATCTGTTCCCAAAATCCTGTGACAAGACTCATA

CCTGTCCACCGTGTCCCGCCCCCGAACTCTTGGGCGGGCCTTCTGTGTTCCTCTTCCCA

CCCAAACCAAAAGACACACTGATGATCTCCAGGACCCCTGAAGTGACTTGCGTCGTGGT

TGACGTGTCTCATGAAGACCCCGAGGTGAAGTTCAACTGGTACGTCGATGGAGTGGAGG

TTCATAACGCCAAGACAAAACCAAGGGAGGAACAATACAACTCTACATACAGGGTGGTC

AGTGTGCTGACTGTGCTGCACCAGGACTGGCTCAACGGCAAAGAGTACAAATGCAAGGT

GTCTAACAAGGCACTTCCTGCTCCAATTGAAAAAACCATCTCCAAGGCTAAGGGGCAGC

CAAGGGAACCACAGGTGTATACTCTTCCTCCTTCTCGCGACGAACTGACTAAAAATCAG

GTGTCATTGACCTGTCTGGTGAAGGGCTTTTACCCCTCCGATATAGCTGTGGAGTGGGA

GAGCAACGGGCAGCCCGAGAACAATTATAAAACCACACCACCTGTCCTCGACAGTGATG

GATCATTTTTCCTCTACAGTAAGCTGACCGTGGATAAATCTAGGTGGCAGCAGGGGAAC

-continued

GTGTTTTCTTGCTCCGTGATGCACGAGGCCCTTCACAACCATTACACACAGAAGAGCCT

GAGCCTGTCCCCAGGAAAG*TGA**GAATTCGCGGCCGC*
(BamHI/HindIII linker sites are in italics; Kozak sequence in lower case; Start codon in bold; EcoRI/NotI linker sites are in italics; Stop Codon in bold italics).

In another embodiment, a HJV fusion protein useful in the methods and compositions as disclosed herein can correspond to a human HJV fusion protein which has been modified to more proteolytically stable and is a non-cleavable variant of HJV, and can be encoded by the polynucleotide sequence of SEQ ID NO: 9. The polynucleotide of SEQ ID NO:9 has a nucleotide differences to result in the encoded HJV protein to have a D172A variation which is non-cleavable. Accordingly, in one embodiment, a polynucleotide useful for encoding and producing a HJV fusion protein for use in the methods and compositions as disclosed herein comprises SEQ ID NO: 9 or analogues, variants or derivatives thereof, where SEQ ID NO:9 is as follows:

ATG TCT GCA CTT ctg atc cta gct ctt gtt gga gct gca gtt gct gac tac aaa gac cat gac ggt gat tat aaa gat cat gac atc gat tac aag gat gac gat gac aag ctt gcg gcc gcT CAT TCT CAA TGC AAG ATC CTC

CGC TGC AAT GCT GAG TAC GTA TCG TCC ACT CTG AGC CTT AGA GGT GGG

GGT TCA TCA GGA GCA CTT CGA GGA GGA GGA GGA GGA GGC CGG GGT GGA

GGG GTG GGC TCT GGC GGC CTC TGT CGA GCC CTC CGC TCC TAT GCG CTC

TGC ACT CGG CGC ACC GCC CGC ACC TGC CGC GGG GAC CTC GCC TTC CAT

TCG GCG GTA CAT GGC ATC GAA GAC CTG ATG ATC CAG CAC AAC TGC TCC

CGC CAG GGC CCT ACA GCC CCT CCC CCG CCC CGG GGC CCC GCC CTT CCA

GGC GCG GGC TCC GGC CTC CCT GCC CCG GAC CCT TGT GAC TAT GAA GGC

CGG TTT TCC CGG CTG CAT GGT CGT CCC CCG GGG TTC TTG CAT TGC GCT

TCC TTC GGG GCC CCC CAT GTG CGC AGC TTC CAC CAT CAC TTT CAC ACA

TGC CGT GTC CAA GGA GCT TGG CCT CTA CTG GAT AAT GAC TTC CTC TTT

GTC CAA GCC ACC AGC TCC CCC ATG GCG TTG GGG GCC AAC GCT ACC GCC

ACC CGG AAG CTC ACC ATC ATA TTT AAG AAC ATG CAG GAA TGC ATT GAT

CAG AAG GTG TAT CAG GCT GAG GTG GAT AAT CTT CCT GTA GCC TTT GAA

GAT GGT TCT ATC AAT GGA GGT GAC CGA CCT GGG GGA TCC AGT TTG TCG

ATT CAA ACT GCT AAC CCT GGG AAC CAT GTG GAG ATC CAA GCT GCC TAC

ATT GGC ACA ACT ATA ATC ATT CGG CAG ACA GCT GGG CAG CTC TCC TTC

TCC ATC AAG GTA GCA GAG GAT GTG GCC ATG GCC TTC TCA GCT GAA CAG

GAC CTG CAG CTC TGT GTT GGG GGG TGC CCT CCA AGT CAG CGA CTC TCT

CGA TCA GAG CGC AAT CGT CGG GGA GCT ATA ACC ATT GAT ACT GCC AGA

CGG CTG TGC AAG GAA GGG CTT CCA GTG GAA GAT GCT TAC TTC CAT TCC

TGT GTC TTT GAT GTT TTA ATT TCT GGT GAT CCC AAC TTT ACC GTG GCA

GCT CAG GCA GCA CTG GAG GAT GCC CGA GCC TTC CTG CCA GAC TTA GAG

AAG CTG CAT CTC TTC CCC TCA ctc gag ctg gtt ccg cgt ggt tcg GgG

GAT CCC ATC GAA GGT CGT GGT GGT GGT GGT GGT GAT CCC AAA TCT TGT

GAC AAA CCT CAC ACA TGC CCA CTG TGC CCA GCA CCT GAA CTC CTG GGG

GGA CCG TCA GTC TTC CTC TTC CCC CCA AAA CCC AAG GAC ACC CTC ATG

ATC TCC CGG ACC CCT GAG GTC ACA TGC GTG GTG GTG GAC GTG AGC CAC

GAA GAC CCT GAG GTC AAG TTC AAC TGG TAC GTG GAC GGC GTG GAG GTG

-continued

```
CAT AAT GCC AAG ACA AAG CCG CGG GAG GAG CAG TAC AAC AGC ACG TAC

CGT GTG GTC AGC GTC CTC ACC GTC CTG CAC CAG GAC TGG CTG AAT GGC

AAG GAG TAC AAG TGC AAG GTC TCC AAC AAA GCC CTC CCA GCC CCC ATC

GAG AAA ACC ATC TCC AAA GCC AAA GGG CAG CCC CGA GAA CCA CAG GTG

TAC ACC CTG CCC CCA TCC CGG GAT GAG CTG ACC AAG AAC CAG GTC AGC

CTG ACC TGC CTA GTC AAA GGC TTC TAT CCC AGC GAC ATC GCC GTG GAG

TGG GAG AGC AAT GGG CAG CCG GAG AAC AAC TAC AAG GCC ACG CCT CCC

GTG CTG GAC TCC GAC GGC TCC TTC TTC CTC TAC AGC AAG CTC ACC GTG

GAC AAG AGC AGG TGG CAG CAG GGG AAC GTC TTC TCA TGC TCC GTG ATG

CAT GAG GCT CTG CAC AAC CAC TAC ACG CAG AAG AGC CTC TCC CTG TCT

CCG GGT AAA TGA
```

(Kozak sequence are identified as being in lower case; Start codon in bold; Stop Codon in bold italics).

In another embodiment, a HJV fusion protein useful in the methods and compositions as disclosed herein can correspond to a human HJV fusion protein encoded by the polynucleotide sequence of SEQ ID NO: 8. Accordingly, in one embodiment, a polynucleotide useful for encoding and producing a HJV fusion protein for use in the methods and compositions as disclosed herein comprises SEQ ID NO: 8 or analogues, variants or derivatives thereof, where SEQ ID NO: 8 is as follows:

```
ATG TCT GCA CTT ctg atc cta gct ctt gtt gga gct gca gtt gct
gac tac aaa gac cat gac ggt gat tat aaa gat cat gac atc gat tac
aag gat gac gat gac aag ctt gcg gcc gcT CAT TCT CAA TGC AAG ATC
CTC CGC TGC AAT GCT GAG TAC GTA TCG TCC ACT CTG AGC CTT AGA GGT
GGG GGT TCA TCA GGA GCA CTT CGA GGA GGA GGA GGA GGA GGC CGG GGT
GGA GGG GTG GGC TCT GGC GGC CTC TGT CGA GCC CTC CGC TCC TAT GCG
CTC TGC ACT CGG CGC ACC GCC CGC ACC TGC CGC GGG GAC CTC GCC TTC
CAT TCG GCG GTA CAT GGC ATC GAA GAC CTG ATG ATC CAG CAC AAC TGC
TCC CGC CAG GGC CCT ACA GCC CCT CCC CCG CCC CGG GGC CCC GCC CTT
CCA GGC GCG GGC TCC GGC CTC CCT GCC CCG GAC CCT TGT GAC TAT GAA
GGC CGG TTT TCC CGG CTG CAT GGT CGT CCC CCG GGG TTC TTG CAT TGC
GCT TCC TTC GGG GAC CCC CAT GTG CGC AGC TTC CAC CAT CAC TTT CAC
ACA TGC CGT GTC CAA GGA GCT TGG CCT CTA CTG GAT AAT GAC TTC CTC
TTT GTC CAA GCC ACC AGC TCC CCC ATG GCG TTG GGG GCC AAC GCT ACC
GCC ACC CGG AAG CTC ACC ATC ATA TTT AAG AAC ATG CAG GAA TGC ATT
GAT CAG AAG GTG TAT CAG GCT GAG GTG GAT AAT CTT CCT GTA GCC TTT
GAA GAT GGT TCT ATC AAT GGA GGT GAC CGA CCT GGG GGA TCC AGT TTG
TCG ATT CAA ACT GCT AAC CCT GGG AAC CAT GTG GAG ATC CAA GCT GCC
TAC ATT GGC ACA ACT ATA ATC ATT CGG CAG ACA GCT GGG CAG CTC TCC
TTC TCC ATC AAG GTA GCA GAG GAT GTG GCC ATG GCC TTC TCA GCT GAA
CAG GAC CTG CAG CTC TGT GTT GGG GGG TGC CCT CCA AGT CAG CGA CTC
TCT CGA TCA GAG CGC AAT CGT CGG GGA GCT ATA ACC ATT GAT ACT GCC
AGA CGG CTG TGC AAG GAA GGG CTT CCA GTG GAA GAT GCT TAC TTC CAT
TCC TGT GTC TTT GAT GTT TTA ATT TCT GGT GAT CCC AAC TTT ACC GTG
GCA GCT CAG GCA GCA CTG GAG GAT GCC CGA GCC TTC CTG CCA GAC TTA
GAG AAG CTG CAT CTC TTC CCC TCA ctc gag ctg gtt ccg cgt ggt tcg
GgG GAT CCC ATC GAA GGT CGT GGT GGT GGT GGT GAT CCC AAA TCT
TGT GAC AAA CCT CAC ACA TGC CCA CTG TGC CCA GCA CCT GAA CTC CTG
GGG GGA CCG TCA GTC TTC CTC TTC CCC CCA AAA CCC AAG GAC ACC CTC
ATG ATC TCC CGG ACC CCT GAG GTC ACA TGC GTG GTG GTG GAC GTG AGC
CAC GAA GAC CCT GAG GTC AAG TTC AAC TGG TAC GTG GAC GGC GTG GAG
GTG CAT AAT GCC AAG ACA AAG CCG CGG GAG GAG CAG TAC AAC AGC ACG
TAC CGT GTG GTC AGC GTC CTC ACC GTC CTG CAC CAG GAC TGG CTG AAT
GGC AAG GAG TAC AAG TGC AAG GTC TCC AAC AAA GCC CTC CCA GCC CCC
ATC GAG AAA ACC ATC TCC AAA GCC AAA GGG CAG CCC CGA GAA CCA CAG
GTG TAC ACC CTG CCC CCA TCC CGG GAT GAG CTG ACC AAG AAC CAG GTC
AGC CTG ACC TGC CTA GTC AAA GGC TTC TAT CCC AGC GAC ATC GCC GTG
GAG TGG GAG AGC AAT GGG CAG CCG GAG AAC AAC TAC AAG GCC ACG CCT
CCC GTG CTG GAC TCC GAC GGC TCC TTC TTC CTC TAC AGC AAG CTC ACC
GTG GAC AAG AGC AGG TGG CAG CAG GGG AAC GTC TTC TCA TGC TCC GTG
ATG CAT GAG GCT CTG CAC AAC CAC TAC ACG CAG AAG AGC CTC TCC CTG
TCT CCG GGT AAA TGA
```

(Kozak sequence are identified as being in lower case; Start codon in bold; Stop Codon in bold italics).

The HJV protein may be fused to one or more fusion partners. In certain embodiments, one of the fusion partners is the Fc protein (e.g., mouse Fc or human Fc). The fusion protein may further include a second fusion partner such as a purification or detection tag, for example, proteins that may be detected directly or indirectly such as green fluorescent protein, hemagglutinin, or alkaline phosphatase), DNA binding domains (for example, GAL4 or LexA), gene activation domains (for example, GAL4 or VP16), purification tags, or secretion signal peptides (e.g., preprotyrypsin signal sequence). In other embodiments the fusion partner may be a tag, such as c-myc, poly histidine, or FLAG. Each fusion partner may contain one or more domains, e.g., a preprotrypsin signal sequence and FLAG tag.

In one embodiment, a HJV fusion protein useful in the methods and compositions as disclosed herein can comprise a human Fc protein or a functional fragment thereof. Accordingly, in one embodiment, a HJV fusion protein useful in the methods and compositions as disclosed herein can comprises a human Fc molecule as the first fusion partner, where the Fc fragment can be SEQ ID NO: 6 or functional variants or functional derivatives thereof, where SEQ ID NO: 6 is as follows:

by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art and are encompassed for use in the present invention.

According to the present invention, the HJV polypeptide (i.e. SEQ ID NO: 2-5 or fragments, derivatives or variants thereof), can be linked to the first fusion partner via any suitable means, as known in the art, see for example U.S. Pat. Nos. 4,625,014, 5,057,301 and 5,514,363, which are incorporated herein in their entirety by reference. For example, the HJV polypeptide can be covalently conjugated to the IgG1 Fc, either directly or through one or more linkers. In one embodiment, a HJV polypeptide as disclosed herein is conjugated directly to the first fusion partner (e.g. Fc), and in an alternative embodiment, a HJV polypeptide as disclosed

```
LELVPRGSGDPIEGRGGGGGDPKSCDKPHTCPLCPAPELLGGPSVFLFPPKPKDTLMISRTPEV

TCVVVDVSHEDPEVKFNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGFYPSDIAVEWESNGQP

ENNYKATPPVLDSDGSFFLYSKLTVDKSRWQQGNVFSCSVMHEALHNHYTQKSLSLSPGK
```

Variations and modifications to the HJV protein and vectors can be used to increase or decrease HJV fusion protein expression, and to provide means for targeting. For example, the HJV fusion protein can be linked with a molecular targeting molecule for muscle cells, to make these HJV fusion proteins tissue specific.

In one embodiment, the HJV fusion proteins is fused to a second fusion partner, such as a carrier molecule to enhance its bioavailability. Such carriers are known in the art and include poly (alkyl) glycol such as poly ethylene glycol (PEG). Fusion to serum albumin can also increase the serum half-life of therapeutic polypeptides.

The HJV fusion polypeptide can also be fused to a second fusion partner, for example, to a polypeptide that targets the product to a desired location, or, for example, a tag that facilitates its purification, if so desired. Tags and fusion partners can be designed to be cleavable, if so desired. Another modification specifically contemplated is attachment, e.g., covalent attachment, to a polymer. In one aspect, polymers such as polyethylene glycol (PEG) or methoxypolyethylene glycol (mPEG) can increase the in vivo half-life of proteins to which they are conjugated. Methods of PEGylation of polypeptide agents are well known to those skilled in the art, as are considerations of, for example, how large a PEG polymer to use.

As used herein, the term “conjugate” or “conjugation” refers to the attachment of two or more entities to form one entity. For example, the methods of the present invention provide conjugation of a HJV polypeptide (i.e. SEQ ID NO: 2-5 or fragments, derivatives or variants thereof) joined with another entity, for example a moiety such as a first fusion partner that makes the HJV stable, such as Ig carrier particle, for example IgG1 Fc. The attachment can be by means of linkers, chemical modification, peptide linkers, chemical linkers, covalent or non-covalent bonds, or protein fusion or herein can be conjugated to a first fusion partner (such as IgG1 Fc) via a linker, e.g. a transport enhancing linker.

A large variety of methods for conjugation of a HJV polypeptide as disclosed herein with a first fusion partner (e.g. Fc) are known in the art. Such methods are e.g. described by Hermanson (1996, Bioconjugate Techniques, Academic Press), in U.S. Pat. No. 6,180,084 and U.S. Pat. No. 6,264,914 which are incorporated herein in their entirety by reference and include e.g. methods used to link haptens to carriers proteins as routinely used in applied immunology (see Harlow and Lane, 1988, “Antibodies: A laboratory manual”, Cold Spring Harbor Laboratory Press, Cold Spring Harbor, N.Y.). It is recognized that, in some cases, a HJV polypeptide can lose efficacy or functionality upon conjugation depending, e.g., on the conjugation procedure or the chemical group utilized therein. However, given the large variety of methods for conjugation the skilled person is able to find a conjugation method that does not or least affects the efficacy or functionality of the entities, such as the HJV polypeptide to be conjugated.

Suitable methods for conjugation of a HJV polypeptide as disclosed herein with a first fusion partner (e.g. Fc) include e.g. carbodimide conjugation (Bauminger and Wilchek, 1980, Meth. Enzymol. 70: 151-159). Alternatively, a moiety can be coupled to a targeting agent as described by Nagy et al., Proc. Natl. Acad. Sci. USA 93:7269-7273 (1996), and Nagy et al., Proc. Natl. Acad. Sci. USA 95:1794-1799 (1998), each of which are incorporated herein by reference. Another method for conjugating one can use is, for example sodium periodate oxidation followed by reductive alkylation of appropriate reactants and glutaraldehyde crosslinking.

One can use a variety of different linkers to conjugate a HJV polypeptide as disclosed herein with a first fusion partner (e.g. Fc), for example but not limited to aminocaproic horse radish peroxidase (HRP) or a heterobiofunctional cross-linker, e.g. carbonyl reactive and sulfhydryl-reactive cross-linker. Heterobiofunctional cross linking reagents usually contain two reactive groups that can be coupled to two different function targets on proteins and other macromolecules in a two or three-step process, which can limit the degree of polymerization often associated with using homobiofunctional cross-linkers. Such multi-step protocols can offer a great control of conjugate size and the molar ratio of components.

The term "linker" refers to any means to join two or more entities, for example a HJV polypeptide as disclosed herein with a first fusion partner (e.g. Fc). A linker can be a covalent linker or a non-covalent linker. Examples of covalent linkers include covalent bonds or a linker moiety covalently attached to one or more of the proteins to be linked. The linker can also be a non-covalent bond, e.g. an organometallic bond through a metal center such as platinum atom. For covalent linkages, various functionalities can be used, such as amide groups, including carbonic acid derivatives, ethers, esters, including organic and inorganic esters, amino, urethane, urea and the like. To provide for linking, the effector molecule and/or the probe can be modified by oxidation, hydroxylation, substitution, reduction etc. to provide a site for coupling. It will be appreciated that modification which do not significantly decrease the function of the HJV polypeptide as disclosed herein or the first fusion partner (e.g. Fc) are preferred.

IV. Polypeptide Expression

In general, HJV fusion proteins may be produced by transformation of a suitable host cell with all or part of a polypeptide-encoding polynucleotide molecule or fragment thereof in a suitable expression vehicle.

Those skilled in the field of molecular biology will understand that any of a wide variety of expression systems may be used to provide the recombinant polypeptide. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS or CHO cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (Pouwels, P. H. et al., 1985, Supp. 1987).

One particular bacterial expression system for polypeptide production is the *E. coli* pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains which express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system which is designed for high-level expression of genes or gene fragments as fusion proteins with rapid purification and recovery of functional gene products. The polypeptide of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, polypeptides expressed in pGEX-2T plasmids may be cleaved with thrombin; those expressed in pGEX-3X may be cleaved with factor Xa.

Commercial scale production of proteins using mammalian cells, such as CHO cells, is desirable in certain embodiments (see, e.g., Wurm, Nat. Biotechnol. 22:1393-1398, 2004). Techniques for optimizing expression in mammalian cells, such as introducing an intron into the cDNA sequence (e.g., between the promoter and the coding sequence), linearization of the plasmid DNA prior to transfection, and use of flank sequences to direct the integration of the construct into a region of the genome that will provide higher expression may be employed. In addition, the choice of media can be critical as well.

Wurm (supra) describes formats used for commercial scale mammalian cell culture as follows.

Adherent Cell Culture.

CHO cells are seeded into roller bottles that are filled to 10-30% of capacity with medium and slowly rotated, allowing cells to adhere. The rotation assures a regular wetting of the cells and oxygen is supplied by the ample 'head space' in the bottle. After a period of growth and maintenance of the culture at confluency for a few days, the product is harvested from the decanted supernatant. The process can be scaled-up easily because the number of roller bottles handled in parallel determines scale. Product concentrations in the 50-200 mg/l range are possible, providing protein in the kilogram range annually.

Adherent cells have also been cultivated on polymer spheres termed microcarriers that are maintained in suspension in stirred-tank bioreactors. They allow for easy scale-up in bioreactors. CHO cells on microcarriers are being used for the production of follicle stimulating hormone and of virus-vaccines.

Suspension Culture.

CHO cells now dominate the domain of mass production of recombinant protein products because of their capacity for single-cell suspension growth. Other cell lines grown well in suspension are mouse myeloma-derived N50 cells, BHK, HEK-293 and human retina-derived PER-C6 cells. With the exception of blood-derived cells (NS0), most established cell lines maintain their anchorage-dependent character unless special efforts are undertaken to adapt them to suspension growth. Commercially available media formulations allow for suspension growth. It may requires screening several media formulations that support the suspension growth.

In a 'simple' batch or extended batch production process, the scale-up to very large volumes can occur by the dilution of the content of a bioreactor into 5-20 volumes of fresh medium held prewarmed in a larger reactor. The entire process from the thawing of banked cells to the production vessel consists of three separate phases-seed train, inoculum train and production phase. The seed train is usually performed at a small scale to provide fresh cells for scale-up during the period chosen for the production. The inoculum train starts with a small volume of cell suspension from the seed train and its volume is expanded so that a sufficient cell number will be generated for the final production phase. Process conditions optimized for a given cell line can rarely be considered generic, because mammalian cell lines have a highly individual character highlighted by different glucose consumption rates, lactate production rates and sensitivity towards stress signals.

Although the timing of the termination (that is, harvest) of a culture is driven mainly by plant capacity and productivity kinetics, another important factor is the quality of the derived product. The continuously changing composition of the culture medium during the production phase can affect the quality of earlier synthesized product through degradative activities mediated by cell-released enzymes. Also, a diminishing supply of nutrients as energy providers or as building blocks for the synthesized product can change its molecular composition. Reproducible processes will, however, produce populations of protein molecules within a definable range of molecular variation.

Most high-yielding processes today are extended batch cultures whereby medium components are added in small batches or semi-continuously. The development of these extended batch processes requires a good understanding of the cell line and the product, and is usually only applied to processes that supply material for phase 3 clinical trials and for the market.

An entirely different philosophy for manufacturing is represented by continuously perfused production processes. Perfused cultures can achieve even higher cell densities than batch or extended batch cultures and can be maintained for many weeks and months, with product harvests occurring repeatedly throughout that period. Several reactor volumes of fresh medium can be fed into the culture per day, while the same volume is being withdrawn from the reactor. The anti-hemophilic factor VIII (Kogenate, Bayer, Berkeley, Calif., USA), of which the market requires about 150 g per year, is reliably being manufactured using perfusion technology with suspension-cultivated BHK cells. Factor VIII maybe the largest protein (2,332 amino acids) ever produced in bioreactors. It is harvested continuously from ongoing perfusion cultures. This very sophisticated, highly controlled process runs for up to 6 months and assures that the fragile protein is of reproducibly high quality.

Once the recombinant polypeptide of the invention is expressed, it is isolated, e.g., using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra).

Once isolated, the recombinant polypeptide can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short peptide fragments, can also be produced by chemical synthesis (e.g., by the methods described in *Solid Phase Peptide Synthesis,* 2nd ed., 1984 The Pierce Chemical Co., Rockford, Ill.).

These general techniques of polypeptide expression and purification can also be used to produce and isolate useful peptide fragments or analogs (described herein). In certain embodiments, a combination of techniques may be used to generate the fusion protein. For example, HJV and its first fusion partner may be produced recombinantly and purified, or may be purified from a natural source, and then chemically coupled together to form the fusion protein.

V. Treatment Methods of the Invention

One aspect of the present invention relates to the use of an HJV fusion protein or polynucleotide encoding an HJV fusion protein to be administered to a mammal (e.g., a human) for the treatment of a subject suffering from any HJV, hepcidin, or BMP-related disorder (e.g., anemia of inflammatory states).

Examples of these disorders include, but are not limited to, iron-related disorders such as hemochromatosis, ferroportin mutation hemochromatosis, transferrin receptor 2 mutation hemochromatosis, juvenile hemochromatosis, neonatal hemochromatosis, hepcidin deficiency, transfusional iron overload, thalassemia, thalassemia intermedia, alpha thalassemia, sideroblastic anemia, porphyria, porphyria cutanea tarda, African iron overload, hyperferritinemia, ceruloplasmin deficiency, atransferrinemia, congenital dyserythropoietic anemia, anemia of chronic disease, anemia, hypochromic microcytic anemia, iron-deficiency anemia, conditions with hepcidin excess, Friedreich ataxia, gracile syndrome, Hallervorden-Spatz disease, Wilson's disease, pulmonary hemosiderosis, hepatocellular carcinoma, cancer, hepatitis, cirrhosis of liver, pica, chronic renal failure, anemia of end-stage renal disease, insulin resistance, diabetes, atherosclerosis, neurodegenerative disorders, multiple sclerosis, Parkinson's disease, Huntington's disease, Alzheimer's disease, restless leg syndrome, rheumatoid arthritis, and macular degeneration.

Accordingly, one aspect of the present invention relates to the treatment or prevention of a HJV-related disorder (e.g. iron-related disorder), or a hepcidin related disorder, or BMP-related disorder (e.g., anemia of inflammatory states) by administering an effective amount of a soluble form of HJV protein, such as a HJV fusion protein (e.g. HJV.Fc) as disclosed herein, or the nucleic acid sequence encoding such HJV fusion protein to a subject to decrease at least one symptom of the HJV, hepcidin, or BMP-related disorder (e.g., anemia of inflammatory states).

Increasing soluble HJV in a subject, such as administering a soluble HJV polypeptide such as a HJV fusion protein as disclosed herein, or administering a nucleic acid construct encoding such HJV fusion protein, in a subject in need thereof is expected to treat or otherwise ameliorate the symptoms of conditions and physical dysfunctions described herein (e.g., those arising from an HJV-related disorder such as an iron-related disorder in the subject). As used herein, the term "treatment" refers to treating a condition that has already manifested in the subject. Treatment is performed generally on a subject who is suffering from a condition or physical dysfunction. Such subjects are said to be in need of treatment. Manifestation of a condition would be by the appearance of one or more symptoms of the condition. Many such conditions and symptoms of an HJV-related disorder, such as an iron-related disorder are described herein. Treatment is also used to refer to a slowing of onset and/or severity of additional symptoms wherein the subject already has one or more symptoms. The skilled artisan will realize that complete cure is not necessary to qualify as treatment. As such, subjects suitable for treatment include those who exhibit one or more symptoms of a condition and are at risk for developing additional symptoms of a condition. Such subjects also include those with one or more symptoms of a condition, but who have not been diagnosed with the condition by a qualified medical professional.

In one embodiment, the methods of treatment described herein, further comprise selection of such a subject suffering from a condition (e.g., one arising from iron deprivation or condition associated with a HJV disorder or disease), or physical dysfunction as described herein, prior to administering a soluble HJV protein, such as a HJV fusion polypeptide as disclosed herein, to thereby treat the condition or dysfunction. Such selection is performed by the skilled practitioner by a number of available methods. For instance, assessment of symptoms which are described herein.

Successful treatment is evidenced by amelioration of one or more symptoms of the condition or dysfunction as discussed herein.

Increasing soluble HJV in a subject, such as administering a soluble HJV polypeptide such as a HJV fusion protein as disclosed herein, or administering a nucleic acid construct encoding such HJV fusion protein, in a subject in need thereof is expected to prevent or retard the development of the conditions and physical dysfunctions described herein (e.g., those arising from iron deprivation in the subject). The term "prevention" is used to refer to a situation wherein a subject does not yet have the specific condition being prevented, meaning that it has not manifested in any appreciable form. Prevention encompasses prevention or slowing of onset and/or severity of a symptom, (including where the subject already has one or more symptoms of another condition). Prevention is performed generally in a subject who is at risk for development of a condition or physical dysfunction. Such subjects are said to be in need of prevention.

In one embodiment, the methods of prevention described herein, further comprise selection of such a subject at risk for a condition (e.g., one arising from iron deprivation or a condition associated with a HJV-related disorder or disease), or physical dysfunction as described herein, prior to administering a soluble HJV polypeptide such as a HJV fusion protein as disclosed herein, in the subject, to thereby prevent the condition or dysfunction. Such selection is performed by the skilled practitioner by a number of available methods. For instance, assessment of risk factors or diagnosis of a disease which is known to cause the condition or dysfunction, or treatment or therapy known to cause the condition or dysfunction. Subjects which have a disease or injury or a relevant family history which is known to contribute to the condition are generally considered to be at increased risk. For example, subjects which a disease causing mutation in HJV sequence (Lanzara et al, 2004, Blood 103, 4317-4317 and Papanikolaou et al, 2004, Nat Genetics, 36; 77-81) or a G320V mutation in HJV (Zhang et al, 2005; JBC, 280; 33885-33894), or subjects with mutations in HFE, Tfr2 (encoding transferrin receptor 2), SLC401A (encoding ferroportin), HAMP (encoding hepcidin), which are well known in the art and disclosed in Yang et al, Biochem, 2008, 47; 4237-4245, which is incorporated herein by reference.

In one embodiment of the invention, the subject is also undergoing another therapy. Such therapies include, without limitation, other therapies to treat or prevent the condition arising from iron deprivation. Such therapies are commonly known by persons of ordinary skill in the art, and include but are not limited to iron supplements, vitamin B-12, folic acid and erythropoietin.

As used herein, the terms "treat" or "treatment" or "treating" refers to both therapeutic treatment and prophylactic (i.e. preventative) measures, wherein the object is to prevent or slow the development of the disease, such as slow down the development of a tumor, the spread of cancer, or reducing at least one effect or symptom of a condition, disease or disorder associated with inappropriate proliferation or a cell mass, for example cancer. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with cancer, as well as those likely to develop secondary tumors due to metastasis.

The term "effective amount" as used herein refers to the amount of a pharmaceutical composition comprising a soluble HJV protein, such as a HJV fusion protein as disclosed herein, to decrease at least one or more symptom of the disease or disorder, and relates to a sufficient amount of pharmacological composition to provide the desired effect. The phrase "therapeutically effective amount" as used herein, e.g., soluble HJV protein, such as a HJV fusion protein as disclosed herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically or prophylatically significant reduction in a symptom or clinical marker associated with decreased iron levels when administered to a typical subject who has anemia, anemia of inflammation or hypoferremia.

A therapeutically or prophylatically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated.

With reference to the treatment of a subject with anemia, the term "therapeutically effective amount" refers to the amount that is safe and sufficient to prevent or delay the development and further decrease in serum iron concentrations, or decrease in transferrin saturation in anemic patients. The amount can thus cure or cause a decrease in at least one anemic symptom, or cause the anemia to go into remission, slow the course of anemia progression. The effective amount for the treatment of anemia depends on the type of anemia and other diseases or disorders causing the anemia as a secondary disease (i.e. vitamin D12 deficiency, sickle cell anemia), the species being treated, the age and general condition of the subject, the mode of administration and so forth. Thus, it is not possible to specify the exact "effective amount". However, for any given case, an appropriate "effective amount" can be determined by one of ordinary skill in the art using only routine experimentation. The efficacy of treatment can be judged by an ordinarily skilled practitioner, for example, efficacy can be assessed in animal models of anemia, for example treatment an as disclosed herein in the Examples, administration to a rodent with low serum iron, and any treatment or administration of the compositions or formulations that leads to an increase in serum iron and/or increase in transferrin saturation (for example by the methods as disclosed herein), and/or a decrease of at least one symptom of associated with anemia, for example easy fatigue and loss of energy; rapid heart beat, particularly with exercise; shortness of breath and headache, particularly with exercise; difficulty concentrating; dizziness; pale skin; leg cramps; pica (hunger for strange substances such as paper, ice, or dirt); koilonychias (upward curvature of the nails); soreness of the mouth with cracks at the corners, etc. indicates effective treatment. Other symptoms of anemia can include; Black and tarry stools; Maroon or visibly bloody stools; rapid heart rate; rapid breathing; cold skin; jaundice; low blood pressure; heart murmur and enlargement of the spleen. In embodiments where the compositions are used for the treatment of anemia, the efficacy of the composition can be judged using an experimental animal model of anemia, e.g., wild-type mice or rats that have anemia and/or iron deficiency, or as disclosed herein, 129S6/SvEvTac mice (Taconic) mice fed 380 parts per million iron; Fanconi Anemia Group C mouse model (Fac−/−); administration of IgM and IgA anti-erythrocyte auto-antibodies to mice (Baudino et al., Blood, 2007, 109; 5355-5362), or $HJV^{-/-}$ mice (Huang et al, 2005, J Clin Invest, 115, 2187-2119 (which is incorporated herein in its entirety by reference). When using an experimental animal model, efficacy of treatment is evidenced when a reduction in a symptom of the anemia, for example an increase in the level of serum iron and/or increase in transferrin saturation, increase of iron release from reticuloendothelial stores, and/or an increase in ferroportin expression, and/or increase in hepatic tissue iron which occurs earlier in treated, versus untreated animals. By "earlier" is meant that an increase, for example in the serum iron concentration occurs at least 5% earlier, but preferably more, e.g., one day earlier, two days earlier, 3 days earlier, or more.

As used herein, the term "treating" when used in reference to anemia is used to refer to the reduction of a symptom and/or a biochemical marker of anemia, for example a reduction in at least one biochemical marker of anemia by at least about 10% would be considered an effective treatment. Examples of such biochemical markers of anemia include, but are not limited to, hematological markers (hemoglobin (HGB), mean corpuscular volume (MCV), mean corpuscular hemoglobin (MCH), red cell distribution width (RDW)) and biochemical markers (serum ferritin (SF), serum iron (SI), transferrin saturation (TS), total iron-binding capacity (TIBC) and reticulocyte hemoglobin content (CHr). As alternative examples, blood test for anemia may show a normal or low hemoglobin, decreased iron, ferritin, and all red blood cell indices. Thus, an increase in hemoglobin or iron or ferritin, or increase in number of red blood cells by at least about 10% would also be considered as affective treatments by the methods as disclosed herein. One can measure blood hematocrit (the % of blood volume made up by red blood cells and hemoglobin). Normal levels of hemoglobin range between 11.1 and 15.0 grams per deciliter (g/dL). A lower than normal hemoglobin level indicates anemia. For example, a women that has a level equal to, or less than 10 g/dL is considered to be anemic, and a male that has a level equal to, or less than 12 g/dL is considered to be anemic. Alternatively, the total iron-binding capacity (TIBC) or transferrin will be increased in anemic subjects, so a decrease in the total iron-binding capacity (TIBC) or transferrin by at least about 10% would also be considered as affective treatments by the methods as disclosed herein. In some embodiments, it is preferred, but not required that the therapeutic agent actually eliminate the tumor.

As used herein, the terms "administering," and "introducing" are used interchangeably herein and refer to the placement of the therapeutic agents such as the soluble HJV protein, such as HJV.Fc fusion protein as disclosed herein into a subject by a method or route which results in delivering of such agent(s) at a desired site. The compounds can be administered by any appropriate route which results in an effective treatment in the subject.

The HJV fusion protein or polynucleotide may be administered by any route known in the art or described herein, for example, oral, parenteral (e.g., intravenously or intramuscularly), intraperitoneal, rectal, cutaneous, nasal, vaginal, inhalant, skin (patch), or ocular. The HJV fusion protein may be administered in any dose or dosing regimen.

IV. Dosage

With respect to the therapeutic methods of the invention, it is not intended that the administration of the HJV fusion protein or polynucleotide encoding such a protein be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to treat the BMP, hepcidin, or HJV-related disorder. The therapeutic may be administered to the patient in a single dose or in multiple doses. When multiple doses are administered, the doses may be separated from one another by, for example, one hour, three hours, six hours, eight hours, one day, two days, one week, two weeks, or one month. For example, the therapeutic may be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

While the attending physician ultimately will decide the appropriate amount and dosage regimen, therapeutically effective amounts of the HJV fusion protein may provided at a dose of 0.0001, 0.01, 0.01 0.1, 1, 5, 10, 25, 50, 100, 500, or 1,000 mg/kg. Effective doses may be extrapolated from dose-response curves derived from in vitro or animal model test bioassays or systems.

Dosages for a particular patient or subject can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the soluble HJV protein, such as HJV fusion protein as disclosed herein, or functional derivatives thereof, and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising soluble HJV proteins, such as HJV fusion proteins or functional derivatives thereof are optionally tested in one or more appropriate in vitro and/or in vivo animal models of disease, such as models of anemia or anemia of chronic disease (ACD), to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of a soluble HJV protein, such as HJV fusion protein or functional derivatives thereof at various concentrations, e.g., as applied to the mass and overall health of the patient. Administration can be accomplished via single or divided doses.

In determining the effective amount of a soluble HJV protein, such as HJV fusion protein or functional derivatives thereof to be administered in the treatment or prophylaxis of disease the physician evaluates circulating plasma levels, formulation toxicities, and progression of the disease.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the subject.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

VII. Formulation of Pharmaceutical Compositions

The administration of an HJV fusion protein may be by any suitable means that results in a concentration of the protein that treats the disorder. The compound may be contained in any appropriate amount in any suitable carrier substance, and is generally present in an amount of 1-95% by weight of the total weight of the composition. The composition may be provided in a dosage form that is suitable for the oral, parenteral (e.g., intravenously or intramuscularly), intraperitoneal, rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

Pharmaceutical compositions according to the invention may be formulated to release the active compound immediately upon administration or at any predetermined time or time period after administration. The latter types of compositions are generally known as controlled release formulations, which include (i) formulations that create substantially constant concentrations of the agent(s) of the invention within the body over an extended period of time; (ii) formulations that after a predetermined lag time create substantially constant concentrations of the agent(s) of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the therapeutic to a particular target cell type. Administration of the protein in the form of a controlled release formulation is especially preferred for compounds having a narrow absorption window in the gastrointestinal tract or a relatively short biological half-life.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the protein is formulated with appropriate excipients into a pharmaceutical composition that, upon administration, releases the protein in a controlled manner. Examples include single or multiple unit tablet or capsule compositions, oil solutions, suspensions, emulsions, microcapsules, molecular complexes, microspheres, nanoparticles, patches, and liposomes. As used herein, the terms "administering," and "introducing" are used interchangeably herein and refer to the placement of the therapeutic agents as disclosed herein into a subject by a method or route which results in delivering of such agent(s) at a desired site. The compounds can be administered by any appropriate route which results in an effective treatment in the subject.

As used herein, the phrases "parenteral administration" and "administered parenterally" as used herein mean modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration therapeutic compositions other than directly into a tumor such that it enters the animal's system and, thus, is subject to metabolism and other like processes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent or encapsulating material, involved in maintaining the activity of or carrying or transporting the subject agents from one organ, or portion of the body, to another organ, or portion of the body. In addition to being "pharmaceutically acceptable" as that term is defined herein, each carrier must also be "acceptable" in the sense of being compatible with the other ingredients of the formulation. The pharmaceutical formulation comprising the soluble HJV proteins, such as HJV fusion proteins as disclosed herein in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, targeted delivery composition of the invention is formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the invention in combination with one or more pharmaceutically acceptable ingredients. The carrier can be in the form of a solid, semi-solid or liquid diluent, cream or a capsule.

The term "pharmaceutically acceptable carriers" is intended to include all solvents, diluents, or other liquid vehicle, dispersion or suspension aids, surface active agents, isotonic agents, thickening or emulsifying agents, preservatives, solid binders, lubricants and the like, as suited to the particular dosage form desired. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its functional derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The terms "composition" or "pharmaceutical composition" used interchangeably herein refer to compositions or formulations that usually comprise an excipient, such as a pharmaceutically acceptable carrier that is conventional in the art and that is suitable for administration to mammals, and preferably humans or human cells. Such compositions can be specifically formulated for administration via one or more of a number of routes, including but not limited to, oral, ocular parenteral, intravenous, intraarterial, subcutaneous, intranasal, sublingual, intraspinal, intracerebroventricular, and the like. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, *University of the Sciences in Philadelphia* (2005) *Remington: The Science and Practice of Pharmacy with Facts and Comparisons,* 21st Ed. In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylanunonium, tetraethyl ammonium, methyl amine, dimethyl amine, trimethylamine, triethylamine, ethylamine, and the like (see, e.g., Berge S. M., et al. (1977) J. Pharm. Sci. 66, 1, which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs are salts or prodrugs that are, within the scope of sound medical judgment, suitable for use in contact with the tissues of subject without undue toxicity, irritation, allergic response, and the like, commensurate with a reasonable benefit/risk ratio, and effective for their intended use.

The term "prodrug" refers to compounds that are rapidly transformed in vivo to yield the functionally active soluble HJV proteins, such as HJV fusion molecules of the present invention, for example the HJV fusion protein of the invention could be hydrolyzed by the blood to render a fully functional soluble form of HJV protein. A thorough discussion is provided in T. Higachi and V. Stella, "Pro-drugs as Novel Delivery Systems," Vol. 14 of the A.C.S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. A prodrug of the soluble HJV can be designed to alter the metabolic stability or the transport characteristics of a soluble HJV protein, to mask side effects or toxicity, to improve the flavor of a compound or to alter other characteristics or properties of a compound. By virtue of knowledge of pharmacodynamic processes and drug metabolism in vivo, once a pharmaceutically active form of the HJV protein, such as derivatives and variants thereof, those of skill in the pharmaceutical art generally can design prodrugs of the compound (see, e.g., Nogrady (1985) Medicinal Chemistry A Biochemical Approach, Oxford University Press, N.Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

a. Parenteral Compositions

The pharmaceutical composition may be administered parenterally by injection, infusion, or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active agent(s), the composition may include suitable parenterally acceptable carriers and/or excipients. The active agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions according to the invention may be in a form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

Pharmaceutical compositions of this invention suitable for parenteral administration comprise one or more soluble HJV proteins, such as HJV fusion proteins as disclosed herein in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions comprising soluble HJV protein, such as HJV fusion protein as disclosed herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug, such as soluble HJV protein, such as HJV fusion protein as disclosed herein in liposomes or microemulsions which are compatible with body tissue.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

b. Controlled Release Parenteral Compositions

Controlled release parenteral compositions may be in form of aqueous suspensions, microspheres, microcapsules, magnetic microspheres, oil solutions, oil suspensions, or emulsions. The composition may also be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine), poly(lactic acid), polyglycolic acid, and mixtures thereof. Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters)) or combinations thereof.

c. Solid Dosage Forms for Oral Use

Formulations for oral use include tablets containing the active ingredient(s) in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, 6,372,218, hereby incorporated by reference). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the protein in a predetermined pattern (e.g., in order to achieve a controlled release formulation) or it may be adapted not to release the agent(s) until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate, may be employed.

The solid tablet compositions may include a coating adapted to protect the composition from unwanted chemical changes, (e.g., chemical degradation prior to the release of the active substances). The coating may be applied on the solid dosage form in a similar manner as that described in Encyclopedia of Pharmaceutical Technology, supra.

The compositions of the invention may be mixed together in the tablet, or may be partitioned. In one example, a first agent is contained on the inside of the tablet, and a second agent is on the outside, such that a substantial portion of the second agent is released prior to the release of the first agent.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate, or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus, or spray drying equipment.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients. In one aspect, a solution of resolvin and/or protectin or precursor or analog thereof can be administered as eye drops for ocular neovascularization or ear drops to treat otitis.

Liquid dosage forms for oral administration of the compounds of the invention include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration of the soluble HJV protein, such as HJV fusion protein as disclosed herein include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the compounds (resolvins and/or protectins and/or precursors or analogues thereof) of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel. In another aspect, biodegradable or absorbable polymers can provide extended, often localized, release of polypeptide agents. The potential benefits of an increased half-life or extended release for a therapeutic agent are clear. A potential benefit of localized release is the ability to achieve much higher localized dosages or concentrations, for greater lengths of time, relative to broader systemic administration, with the potential to also avoid possible undesirable side effects that may occur with systemic administration.

Bioabsorbable polymeric matrix suitable for delivery of the soluble HJV polypeptide, such as HJV fusion polypeptides as disclosed herein can be selected from a variety of synthetic bioabsorbable polymers, which are described extensively in the literature. Such synthetic bioabsorbable, biocompatible polymers, which may release proteins over several weeks or months can include, for example, poly-α-hydroxy acids (e.g. polylactides, polyglycolides and their copolymers), polyanhydrides, polyorthoesters, segmented block copolymers of polyethylene glycol and polybutylene terephtalate (Polyactive™), tyrosine derivative polymers or poly(ester-amides). Suitable bioabsorbable polymers to be used in manufacturing of drug delivery materials and implants are discussed e.g. in U.S. Pat. Nos. 4,968,317, 5,618, 563, among others, and in "Biomedical Polymers" edited by S. W. Shalaby, Carl Hanser Verlag, Munich, Vienna, New York, 1994 and in many references cited in the above publications. The particular bioabsorbable polymer that should be selected will depend upon the particular patient that is being treated.

VII. Gene Therapy

An HJV fusion protein can be effectively used in treatment by gene therapy. See, generally, for example, U.S. Pat. No. 5,399,346, which is incorporated herein by reference. The general principle is to introduce the polynucleotide into a target cell in a patient, and allow it to supplement the activity of the endogenous HJV protein.

Entry into the cell is facilitated by suitable techniques known in the art such as providing the polynucleotide in the form of a suitable vector, or encapsulation of the polynucleotide in a liposome.

A desired mode of gene therapy is to provide the polynucleotide in such a way that it will replicate inside the cell, enhancing and prolonging the desired effect. Thus, the polynucleotide is operably linked to a suitable promoter, such as the natural promoter of the corresponding gene, a heterologous promoter that is intrinsically active in liver, neuronal, bone, muscle, skin, joint, or cartilage cells, or a heterologous promoter that can be induced by a suitable agent.

Expression vectors compatible with eukaryotic cells, preferably those compatible with vertebrate cells, can be used to produce recombinant constructs for the expression of soluble HJV proteins such as HJV fusion proteins as disclosed herein, including fusion proteins with fragments or derivatives or variants of HJV thereof as described herein. Eukaryotic cell expression vectors are well known in the art and are available from several commercial sources. Typically, such vectors are provided containing convenient restriction sites for insertion of the desired DNA segment. These vectors can be viral vectors such as adenovirus, adeno-associated virus, pox virus such as an orthopox (vaccinia and attenuated vaccinia), avipox, lentivirus, murine moloney leukemia virus, etc. Alternatively, plasmid expression vectors can be used.

Viral vector systems which can be utilized in the present invention include, but are not limited to, (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. In a preferred embodiment, the vector is an adenovirus. Replication-defective viruses can also be advantageous.

The vector may or may not be incorporated into the cells genome. The constructs may include viral sequences for transfection, if desired. Alternatively, the construct may be incorporated into vectors capable of episomal replication, e.g EPV and EBV vectors.

Constructs for the recombinant expression of soluble HJV proteins such as HJV fusion proteins as disclosed herein (including fusion proteins with fragments or derivatives or variants of HJV thereof) will generally require regulatory elements, e.g., promoters, enhancers, etc., to ensure the expression of the construct in target cells. Other specifics for vectors and constructs are described in further detail below.

By "operably linked" is meant that a nucleic acid molecule and one or more regulatory sequences (e.g., a promoter) are connected in such a way as to permit expression and/or secretion of the product (e.g., a protein) of the nucleic acid molecule when the appropriate molecules (e.g., transcriptional activator proteins) are bound to the regulatory sequences. Stated another way, the term "operatively linked" as used herein refers to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined. An operatively linked polynucleotide which is to be expressed typically includes an appropriate start signal (e.g., ATG) and maintains the correct reading frame to permit expression of the polynucleotide sequence under the control of the expression control sequence, and production of the desired polypeptide encoded by the polynucleotide sequence.

As used herein, the terms "promoter" or "promoter region" or "promoter element" have been defined herein, refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated.

The term "regulatory sequences" is used interchangeably with "regulatory elements" herein refers element to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, inducible promoters and transcriptional elements, an optional operate sequence to control transcription, a sequence encoding suitable mRNA ribosomal binding sites, and sequences to control the termination of transcription and/or translation. Included in the term "regulatory elements" are nucleic acid sequences such as initiation signals, enhancers, and promoters, which induce or control transcription of protein coding sequences with which they are operatively linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc.

Regulatory sequences useful in the methods as disclosed herein are promoter elements which are sufficient to render promoter-dependent gene expression controllable for cell type-specific, tissue-specific or inducible by external signals or agents (e.g. enhancers or repressors); such elements may be located in the 5' or 3' regions of the native gene, or within an intron.

As used herein, the term "tissue-specific promoter" means a nucleic acid sequence that serves as a promoter, i.e., regulates expression of a selected nucleic acid sequence operably linked to the promoter, and which selectively affects expression of the selected nucleic acid sequence in specific cells of a tissue, such as cells of neural origin, e.g. neuronal cells.

In some embodiments, it can be advantageous to direct expression of a soluble HJV proteins such as HJV fusion proteins as disclosed herein (including fusion proteins with fragments or derivatives or variants of HJV thereof as described herein) in a tissue- or cell-specific manner. Muscle-specific expression can be achieved, for example, using the skeletal muscle MKC promoter (as disclosed in U.S. Patent Application WO2007/100722, which is incorporated herein by reference), or other muscle-specific promoters, such as α-myosin heavy chain, myosin light chain-2 (which is specific for skeletal muscle (Shani et al., Nature, 314; 283-86, 1985), gonadotrophic releasing hormone gene control region which is active in the hypothalamus (Mason et al, Science, 234; 1372-78, 1986), and smooth muscle promoter SM22a, which are all commonly known in the art.

The term "constitutively active promoter" refers to a promoter of a gene which is expressed at all times within a given cell. Exemplary promoters for use in mammalian cells include cytomegalovirus (CMV), and for use in prokaryotic cells include the bacteriophage T7 and T3 promoters, and the like. The term "inducible promoter" refers to a promoter of a gene which can be expressed in response to a given signal, for example addition or reduction of an agent. Non-limiting examples of an inducible promoter are "tet-on" and "tet-off" promoters, or promoters that are regulated in a specific tissue type.

In a specific embodiment, viral vectors that contain nucleic acid sequences encoding the soluble HJV proteins, such as HJV fusion proteins as disclosed herein (including fusion proteins with fragments or derivatives or variants of HJV thereof as described herein) are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding a human HJV fusion polypeptide are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

The production of a recombinant retroviral vector carrying a gene of interest is typically achieved in two stages. First, sequence encoding a human HJV fusion polypeptide can be inserted into a retroviral vector which contains the sequences necessary for the efficient expression of the metabolic regulators (including promoter and/or enhancer elements which can be provided by the viral long terminal repeats (LTRs) or by an internal promoter/enhancer and relevant splicing signals), sequences required for the efficient packaging of the viral RNA into infectious virions (e.g., a packaging signal (Psi), a tRNA primer binding site (−PBS), a 3' regulatory sequence required for reverse transcription (+PBS)), and a viral LTRs). The LTRs contain sequences required for the association of viral genomic RNA, reverse transcriptase and integrase functions, and sequences involved in directing the expression of the genomic RNA to be packaged in viral particles.

Following the construction of the recombinant retroviral vector, the vector DNA is introduced into a packaging cell line. Packaging cell lines provide viral proteins required in trans for the packaging of viral genomic RNA into viral particles having the desired host range (e.g., the viral-encoded core (gag), polymerase (pol) and envelope (env) proteins). The host range is controlled, in part, by the type of envelope gene product expressed on the surface of the viral particle. Packaging cell lines can express ecotrophic, amphotropic or xenotropic envelope gene products. Alternatively, the packaging cell line can lack sequences encoding a viral envelope (env) protein. In this case, the packaging cell line can package the viral genome into particles which lack a membrane-associated protein (e.g., an env protein). To produce viral particles containing a membrane-associated protein which permits entry of the virus into a cell, the packaging cell line containing the retroviral sequences can be transfected with sequences encoding a membrane-associated protein (e.g., the G protein of vesicular stomatitis virus (VSV)). The transfected packaging cell can then produce viral particles which contain the membrane-associated protein expressed by the transfected packaging cell line; these viral particles which contain viral genomic RNA derived from one virus encapsidated by the envelope proteins of another virus are said to be pseudotyped virus particles.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Another preferred viral vector is a pox virus such as a vaccinia virus, for example an attenuated vaccinia such as Modified Virus Ankara (MVA) or NYVAC, an avipox such as fowl pox or canary pox. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In another embodiment, lentiviral vectors are used, such as the HIV based vectors described in U.S. Pat. Nos. 6,143,520; 5,665,557; and 5,981,276, which are herein incorporated by reference. Use of Adeno-associated virus (AAV) vectors is also contemplated (Walsh et al., Proc. Soc. Exp. Biol. Med. 204:289-300 (1993); U.S. Pat. No. 5,436,146 which is incorporated herein by reference).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

U.S. Pat. No. 5,676,954 (which is herein incorporated by reference) reports on the injection of genetic material, complexed with cationic liposome carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals. Such cationic lipid complexes or nanoparticles can also be used to deliver protein.

A gene or nucleic acid sequence can be introduced into a target cell by any suitable method. For example, an human HJV fusion polypeptide construct can be introduced into a cell by transfection (e.g., calcium phosphate or DEAE-dextran mediated transfection), lipofection, electroporation, microinjection (e.g., by direct injection of naked DNA), biolistics, infection with a viral vector containing a muscle related transgene, cell fusion, chromosome-mediated gene transfer, microcell-mediated gene transfer, nuclear transfer, and the like. A nucleic acid encoding an human HJV fusion polypeptide can be introduced into cells by electroporation (see, e.g., Wong and Neumann, Biochem. Biophys. Res. Commun. 107:584-87 (1982)) and biolistics (e.g., a gene gun; Johnston and Tang, Methods Cell Biol. 43 Pt A:353-65 (1994); Fynan et al., Proc. Natl. Acad. Sci. USA 90:11478-82 (1993)).

In certain embodiments, a gene or nucleic acid sequence encoding human HJV fusion polypeptide can be introduced into target cells by transfection or lipofection. Suitable agents for transfection or lipofection include, for example, calcium phosphate, DEAE dextran, lipofectin, lipfectamine, DIMRIE C, Superfect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecylammonium bromide), DHDEAB (N,N-di-n-hexadecyl-N,N-dihydroxyethyl ammonium bromide), HDEAB (N-n-hexadecyl-N,N-dihydroxyethylammonium bromide), polybrene, poly(ethylenimine) (PEI), and the like. (See, e.g., Banerjee et al., Med. Chem. 42:4292-99 (1999); Godbey et al., Gene Ther. 6:1380-88 (1999); Kichler et al., Gene Ther. 5:855-60 (1998); Birchaa et al., J. Pharm. 183:195-207 (1999)).

Methods known in the art for the therapeutic delivery of agents such as proteins and/or nucleic acids can be used for the delivery of a polypeptide or nucleic acid encoding an human HJV fusion polypeptide for modulating iron metabolism and/or for increasing serum iron concentration in a subject, e.g., cellular transfection, gene therapy, direct administration with a delivery vehicle or pharmaceutically acceptable carrier, indirect delivery by providing recombinant cells comprising a nucleic acid encoding a targeting fusion polypeptide of the invention.

Various delivery systems are known and can be used to directly administer therapeutic polypeptides such as the human HJV fusion polypeptide and/or a nucleic acid encoding a human HJV fusion polypeptide as disclosed herein, e.g., encapsulation in liposomes, microparticles, microcapsules, recombinant cells capable of expressing the compound, and receptor-mediated endocytosis (see, e.g., Wu and Wu, 1987, J. Biol. Chem. 262:4429-4432). Methods of introduction can be enteral or parenteral and include but are not limited to intradermal, intramuscular, intraperitoneal, intravenous, subcutaneous, pulmonary, intranasal, intraocular, epidural, and oral routes. The agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105).

Thus, a wide variety of gene transfer/gene therapy vectors and constructs are known in the art. These vectors are readily adapted for use in the methods of the present invention. By the appropriate manipulation using recombinant DNA/molecular biology techniques to insert an operatively linked human HJV fusion polypeptide encoding nucleic acid segment into the selected expression/delivery vector, many equivalent vectors for the practice of the methods described herein can be generated.

It will be appreciated by those of skill that cloned genes readily can be manipulated to alter the amino acid sequence of a protein. The cloned gene for human HJV that comprise part of the HJV fusion polypeptide can be manipulated by a variety of well known techniques for in vitro mutagenesis, among others, to produce variants of the naturally occurring human protein, herein referred to as muteins or variants or mutants of HJV, which may be used in accordance with the methods and compositions described herein.

The variation in primary structure of muteins of HJV useful in the invention, for instance, may include deletions, additions and substitutions. The substitutions may be conservative or non-conservative. The differences between the natural protein and the mutein generally conserve desired properties, mitigate or eliminate undesired properties and add desired or new properties.

VIII. Other Embodiments

From the foregoing description, it will be apparent that variations and modifications may be made to the invention described herein to adopt it to various usages and conditions. Such embodiments are also within the scope of the following claims.

The invention also contemplates an article of manufacture which is a labeled container for providing an soluble HJV protein such as a HJV fusion polypeptide as disclosed herein. An article of manufacture comprises packaging material and a pharmaceutical agent of the soluble HJV polypeptide, such as a HJV fusion polypeptide, contained within the packaging material.

The pharmaceutical agent in an article of manufacture is any of the compositions of the present invention suitable for providing a soluble HJV protein, such as a HJV fusion polypeptide (e.g. HJV.Fc) and formulated into a pharmaceutically acceptable form as described herein according to the disclosed indications. Thus, the composition can comprise a HJV fusion polypeptide (e.g. HJV.Fc) or a DNA molecule which is capable of expressing such a polypeptide.

The article of manufacture contains an amount of pharmaceutical agent sufficient for use in treating a condition indicated herein, either in unit or multiple dosages. The packaging material comprises a label which indicates the use of the pharmaceutical agent contained therein, e.g., for the treatment of a HJV-related disorder, such as an iron-related disorder as discussed herein, or for other indicated therapeutic or prophylactic uses.

The label can further include instructions for use and related information as may be required for marketing. The packaging material can include container(s) for storage of the pharmaceutical agent.

As used herein, the term packaging material refers to a material such as glass, plastic, paper, foil, and the like capable of holding within fixed means a pharmaceutical agent. Thus, for example, the packaging material can be plastic or glass vials, laminated envelopes and the like containers used to contain a pharmaceutical composition including the pharmaceutical agent.

In preferred embodiments, the packaging material includes a label that is a tangible expression describing the contents of the article of manufacture and the use of the pharmaceutical agent contained therein.

IX. Materials and Methods

The following describes Materials and Methods useful not only for the studies that elucidated the iron metabolism effects of a soluble form of HJV, such as a HJV fusion protein as disclosed herein, but also for the practice of the invention as described herein.

cDNA subcloning. The inventors generated cDNA encoding mutant mouse hemojuvelin with a G313V substitution by an overlapping PCR strategy using primers G313V-N-F, G313V-N-R, G313V-C-F and G313V-C-R, followed by subcloning into pcDNA 3.1 (Invitrogen).

The inventors generated cDNA encoding soluble Hjv.Fc fusion protein by PCR of the extracellular domain of mouse hemojuvelin using the primers HjvECD-F and HjvECD-R, followed by subcloning into the mammalian expression vector pIgplus (R & D Systems) in-frame with the Fc portion of human immunoglobulin.

The inventors generated cDNA encoding Flag-tagged human hemojuvelin (Flag-HJV) by using PCR to amplify human hemojuvelin transcript variant b, which does not contain exon 2, with primers HJVB-F and HJVB-R. Exon 2, which codes for the signal peptide of the full-length hemojuvelin transcript variant a, was amplified by PCR from human genomic DNA using the primers HJVEx2-F and HJVEx2-R. The two overlapping fragments were fused together by PCR, and the full-length cDNA product was subcloned via EcoRI/XhoI restriction sites into pcDNA3.1 (Invitrogen), to generate pcDNA3.1-HJV. To generate Flag-HJV, an upstream fragment corresponding to the beginning of exon 3 was generated by PCR using the primers HJVEx3-F and HJVEx3-R followed by digestion by NotI and SacII. A downstream fragment was cut with SacII and XbaI from pcDNA3.1-HJV. The two fragments were ligated and subcloned into the NotI and XbaI sites of p3XFlag-CMV9 (Sigma) downstream of the preprotrypsin signal sequence and Flag tag.

cDNA encoding mutant Flag-tagged hemojuvelin with a valine to glycine substitution at amino acid 99 (Flag-G99V-HJV) was generated from Flag-HJV by site-directed mutagenesis using the QuikChange kit (Stratagene).

cDNA encoding the hepcidin promoter luciferase construct was generated by subcloning the −2649 to +45 region of the human hepcidin promoter46 into the pGL2-Bsic vector (Promega) upstream of the firefly luciferase reporter gene.

All cDNAs were sequenced to verify the fidelity of the constructs (Massachusetts General Hospital Molecular Biology DNA Sequencing Core Facility). See Table 1 for primer sequences.

TABLE 1

Primer sequences.

| Name | Strand | Sequence (5' - 3') |
|---|---|---|
| G313V-N-F | + | ACCGAATTCGGGGGACCTGGCTGGATAG (SEQ ID NO: 12) |
| G313V-N-R | − | CGGAGGGCATACCCCAACACACAG(SEQ ID NO: 13) |
| G313V-C-F | + | CTGTGTGTTGGGGTATGCCCTCCG (SEQ ID NO: 14) |
| G313V-C-R | − | CCCTCTAGATGGTGCCAGTCTCCAAAAGC (SEQ ID NO: 15) |
| HjvECD-F | + | GGAAGCTTATGGGCCAGTCCCCTAGT (SEQ ID NO: 16) |
| HjvECD-R | − | CCGGATCCGCTAAGTTCTCTAAATCCGTC (SEQ ID NO: 17) |
| HJVB-F | + | CCTCTGTGGACATGCTCATTCTCAATGCAAGATCCTCCGCTG (SEQ ID NO: 18) |
| HJVB-R | − | CGTCTCGAGTTACTGAATGCAAAGCCACAGAACAAAGAGC (SEQ ID NO: 19) |
| HJVEx2-F | + | CGAGAATTCACTTACAGGGCTTCCGGTCA (SEQ ID NO: 20) |
| HJVEx2-R | − | GCATTGAGAATGAGCATGTCCACAGAGGAGCAGCAG (SEQ ID NO: 21) |
| HJVEx3-F | + | GACAGATCTGCGGCCGCTCATTCTCAATGCAAGATCCTCCG (SEQ ID NO: 22) |

TABLE 1-continued

| Primer sequences. | | |
|---|---|---|
| Name | Strand | Sequence (5' - 3') |
| HJVEx3-R | - | GAGCAGTTGTGCTGGATCATCAGG (SEQ ID NO: 23) |
| HAMP-F | + | CTGCAACCCCAGGACAGAG (SEQ ID NO: 24) |
| HAMP-R | - | GGAATAAATAAGGAAGGGAGGGG (SEQ ID NO: 25) |
| ACTB-F | + | AGGATGCAGAAGGAGATCACTG (SEQ ID NO: 26) |
| ACTB-R | - | GGGTGTAACGCAACTAAGTCATAG (SEQ ID NO: 27) |
| BMP2-F | + | CGTGACCAGACTTTTGGACAC (SEQ ID NO: 28) |
| BMP2-R | - | GGCATGATTAGTGGAGTTCAG (SEQ ID NO: 29) |
| BMP4-F | + | AGCAGCCAAACTATGGGCTA (SEQ ID NO: 30) |
| BMP4-R | - | TGGTTGAGTTGAGGTGGTCA (SEQ ID NO: 31) |
| Hamp1-F | + | TCCTTAGACTGCACAGCAGAA (SEQ ID NO: 32) |
| Hamp1-R | - | ATAAATAAGGACGGGAGGGG (SEQ ID NO: 33) |

To generate cDNA encoding HJV.Fc, an upstream fragment of human hemojuvelin (containing a preprotrypsin signal sequence and FLAG tag) was digested SpeI/BstEII from the plasmid FLAG-HJV (Babitt et al., 2006. Nat. Genet. 38:531-539). A downstream fragment of human hemojuvelin that does not include the glycophosphatidylinositol (GPI) domain was amplified by PCR from the plasmid FLAG-HJV using the primers 5'-AGAAGGTGTATCAGGCTGAGGTGG-3' (SEQ ID NO: 34) and 5'-CAGCTCGAGTGAGGGGAAGAGATGCAGCTTCTC-3' (SEQ ID NO: 35), followed by BstEII/XhoI digestion. Both fragments were ligated into the SpeI/XhoI sites of Signal PigPlus (R & D Systems) in-frame with Fc portion of human IgG. Sequences were verified by bi-directional sequencing at the DNA sequencing core facility of Massachusetts General Hospital.

Purification of HJV.Fc.

Two methods were used. CHO cells stably expressing Hjv.Fc were cultured in F-12K NutrientMixture, Kaighn's Modification, supplemented with 5% ultra-low immunoglobulin FBS (Invitrogen) using 175-cm2 multifloor flasks (Denville Scientific). Hjv.Fc was purified from the medium of stably transfected cells via one-step Protein A affinity chromatography using HiTrap rProtein A FF columns (Amersham Biosciences) as described in Babitt et al., J. Biol. Chem. 280, 29820-29827 (2005) and del Re et al., J. Biol. Chem. 279, 22765-22772 (2004). Hjv.Fc was subjected to reducing SDS-PAGE and gels were stained with Bio-safe Coomassie blue (Bio-Rad) to determine purity and quantify protein concentration.

Alternatively, HEK293 cells (ATCC #CRL-1573) cultured in RPMI medium 1640 (GIBCO) supplemented with L-glutamine (GIBCO) and 10% FBS (Atlanta Biologicals) were stably transfected with cDNA encoding HJV.Fc using Lipofectamine 2000 (Invitrogen) according to manufacturer instructions. Stably transfected cells were selected and cultured in 1 mg/ml Geneticin (Cellgro Mediatech). HJV.Fc was purified from the conditioned media of stably transfected cells by Bioexpress.

Generation of Antibody to Hemojuvelin (α-HJV) and Protein Blot Analysis.

An affinity-purified rabbit polyclonal antibody to hemojuvelin (α-HJV) was raised against the peptide 292-RVAEDVARAFSAEQDLQLC-310 (SEQ ID NO: 36) in the C terminus of mouse hemojuvelin upstream of its hydrophobic tail (Papanikolaou et al., Nat. Genet. 36, 77-82 (2004); Samad et al., J. Neurosci. 24, 2027-2036 (2004)). Livers from 12956/SvEvTac wild-type or Hfe2$^{-/-}$ mice 19, or cells transfected with cDNA encoding wild-type or mutant hemojuvelin, were homogenized and sonicated in lysis buffer (200 mM Tris-HCl, pH 8, 100 mM NaCl, 1 mM EDTA, 0.5% NP-40 and 10% glycerol) containing a mixture of protease inhibitors (Roche) as described in Babitt et al., J. Biol. Chem. 280, 29820-29827 (2005). For assays examining phosphorylated Smad expression, 1 mM sodium orthovanadate (Sigma) and 1 mM sodium fluoride (Sigma) were added to the lysis buffer as phosphatase inhibitors. Purified Hjv.Fc, transfected cell lysates or liver lysates, were subjected to reducing SDS-PAGE and protein blot using (i) α-HJV (1:1,000, 4 mg ml$^{-1}$) at 4° C. overnight, (ii) goat anti-human Fc antibody (1:1,000; Jackson ImmunoResearch Laboratories) at 23° C. for 1 h or (iii) rabbit polyclonal antibody to phosphorylated Smad1/5/8 (1:1,000; Cell Signaling) at 4° C. overnight (Babitt et al., J. Biol. Chem. 280, 29820-29827 (2005)). Blots were stripped and reprobed with mouse monoclonal antibody to β-actin (1:5,000; Sigma), rabbit polyclonal antibody to Smad1 (1:250; Upstate Biotechnology) at 4° C. overnight, or rabbit polyclonal antibody to actin (1:50; Biomedical Technologies) at room temperature for 1 h as loading controls.

Ligand Iodination and Crosslinking.

The inventors iodinated 2 mg of carrier-free human BMP-2 or BMP-4 ligand (R & D Systems) per reaction with $^{125}$I by the modified chloramine-Tmethod as previously described (Frolik et al., J. Biol. Chem. 259, 10995-11000 ((1984)). $^{125}$I-BMP-2 was incubated with 60 ng Hjv.Fc for ALK5.Fc (R & D Systems) in 20 mM HEPES (pH 7.8) with 0.1% BSA and a mixture of protease inhibitors (Roche Diagnostics) or with buffer alone. This mixture was incubated in the absence or presence of 2.5 M DSS (Sigma) followed by incubation with Protein A Sepharose beads (Amersham) as described in Babitt et al., J. Biol. Chem. 280, 29820-29827 (2005). Beads were washed with PBS and protein was eluted by nonreducing Laemmli sample buffer (Bio-Rad). Eluted protein was separated by SDS-PAGE and analyzed by autoradiography.

Hepcidin Induction Assays, Quantitative Real-Time PCR and RT-PCR.

HepG2 or Hep3B cells were grown to 60% confluence on 6-cm tissue culture plates. Where indicated, cells were transfected with varying amounts of cDNA encoding Flag-HJV or Flag-G99V-HJV. Cells were serum-starved 24 h after transfection in α-MEM with 1% FBS followed by incubation with 50 ng $ml^{-1}$ BMP-2 at 37° C. for various times or with 1 mg $ml^{-1}$ noggin at 37 1 C for 48 h. For cycloheximide experiments, 10 mg $ml^{-1}$ cycloheximide was added for 30 min before addition of BMP-2. Total RNA was isolated using the RNeasy Mini Kit (QIAgen), with DNAse digestion by the RNase-Free DNase Set (QIAgen) according to the manufacturer's instructions. Real-time quantification of mRNA transcripts was performed using two-step RT-PCR using the ABI Prism 7900HT Sequence Detection System and SDS software version 2.0. Firststrand cDNA synthesis was performed using iScript cDNA Synthesis Kit (Bio-Rad) according to the manufacturer's instructions, using 2 mg total RNA template per sample. In a second step, hepcidin (HAMP) transcripts were amplified with the primers HAMP-F and HAMP-R and detected using iTaq SYBR Green Supermix with ROX (Bio-rad) according to the manufacturer's instructions. In parallel, β-actin (ACTB) transcripts were amplified with the primers ACTB-F and ACTB-R and detected in a similar manner to serve as an internal control. Standard curves for hepcidin and β-actin were generated from accurately determined dilutions of plasmids containing cDNA encoding hepcidin and β-actin as templates. Samples were analyzed in triplicate, and results are reported as the ratio of mean values for hepcidin to β-actin. BMP2 and BMP4 transcripts were amplified from HepG2 cDNA generated above using the primers BMP2-F and BMP2-R (for BMP2) and BMP4-F and BMP4-R (for BMP4) (see Table 1 for primer sequences).

Animals.

Six to eight week old 12956/SvEvTac mice (Taconic) were fed on either the Prolab 5P75 Isopro RMH 3000 or Prolab RMH 3000 diet, each with 380 parts per million iron.

BMP Injection.

Mice were anesthetized with Avertin (Sigma) and given a single retro-orbital injection of 1 mg/kg of BMP-2 (kindly provided by Dr. Vicki Rosen, Harvard School of Dental Medicine, Boston, Mass.) in 0.1% BSA in 1×PBS or an equal volume of vehicle alone. Dosage of BMP-2 was based on published data for BMP-7 showing that doses ranging from 0.25-1.0 mg/kg IV or IP are effective in inhibiting fibrosis and preserving renal function in several animal models of kidney injury (Matsunaga et al., Nat. Cell Biol. 6, 749-755 (2004); Courselaud et al., J. Biol. Chem. 277, 41163-41170 (2002); del Re et al., J. Biol. Chem. 279, 22765-22772 (2004); Frolik et al., J. Biol. Chem. 259, 10995-11000 (1984); Lin et al., Cell 119, 121-135 (2004)). Four hours after injection the mice were sacrificed, and blood and livers were harvested for measurement of iron parameters and hepcidin expression.

HJV.Fc Injection.

Mice were injected with an intraperitoneal dose of 25 mg/kg purified HJV.Fc or an equal volume of normal saline three times per week for three weeks. Twenty-four hours after the last injection, mice were sacrificed and blood, livers, and spleen were harvested for measurement of iron parameters, phosphorylated Smad1/5/8, and hepcidin expression.

Serum Iron Measurements.

Blood was collected in BD Microtainer serum separator tubes (Fisher Scientific) and serum was isolated according to the manufacturer's instructions. Serum iron and unsaturated iron-binding capacity (UIBC) were measured by colorimetric assay using the Iron/UIBC kit (Thermo Electron Corporation). Total iron binding capacity (TIBC) was calculated as the sum of serum iron and UIBC measurements, and transferrin saturation percentage was calculated as serum iron/TIBC×100.

Tissue Iron Measurement.

Immediately after harvest, livers and spleen were sectioned and weighed. Quantitative measurement of non-heme iron was measured according to the method of Torrence and Bothwell (Alonso et al., J. Mol. Evol. 23, 11-22 (1986)). Results are reported as μg iron/gram wet weight tissue.

Luciferase Assay.

Hepcidin promoter luciferase assays in hepatoma-derived Hep3B cells were carried out using the Dual-Luciferase system (Promega) as described in Babitt et al., 2006. Nat. Genet. 38:531-539 with the following modifications. For BMP/TGF-β-stimulation assays, cells transfected with the hepcidin promoter luciferase reporter and control *Renilla* luciferase vector (pRL-TK) were serum starved in α-MEM with L-glutamine (Invitrogen) supplemented with 1% FBS for 6 hours, followed by stimulation with 50 ng/ml BMP ligands, 30 ng/ml Activin A, or 5 ng/ml TGF-β ligands (R & D Systems), for 16 hours. Relative concentrations of BMP/TGF-β superfamily ligands are similar to those previously used by others to compare superfamily ligand responses (Wang et al., 2005. Cell Metab. 2:399-409, Korchynskyi et al., 2002. J. Biol. Chem. 277:4883-4891; Dennler et al., 1998. EMBO J. 17:3091-3100). For HJV.Fc inhibition assays, cells transfected with the hepcidin promoter luciferase reporter and pRL-TK were serum starved as above and incubated with 25 ng/ml BMP-2, -4, -6, -7 ligands, 50 ng/ml BMP-5, or 5 ng/ml BMP-9, either alone or with 0.5-25 μg/ml of HJV.Fc for 16 hours. Relative concentrations of BMP ligands were chosen to elicit similar degrees of hepcidin promoter relative luciferase activity. Experiments using equal concentrations of ligands were also carried out and had similar results (data not shown).

Primary Hepatocyte Isolation and Culture.

Primary hepatocytes were isolated by collagenase digestion of livers from 8- to 10-week-old 12956/SvEvTac wild-type or $Hfe2^{-/-}$ mice using methods described in Lin et al., Cell 119, 121-135 (2004). Briefly, mice were perfused through the inferior vena cava with calcium-free Hank's Balanced Salt Solution (HBSS; Mediatech) supplemented with 0.5 mM EDTA and 16.7 mM sodium bicarbonate for 4 min at a rate of B1.5 ml $min^{-1}$. Mice were subsequently perfused with calcium-containing HBSS containing 0.05% collagenase (Sigma), 1% bovine serum albumin and 16.7 mM sodium bicarbonate for 8 min. After enzymatic digestion, hepatocytes were liberated into culture medium (1:1 Dulbecco's Modified Eagle's/Ham's F12 medium (Gibco) supplemented with 100 IU $ml^{-1}$ penicillin, 100 mg $ml^{-1}$ streptomycin, 18 mM HEPES, 1 mM sodium pyruvate, 10 mg $ml^{-1}$ insulin, 5.5 mg $ml^{-1}$ transferrin, 5 ng $ml^{-1}$ selenium (ITS; Sigma), 2 mM L-glutamine, 0.1 mM non-essential amino acids (Gibco) and 10% FBS (HyClone)), passed through a 100-mm BD Falcon mesh cell strainer (BD Biosciences), centrifuged, gently washed with culture medium and counted. Cells (490% hepatocytes by microscopy) were seeded on collagen-coated plates (Sigma) at $5\times10^5$ cells per 60-mm dish. After 2 to 3 h, cells were washed with PBS, serum-starved with culture medium containing 1% FBS for 6 h and stimulated with recombinant human BMP-2 at varying concentrations for 12 h. RNA was isolated using the RNeasy kit according to manufacturer's directions (QIAgen).

RNA Blot Analysis.

Total RNA (2.5 mg) from primary hepatocytes was separated on a 1% formaldehyde agarose gel and transferred onto Hybond N+ membranes (Amersham Pharmacia Biotech). Membranes were baked for 2 h at 80 1 C under vacuum and hybridized with radioactively labeled probes specific for mouse hepcidin 1 (Hamp1, amplified with primers Hamp1-F and Hamp1-R (see table 1 for primer sequences) and for β-actin. Expression was quantified using a phosphorimager (Molecular Dynamics/Amersham Biosciences) and normalized to β-actin or 28S rRNA as loading controls. See Table 1 for primer sequences.

RT-PCR.

Total RNA was isolated from HepG2 or Hep3B cells and was analyzed for BMP2, BMP4, BMP5, BMP6, and BMP9 expression as previously described (29) using the primers BMP2-F, BMP2-R, BMP4-F, BMP4-R, BMP6-F, BMP6-R, BMP9-F, and BMP9-R (see Table 1 for primer sequences).

Quantitative Real-Time RT-PCR.

Hep3B or HepG2 cells were serum starved for 6 hours in α-MEM supplemented with 1% FBS and treated for 16 hours with varying amounts of BMP/TGF-β superfamily ligands or 100 ng/ml IL-6, in the absence or presence of 25 μg/ml purified HJV.Fc. For BMP siRNA experiments, HepG2 cells were plated in 24-well plates and transfected with 200 ng pcDNA3 (Invitrogen) and 40 nM BMP-2, BMP-4, BMP-6, BMP-7, or Control scramble siRNA (Ambion, see Table 2 for siRNA sequences) in α-MEM using Lipofectamine 2000® (Invitrogen) according to the manufacturer's instructions. Cells were serum starved overnight in α-MEM supplemented with 0.1% BSA. Total RNA was isolated from treated cells, and real-time quantitation of hepcidin relative to β-actin mRNA transcripts was performed using 2-step quantitative real-time RT-PCR as previously described (Babitt et al., 2006. Nat. Genet. 38:531-539). For BMP siRNA experiments, real-time quantitation of BMP2, BMP4, and BMP6 relative to β-actin mRNA transcripts was also performed as described above using the primers qBMP2-F, qBMP2-R, qBMP4-F, qBMP4-R, qBMP6-F, qBMP6-R (see Table 1 for primer sequences). For mouse livers, total RNA was isolated using the Illustra RNAspin Mini Kit (GE Healthcare) according to the manufacturer's instructions. Real-time quantification of hepcidin (Hamp1) relative to Gapdh mRNA transcripts was performed as described above using primers Hamp1-F (6) Hamp1-R (6), Gapdh-F, and Gapdh-R.

TABLE 2

Sequence of siRNAs for BMP ligands (Ambion)

| Name | Sequence (sense) |
|---|---|
| BMP2 | GGUUUUCCGAGAACAGAUGtt (SEQ ID NO: 65) |
| BMP4 | GGGACCAGUGAAAACUCUGtt (SEQ ID NO: 67) |
| BMP6 | GCGACACCACAAAGAGUUCtt (SEQ ID NO: 68) |
| BMP7 | GGCAAAACCUAGCAGGAAAtt (SEQ ID NO: 69) |

Western Blot.

Western blot of purified HJV.Fc using anti-hemojuvelin antibody (Babitt et al., 2006. Nat. Genet. 38:531-539) and anti-Fc antibody (Jackson ImmunoResearch Laboratories) was performed as described in Babitt et al., 2006. Nat. Genet. 38:531-539. Western blot of liver lysates for phosphorylated Smad1/5/8 expression relative to total Smad1 and β-actin expression was performed as described in Babitt et al., 2006. Nat. Genet. 38:531-539. For ferroportin assays, spleen membrane preparations were prepared as previously described (Canonne-Hergaux et al., 1999. Blood. 93:4406-4417). Protein concentrations were determined by BCA assay (Pierce). After solubilization in 1× Laemmli buffer for 30 minutes at room temperature, 35 μg of protein per sample were separated by SDSPAGE using pre-cast NuPAGE Novex 4-12% Bis-Tris gels (Invitrogen) and transferred onto PDVF membranes. Western blot for was performed using anti-ferroportin antibody (kindly donated by Francois Canonne-Hergaux) as previously described (Canonne-Hergaux et al., 2005. Am. J. Physiol. Gastrointest. Liver Physiol. 290:156-163). Blots were stripped and reprobed for β-actin expression as a loading control as described in Babitt et al., 2006. Nat. Genet. 38:531-539 and herein.

Cell Culture and Transfection.

CHO cells (ATCC) were cultured in F-12K Nutrient Mixture, Kaighn's Modification (Invitrogen) supplemented with 10% fetal bovine serum (FBS; Atlanta Biologicals). HepG2 cells and Hep3B cells (ATCC) were cultured in Minimal Essential Alpha Medium with L-glutamine (α-MEM, Invitrogen) containing 10% FBS. HEK293 cells (ATCC) were cultured in DMEM (Cellgro Mediatech) supplemented with 10% FBS. All plasmid transfections were performed with Lipofectamine 2000 (Invitrogen) or Effectene transfection reagent (QIAgen) according to manufacturer instructions. Stably transfected cells were selected and cultured in 1 mg ml-1 geneticin (Cellgro Mediatech).

Luciferase Assay.

HepG2 or Hep3B cells were transiently transfected with 2.5 mg BMP responsive luciferase reporter (BRE-Luc), 2.5 mg TGF-β responsive luciferase reporter, (CAGA)12 MPL-Luc (CAGA-Luc) (both provided by P. ten Dijke, Leiden University Medical Center, The Netherlands) or 2.5 mg hepcidin promoter luciferase reporter construct, in combination with 0.25 mg pRL-TK *Renilla* luciferase vector (Promega) to control for transfection efficiency, with or without cotransfection with cDNA encoding wild-type or mutant hemojuvelin. Cells were serum-starved 48 h after transfection in α-MEM supplemented with 1% FBS for 6 h and treated with 1 ng $ml^{-1}$ TGF-β1 or 25-50 ng ml-1 BMP ligands (R & D Systems) for 16 h, in the absence or presence of 1 mg ml-1 noggin (R & D Systems) or 20 mg ml-1 neutralizing antibody to BMP-2 or BMP-4 (R & D Systems). Cells were lysed and luciferase activity was determined with the Promega Dual Reporter Assay according to the manufacturer's instructions. Experiments were performed in duplicate or triplicate wells. Relative luciferase activity was calculated as the ratio of firefly (reporter) to *Renilla* (transfection control) luciferase activity and is expressed as a multiple of the activity of unstimulated cells transfected with reporter alone.

Binding Assay.

60 ng purified Hjv.Fc in Tris buffered saline/Casein blocking buffer (BioFX, Owings Mills, Md.) or buffer alone was incubated with $^{125}$I-BMP-2 or $^{125}$I-BMP-4 at 4° C., either alone or in the presence of 80 ng cold BMP-2, BMP-4, BMP-7 or TGF-β1 (R&D Systems) as described in Babitt et al. J. Biol. Chem. 280, 29820-29827, 2005. The reaction mix was then incubated for 1.5 hrs at 4° C. on a protein A coated plates (Pierce), plates were washed with wash solution (KPL, Gaithersberg, Md.), and individual wells were counted with a standard gamma counter.

Crosslinking at the Cell Surface.

HEK293 cells in 10 cm dishes were transfected with 1.5 μg cDNA encoding HA-tagged ALK6 (ALK6-HA, kindly provided by Hideyuki Beppu and Kenneth Bloch, Massachusetts General Hospital, Boston, Mass.), FLAG-tagged human HJV (FLAG-HJV), or both. Forty-eight hours after transfection, cells were serum starved for 3 hours in 1% FBS at 37° C. and incubated for 3 hours at 4° C. in the absence or presence of 300 ng/ml BMP-2. Cells were detached in 200 μl cold PBS and incubated with 15 μl of 100 mM DSS in DMSO for 30 minutes at room temperature. After quenching of DSS, cells were lysed in 10 mM Tris-HCl, pH 7.4, 150 mM NaCl, 1% Triton-100, 2% Octyl-β-Glucoside (Pierce) and a mixture of protease inhibitors (Roche Diagnostics). 380 μl cell lysates were immunoprecipitated with 1 μg rabbit polyclonal anti-HA antibody (#-HA, Santa Cruz, SC-805) at 4° C. overnight followed by incubation with Protein A beads (Pierce) for 6 hours at 4° C. Immunoprecipitates were analyzed by reducing SDS-PAGE and Western blot with mouse monoclonal M5 anti-FLAG antibody (#-FLAG, 1:500 dilution, Sigma). Total cell lysates were analyzed by reducing SDSPAGE and Western blot with #-FLAG (1:500) or #-HA (1:1000).

Statistical Analysis.

A two-tailed Student's t-test with $P<0.05$ was used to determine statistical significance.

Accession Codes.

GenBank: *Homo sapiens* hemojuvelin (HEF2) transcript variant a, NM__213653 (SEQ ID NO: 37); *Homo sapiens* hemojuvelin (HEF2) transcript variant b, NM__145277 (SEQ ID NO: 38); BC085604 (SEQ ID NO: 39); *Mus musculus* hemojuvelin (RgmC) mRNA, AJ557515 (SEQ ID NO: 40); *Homo sapiens* HAMP mRNA, NM__021175 (SEQ ID NO: 41), BC020612 (SEQ ID NO: 42); *Mus musculus* hamp1 mRNA, NM__032541 (SEQ ID NO: 43), EST W12193 (SEQ ID NO: 44); *Homo sapiens* BMP2 mRNA, NM__001200 (SEQ ID NO: 45), BC069214 (SEQ ID NO: 46); *Homo sapiens* BMP4 mRNA, NM__001202 (SEQ ID NO: 47), BC020546 (SEQ ID NO: 48); *Homo sapiens* ACTB mRNA, NM__001101 (SEQ ID NO: 49), BC001301 (SEQ ID NO: 50).

X. Examples

Example 1

Hemojuvelin is a BMP Coreceptor

Figure 2A:
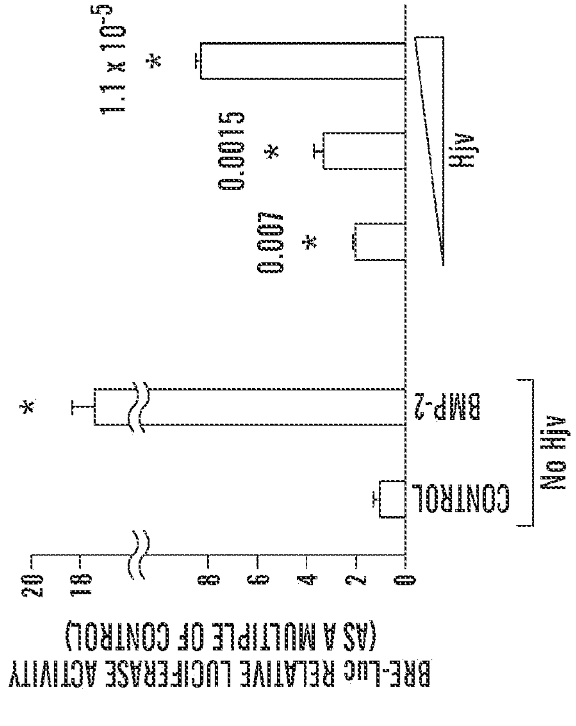
FIGS. 2A and 2B show that hemojuvelin signals via the BMP, but not the TGF-β, pathway. HepG2 cells were transfected with a BMP-responsive firefly luciferase reporter (a, BRE-Luc) or TGF-β-responsive firefly luciferase reporter (b, CAGA-Luc) and a control *Renilla* luciferase vector (pRL-TK), without or with 2 ng-2 mg cDNA encoding mouse hemojuvelin (Hjv). As negative and positive controls, cells without Hjv were incubated in the absence (control) or presence of 50 ng $ml^{-1}$ BMP-2 (FIG. 2A) or 1 ng $ml^{-1}$ TGF-β1 (FIG. 2B). Cells transfected with Hjv were incubated in the absence of exogenous BMP-2 or TGF-β ligands. Cell lysates were analyzed for luciferase activity. Relative luciferase activity was calculated as the ratio of firefly to *Renilla* luciferase activity, to control for transfection efficiency, and is expressed as a multiple of the activity of unstimulated cells transfected with reporter alone (control). Results are reported as the mean±s.d. n=2 to 4 in each group. * $P<0.05$ (compared with control). Exact P-values are shown above bars.
Figure 2B:
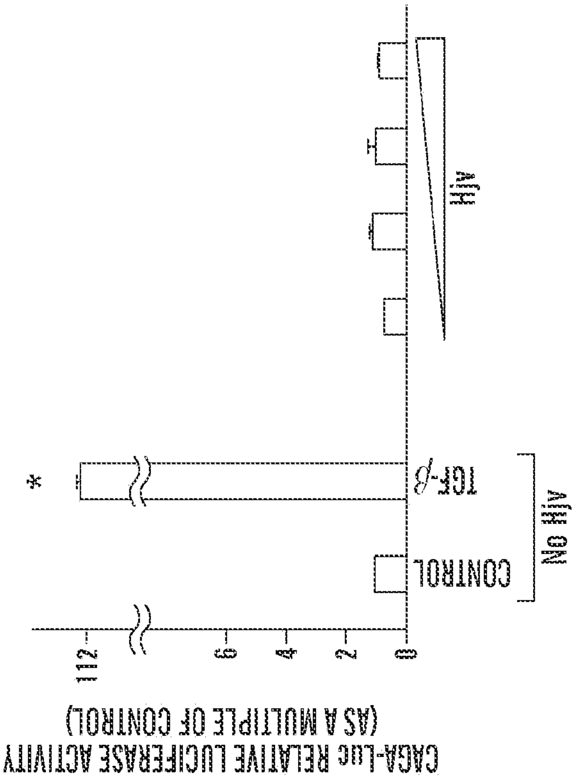

To test whether hemojuvelin mediates BMP signaling in liver cells, hepatoma-derived HepG2 cells were transfected with a BMP-responsive luciferase reporter (BRE-Luc) (Korchynskyi et al., J. Biol. Chem. 277, 4883-4891 (2002)), either alone or in combination with cDNA encoding mouse hemojuvelin (Hjv). Transfected cells were incubated with or without BMP-2 and measured luciferase activity. Stimulation with exogenous BMP-2 increased BRE luciferase activity B18-fold over baseline (FIGS. 2A and 2B). Hjv increased BRE luciferase activity in a dose-dependent fashion, even in the absence of exogenous BMP-2 (FIG. 2A). In contrast, Hjv did not increase TGF-β-responsive CAGA luciferase activity (FIG. 2B) (Dennler et al., EMBO J. 17, 3091-3100 (1998)). The inventors obtained similar results in another hepatoma-derived cell line, Hep3B cells (data not shown). Thus, hemojuvelin enhances BMP, but not TGF-β, signaling.

Figure 3A:
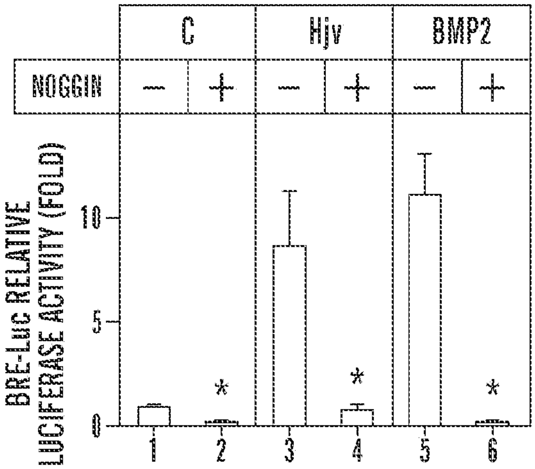
FIGS. 3A-3C show that hemojuvelin-mediated BMP signaling is ligand-dependent.
Figure 3B:
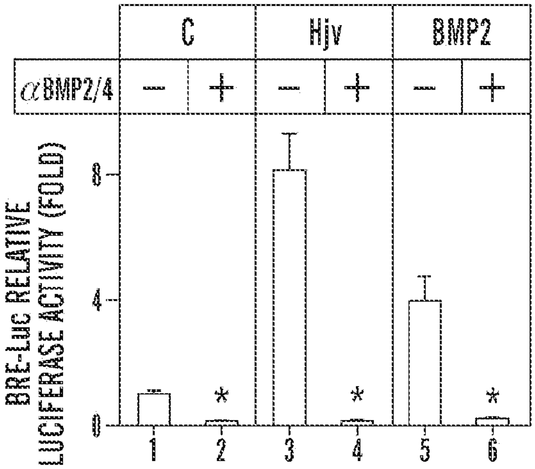
Figure 3C:
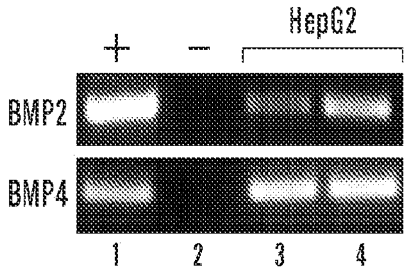

Hemojuvelin's ability to generate BMP signals without exogenous BMP ligand raises the question of whether hemojuvelin enhances signaling by endogenous BMP ligands, or whether it acts in a ligand-independent manner. The inventors therefore determined whether hemojuvelin-mediated BMP signaling was inhibited by noggin, a soluble BMP inhibitor that binds to BMP ligands and blocks the binding epitopes for BMP receptors (Balemans et al., Dev. Biol. 250, 231-250 (2002); Groppe et al., Nature 420, 636-642 (2002)). In a manner similar to its effects on exogenous BMP-2, noggin protein inhibited BRE luciferase stimulation by Hjv, suggesting that hemojuvelin-mediated signaling requires BMP ligands (FIGS. 3A-3C). Similar results were obtained using a neutralizing antibody against BMP-2 and BMP-4 (aBMP2/4) in place of noggin, suggesting that hemojuvelin, like family members RGMA and DRAGON, may have ligand selectivity for BMP-2, BMP-4 or both (FIGS. 3A-3C). Expression of both endogenous BMP2 and BMP4 mRNA by RT-PCR in these cells was detected (FIGS. 3A-3C).

Figure 4A:
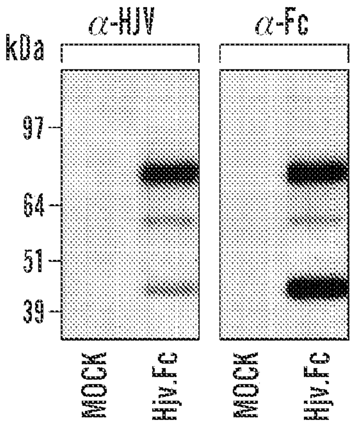
FIGS. 4A-4C show that HJV.Fc binds $^{125}$I-BMP-2 and $^{125}$I-BMP-4 in solution.
Figure 4B:
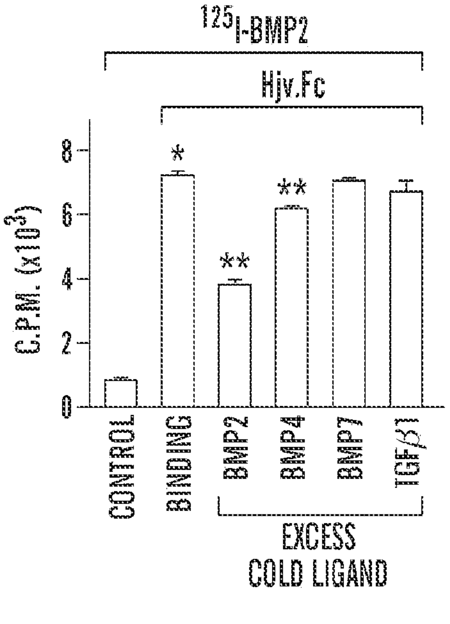
Figure 4C:
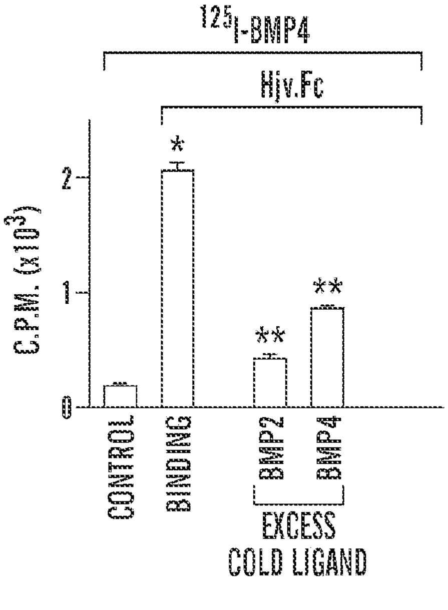
Figure 5:
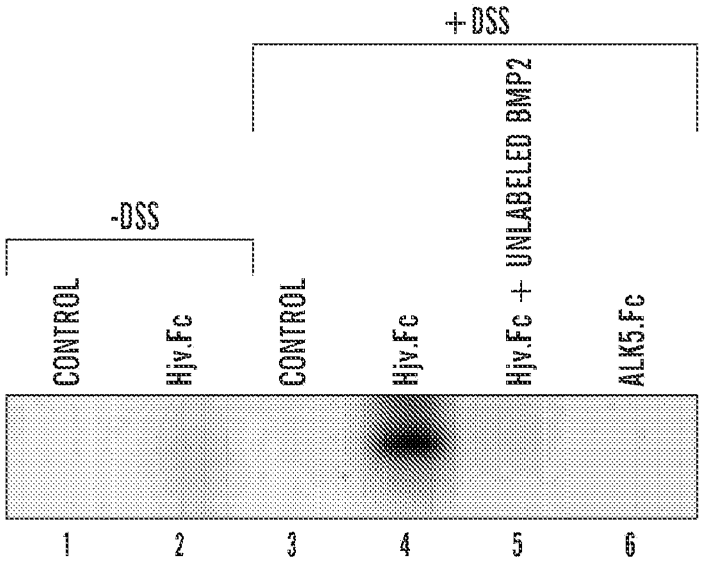
FIG. 5 shows that Hjv.Fc forms a complex with $^{125}$I-BMP-2 in solution. the inventors incubated buffer alone (control), 60 ng Hjv.Fc or TGF-β type I receptor ALK5.Fc with $^{125}$I-BMP-2, with or without excess unlabeled BMP-2, in the absence or presence of the crosslinker DSS. $^{125}$I-BMP-2 bound to Hjv.Fc was precipitated with Protein A beads, and the eluted protein complex was analyzed by non-reducing SDS-PAGE, followed by autoradiography. The band migrating at B180 kDa corresponds to the predicted size of a complex containing a dimer of disulfide-linked Hjv.Fc and a dimer of disulfide-linked $^{125}$I-BMP-2.
Figure 6A:
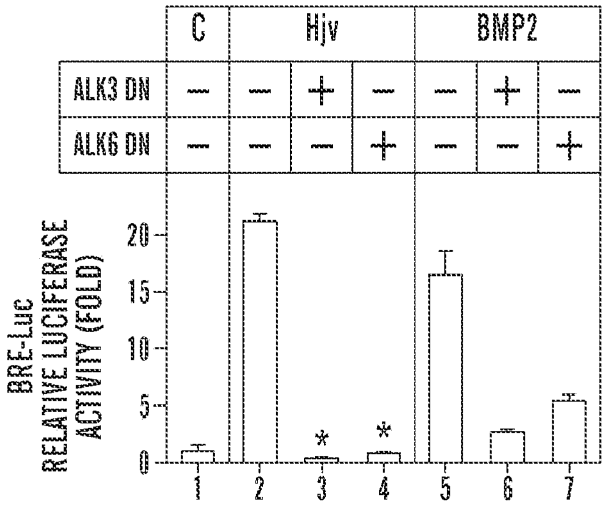
FIGS. 6A and 6B show that hemojuvelin mediates BMP signaling via BMP type I receptors, ALK3 and ALK6, and can be crosslinked with ALK6 at the cell surface in the presence of BMP-2.
Figure 6B:
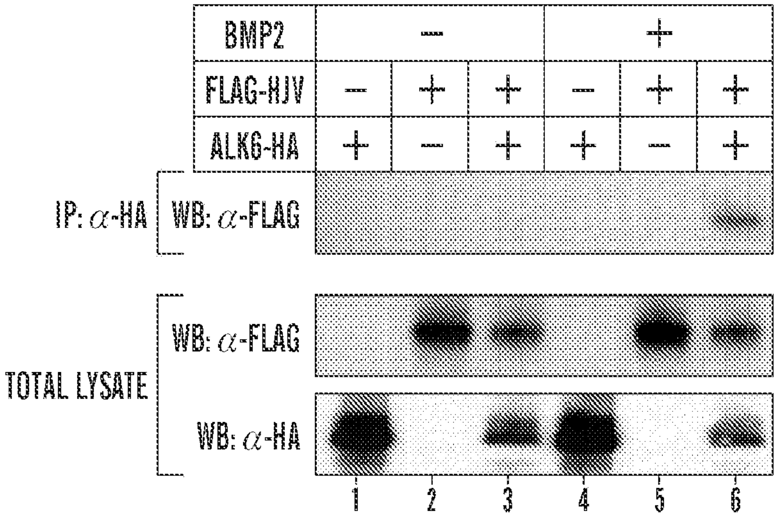

The inventors then investigated whether hemojuvelin interacts directly with BMP-2 and/or BMP-4 ligands. The inventors generated soluble hemojuvelin fusion protein (Hjv.Fc) by fusing the extracellular domain of mouse Hjv to the Fc portion of human immunoglobulin G (FIGS. 4A-4C). The inventors incubated purified Hjv.Fc overnight with $^{125}$I-labeled BMP-2 ($^{125}$I-BMP-2) or $^{125}$I-labeled BMP-4 ($^{125}$I-BMP-4) in the absence or presence of excess unlabeled BMP-2, BMP-4, BMP-7 or TGF-β1, transferred it to Protein A-coated plates and measured bound radioactivity. Hjv.Fc bound to $^{125}$I-BMP-2 and $^{125}$I-BMP-4, and this binding was competitively inhibited by excess unlabeled BMP-2 and, to a lesser extent, by BMP-4, but not by BMP-7 or TGF-131 (FIGS. 4A-4C). As further confirmation of an interaction between hemojuvelin and BMP-2, $^{125}$I-BMP-2 was chemically crosslinked with Hjv.Fc in the presence of disuccinimidyl suberate (DSS; FIG. 5), and this crosslinking was inhibited by excess unlabeled BMP-2 (FIG. 5). No bands were observed when the inventors used buffer alone or ALK5.Fc (a TGF-β type I receptor) in place of Hjv.Fc or if DSS was absent (FIG. 5). These data collectively suggest that Hjv.Fc binds to radiolabeled BMP-2 and, to a lesser extent, BMP-4. To examine whether hemojuvelin-mediated BMP signaling requires BMP receptors, the inventors tested the effects of dominant-negative mutant BMP type I receptors ALK3 and ALK6 in our reporter assay system. These dominant-negative mutants are deficient in kinase activity and therefore unable to phosphorylate Smad proteins (Samad et al., J. Biol. Chem. 280, 14122-14129 (2005); Babitt et al., J. Biol. Chem. 280, 29820-29827 (2005); Clarke et al., Mol. Endocrinol. 15, 946-959 (2001)). BRE luciferase activity induced by transfection with Hjv or incubation of cells with exogenous BMP-2 was inhibited by coexpression with dominant-negative ALK3 or ALK6 (FIGS. 6A and 6B). Thus, hemojuvelin-mediated BMP signaling involves BMP type I receptors.

The inventors then determined whether hemojuvelin interacts directly with BMP type I receptors at the cell surface and whether this interaction depends on the presence of BMP ligands using a coimmunoprecipitation assay in HEK293 cells, a human embryonic kidney cell line with high recombinant protein expression. The inventors generated Flag-tagged human hemojuvelin (Flag-HJV) and coexpressed it in HEK293 cells with hemagglutinin-tagged ALK6 (ALK6-HA), in the absence or presence of exogenous BMP-2 ligand, followed by crosslinking with DSS and immunoprecipitation with antibody to hemagglutinin. Protein blot of immunoprecipitates with antibody to Flag demonstrated that Flag-HJV formed a complex with ALK6-HA in the presence of BMP-2 (FIGS. 6A and 6B).

Figure 7:
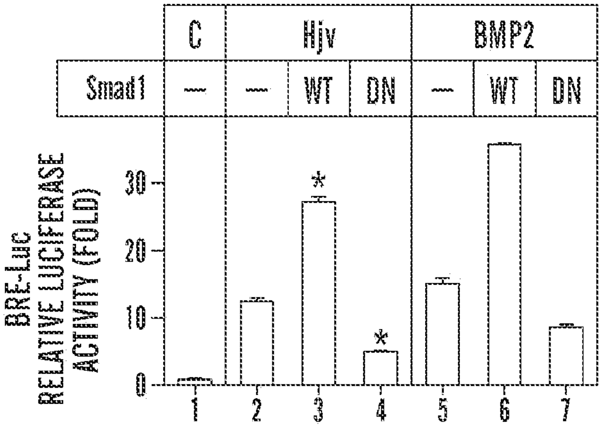
FIG. 7 shows that hemojuvelin mediates BMP signaling via BMP receptor-activated Smad1. HepG2 cells were transfected with BRE-Luc and pRL-TK without (bars 1, 5-7), or in combination with, 40 ng/ml Hjv (bars 2-4), in the absence (bars 1, 2, 5) or presence of 200 ng/ml cDNA encoding wild-type (WT, bars 3, 6) or dominant negative (DN) Smad1 (bars 4, 7). Transfected cells were incubated in the absence (bars 1-4) or presence of 25 ng/ml BMP-2 (bars 5-7) for 16 hours. Cell lysates were analyzed for luciferase activity as in FIGS. 3A-3C. Results are reported as the mean+/−standard deviation (n=2 in each group; * $P<0.05$ compared to cells transfected with Hjv alone (bar 2): bar 3 compared to bar 2 P=0.002, bar 4 compared to bar 2 P=0.0024).

Next, the inventors tested whether hemojuvelin mediates BMP signaling via the classical BMP signaling pathway involving BMP receptor-activated Smad1 using our luciferase assay system. Coexpression of wild-type Smad1 and Hjv further augmented the BRE luciferase activity induced by Hjv alone, whereas coexpression of dominant-negative Smad1 (with deleted phosphoacceptor residues 24, 25, 35, 36) and Hjv blocked the BRE luciferase activity induced by Hjv alone (FIG. 7) (Samad et al., J. Biol. Chem. 280, 14122-14129 (2005); Babitt et al., J. Biol. Chem. 280, 29820-29827 (2005); Macias-Silva et al., J. Biol. Chem. 273, 25628-25636 (1998); Piscione et al., Am. J. Physiol. Renal Physiol. 280, F19-F33 (2001)). Wild-type and dominant-negative Smad1 had similar effects on exogenous BMP-2 stimulation (FIG. 7). Thus, hemojuvelin mediates BMP signaling via the classical BMP signaling pathway that involves BMP receptor-activated Smad1.

Example 2

Hemojuvelin Mutants have Impaired BMP Signaling Ability

Figure 8B:
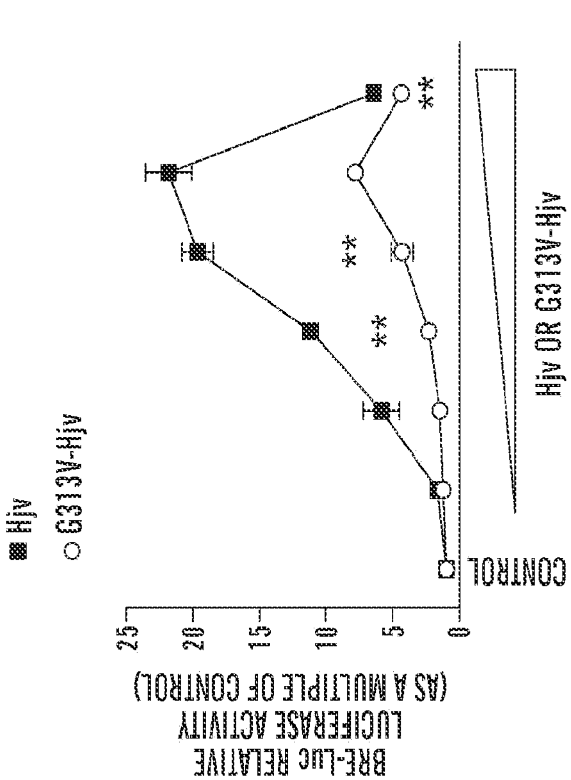
FIGS. 8A-8D show that hemojuvelin mutants associated with hemochromatosis have impaired BMP signaling ability.
Figure 8A:
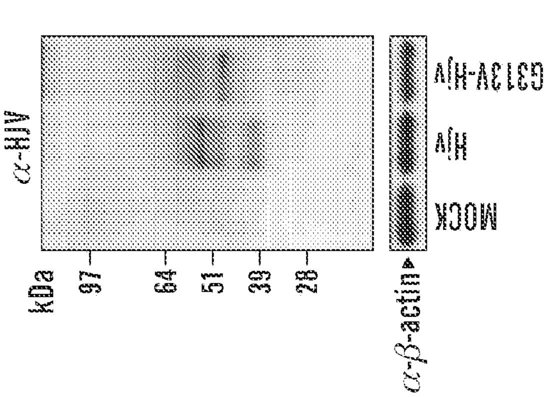

A common mutation in HFE2 that results in juvenile hemochromatosis is a point mutation substituting valine for glycine at amino acid 320 (corresponding to amino acid 313 in mouse hemojuvelin) (Papanikolaou et al., Nat. Genet. 36, 77-82 (2004); Lanzara et al., Blood 103, 4317-4321 (2004); Lee et al., Blood 103, 4669-4671 (2004)). The inventors generated cDNA encoding the equivalent mouse mutation, G313V-Hjv, and investigated whether this mutant had an altered ability to mediate BMP signaling. Using CHO cells, which lack native hemojuvelin and efficiently express transfected proteins, the inventors first demonstrated that G313V-Hjv was expressed by protein blot using an antibody to hemojuvelin (α-HJV, FIG. 8A). G313V-Hjv migrated with a different pattern than wild-type Hjv, suggesting that it may be processed differently, at least in this cell type (FIG. 8A). The inventors then examined the ability of G313V-Hjv versus wild-type Hjv to enhance endogenous BMP signaling in HepG2 cells. Hjv increased BRE luciferase activity in a dose-dependent fashion up to 23-fold (FIG. 8B). In contrast, G313V-Hjv was able to stimulate BRE luciferase activity to a maximum of only eightfold (FIG. 8B). The inventors found similar results in Hep3B cells (data not shown).

Figure 8C:
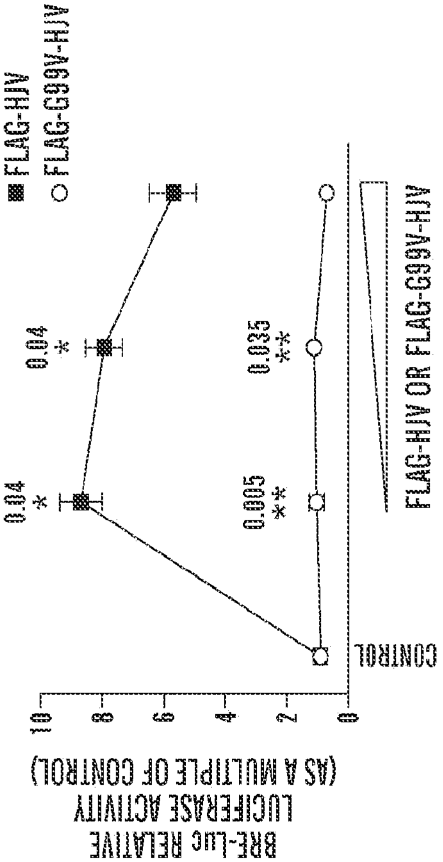
Figure 8D:
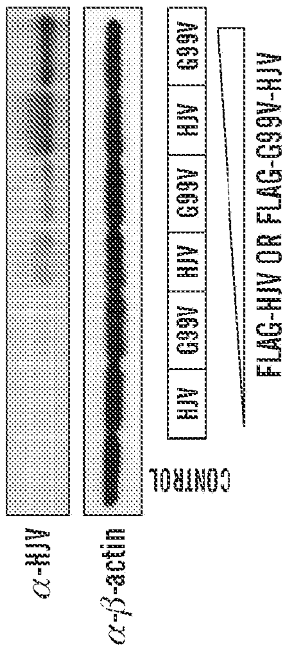

Although Hjv and G313V-Hjv were expressed at approximately equivalent levels in CHO cells, the inventors could not detect expression of these proteins by protein blot in HepG2 or Hep3B cells, presumably owing to low expression efficiency or the sensitivity of our antibody. The inventors therefore generated cDNA encoding Flag-tagged human hemojuvelin (Flag-HJV), replacing the signal peptide of native hemojuvelin with that from preprotrypsin and adding a Flag tag to the N-terminus. The inventors also used this construct to generate cDNA encoding Flag-G99V-HJV, containing a valine-for-glycine substitution at amino acid 99, another hemojuvelin mutation associated with juvenile hemochromatosis Like wild-type mouse hemojuvelin (Hjv), Flag-HJV was able to stimulate BRE luciferase activity (FIG. 8C) in Hep3B cells. In contrast, mutant Flag-G99V-HJV had a significantly reduced ability to stimulate BRE luciferase activity compared with Flag-HJV (FIG. 8C). The inventors saw similar results in HepG2 cells (data not shown). Protein blot using α-HJV (FIG. 8D) and antibody to Flag (data not shown) showed that Flag-HJV and Flag-G99V-HJV had similar expression levels in Hep3B cells.

Figure 9:
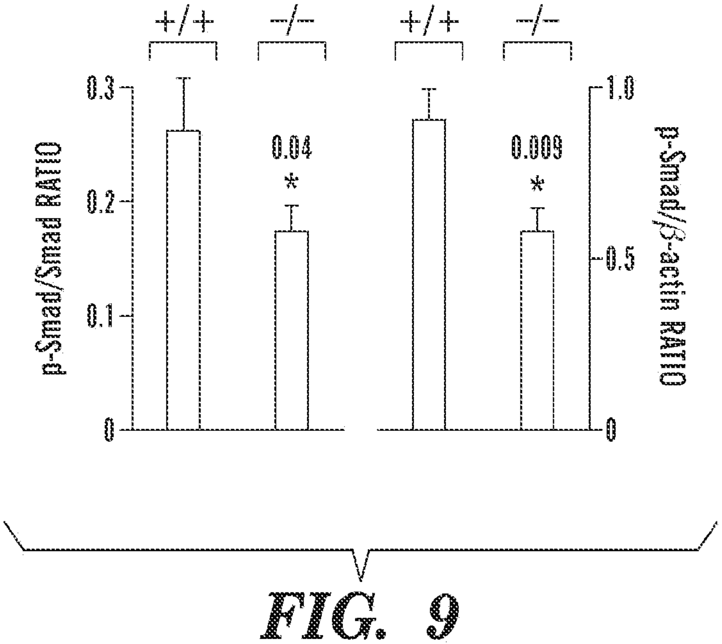
FIG. 9 shows that $Hfe2^{-/-}$ livers show decreased basal BMP signaling compared with wild-type livers. Liver lysates from wild-type (+/+) or $Hfe2^{-/-}$ mice (−/−) were analyzed by protein blot with antibody to phosphorylated Smad1/5/8. Blots were stripped and reprobed with antibody to Smad1 and antibody to β-actin as loading controls. Chemiluminescence was quantified using IPLab Spectrum software to calculate the ratio (mean±s.d.) of phosphorylated Smad1/5/8 (p-Smad) relative to total Smad1 (left) and relative to β-actin (right). n=3 in each group; * $P<0.05$ for livers from $Hfe2^{-/-}$ mice compared with wild-type mice.

$Hfe2^{-/-}$ mice mirror the iron overload phenotype seen in juvenile hemochromatosis (Huang et al., J. Clin. Invest. 115, 2187-2191 (2005)). To further support a physiologic role for hemojuvelin in BMP signaling in liver cells in vivo, the inventors assayed liver lysates from wild-type and $Hfe2^{-/-}$ mice for phosphorylated Smad1, Smad5 and Smad8 (Smad1/5/8) by protein blot as an indicator of basal BMP signaling. The inventors quantified chemiluminescence and normalized results to total Smad1 and β-actin as loading controls. $Hfe2^{-/-}$ livers had significantly lower levels of basal phosphorylated Smad1/5/8 than wild-type livers (FIG. 9).

Collectively, these findings demonstrate that mutations in hemojuvelin, the equivalent of which in humans cause juvenile hemochromatosis, result in decreased BMP signaling in liver cells. Furthermore, the absence of hemojuvelin in $Hfe2^{-/-}$ mouse livers results in reduced BMP signaling. This raises the possibility of a link between hemojuvelin's BMP signaling ability and its role in iron metabolism.

Example 3

Hemojuvelin Increases Hepcidin Expression in Liver Cells

Figure 10B:
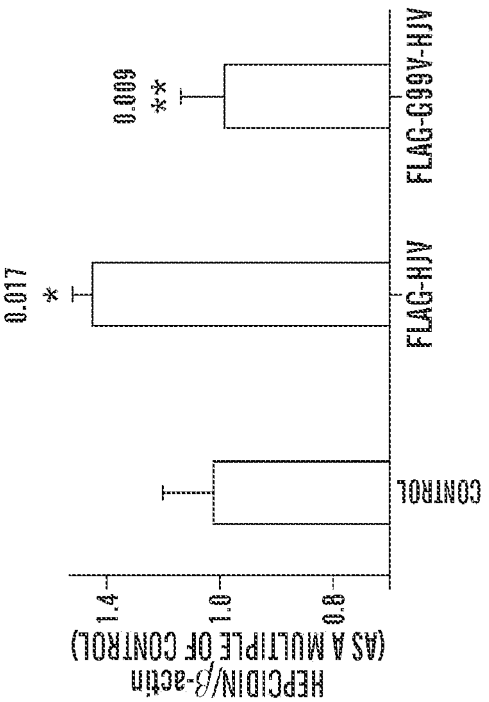
FIGS. 10A-10D show that hemojuvelin positively regulates hepcidin mRNA expression.
Figure 10A:
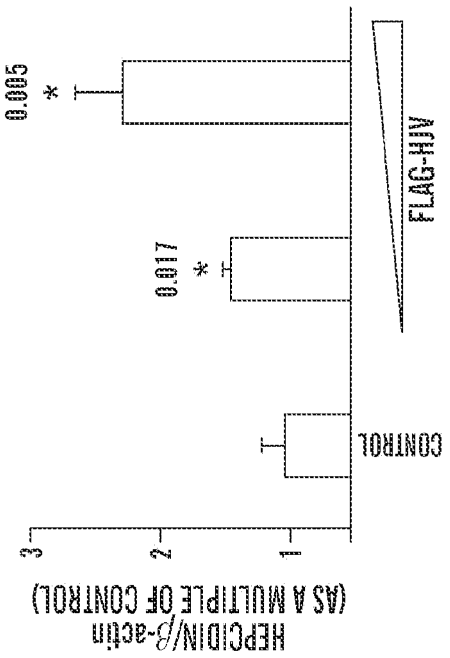

It has been hypothesized that hemojuvelin positively regulates hepcidin expression and that iron overload in individuals with HFE2 mutations is due to reduced hepcidin levels and consequent ferroportin overexpression (Papanikolaou et al., Nat. Genet. 36, 77-82 (2004), Huang et al., J. Clin. Invest. 115, 2187-2191 (2005); Niederkofler et al., J. Clin. Invest. 115, 2180-2186 (2005); Lin et al., Blood 106, 2884-2889 (2005)19-21). The inventors therefore used quantitative real-time PCR to directly test whether transfection of cDNA encoding hemojuvelin into liver cells upregulates hepcidin mRNA expression and whether hemojuvelin mutants have an altered ability to upregulate hepcidin expression. Flag-HJV significantly increased hepcidin mRNA expression in a dose-dependent fashion in Hep3B cells (FIG. 10A). By contrast, mutant Flag-G99V-HJV had an impaired ability to increase the hepcidin expression compared with Flag-HJV (FIG. 10B).

Figure 10D:
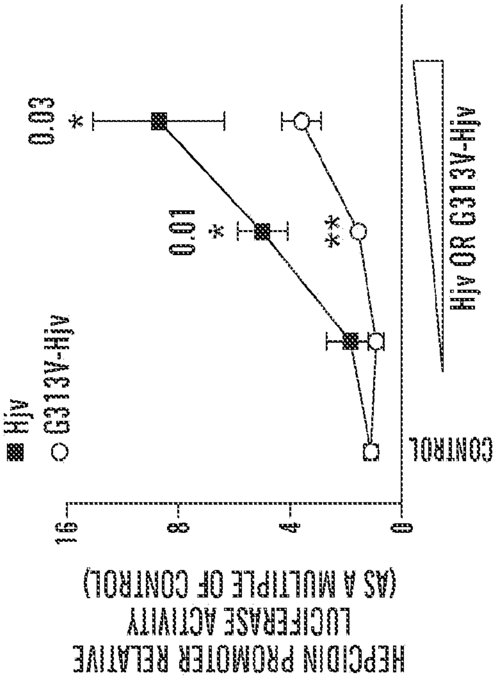
Figure 10C:
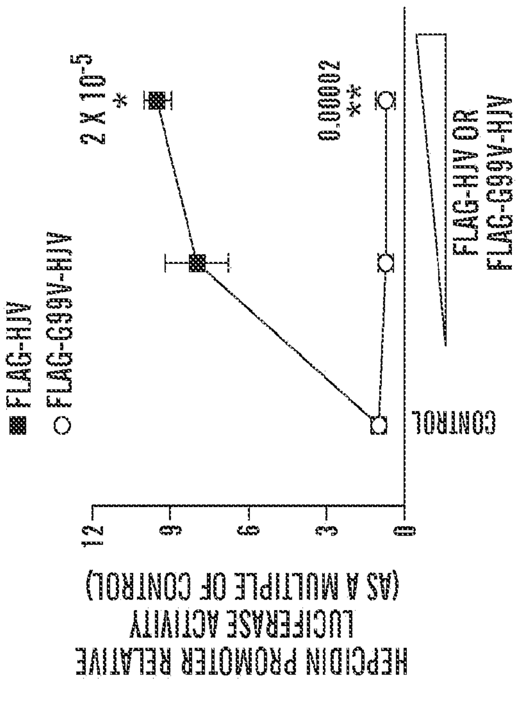

As the sensitivity of this assay is limited by transfection efficiency, the inventors also examined the relative ability of wild-type Hjv or Flag-HJV versus mutant G313V-Hjv or Flag-G99V-HJV to activate the hepcidin promoter using a dual luciferase assay. The inventors transfected Hep3B cells with a hepcidin promoter/firefly luciferase construct and a *Renilla* luciferase vector. The inventors calculated relative luciferase activity as the ratio of firefly luciferase activity to *Renilla* luciferase activity, to control for transfection efficiency. Coexpression with Flag-HJV (FIG. 10C) or Hjv (FIG. 10D) significantly increased hepcidin promoter relative luciferase activity compared with cells not transfected with hemojuvelin, consistent with the findings by real-time PCR. Furthermore, mutant Flag-G99V-HJV (FIG. 10C) and G313V-Hjv (FIG. 10D) had a significantly impaired ability to activate hepcidin promoter luciferase activity compared with Flag-HJV and Hjv.

Example 4

BMP-2 Increases Hepcidin Expression in Liver Cells

Figure 11B:
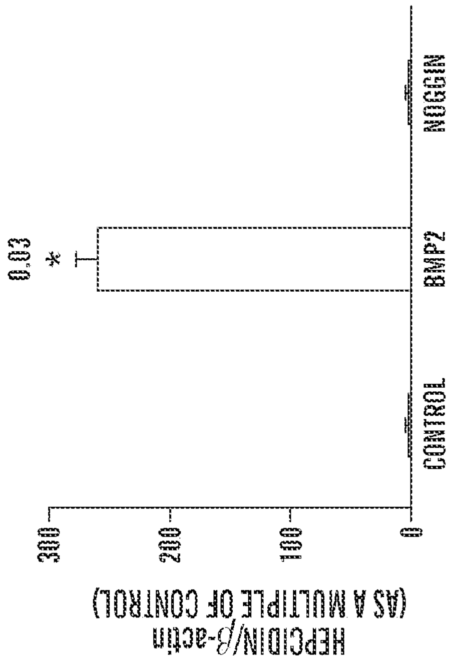
FIGS. 11A-11D show that BMP-2 positively regulates hepcidin mRNA expression.
Figure 11A:
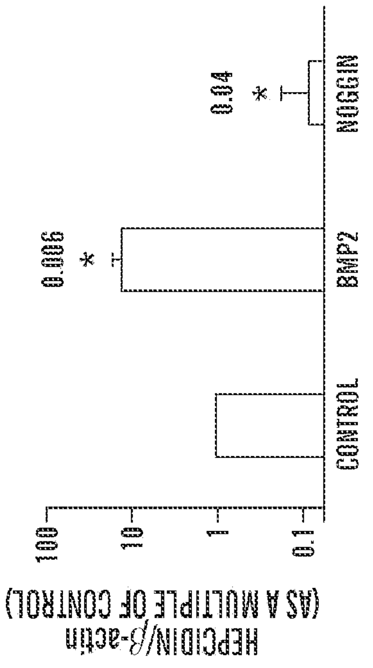
Figure 11C:
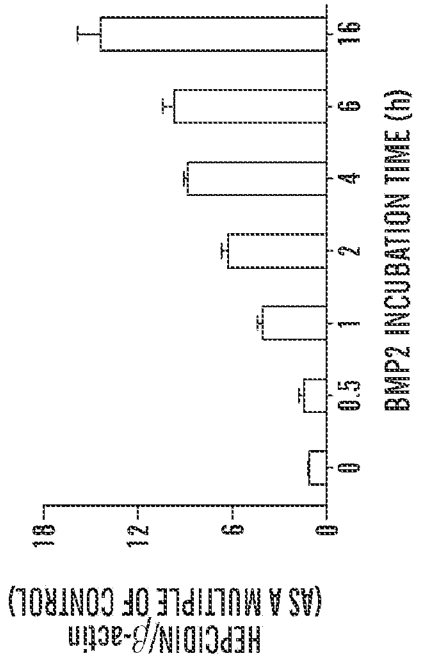

The inventors then investigated whether hemojuvelin's BMP signaling ability might be the mechanism by which hemojuvelin regulates hepcidin expression in liver cells. The inventors performed quantitative real-time PCR to test for hepcidin mRNA expression in HepG2 (FIG. 11A) or Hep3B cells (FIG. 11B) after no treatment, stimulation with exogenous BMP-2 or incubation with exogenous noggin. Exogenous BMP-2 significantly increased the hepcidin/β-actin mRNA ratio by 12-fold in HepG2 cells (FIG. 11A) and by 260-fold in Hep3B cells (FIG. 11B). The hepcidin/β-actin ratio began to increase 0.5 to 1 h after addition of exogenous BMP-2 (FIG. 11C). In contrast, inhibition of endogenous BMP signaling with noggin significantly decreased the hepcidin/β-actin ratio 12-fold below baseline in HepG2 cells (FIG. 11A), although the inventors did not see any inhibition in Hep3B cells (FIG. 11B), in which basal hepcidin mRNA levels were much lower (data not shown). These changes were predominantly due to alterations in hepcidin mRNA levels, as bactin mRNA expression varied up to only 1.6-fold over all experiments (data not shown). Thus, BMP-2 positively regulates hepcidin expression in liver cells.

Figure 11D:
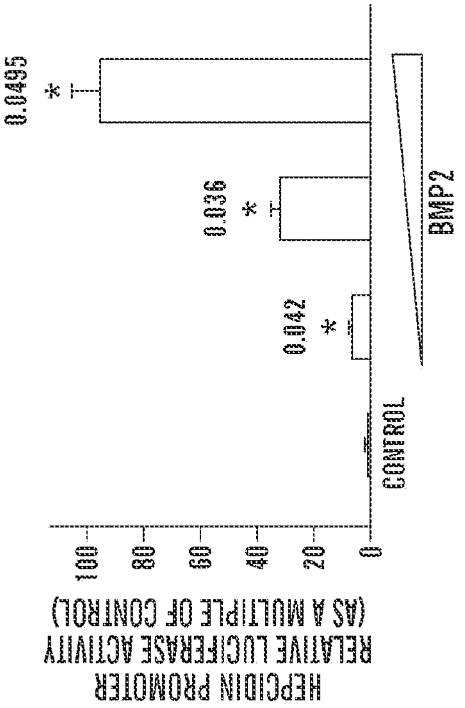
Figure 13:
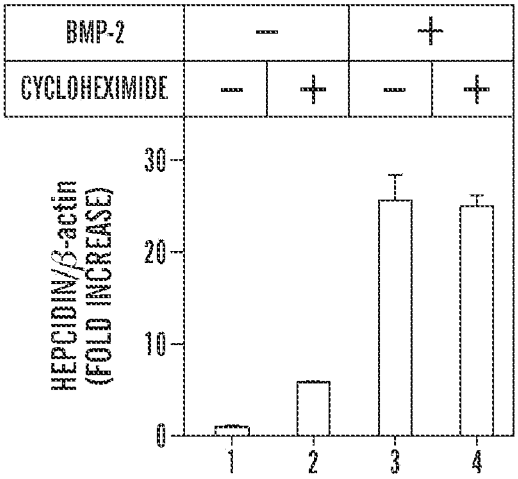
FIG. 13 shows that BMP-2 regulation of hepcidin expression is not affected by cycloheximide. HepG2 cells were incubated without (Control) or with 10 μg/ml cycloheximide for 30 minutes followed by incubation without or with 50 ng/ml BMP-2 for 6 hours as indicated. Quantitative real-time PCR for hepcidin and β-actin were performed as described in FIGS. 10A-10D. Results are reported as the mean+/−standard deviation (n=2 in each group).

Examination of the hepcidin promoter demonstrated several potential BMP responsive elements (FIG. 12), suggesting that hemojuvelin might regulate hepcidin expression directly at the transcriptional level. The inventors therefore tested the ability of cycloheximide, an inhibitor of de novo protein synthesis, to inhibit BMP-2 induction of hepcidin mRNA expression using quantitative real-time PCR, and the inventors tested the ability of BMP-2 to activate the hepcidin promoter using the hepcidin promoter luciferase construct. Cycloheximide had no effect on BMP-2 induction of hepcidin expression (FIG. 13), suggesting that de novo protein synthesis is not required for BMP-2 regulation of hepcidin levels. Exogenous BMP-2 increased hepcidin promoter luciferase activity in a dose-dependent fashion up to 100-fold, suggesting that BMP-2 increases transcription of hepcidin mRNA (FIG. 11D). The inventors saw similar results in HepG2 cells, although the degree of stimulation was lower (data not shown). Thus, BMP-2 directly upregulates transcription of hepcidin mRNA.

Example 5

Hepcidin Induction by BMP-2 is Enhanced by Hemojuvelin

Figure 14B:
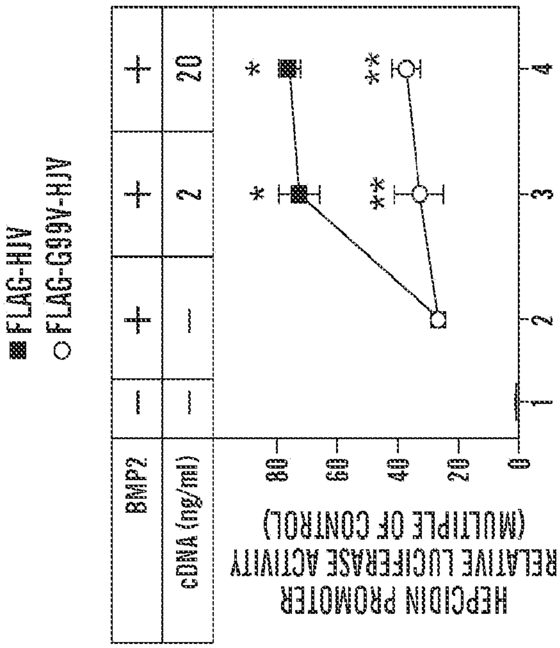
FIGS. 14A-14D show that hepcidin induction by BMP-2 is enhanced by hemojuvelin and blunted in $Hfe2^{-/-}$ hepatocytes.
Figure 14A:
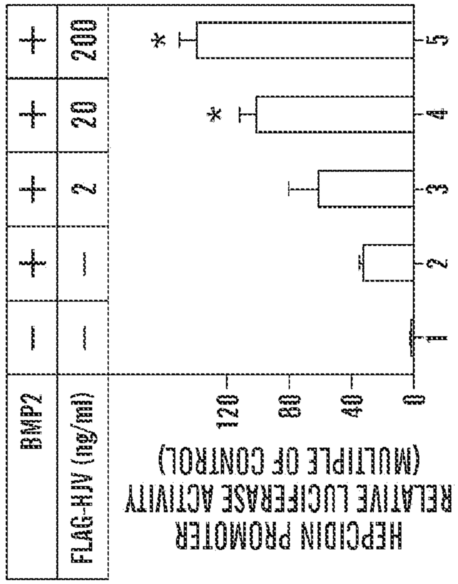
Figure 14C:
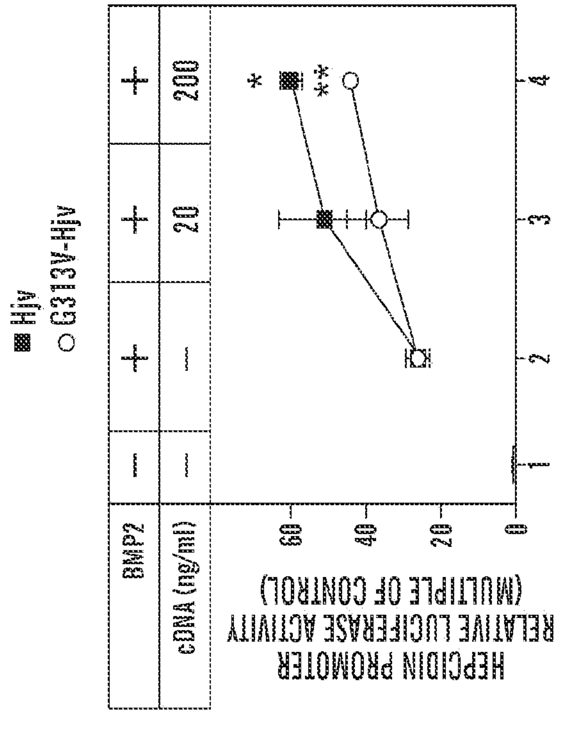

As hemojuvelin enhances cellular responses to BMP-2, and BMP-2 positively regulates hepcidin expression, the inventors tested whether hemojuvelin enhances the upregulation of hepcidin expression by BMP-2. Coexpression of the hepcidin promoter luciferase construct with Flag-HJV or Hjv increased hepcidin promoter luciferase activity in response to a fixed dose of BMP-2 (FIGS. 14A-14C). In contrast, coexpression of the hepcidin promoter luciferase construct with mutant Flag-G99V-HJV or G313V-Hjv resulted in significantly less activation of the hepcidin promoter in response to BMP-2 compared with the results of coexpression with Flag-HJV or Hjv (FIGS. 14B and 14C).

Figure 14D:
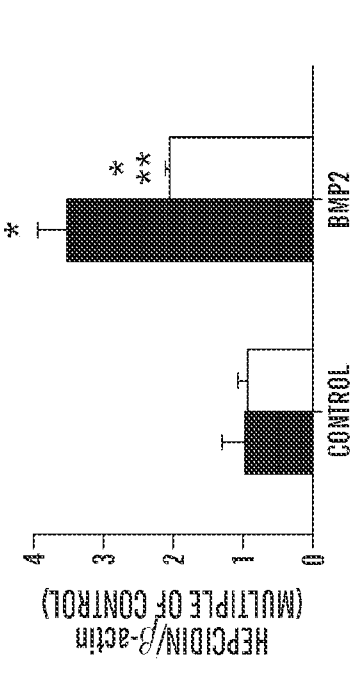

Next, the inventors tested whether liver cells lacking hemojuvelin had impaired induction of hepcidin expression in response to BMP-2. The inventors incubated primary hepatocyte cultures from wild-type ($Hfe2^{+/+}$) or $Hfe2^{-/-}$ mice with or without exogenous BMP-2 and then assayed for hepcidin mRNA by RNA blot. Consistent with our results in HepG2 and Hep3B cells (FIGS. 11A-11D), BMP-2 increased hepcidin mRNA expression in wild-type primary hepatocytes. In contrast, although BMP-2 was able to increase hepcidin mRNA expression to some extent in $Hfe2^{-/-}$ hepatocytes, the response was significantly blunted compared with wild-type hepatocytes (FIG. 14D). Hemojuvelin therefore enhances hepcidin induction in response to BMP-2, although hemojuvelin does not seem absolutely necessary to generate cellular responses to BMP-2.

Example 6

Selective Regulation of Hepcidin by BMP/TGF-β Superfamily Members

Figure 15A:
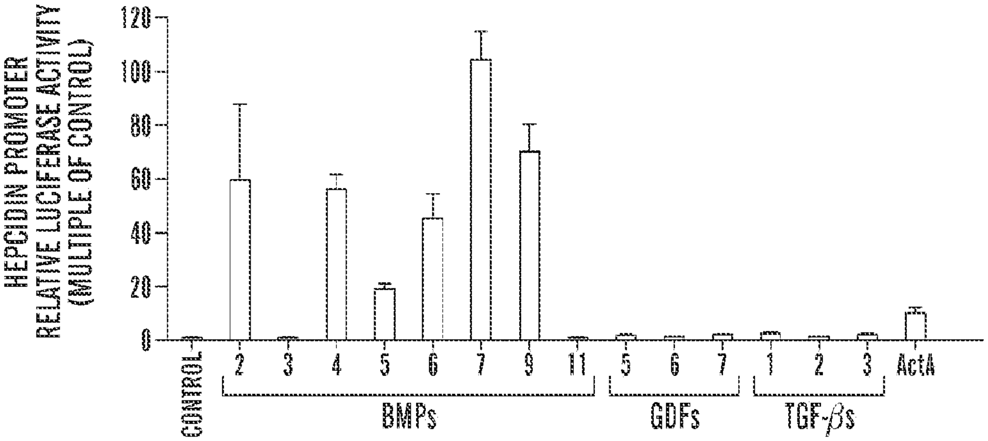
FIGS. 15A and 15B show induction of hepcidin expression by TGF-β/BMP superfamily ligands.
Figure 15B:
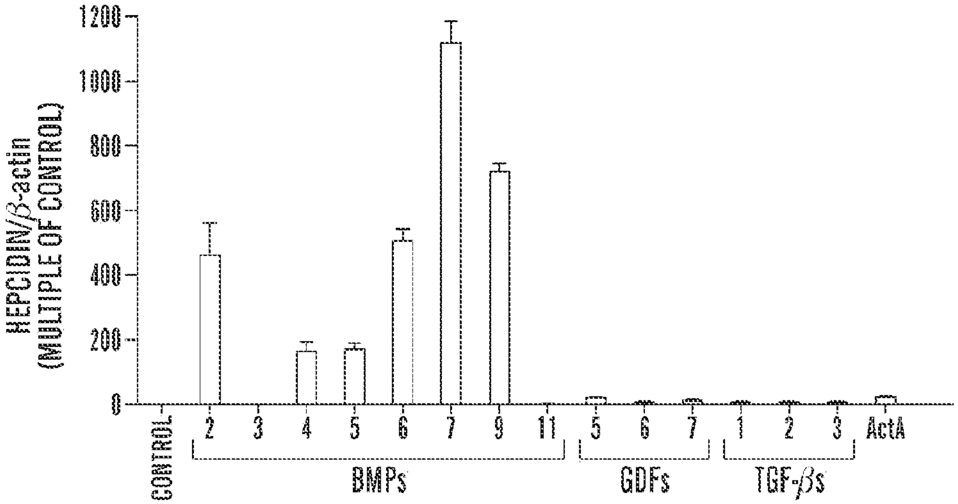

TGF-β superfamily members were tested for their ability to regulate hepcidin using both a hepcidin promoter reporter assay (FIG. 15A) and quantitative real-time RT-PCR (FIG. 15B) in Hep3B hepatoma-derived cells. Relative concentrations of BMP/TGF-β superfamily ligands used are similar to those previously used by others to compare responses among superfamily ligands (Wang et al., 2005. Cell Metab. 2:399-409, Korchynskyi et al., 2002. J. Biol. Chem. 277:4883-4891, Dennler et al., 1998. EMBO J. 17:3091-3100). BMP-2, BMP-4, BMP-5, BMP-6, BMP-7, and BMP-9 robustly increased hepcidin promoter luciferase activity 20-100-fold over baseline and increased hepcidin mRNA expression by 160-1100-fold. In contrast, TGF-β1, -β2, and -β3 increased hepcidin expression by only 1.5-3-fold over baseline by both methods. BMP-3, BMP-11, GDF-5, GDF-6, and GDF-7 showed no or comparatively small hepcidin induction by both methods. ActivinA increased hepcidin promoter relative luciferase activity by 10-fold, but increased hepcidin mRNA expression by real-time RT-PCR to a comparatively lesser extent relative to BMP-2, -4, -5, -6, -7 and -9. Biologic activity of all ligands was verified by luciferase assay using BMP-responsive (BRELuc, Wang et al., Cell Metab. 2, 399-409 (2005)) and TGF-β/Activin responsive (CAGA-Luc, Korchynskyi et al., J. Biol. Chem. 277, 4883-4891 (2002)) luciferase reporters. Results using both methods correlated well with each other, suggesting that the hepcidin promoter luciferase assay is a good surrogate for hepcidin mRNA expression by quantitative real-time RT-PCR. Thus, many TGF-β superfamily members can positively regulate hepcidin expression in vitro; however, BMP-2, BMP-4, BMP-5, BMP-6, BMP-7, and BMP-9 are much more potent regulators of hepcidin compared with other superfamily members, including all three TGF-β ligands.

Example 7

Figure 16A:
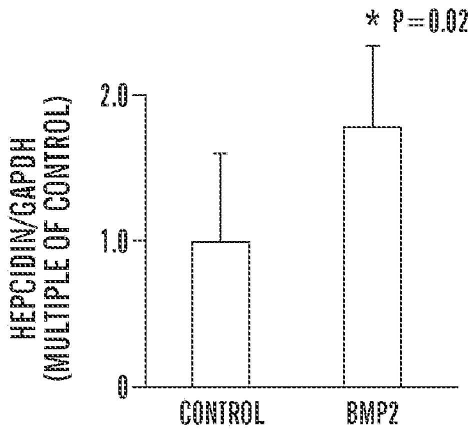
FIGS. 16A and 16B show that BMP-2 administration in mice increases hepcidin mRNA expression and decreases serum iron. 12956/SvEvTac mice were injected retro-orbitally with 1 mg/kg BMP-2 (n=8) or an equal volume of vehicle alone (n=7). Four hours after injection, blood and livers were harvested.
Figure 16B:
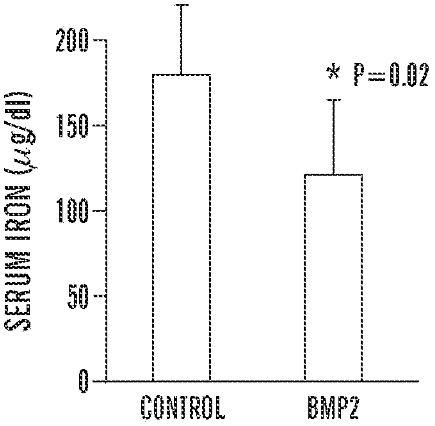

BMP-2 Administration In Vivo Increases Hepcidin Expression and Decreases Serum Iron Next, the inventors investigated whether BMP-2 regulates hepcidin expression and iron metabolism in vivo. Purified BMP-2 at 1 mg/kg was injected retro-orbitally into mice, followed by determination of serum iron levels and hepatic hepcidin mRNA expression four hours after injection. BMP-2 administration increased hepatic hepcidin mRNA expression 1.8-fold over mice injected with vehicle alone (FIG. 16A, * P=0.02). BMP-2 administration also decreased serum iron levels from 170 μg/dl to 114 μg/dl (FIG. 16B, * P=0.02). This is consistent with a role for BMP-2 as a positive regulator of hepcidin expression in vivo.

Example 8

Soluble HJV.Fc Selectively Inhibits BMP Signaling In Vitro

Figure 17A:
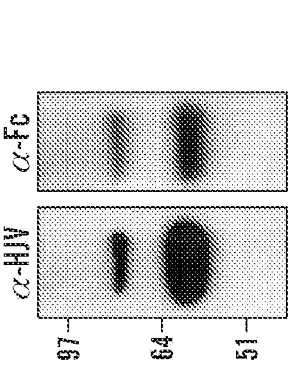
FIGS. 17A-17D show that soluble HJV.Fc inhibits basal hepcidin expression and selectively inhibits BMP induction of hepcidin expression.
Figure 17B:
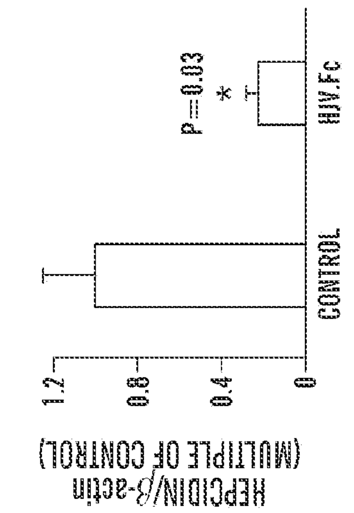
Figure 17C:
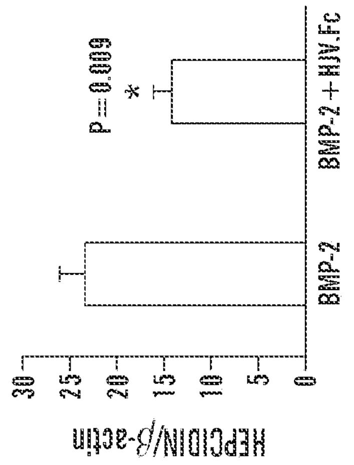
Figure 17D:
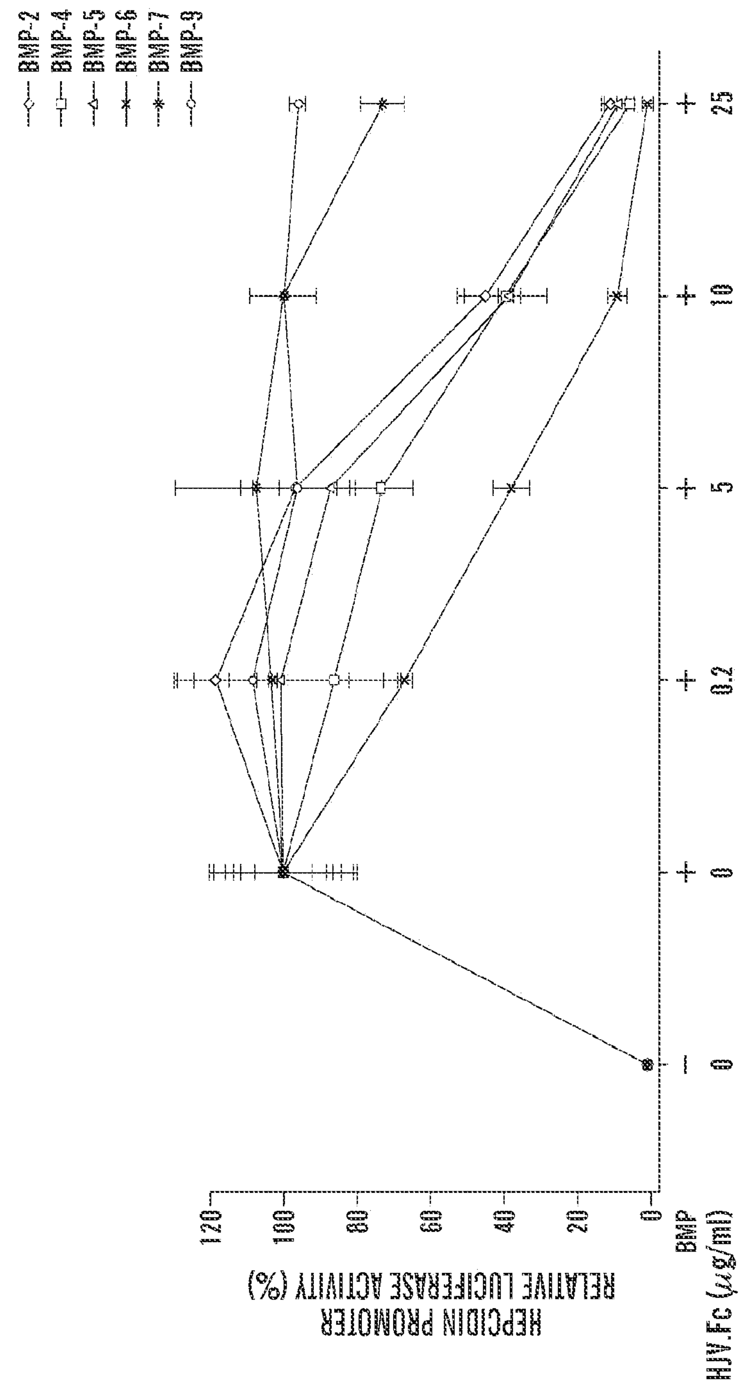

Soluble receptors, such as the soluble TNF receptor etanercept, have been used to inhibit ligand activity in vitro and in vivo, presumably by binding to ligands and preventing their interaction with membrane bound receptors (Moreland et al., 1997. N. Engl. J. Med. 337:141-147). Interestingly, soluble hemojuvelin has been detected in human sera and has been shown to inhibit hepcidin expression in cultured cells, although the mechanism for this inhibition was not investigated (Lin et al., 2005. Blood. 106:2884-2889). The inventors therefore generated purified soluble human hemojuvelin fused to the Fc portion of immunoglobulin (HJV.Fc) (FIG. 17A), the murine homologue of which can bind to BMP-2 and BMP-4 ligands. The inventors then investigated whether HJV.Fc inhibited basal hepcidin expression and BMP induction of hepcidin expression in vitro. Using hepatoma-derived HepG2 cells, which have higher basal hepcidin expression, HJV.Fc inhibited basal hepcidin mRNA expression by 80% (FIG. 17B * P=0.03). These results are consistent with prior reports using soluble hemojuvelin without an Fc fusion (Lin et al., 2005. Blood. 106:2884-2889), suggesting that the Fc domain does not affect the function of soluble hemojuvelin. HJV.Fc also inhibited BMP-2 induction of hepcidin expression (FIG. 17C, P=0.009) and BMP-2 induced activation of the hepcidin promoter in a dose-dependent fashion (FIG. 17D, blue line). HJV.Fc inhibition of BMP ligands was selective; HJV.Fc inhibited more than 90% of hepcidin promoter activation induced by BMP-2, -4, -5, and -6, but did not inhibit BMP-9 even at lower ligand concentrations (FIG. 17D). There was a trend toward low-level inhibition of BMP-7 (FIG. 17D).

Figure 18A:
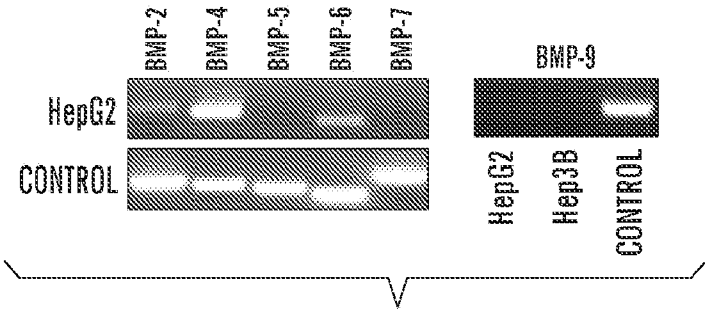
FIGS. 18A-18C show siRNA inhibition of endogenous BMP ligands decreases basal hepcidin expression.
Figure 18B:
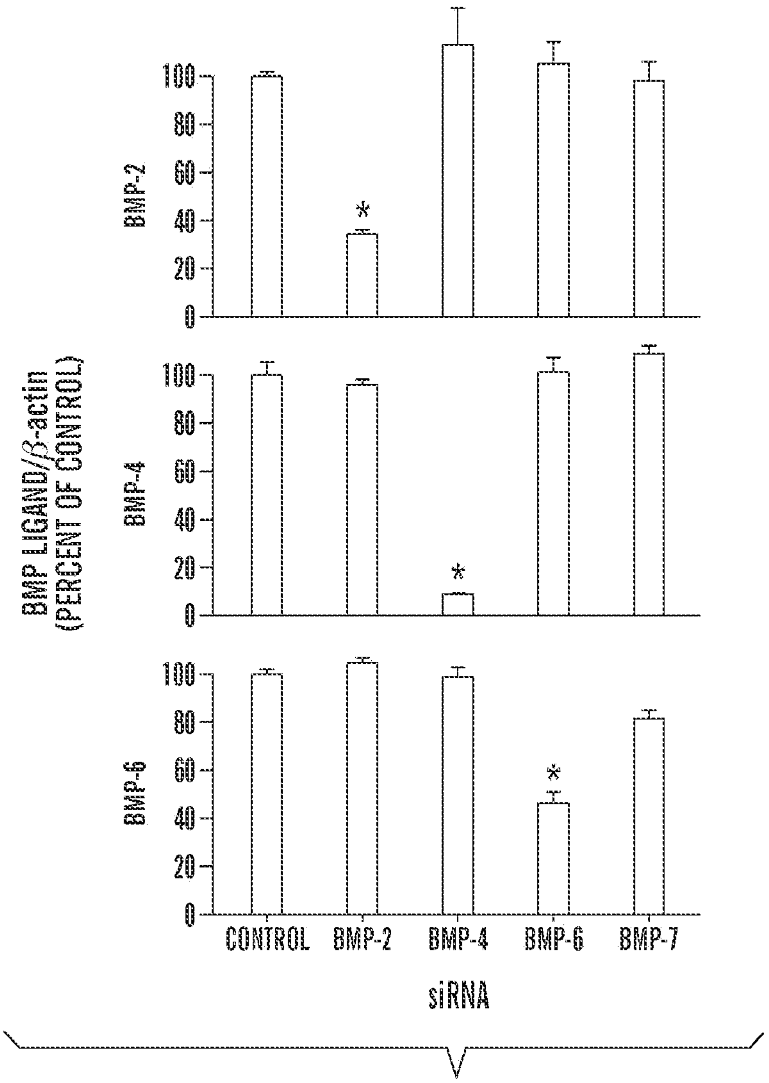
Figure 18C:
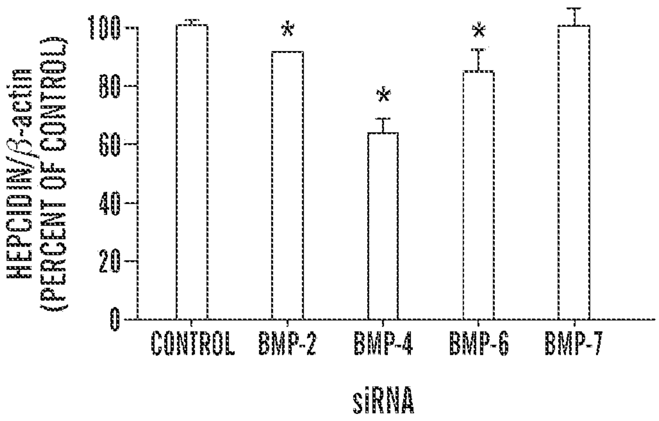

BMP-2 and BMP-4 are endogenously expressed in HepG2 cells. To test whether inhibition of these endogenous BMP ligands was the mechanism by which HJV.Fc decreased basal hepcidin expression in HepG2 cells, the inventors sought to determine if other BMP ligands are endogenously expressed in HepG2 using RT-PCR. The inventors then tested whether siRNA inhibition of these endogenously expressed BMP ligands inhibited basal hepcidin expression in a manner similar to HJV.Fc. BMP-2, BMP-4, and BMP-6 were endogenously expressed in HepG2 cells, with BMP-4 being the most abundant (FIG. 18A). BMP-2, BMP-4, and BMP-6 siRNA each selectively and significantly reduced endogenous ligand expression in HepG2 cells by 65%, 90%, and 55% respectively as measured by real-time RT-PCR (FIG. 18B). BMP-2, BMP-4, and BMP-6 siRNA each significantly inhibited basal hepcidin expression in HepG2 cells by approximately 10% (P=0.012), 35% (P=0 0027), and 15% (P=0.0026) respectively as measured by real-time RT-PCR (FIG. 18C). As a negative control, neither a Control siRNA nor a BMP-7 specific siRNA inhibited basal hepcidin expression. The relative ability of each ligand to inhibit basal hepcidin correlated with the relative mRNA abundance of the ligand and the strength of siRNA inhibition of ligand expression. Endogenous BMP-2, BMP-4, and BMP-6 ligands all may therefore contribute to basal hepcidin expression in HepG2 cells. These data are consistent with HJV.Fc inhibiting basal hepcidin expression by inhibiting endogenous BMP signaling, which may occur by binding and sequestering endogenously produced BMP ligands and preventing their interaction with BMP type I and type II receptors.

Example 9

Figure 19A:
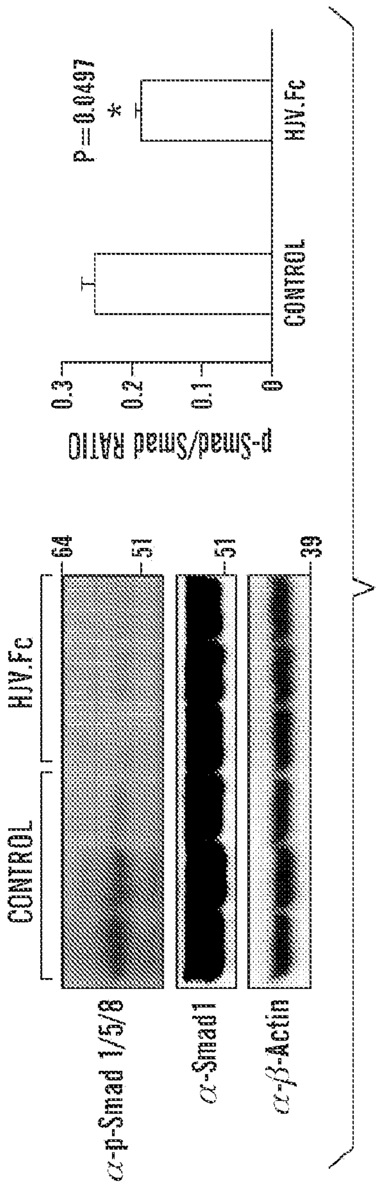
FIGS. 19A-19G show soluble HJV.Fc administration in mice decreases hepatic phosphorylated Smad1/5/8 expression, decreases hepcidin expression, increases serum iron, increases liver iron content, and decreases spleen iron content. 129S6/SvEvTac mice received an intraperitoneal injection of 25 mg/kg HJV.Fc or normal saline (Control) three times weekly for three weeks.
Figure 19B:
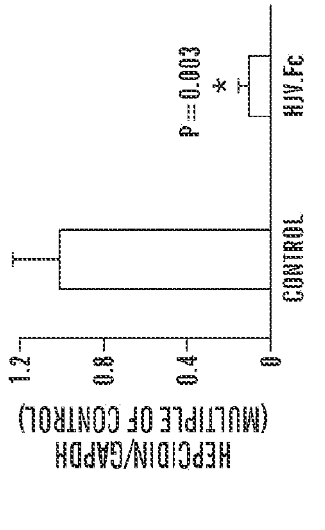
Figure 19C:
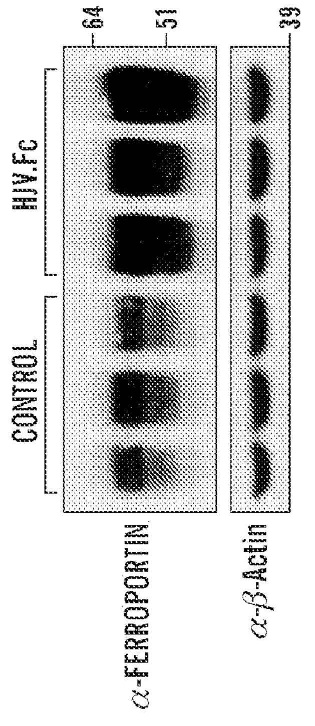
Figure 19D:
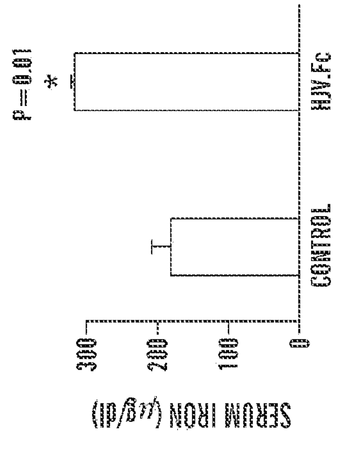
Figure 19E:
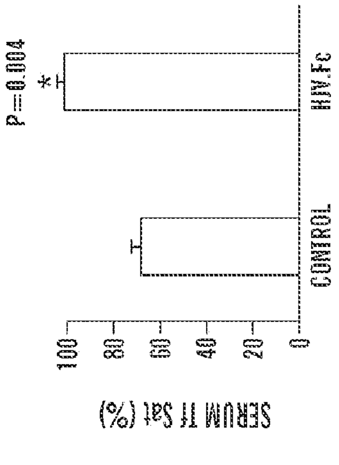
Figure 19F:
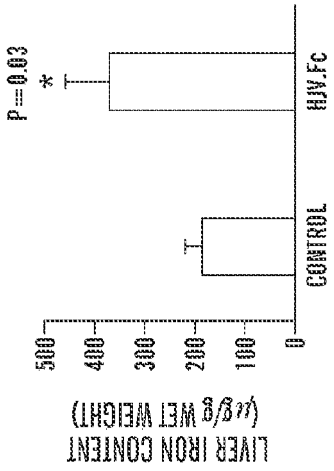
Figure 19G:
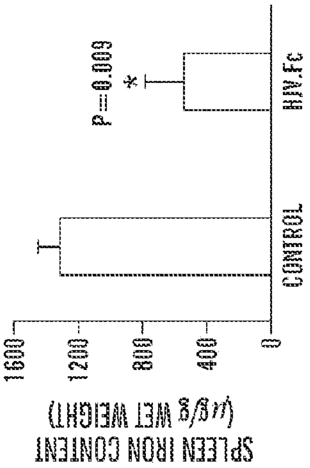

Soluble HJV.Fc Inhibits Hepatic BMP Signaling, Inhibits Hepcidin Expression, Increases Ferroportin Expression, Mobilizes Reticuloendothelial Cell Iron Stores, and Increases Serum Iron In Vivo To test whether HJV.Fc administration could regulate hepcidin expression and iron metabolism in vivo, mice were injected with 25 mg/kg purified HJV.Fc or an equal volume of normal saline by intraperitoneal injection three times weekly for three weeks. Western blot analysis of liver lysates from these mice showed decreased phosphorylated Smad1/5/8 expression relative to total Smad1 expression in HJV.Fc treated mice compared with control mice (FIG. 19A, * P=0.0497), demonstrating that HJV.Fc decreases hepatic BMP signaling in vivo. Quantitative real-time RT-PCR analysis revealed a 10-fold decrease in hepatic hepcidin mRNA expression in HJV.Fc treated mice compared with control mice (FIG. 19B, * P=0.003). Consistent with the predicted effects of depressed hepcidin levels to increase ferroportin cell-surface expression, increase intestinal iron absorption, and increase release of iron from reticuloendothelial stores, HJV.Fc treatment increased ferroportin expression in the spleen compared with control mice as measured by Western blot (FIG. 19C). HJV.Fc treatment also increased serum iron levels from 177+/−26 μg/dl to 309+/−2 μg/dl (FIG. 19D, * P=0.01) and increased serum transferrin saturation from 70% to 100% (FIG. 19E, * P=0.004). Furthermore, HJV.Fc treatment increased hepatic tissue iron content by approximately 2-fold (FIG. 19F, * P=0.03) and reduced splenic tissue iron content by almost 60% (FIG. 19G, * P=0.009). The inventors also determined that mice injected with 5 mg/kg purified HJV.Fc or an equal volume of normal saline by intraperitoneal injection three times weekly for three weeks demonstrated about a 2-fold increase in serum iron with 5 mg/kg as compared with the saline control (FIG. 22A), and also increased serum transferrin saturation from about 60% to about 85% (FIG. 22B), demonstrating that administration of soluble HJV is effective at increasing serum iron concentrations and serum transferrin saturation in vivo at a wide range of doses, for example from about 0.1 mg/kg to about 50 mg/kg, such as from 1 mg/kg to 25 mg/kg or higher.

Example 10

Soluble HJV.Fc Inhibits IL-6 Induction of Hepcidin Expression

Figure 20:
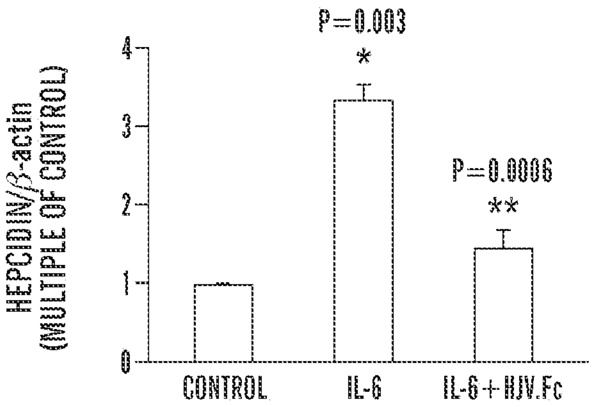
FIG. 20 shows that soluble HJV.Fc inhibits IL-6 induction of hepcidin expression. HepG2 cells were incubated for 16 hours under control conditions, with 100 ng/ml IL-6, or with 100 ng/ml IL-6 in combination with HJV.Fc after pre-incubation with HJV.Fc for 1 hour as indicated. Total RNA was analyzed for hepcidin expression relative to β-actin expression by quantitative real-time RT-PCR. Results are expressed as mean+/−standard deviation, n=3 per group, * P=0.003 for IL-6 treated cells compared with Control cells, ** P=0.0006 for cells treated with HJV.Fc in combination with IL-6 compared with cells treated with IL-6 alone.

Inflammatory cytokines induce hepcidin expression, and this hepcidin excess is thought to play a role in the anemia of chronic disease (Weiss et al., 2005. N. Engl. J. Med. 352: 1011-1023; Pigeon et al., 2001. J. Biol. Chem. 276:7811-7819; Nicolas et al., 2002. J. Clin. Invest. 110:1037-1044; Nemeth et al., 2004. J. Clin. Invest. 113:1271-1276; Nemeth et al., 2003. Blood. 101:2461-2463; Lee et al., 2005. Proc. Natl. Acad. Sci. USA. 102:1906-1910). The inventors therefore investigated whether HJV.Fc could inhibit hepcidin induction by the inflammatory cytokine IL-6. IL-6 increased hepcidin expression 3.3-fold in HepG2 cells as measured by real-time RT-PCR (FIG. 20, *P=0.003). Hepcidin induction by IL-6 was significantly abrogated when cells were incubated with HJV.Fc in combination with IL-6 (FIG. 20, **P=0.0006 compared with cells treated with IL-6 alone).

REFERENCES

All publications, patents, and patent applications mentioned in this specification are incorporated by reference to the same extent as if each individual publication or patent was specifically and individually indicated to be incorporated by reference.

What is claimed is:

1. A fusion protein comprising:

(a) a hemojuvelin (HJV) polypeptide or fragment thereof, wherein said polypeptide or fragment thereof has at least 95% amino acid sequence identity to a portion of the HJV protein of SEQ ID NOs: 2, 3 or 4 and is at least 50 amino acids in length; and (b) a first fusion partner, wherein said first fusion partner is conjugated to said HJV polypeptide or fragment thereof, wherein said first fusion partner is an IgG1 Fc; and (c) a second fusion partner.

2. The fusion protein of claim 1, wherein said first fusion partner is fused to the N-terminus or to the C-terminus of the HJV protein fragment.

3. The fusion protein of claim 1, wherein said IgG1 Fc is human IgG1 Fc.

4. The fusion protein of claim 1, wherein said IgG1 Fc is at least 95% identical to SEQ ID NO: 6.

5. The fusion protein of claim 1, wherein said HJV fragment is a soluble fragment.

6. The fusion protein of claim 1, wherein said HJV fragment lacks the C-terminal GPI anchoring domain.

7. The fusion protein of claim 1, wherein said HJV fragment lacks the N-terminal signal sequence.

8. The fusion protein of claim 1, wherein said HJV fragment lacks both the C-terminal GPI anchoring domain and the N-terminal signal sequence.

9. The fusion protein of claim 1, further comprising purification or detection tag.

10. The fusion protein of claim 9, wherein the purification or detection tag is selected from the group consisting of detectable proteins, DNA binding domains, gene activation domains, purification tags and secretion signal peptides.

11. The fusion protein of claim 1, wherein the first fusion partner is conjugated to said HJV polypeptide or fragment via a covalent bond.

12. The fusion protein of claim 11, wherein said HJV fragment lacks the N terminal signal sequence.

13. The fusion protein of claim 1, wherein the HJV polypeptide or fragment thereof is not SEQ ID NO: 62, 63 or 64.

14. The fusion protein of claim 1, wherein said fusion protein has enhanced proteolytic stability.

15. The fusion protein of claim 14, wherein said enhanced proteolytic stability is conferred by a sequence alteration at the amino acid corresponding to amino acid 172 of isoform A of human HJV.

16. The fusion protein of claim 1, wherein said fusion protein has an amino acid sequence with at least 95% identity to the sequence of SEQ ID NO: 10.

17. The fusion protein of claim 16, wherein said fusion protein has an amino acid sequence comprising the sequence of SEQ ID NO: 10.

18. The fusion protein of claim 16, wherein said fusion protein has an amino acid sequence consisting of the sequence of SEQ ID NO: 10.

19. The fusion protein of claim 1, wherein said fusion protein has an amino acid sequence with at least 95% identity to the sequence of SEQ ID NO: 7.

20. The fusion protein of claim 19, wherein said fusion protein has an amino acid sequence comprising the sequence of SEQ ID NO: 7.

21. The fusion protein of claim 1, wherein said fusion protein has an amino acid sequence with at least 95% identity to the sequence of SEQ ID NO: 1.

22. The fusion protein of claim 21, wherein said fusion protein has an amino acid sequence comprising the sequence of SEQ ID NO: 1.

23. A pharmaceutical composition comprising the fusion protein of claim 1 and a pharmaceutically acceptable carrier.

24. The fusion protein of claim 1, wherein the second fusion partner comprises a HJV polypeptide or fragment thereof, wherein wherein said polypeptide or fragment thereof has at least 95% amino acid sequence identity to a portion of the HJV protein of SEQ ID NOs. 2, 3 or 4 and is at least 50 amino acids in length fused to a polypeptide comprising an amino acid sequence 95% identical to IgG1 Fc.

25. The fusion protein of claim 24, wherein the second polypeptide or fragment is conjugated to said first fusion partner via a crosslinker.

26. The fusion protein of claim 25, wherein the crosslinker is a DSS crosslinker.

27. The fusion protein of claim 25, wherein wherein the second polypeptide or fragment is conjugated to said first fusion partner via one or more disulfide bonds.

28. The fusion protein of claim 24, wherein the IgG1 Fc is at least 95% identical to SEQ ID NO: 6.

29. The fusion protein of claim 1, further comprising a BMP-2.

30. A method for producing the fusion protein of claim 1 comprising:

(a) introducing into a cell a vector comprising a polynucleotide encoding the fusion protein operably linked to a promoter; and (b) culturing said cell under conditions where said protein is expressed.

31. The method of claim 30, further comprising purifying said protein of step (b).

32. An isolated polynucleotide encoding the fusion protein of claim 1.

33. A vector comprising the polynucleotide of claim 32.

34. The vector of claim 33, wherein the vector is a viral vector.

35. The vector of claim 34, wherein the viral vector is selected from the group consisting of an adenoviral vector, a poxvirus vector and a lentiviral vector.

36. The vector of claim 33, wherein the vector comprises a tissue- or cell-type specific promoter is a muscle or liver specific promoter.

37. A pharmaceutical composition comprising the vector of claim 33 and a pharmaceutically acceptable carrier.

38. An isolated host cell comprising the vector of claim 33.

* * * * *

UNITED STATES PATENT AND TRADEMARK OFFICE

CERTIFICATE OF CORRECTION

PATENT NO. : 8,895,002 B2
APPLICATION NO. : 12/595423
DATED : November 25, 2014
INVENTOR(S) : Herbert Y. Lin et al.

It is certified that error appears in the above-identified patent and that said Letters Patent is hereby corrected as shown below:

In the Claims

In claim 24, column 172, line 17, replace “wherein wherein” with --wherein--

In claim 27, column 172, line 27, replace “wherein wherein” with --wherein--

Signed and Sealed this
Thirty-first Day of March, 2015

Michelle K. Lee
*Director of the United States Patent and Trademark Office*

SEQUENCE LISTING

```
<160> NUMBER OF SEQ ID NOS: 69

<210> SEQ ID NO 1
<211> LENGTH: 659
```

<212> TYPE: PRT
<213> ORGANISM: Homo sapiens

<400> SEQUENCE: 1

```
Met Ser Ala Leu Leu Ile Leu Ala Leu Val Gly Ala Ala Val Ala Asp
1               5                   10                  15

Tyr Lys Asp His Asp His Asp Tyr Lys Asp His Asp Ile Asp Tyr Lys
            20                  25                  30

Asp Asp Asp Asp Lys Ile Ala Ala Ala His Ser Gln Cys Lys Ile Leu
        35                  40                  45

Arg Cys Asn Ala Glu Tyr Val Ser Ser Thr Leu Ser Leu Arg Gly Gly
    50                  55                  60

Gly Ser Ser Gly Ala Leu Arg Gly Gly Gly Gly Gly Gly Arg Gly Gly
65                  70                  75                  80

Gly Val Gly Ser Gly Gly Leu Cys Arg Ala Leu Arg Ser Tyr Ala Leu
                85                  90                  95

Cys Thr Arg Arg Thr Ala Arg Thr Cys Arg Gly Asp Leu Ala Phe His
            100                 105                 110

Ser Ala Val His Gly Ile Glu Asp Leu Met Ile Gln His Asn Cys Ser
        115                 120                 125

Arg Gln Gly Pro Thr Ala Pro Pro Pro Pro Arg Gly Pro Ala Leu Pro
    130                 135                 140

Gly Ala Gly Ser Gly Leu Pro Ala Pro Asp Pro Cys Asp Tyr Glu Gly
145                 150                 155                 160

Arg Phe Ser Arg Leu His Gly Arg Pro Pro Gly Phe Leu His Cys Ala
                165                 170                 175

Ser Phe Gly Asp Pro His Val Arg Ser Phe His His His Phe His Thr
            180                 185                 190

Cys Arg Val Gln Gly Ala Trp Pro Leu Leu Asp Asn Asp Phe Leu Phe
        195                 200                 205

Val Gln Ala Thr Ser Ser Pro Met Ala Leu Gly Ala Asn Ala Thr Ala
    210                 215                 220

Thr Pro Lys Leu Thr Ile Ile Phe Lys Asn Met Gln Glu Cys Ile Asp
225                 230                 235                 240

Gln Lys Val Tyr Gln Ala Glu Val Asp Asn Leu Pro Val Ala Phe Glu
                245                 250                 255

Asp Gly Ser Ile Asn Gly Gly Asp Arg Pro Gly Gly Ser Ser Leu Ser
            260                 265                 270

Ile Gln Thr Ala Asn Pro Gly Asn His Val Glu Ile Gln Ala Ala Tyr
        275                 280                 285

Ile Gly Thr Thr Ile Ile Ile Arg Gln Thr Ala Gly Gln Leu Ser Phe
    290                 295                 300

Ser Ile Lys Val Ala Glu Asp Val Ala Met Ala Phe Ser Ala Glu Gln
305                 310                 315                 320

Asp Leu Gln Leu Cys Val Gly Gly Cys Pro Pro Ser Gln Arg Leu Ser
                325                 330                 335

Arg Ser Glu Arg Asn Arg Arg Gly Ala Ile Thr Ile Asp Thr Ala Arg
            340                 345                 350

Arg Leu Cys Lys Glu Gly Leu Pro Val Glu Asp Ala Tyr Phe His Ser
        355                 360                 365

Cys Val Phe Asp Val Leu Ile Ser Gly Asp Pro Asn Phe Thr Val Ala
    370                 375                 380

Ala Gln Ala Ala Leu Glu Asp Ala Arg Ala Phe Leu Pro Asp Leu Glu
385                 390                 395                 400
```

```
Lys Leu His Leu Phe Pro Ser Leu Glu Leu Val Pro Arg Gly Ser Gly
                405                 410                 415

Asp Pro Ile Glu Gly Arg Gly Gly Gly Gly Gly Asp Pro Lys Ser Cys
            420                 425                 430

Asp Lys Pro His Thr Cys Pro Leu Cys Pro Ala Pro Glu Leu Leu Gly
        435                 440                 445

Gly Pro Ser Val Phe Leu Phe Pro Pro Lys Pro Lys Asp Thr Leu Met
    450                 455                 460

Ile Ser Arg Thr Pro Glu Val Thr Cys Val Val Val Asp Val Ser His
465                 470                 475                 480

Glu Asp Pro Glu Val Lys Phe Asn Trp Tyr Val Asp Gly Val Glu Val
                485                 490                 495

His Asn Ala Lys Thr Lys Pro Arg Glu Glu Gln Tyr Asn Ser Thr Tyr
            500                 505                 510

Arg Val Val Ser Val Leu Thr Val Leu His Gln Asp Trp Leu Asn Gly
        515                 520                 525

Lys Glu Tyr Lys Cys Lys Val Ser Asn Lys Ala Leu Pro Ala Pro Ile
    530                 535                 540

Glu Lys Thr Ile Ser Lys Ala Lys Gly Gln Pro Arg Glu Pro Gln Val
545                 550                 555                 560

Tyr Thr Leu Pro Pro Ser Arg Asp Glu Leu Thr Lys Asn Gln Val Ser
                565                 570                 575

Leu Thr Cys Leu Val Lys Gly Phe Tyr Pro Ser Asp Ile Ala Val Glu
            580                 585                 590

Trp Glu Ser Asn Gly Gln Pro Glu Asn Asn Tyr Lys Ala Thr Pro Pro
        595                 600                 605

Val Ile Asp Ser Asp Gly Ser Phe Phe Leu Tyr Ser Lys Leu Thr Val
    610                 615                 620

Asp Lys Ser Arg Trp Gln Gln Gly Asn Val Phe Ser Cys Ser Val Met
625                 630                 635                 640

His Glu Ala Leu His Asn His Tyr Thr Gln Lys Ser Leu Ser Leu Ser
                645                 650                 655

Pro Gly Lys


<210> SEQ ID NO 2
<211> LENGTH: 426
<212> TYPE: PRT
<213> ORGANISM: Homo sapiens

<400> SEQUENCE: 2

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Leu Cys Gly His
            20                  25                  30

Ala His Ser Gln Cys Lys Ile Leu Arg Cys Asn Ala Glu Tyr Val Ser
        35                  40                  45

Ser Thr Leu Ser Leu Arg Gly Gly Gly Ser Ser Gly Ala Leu Arg Gly
    50                  55                  60

Gly Gly Gly Gly Gly Arg Gly Gly Gly Val Gly Ser Gly Gly Leu Cys
65                  70                  75                  80

Arg Ala Leu Arg Ser Tyr Ala Leu Cys Thr Arg Arg Thr Ala Arg Thr
                85                  90                  95

Cys Arg Gly Asp Leu Ala Phe His Ser Ala Val His Gly Ile Glu Asp
            100                 105                 110
```

```
Leu Met Ile Gln His Asn Cys Ser Arg Gln Gly Pro Thr Ala Pro Pro
        115                 120                 125

Pro Pro Arg Gly Pro Ala Leu Pro Gly Ala Gly Ser Gly Leu Pro Ala
    130                 135                 140

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
            180                 185                 190

Leu Leu Asp Asn Asp Phe Leu Phe Val Gln Ala Thr Ser Ser Pro Met
        195                 200                 205

Ala Leu Gly Ala Asn Ala Thr Ala Thr Arg Lys Leu Thr Ile Ile Phe
    210                 215                 220

Lys Asn Met Gln Glu Cys Ile Asp Gln Lys Val Tyr Gln Ala Glu Val
225                 230                 235                 240

Asp Asn Leu Pro Val Ala Phe Glu Asp Gly Ser Ile Asn Gly Gly Asp
                245                 250                 255

Arg Pro Gly Gly Ser Ser Leu Ser Ile Gln Thr Ala Asn Pro Gly Asn
            260                 265                 270

His Val Glu Ile Gln Ala Ala Tyr Ile Gly Thr Thr Ile Ile Ile Arg
        275                 280                 285

Gln Thr Ala Gly Gln Leu Ser Phe Ser Ile Lys Val Ala Glu Asp Val
    290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg Gly
                325                 330                 335

Ala Ile Thr Ile Asp Thr Ala Arg Arg Leu Cys Lys Glu Gly Leu Pro
            340                 345                 350

Val Glu Asp Ala Tyr Phe His Ser Cys Val Phe Asp Val Leu Ile Ser
        355                 360                 365

Gly Asp Pro Asn Phe Thr Val Ala Ala Gln Ala Ala Leu Glu Asp Ala
    370                 375                 380

Arg Ala Phe Leu Pro Asp Leu Glu Lys Leu His Leu Phe Pro Ser Asp
385                 390                 395                 400

Ala Gly Val Pro Leu Ser Ser Ala Thr Leu Leu Ala Pro Leu Leu Ser
                405                 410                 415

Gly Leu Phe Val Leu Trp Leu Cys Ile Gln
            420                 425
```

<210> SEQ ID NO 3
<211> LENGTH: 309
<212> TYPE: PRT
<213> ORGANISM: Homo sapiens

<400> SEQUENCE: 3

```
Met Ile Gln His Asn Cys Ser Arg Gln Gly Pro Thr Ala Pro Pro Pro
1               5                   10                  15

Pro Arg Gly Pro Ala Leu Pro Gly Ala Gly Ser Gly Leu Pro Ala Pro
            20                  25                  30

Asp Pro Cys Asp Tyr Glu Gly Arg Phe Ser Arg Leu His Gly Arg Pro
        35                  40                  45

Pro Gly Phe Leu His Cys Ala Ser Phe Gly Asp Pro His Val Arg Ser
```

-continued

```
    50                  55                  60

Phe His His His Phe His Thr Cys Arg Val Gln Gly Ala Trp Pro Leu
65                  70                  75                  80

Leu Asp Asn Asp Phe Leu Phe Val Gln Ala Thr Ser Ser Pro Met Ala
                85                  90                  95

Leu Gly Ala Asn Ala Thr Ala Thr Arg Lys Leu Thr Ile Ile Phe Lys
            100                 105                 110

Asn Met Gln Glu Cys Ile Asp Gln Lys Val Tyr Gln Ala Glu Val Asp
        115                 120                 125

Asn Leu Val Ala Phe Glu Asp Gly Ser Ile Asn Gly Gly Asp Arg Pro
    130                 135                 140

Gly Gly Ser Ser Leu Ser Ile Gln Thr Ala Asn Pro Gly Asn His Val
145                 150                 155                 160

Glu Ile Gln Ala Ala Tyr Ile Gly Thr Thr Ile Ile Ile Arg Gln Thr
                165                 170                 175

Ala Gly Gln Leu Ser Phe Ser Ile Lys Val Ala Glu Asp Val Ala Met
            180                 185                 190

Ala Phe Ser Ala Glu Gln Asp Gln Leu Cys Val Gly Gly Cys Pro Pro
        195                 200                 205

Ser Gln Arg Leu Ser Arg Ser Asn Arg Arg Gly Ala Ile Thr Ile Asp
    210                 215                 220

Thr Ala Arg Arg Leu Cys Lys Glu Gly Leu Pro Val Glu Asp Ala Tyr
225                 230                 235                 240

Phe His Ser Cys Val Phe Asp Val Leu Ile Ser Gly Asp Pro Asn Phe
                245                 250                 255

Thr Val Ala Ala Gln Ala Ala Leu Glu Asp Ala Arg Ala Phe Leu Pro
            260                 265                 270

Asp Leu Glu Lys Leu His Leu Phe Pro Ser Asp Ala Gly Val Pro Leu
        275                 280                 285

Ser Ser Ala Thr Leu Leu Ala Pro Leu Leu Ser Gly Leu Phe Val Leu
    290                 295                 300

Trp Leu Cys Ile Gln
305


<210> SEQ ID NO 4
<211> LENGTH: 198
<212> TYPE: PRT
<213> ORGANISM: Homo sapiens

<400> SEQUENCE: 4

Met Gln Glu Cys Ile Asp Gln Lys Val Tyr Gln Ala Glu Val Asp Asn
1               5                   10                  15

Leu Pro Val Ala Phe Glu Asp Gly Ser Ile Asn Gly Gly Asp Arg Pro
            20                  25                  30

Gly Gly Ser Ser Leu Ser Ile Gln Thr Ala Asn Pro Gly Asn His Val
        35                  40                  45

Glu Ile Gln Ala Ala Tyr Ile Gly Thr Thr Ile Ile Ile Arg Gln Thr
    50                  55                  60

Ala Gly Gln Leu Ser Phe Ser Ile Lys Val Ala Glu Asp Val Ala Met
65                  70                  75                  80

Ala Phe Ser Ala Glu Gln Asp Leu Gln Leu Cys Val Gly Gly Cys Pro
                85                  90                  95

Pro Ser Gln Arg Leu Ser Arg Ser Asn Arg Arg Gly Ala Ile Thr Ile
            100                 105                 110
```

Asp Thr Ala Arg Arg Leu Cys Lys Glu Gly Leu Pro Val Glu Asp Ala
        115                 120                 125

Tyr Phe His Ser Cys Val Phe Asp Val Leu Ile Ser Gly Asp Pro Asn
    130                 135                 140

Phe Thr Val Ala Ala Gln Ala Ala Leu Glu Asp Ala Arg Ala Phe Leu
145                 150                 155                 160

Pro Asp Leu Glu Lys Leu His Leu Phe Pro Ser Asp Ala Gly Val Pro
                165                 170                 175

Leu Ser Ser Ala Thr Leu Leu Ala Pro Leu Leu Ser Gly Leu Phe Val
            180                 185                 190

Leu Trp Leu Cys Ile Gln
        195

<210> SEQ ID NO 5
<211> LENGTH: 201
<212> TYPE: PRT
<213> ORGANISM: Mus musculus

<400> SEQUENCE: 5

Met Gln Glu Cys Ile Asp Gln Lys Val Tyr Gln Ala Glu Val Asp Asn
1               5                   10                  15

Leu Pro Ala Ala Phe Glu Asp Gly Ser Ile Asn Gly Gly Asp Arg Pro
            20                  25                  30

Gly Gly Ser Ser Leu Ser Ile Gln Thr Ala Asn Leu Gly Ser His Val
        35                  40                  45

Glu Ile Arg Ala Ala Tyr Ile Gly Thr Thr Ile Ile Ile Arg Gln Thr
    50                  55                  60

Ala Gly Gly Leu Ser Phe Ser Ile Arg Val Ala Glu Asp Val Ala Arg
65                  70                  75                  80

Ala Phe Ser Ala Glu Gln Asp Leu Gln Leu Cys Val Gly Gly Cys Pro
                85                  90                  95

Pro Ser Gln Arg Leu Ser Arg Ser Glu Arg Asn Arg Arg Gly Ala Ile
            100                 105                 110

Ala Ile Asp Thr Ala Arg Arg Leu Cys Lys Glu Gly Leu Pro Val Glu
        115                 120                 125

Asp Ala Tyr Phe Gln Ser Cys Val Phe Asp Val Ser Val Ser Gly Asp
    130                 135                 140

Pro Asn Phe Thr Val Ala Ala Cys Thr Ala Leu Leu Asp Ala Arg Tyr
145                 150                 155                 160

Phe Leu Thr Asp Leu Glu Asn Leu His Leu Phe Pro Ser Asp Ala Gly
                165                 170                 175

Pro Pro Leu Ser Pro Ala Ile Cys Leu Val Pro Leu Leu Ser Ala Leu
            180                 185                 190

Phe Val Leu Trp Leu Cys Phe Ser Lys
        195                 200

<210> SEQ ID NO 6
<211> LENGTH: 252
<212> TYPE: PRT
<213> ORGANISM: Homo sapiens

<400> SEQUENCE: 6

Leu Glu Leu Val Pro Arg Gly Ser Gly Asp Pro Ile Glu Gly Arg Gly
1               5                   10                  15

Gly Gly Gly Gly Asp Pro Lys Ser Cys Asp Lys Pro His Thr Cys Pro
            20                  25                  30

```
Leu Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Glu
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Ala Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250


<210> SEQ ID NO 7
<211> LENGTH: 653
<212> TYPE: PRT
<213> ORGANISM: Homo sapiens

<400> SEQUENCE: 7

Met Ser Ala Leu Leu Ile Leu Ala Leu Val Gly Ala Ala Val Ala Asp
1               5                   10                  15

Tyr Lys Asp His Asp Gly Asp Tyr Lys Asp His Asp Ile Asp Tyr Lys
            20                  25                  30

Asp Asp Asp Asp Lys Leu Ala Ala Ala His Ser Gln Cys Lys Ile Leu
        35                  40                  45

Arg Cys Asn Ala Glu Tyr Val Ser Ser Thr Leu Ser Leu Arg Gly Gly
    50                  55                  60

Gly Ser Ser Gly Ala Leu Arg Gly Gly Gly Gly Gly Gly Arg Gly Gly
65                  70                  75                  80

Gly Val Gly Ser Gly Gly Leu Cys Arg Ala Leu Arg Ser Tyr Ala Leu
                85                  90                  95

Cys Thr Arg Arg Thr Ala Arg Thr Cys Arg Gly Asp Leu Ala Phe His
            100                 105                 110

Ser Ala Val His Gly Ile Glu Asp Leu Met Ile Gln His Asn Cys Ser
        115                 120                 125

Arg Gln Gly Pro Thr Ala Pro Pro Pro Pro Arg Gly Pro Ala Leu Pro
    130                 135                 140

Gly Ala Gly Ser Gly Leu Pro Ala Pro Asp Pro Cys Asp Tyr Glu Gly
145                 150                 155                 160
```

-continued

```
Arg Phe Ser Arg Leu His Gly Arg Pro Pro Gly Phe Leu His Cys Ala
                165                 170                 175

Ser Phe Gly Ala Pro His Val Arg Ser Phe His His His Phe His Thr
            180                 185                 190

Cys Arg Val Gln Gly Ala Trp Pro Leu Leu Asp Asn Asp Phe Leu Phe
        195                 200                 205

Val Gln Ala Thr Ser Ser Pro Met Ala Leu Gly Ala Asn Ala Thr Ala
    210                 215                 220

Thr Arg Lys Leu Thr Ile Ile Phe Lys Asn Met Gln Glu Cys Ile Asp
225                 230                 235                 240

Gln Lys Val Tyr Gln Ala Glu Val Asp Asn Leu Pro Val Ala Phe Glu
                245                 250                 255

Asp Gly Ser Ile Asn Gly Gly Asp Arg Pro Gly Gly Ser Ser Leu Ser
            260                 265                 270

Ile Gln Thr Ala Asn Pro Gly Asn His Val Glu Ile Gln Ala Ala Tyr
        275                 280                 285

Ile Gly Thr Thr Ile Ile Ile Arg Gln Thr Ala Gly Gln Leu Ser Phe
    290                 295                 300

Ser Ile Lys Val Ala Glu Asp Val Ala Met Ala Phe Ser Ala Glu Gln
305                 310                 315                 320

Asp Leu Gln Leu Cys Val Gly Gly Cys Pro Pro Ser Gln Arg Leu Ser
                325                 330                 335

Arg Ser Asn Arg Arg Gly Ala Ile Thr Ile Asp Thr Ala Arg Arg Leu
            340                 345                 350

Cys Lys Glu Gly Leu Pro Val Glu Asp Ala Tyr Phe His Ser Cys Val
        355                 360                 365

Phe Asp Val Leu Ile Ser Gly Asp Pro Asn Phe Thr Val Ala Ala Gln
    370                 375                 380

Ala Ala Leu Glu Asp Ala Arg Ala Phe Leu Pro Asp Leu Glu Lys Leu
385                 390                 395                 400

His Leu Phe Pro Ser Leu Glu Leu Val Pro Arg Gly Ser Gly Asp Pro
                405                 410                 415

Ile Glu Gly Arg Gly Gly Gly Gly Gly Asp Pro Lys Ser Cys Asp Lys
            420                 425                 430

Pro His Thr Cys Pro Leu Cys Pro Ala Pro Glu Leu Leu Gly Gly Pro
        435                 440                 445

Ser Val Phe Leu Phe Pro Pro Lys Pro Lys Asp Thr Leu Met Ile Ser
    450                 455                 460

Arg Thr Pro Glu Val Thr Cys Val Val Val Asp Val Ser His Glu Asp
465                 470                 475                 480

Pro Glu Val Lys Phe Asn Trp Tyr Val Asp Gly Val Glu Val His Asn
                485                 490                 495

Ala Lys Thr Lys Pro Arg Glu Glu Gln Tyr Asn Ser Tyr Val Val Ser
            500                 505                 510

Val Leu Thr Val Leu His Gln Asp Trp Leu Asn Gly Lys Glu Tyr Lys
        515                 520                 525

Cys Lys Val Ser Asn Lys Ala Leu Pro Ala Pro Ile Glu Lys Thr Ile
    530                 535                 540

Ser Lys Ala Lys Gly Gln Pro Arg Glu Pro Gln Val Tyr Thr Leu Pro
545                 550                 555                 560

Pro Ser Arg Asp Glu Leu Thr Lys Asn Gln Val Ser Leu Thr Cys Leu
                565                 570                 575
```

```
Val Lys Gly Phe Tyr Pro Ser Asp Ile Ala Val Glu Trp Glu Ser Asn
            580                 585                 590

Gly Gln Pro Glu Asn Asn Tyr Lys Ala Thr Pro Pro Val Leu Asp Ser
        595                 600                 605

Asp Gly Ser Phe Phe Lys Lys Leu Thr Val Asp Lys Ser Arg Trp Gln
    610                 615                 620

Gln Gly Asn Val Phe Ser Cys Ser Val Met His Glu Ala Leu His Asn
625                 630                 635                 640

His Tyr Thr Gln Lys Ser Leu Ser Leu Ser Pro Gly Lys
                645                 650


<210> SEQ ID NO 8
<211> LENGTH: 1980
<212> TYPE: DNA
<213> ORGANISM: Homo sapiens

<400> SEQUENCE: 8

atgtctgcac ttctgatcct agctcttgtt ggagctgcag ttgctgacta caaagaccat     60

gacggtgatt ataaagatca tgacatcgat tacaaggatg acgatgacaa gcttgcggcc    120

gctcattctc aatgcaagat cctccgctgc aatgctgagt acgtatcgtc cactctgagc    180

cttagaggtg gggttcatc aggagcactt cgaggaggag gaggaggagg ccggggtgga    240

ggggtgggct ctggcggcct ctgtcgagcc ctccgctcct atgcgctctg cactcggcgc    300

accgcccgca cctgccgcgg ggacctcgcc ttccattcgg cggtacatgg catcgargac    360

ctgatgatcc agcacaactg ctcccgccag ggccctacag cccctccccc gccccggggc    420

cccgcccttc caggcgcggg ctccggcctc cctgccccgg acccttgtga ctatgaaggc    480

cggttttccc ggctgcatgg tcgtcccccg gggttcttgc attgcgcttc cttcggggac    540

ccccatgtgc gcagcttcca ccatcacttt cacacatgcc gtgtccaagg agcttggcct    600

ctactggata atgacttcct ctttgtccaa gccaccagct cccccatggc gttgggggcc    660

aacgctaccg ccacccggaa gctcaccatc atatttaaga acatgcagga atgcattgat    720

cagaaggtgt atcaggctga ggtggataat cttcctgtag cctttgaaga tggttctatc    780

aatggaggtg accgacctgg gggatccagt ttgtcgattc aaactgctaa ccctgggaac    840

catgtggaga tccaagctgc ctacattggc acaactatta tcattcggca gacagctggg    900

cagctctcct tctccatcaa ggtagcagag gatgtggcca tggccttctc agctgaacag    960

gacctgcagc tctgtgttgg ggggtgccct ccaagtcagc gactctctcg atcagagcgc   1020

aatcgtcggg gagctataac cattgatact gccagacggc tgtgcaagga agggcttcca   1080

gtggaagatg cttacttcca ttcctgtgtc tttgatgttt taatttctgg tgatcccaac   1140

tttaccgtgg cagctcaggc agcactggag gatgcccgag ccttcctgcc agacttagag   1200

aagctgcatc tcttcccctc actcgagctg gttccgcgtg gttcggggga tcccatcgaa   1260

ggtcgtggtg gtggtggtgg tgatcccaaa tcttgtgaca aacctcacac atgcccactg   1320

tgcccagcac ctgaactcct ggggggaccg tcagtcttcc tcttcccccc aaaacccaag   1380

gacaccctca tgatctcccg gacccctgag gtcacatgcg tggtggtgga cgtgagccac   1440

gaagaccctg aggtcaagtt caactggtac gtggacggcg tggaggtgca taatgccaag   1500

acaaagccgc gggaggagca gtacaacagc acgtaccgtg tggtcagcgt cctcaccgtc   1560

ctgcaccagg actggctgaa tggcaaggag tacaagtgca aggtctccaa caaagccctc   1620

ccagccccca tcgagaaaac catctccaaa gccaaagggc agccccgaga accacaggtg   1680
```

```
tacaccctgc cccatcccg ggatgagctg accaagaacc aggtcagcct gacctgccta   1740

gtcaaaggct tctatcccag cgacatcgcc gtggagtggg agagcaatgg gcagccggag   1800

aacaactaca aggccacgcc tcccgtgctg gactccgacg gctccttctt cctctacagc   1860

aagctcaccg tggacaagag caggtggcag caggggaacg tcttctcatg ctccgtgatg   1920

catgaggctc tgcacaacca ctacacgcag aagagcctct ccctgtctcc gggtaaatga   1980


<210> SEQ ID NO 9
<211> LENGTH: 1980
<212> TYPE: DNA
<213> ORGANISM: Homo sapiens

<400> SEQUENCE: 9

atgtctgcac ttctgatcct agctcttgct ggagctgcag ttgctgacta caaagaccat     60

gacggtgatt ataaagatca tgacatcgat tacaaggatg acgatgacaa gcttgcggcc    120

gctcattctc aatgcaagat cctccgctgc aatgctgagt acgtatcgtc cactctgagc    180

cttagaggtg ggggttcatc aggagcactt cgaggaggag gaggaggagg ccggggtgga    240

ggggtgggct ctggcggcct ctgtcgagcc ctccgctcct atgcgctctg cactcggcgc    300

accgcccgca cctgccgcgg ggacctcgcc ttccattcgg cggtacatgg catcgaagac    360

ctgatgatcc agcacaactg ctcccgccag ggccctacag cccctccccc gccccggggc    420

cccgcccttc caggcgcggg ctccggcctc cctgccccgg acccttgtga ctatgaaggc    480

cggttttccc ggctgcatgg tcgtcccccg gggttcttgc attgcgcttc cttcggggcc    540

ccccatgtgc gcagcttcca ccatcacttt cacacatgcc gtgtccaagg agcttggcct    600

ctactggata atgacttcct ctttgtccaa gccaccagct cccccatggc gttgggggcc    660

aacgctaccg ccacccggaa gctcaccatc atatttaaga acatgcagga atgcattgat    720

cagaaggtgt atcaggctga ggtggataat cttcctgtag cctttgaaga tggttctatc    780

aatggaggtg accgacctgg gggatccagt ttgtcgattc aaactgctaa ccctgggaac    840

catgtggaga tccaagctgc ctacattggc acaactataa tcattcggca gacagctggg    900

cagctctcct tctccatcaa ggtagtagag gatgtggcca tggccttctc agctgaacag    960

gacctgcagc tctgtgttgg ggggtgccct ccaagtcagc gactctctcg atcagagcgc   1020

aatcgtcggg gagctataac cattgatact gccagacggc tgtgcaagga agggcttcca   1080

gtggaagatg cttacttcca ttcctgtgtc tttgatgttt taatttctgg tgatcccaac   1140

tttaccgtgg cagctcaggc agcactggag gatgcccgag ccttcctgcc agacttagag   1200

aagctgcatc tcttcccctc actcgagctg gttccgcgtg gttcgggggga tcccatcgaa   1260

ggtcgtggtg gtggtggtgg tgatcccaaa tcttgtgaca aacctcacac atgcccactg   1320

tgcccagcac ctgaactcct ggggggaccg tcagtcttcc tcttcccccc aaaacccaag   1380

gacaccctca tgatctcccg gacccctgag gtcacatgcg tggtggtgga cgtgagccac   1440

gaagaccctg aggtcaagtt caactggtac gtggacggcg tggaggtgca taatgccaag   1500

acaaagccgc gggaggagca gtacaacagc acgtaccgtg tggtcagcgt cctcaccgtc   1560

ctgcaccagg actggctgaa tggcaaggag tacaagtgca aggtctccaa caaagccctc   1620

ccagccccca tcgagaaaac catctccaaa gccaaagggc agccccgaga accacaggtg   1680

tacaccctgc ccccatcccg ggatgagctg accaagaacc aggtcagcct gacctgccta   1740

gtcaaaggct tctatcccag cgacatcgcc gtggagtggg agagcaatgg gcagccggag   1800

aacaactaca aggccacgcc tcccgtgctg gactccgacg gctccttctt cctctacagc   1860
```

```
aagctcaccg tggacaagag caggtggcag caggggaacg tcttctcatg ctccgtgatg   1920

catgaggctc tgcacaacca ctacacgcag aagagcctct ccctgtctcc gggtaaatga   1980


<210> SEQ ID NO 10
<211> LENGTH: 603
<212> TYPE: PRT
<213> ORGANISM: Homo sapiens

<400> SEQUENCE: 10

Met Ser Ala Leu Leu Ile Leu Ala Leu Val Gly Ala Ala Val Ala His
1               5                   10                  15

Ser Gln Cys Lys Ile Leu Arg Cys Asn Ala Glu Tyr Val Ser Ser Thr
            20                  25                  30

Leu Ser Leu Arg Gly Gly Gly Ser Ser Gly Ala Leu Arg Gly Gly Gly
        35                  40                  45

Gly Gly Gly Arg Gly Gly Gly Val Gly Ser Gly Gly Leu Cys Arg Ala
    50                  55                  60

Leu Arg Ser Tyr Ala Leu Cys Thr Arg Arg Thr Ala Arg Thr Cys Arg
65                  70                  75                  80

Gly Asp Leu Ala Phe His Ser Ala Val His Gly Ile Glu Asp Leu Met
                85                  90                  95

Ile Gln His Asn Cys Ser Arg Gln Gly Pro Thr Ala Pro Pro Pro Pro
            100                 105                 110

Arg Gly Pro Ala Leu Pro Gly Ala Gly Ser Gly Leu Pro Ala Pro Asp
        115                 120                 125

Pro Cys Asp Tyr Glu Gly Arg Phe Ser Arg Leu His Gly Arg Pro Pro
    130                 135                 140

Gly Phe Leu His Cys Ala Ser Phe Gly Asp Pro His Val Arg Ser Phe
145                 150                 155                 160

His His His Phe His Thr Cys Arg Val Gln Gly Ala Trp Pro Leu Leu
                165                 170                 175

Asp Asn Asp Phe Leu Phe Val Gln Ala Thr Ser Ser Pro Met Ala Leu
            180                 185                 190

Gly Ala Asn Ala Thr Ala Thr Arg Lys Leu Thr Ile Ile Phe Lys Asn
        195                 200                 205

Met Gln Glu Cys Ile Asp Gln Lys Val Tyr Gln Ala Glu Val Asp Asn
    210                 215                 220

Leu Pro Val Ala Phe Glu Asp Gly Ser Ile Asn Gly Gly Asp Arg Pro
225                 230                 235                 240

Gly Gly Ser Ser Leu Ser Ile Gln Thr Ala Asn Pro Gly Asn His Val
                245                 250                 255

Glu Ile Gln Ala Ala Tyr Ile Gly Thr Thr Ile Ile Ile Arg Gln Thr
            260                 265                 270

Ala Gly Gln Leu Ser Phe Ser Ile Lys Val Ala Glu Asp Val Ala Met
        275                 280                 285

Ala Phe Ser Ala Glu Gln Asp Leu Gln Leu Cys Val Gly Gly Cys Pro
    290                 295                 300

Pro Ser Gln Arg Leu Ser Arg Ser Asn Arg Arg Gly Ala Ile Thr Ile
305                 310                 315                 320

Asp Thr Ala Arg Arg Leu Cys Lys Glu Gly Leu Pro Val Glu Asp Ala
                325                 330                 335

Tyr Phe His Ser Cys Val Phe Asp Val Leu Ile Ser Gly Asp Pro Asn
            340                 345                 350
```

-continued

```
Phe Thr Val Ala Ala Gln Ala Ala Leu Glu Asp Ala Arg Ala Phe Leu
        355                 360                 365

Pro Asp Leu Glu Lys Leu His Leu Phe Pro Lys Ser Cys Asp Lys Thr
    370                 375                 380

His Thr Cys Pro Pro Cys Pro Ala Pro Glu Leu Leu Gly Gly Pro Ser
385                 390                 395                 400

Val Phe Leu Phe Pro Pro Lys Pro Lys Asp Thr Leu Met Ile Ser Arg
                405                 410                 415

Thr Pro Glu Val Thr Cys Val Val Val Asp Val Ser His Glu Asp Pro
            420                 425                 430

Glu Val Lys Phe Asn Trp Tyr Val Asp Gly Val Glu Val His Asn Ala
        435                 440                 445

Lys Thr Lys Pro Arg Glu Glu Gln Tyr Asn Ser Tyr Val Val Ser Val
    450                 455                 460

Leu Thr Val Leu His Gln Asp Trp Leu Asn Gly Lys Glu Tyr Lys Cys
465                 470                 475                 480

Lys Val Ser Asn Lys Ala Leu Pro Ala Pro Ile Glu Lys Thr Ile Ser
                485                 490                 495

Lys Ala Lys Gly Gln Pro Arg Glu Pro Gln Val Tyr Thr Leu Pro Ser
            500                 505                 510

Arg Asp Glu Leu Thr Lys Asn Gln Val Ser Leu Thr Cys Leu Val Lys
        515                 520                 525

Gly Phe Tyr Pro Ser Asp Ile Ala Val Glu Trp Glu Ser Asn Gly Gln
    530                 535                 540

Pro Glu Asn Asn Tyr Lys Thr Thr Pro Pro Val Leu Asp Ser Asp Gly
545                 550                 555                 560

Ser Phe Phe Lys Lys Leu Thr Val Asp Lys Ser Arg Trp Gln Gln Gly
                565                 570                 575

Asn Val Phe Ser Cys Ser Val Met His Glu Ala Leu His Asn His Tyr
            580                 585                 590

Thr Gln Lys Ser Leu Ser Leu Ser Pro Gly Lys
        595                 600
```

<210> SEQ ID NO 11
<211> LENGTH: 1865
<212> TYPE: DNA
<213> ORGANISM: Homo sapiens

<400> SEQUENCE: 11

```
ggatccaagc ttgccgccat gagcgccctg cttattctgg ccctggttgg agcagccgtg      60

gctcatagcc agtgcaagat cctgcgatgc aatgccgagt acgtgtcttc caccctcagt     120

ctcagaggcg gggggagttc cggcgcactg cgcgggggag gtggaggtgg ccgcggaggc     180

ggagtgggat ctgggggact gtgccgagct ttgcggagtt acgctctgtg cacaagacgc     240

accgccagga cctgcagggg agacctggca ttccacagcg cagtgcacgg cattgaagac     300

ttgatgattc agcataattg tagtagacaa ggccctaccg ctcccccccc tcccaggggc     360

cccgctttgc ctggggcagg ttccggactg cccgccccag atccttgtga ctacgagggg     420

cggttcagcc gactccatgg aaggccccca ggcttcctgc actgcgcaag ttttggcgat     480

ccacacgtca ggtcatttca ccaccacttt catacctgtc gtgtccaggg cgcatggcct     540

ctgctggaca acgacttcct cttcgtccaa gcaacaagtt cacctatggc tctgggggca     600

aatgctactg ccacccgaaa acttaccatt atctttaaga atatgcaaga atgtatcgat     660

cagaaggtct accaggccga agttgacaac ctgcccgtgg ctttcgagga tggttcaatc     720
```

```
aacggagggg accggcctgg aggctccagt ctgagcatcc agaccgccaa tcctggaaat    780

cacgtggaga tccaggctgc ctacatcggc acaacaatca taattaggca gaccgctggc    840

cagctgagct tctccatcaa ggtcgccgaa gacgtggcca tggctttctc tgccgaacag    900

gacctccagc tttgcgtggg tggttgtcca ccctcccagc gcctttctcg atccgaacgc    960

aataggcgag gcgcaatcac tatcgacact gctcgcagat tgtgcaaaga gggcctgcct   1020

gtggaggatg catacttcca ttcttgtgtg ttcgacgtcc tgataagcgg agacccaaat   1080

ttcacagtgg ctgctcaggc cgcactggag gatgccaggg ccttttgcc cgatctggaa    1140

aagttgcatc tgttcccaaa atcctgtgac aagactcata cctgtccacc gtgtcccgcc   1200

cccgaactct tgggcgggcc ttctgtgttc ctcttcccac ccaaaccaaa agacacactg   1260

atgatctcca ggacccctga agtgacttgc gtcgtggttg acgtgtctca tgaagacccc   1320

gaggtgaagt tcaactggta cgtcgatgga gtggaggttc ataacgccaa gacaaaacca   1380

agggaggaac aatacaactc tacatacagg gtggtcagtg tgctgactgt gctgcaccag   1440

gactggctca acggcaaaga gtacaaatgc aaggtgtcta acaaggcact tcctgctcca   1500

attgaaaaaa ccatctccaa ggctaagggg cagccaaggg aaccacaggt gtatactctt   1560

cctccttctc gcgacgaact gactaaaaat caggtgtcat tgacctgtct ggtgaagggc   1620

ttttacccct ccgatatagc tgtggagtgg gagagcaacg ggcagcccga gaacaattat   1680

aaaaccacac cacctgtcct cgacagtgat ggatcatttt tcctctacag taagctgacc   1740

gtggataaat ctaggtggca gcaggggaac gtgttttctt gctccgtgat gcacgaggcc   1800

cttcacaacc attacacaca gaagagcctg agcctgtccc caggaaagtg agaattcgcg   1860

gccgc                                                               1865
```

<210> SEQ ID NO 12
<211> LENGTH: 28
<212> TYPE: DNA
<213> ORGANISM: Artificial Sequence
<220> FEATURE:
<223> OTHER INFORMATION: Chemically Synthesized Primer Sequence

<400> SEQUENCE: 12
accgaattcg ggggacctgg ctggatag 28

<210> SEQ ID NO 13
<211> LENGTH: 24
<212> TYPE: DNA
<213> ORGANISM: Artificial Sequence
<220> FEATURE:
<223> OTHER INFORMATION: Chemically Synthesized Primer Sequence

<400> SEQUENCE: 13
cggagggcat accccaacac acag 24

<210> SEQ ID NO 14
<211> LENGTH: 24
<212> TYPE: DNA
<213> ORGANISM: Artificial Sequence
<220> FEATURE:
<223> OTHER INFORMATION: Chemically Synthesized Primer Sequence

<400> SEQUENCE: 14
ctgtgtgttg gggtatgccc tccg 24

<210> SEQ ID NO 15

-continued

<211> LENGTH: 29
<212> TYPE: DNA
<213> ORGANISM: Artificial Sequence
<220> FEATURE:
<223> OTHER INFORMATION: Chemically Synthesized Primer Sequence

<400> SEQUENCE: 15
ccctctagat ggtgccagtc tccaaaagc 29

<210> SEQ ID NO 16
<211> LENGTH: 26
<212> TYPE: DNA
<213> ORGANISM: Artificial Sequence
<220> FEATURE:
<223> OTHER INFORMATION: Chemically Synthesized Primer Sequence

<400> SEQUENCE: 16
ggaagcttat gggccagtcc cctagt 26

<210> SEQ ID NO 17
<211> LENGTH: 29
<212> TYPE: DNA
<213> ORGANISM: Artificial Sequence
<220> FEATURE:
<223> OTHER INFORMATION: Chemically Synthesized Primer Sequence

<400> SEQUENCE: 17
ccggatccgc taagttctct aaatccgtc 29

<210> SEQ ID NO 18
<211> LENGTH: 42
<212> TYPE: DNA
<213> ORGANISM: Artificial Sequence
<220> FEATURE:
<223> OTHER INFORMATION: Chemically Synthesized Primer Sequence

<400> SEQUENCE: 18
cctctgtgga catgctcatt ctcaatgcaa gatcctccgc tg 42

<210> SEQ ID NO 19
<211> LENGTH: 40
<212> TYPE: DNA
<213> ORGANISM: Artificial Sequence
<220> FEATURE:
<223> OTHER INFORMATION: Chemically Synthesized Primer Sequence

<400> SEQUENCE: 19
cgtctcgagt tactgaatgc aaagccacag aacaaagagc 40

<210> SEQ ID NO 20
<211> LENGTH: 29
<212> TYPE: DNA
<213> ORGANISM: Artificial Sequence
<220> FEATURE:
<223> OTHER INFORMATION: Chemically Synthesized Primer Sequence

<400> SEQUENCE: 20
cgagaattca cttacagggc ttccggtca 29

<210> SEQ ID NO 21
<211> LENGTH: 36
<212> TYPE: DNA
<213> ORGANISM: Artificial Sequence
<220> FEATURE:
<223> OTHER INFORMATION: Chemically Synthesized Primer Sequence

<400> SEQUENCE: 21

-continued gcattgagaa tgagcatgtc cacagaggag cagcag 36

<210> SEQ ID NO 22
<211> LENGTH: 41
<212> TYPE: DNA
<213> ORGANISM: Artificial Sequence
<220> FEATURE:
<223> OTHER INFORMATION: Chemically Synthesized Primer Sequence

<400> SEQUENCE: 22
gacagatctg cggccgctca ttctcaatgc aagatcctcc g 41

<210> SEQ ID NO 23
<211> LENGTH: 24
<212> TYPE: DNA
<213> ORGANISM: Artificial Sequence
<220> FEATURE:
<223> OTHER INFORMATION: Chemically Synthesized Primer Sequence

<400> SEQUENCE: 23
gagcagttgt gctggatcat cagg 24

<210> SEQ ID NO 24
<211> LENGTH: 19
<212> TYPE: DNA
<213> ORGANISM: Artificial Sequence
<220> FEATURE:
<223> OTHER INFORMATION: Chemically Synthesized Primer Sequence

<400> SEQUENCE: 24
ctgcaacccc aggacagag 19

<210> SEQ ID NO 25
<211> LENGTH: 23
<212> TYPE: DNA
<213> ORGANISM: Artificial Sequence
<220> FEATURE:
<223> OTHER INFORMATION: Chemically Synthesized Primer Sequence

<400> SEQUENCE: 25
ggaataaata aggaagggag ggg 23

<210> SEQ ID NO 26
<211> LENGTH: 22
<212> TYPE: DNA
<213> ORGANISM: Artificial Sequence
<220> FEATURE:
<223> OTHER INFORMATION: Chemically Synthesized Primer Sequence

<400> SEQUENCE: 26
aggatgcaga aggagatcac tg 22

<210> SEQ ID NO 27
<211> LENGTH: 24
<212> TYPE: DNA
<213> ORGANISM: Artificial Sequence
<220> FEATURE:
<223> OTHER INFORMATION: Chemically Synthesized Primer Sequence

<400> SEQUENCE: 27
gggtgtaacg caactaagtc atag 24

<210> SEQ ID NO 28
<211> LENGTH: 21
<212> TYPE: DNA

<213> ORGANISM: Artificial Sequence
<220> FEATURE:
<223> OTHER INFORMATION: Chemically Synthesized Primer Sequence

<400> SEQUENCE: 28
cgtgaccaga cttttggaca c 21

<210> SEQ ID NO 29
<211> LENGTH: 21
<212> TYPE: DNA
<213> ORGANISM: Artificial Sequence
<220> FEATURE:
<223> OTHER INFORMATION: Chemically Synthesized Primer Sequence

<400> SEQUENCE: 29
ggcatgatta gtggagttca g 21

<210> SEQ ID NO 30
<211> LENGTH: 20
<212> TYPE: DNA
<213> ORGANISM: Artificial Sequence
<220> FEATURE:
<223> OTHER INFORMATION: Chemically Synthesized Primer Sequence

<400> SEQUENCE: 30
agcagccaaa ctatgggcta 20

<210> SEQ ID NO 31
<211> LENGTH: 20
<212> TYPE: DNA
<213> ORGANISM: Artificial Sequence
<220> FEATURE:
<223> OTHER INFORMATION: Chemically Synthesized Primer Sequence

<400> SEQUENCE: 31
tggttgagtt gaggtggtca 20

<210> SEQ ID NO 32
<211> LENGTH: 21
<212> TYPE: DNA
<213> ORGANISM: Artificial Sequence
<220> FEATURE:
<223> OTHER INFORMATION: Chemically Synthesized Primer Sequence

<400> SEQUENCE: 32
tccttagact gcacagcaga a 21

<210> SEQ ID NO 33
<211> LENGTH: 20
<212> TYPE: DNA
<213> ORGANISM: Artificial Sequence
<220> FEATURE:
<223> OTHER INFORMATION: Chemically Synthesized Primer Sequence

<400> SEQUENCE: 33
ataaataagg acgggagggg 20

<210> SEQ ID NO 34
<211> LENGTH: 24
<212> TYPE: DNA
<213> ORGANISM: Artificial Sequence
<220> FEATURE:
<223> OTHER INFORMATION: Chemically Synthesized Primer Sequence

<400> SEQUENCE: 34
agaaggtgta tcaggctgag gtgg 24

<210> SEQ ID NO 35
<211> LENGTH: 33
<212> TYPE: DNA
<213> ORGANISM: Artificial Sequence
<220> FEATURE:
<223> OTHER INFORMATION: Chemically Synthesized Primer Sequence

<400> SEQUENCE: 35
cagctcgagt gaggggaaga gatgcagctt ctc 33

<210> SEQ ID NO 36
<211> LENGTH: 19
<212> TYPE: PRT
<213> ORGANISM: Mus musculus

<400> SEQUENCE: 36

Arg Val Ala Glu Asp Val Ala Arg Ala Phe Ser Ala Glu Gln Asp Leu
1 5 10 15

Gln Leu Cys

<210> SEQ ID NO 37
<211> LENGTH: 2234
<212> TYPE: DNA
<213> ORGANISM: Homo sapiens
<220> FEATURE:
<221> NAME/KEY: gene
<222> LOCATION: (1)..(2234)
<223> OTHER INFORMATION: Accession No. NM_213653

<400> SEQUENCE: 37
accgtcaact cagtagccac ctccctccct gctcagctgt ccagtactct ggccagccat 60
atactccccc ttccccccat accaaacctt ctctggttcc ctgacctcag tgagacagca 120
gccggcctgg ggacctgggg gagacacgga ggaccccctg gctggagctg acccacagag 180
tagggaatca tggctggaga attggatagc agagtaatgt ttgacctctg gaaacatcac 240
ttacagggct tccggtcaaa attcactagg taggagggtc atcagctggg aagaaccggc 300
gcctgggaaa cctggctgga taggtatggg ggagccaggc cagtccccta gtcccaggtc 360
ctcccatggc agtcccccaa ctctaagcac tctcactctc ctgctgctcc tctgtggaca 420
tgctcattct caatgcaaga tcctccgctg caatgctgag tacgtatcgt ccactctgag 480
ccttagaggt gggggttcat caggagcact tcgaggagga ggaggaggag gccggggtgg 540
aggggtgggc tctggcggcc tctgtcgagc cctccgctcc tatgcgctct gcactcggcg 600
caccgcccgc acctgccgcg gggacctcgc cttccattcg gcggtacatg gcatcgaaga 660
cctgatgatc cagcacaact gctcccgcca gggccctaca gcccctcccc cgccccgggg 720
ccccgccctt ccaggcgcgg gctccggcct ccctgccccg gacccttgtg actatgaagg 780
ccggttttcc cggctgcatg gtcgtccccc ggggttcttg cattgcgctt ccttcgggga 840
cccccatgtg cgcagcttcc accatcactt tcacacatgc cgtgtccaag gagcttggcc 900
tctactggat aatgacttcc tctttgtcca agccaccagc tcccccatgg cgttgggggc 960
caacgctacc gccacccgga agctcaccat catatttaag aacatgcagg aatgcattga 1020
tcagaaggtg tatcaggctg aggtggataa tcttcctgta gcctttgaag atggttctat 1080
caatggaggt gaccgacctg ggggatccag tttgtcgatt caaactgcta accctgggaa 1140
ccatgtggag atccaagctg cctacattgg cacaactata atcattcggc agacagctgg 1200
gcagctctcc ttctccatca aggtagcaga ggatgtggcc atggccttct cagctgaaca 1260

```
ggacctgcag ctctgtgttg gggggtgccc tccaagtcag cgactctctc gatcagagcg   1320
caatcgtcgg ggagctataa ccattgatac tgccagacgg ctgtgcaagg aagggcttcc   1380
agtggaagat gcttacttcc attcctgtgt ctttgatgtt ttaatttctg gtgatcccaa   1440
ctttaccgtg gcagctcagg cagcactgga ggatgcccga gccttcctgc cagacttaga   1500
gaagctgcat ctcttcccct cagatgctgg ggttcctctt tcctcagcaa ccctcttagc   1560
tccactcctt tctgggctct ttgttctgtg gctttgcatt cagtaagggg accatcagtc   1620
ccattactag tttggaaatg atttggagat acagattggc atagaagaat gtaaagaatc   1680
attaaaggaa gcagggccta ggagacacgt gaaacaatga cattatccag agtcagatga   1740
ggctgcagtc cagggttgaa attatcacag aataaggatt ctgggcaagg ttactgcatt   1800
ccggatctct gtggggctct tcaccaattt ttccagcctc atttatagta aacaaattgt   1860
tctaatccat ttactgcaga tttcaccctt ataagtttag aggtcatgaa ggttttaatg   1920
atcagtaaag atttaagggt tgagattttt aagaggcaag agctgaaagc agaagacatg   1980
atcattagcc ataagaaact caaaggagga agacataatt agggaaagaa gtctatttga   2040
tgaatatgtg tgtgtaaggt atgttctgct ttcttgattc aaaaatgaag caggcattgt   2100
ctagctctta ggtgaaggga gtctctgctt ttgaagaatg gcacaggtag gacagaagta   2160
tcatccctac cccctaacta atctgttatt aaagctacaa attcttcaca ccatcaaaaa   2220
aaaaaaaaaa aaaa                                                     2234
```

<210> SEQ ID NO 38
<211> LENGTH: 2048
<212> TYPE: DNA
<213> ORGANISM: Homo sapiens
<220> FEATURE:
<221> NAME/KEY: gene
<222> LOCATION: (1)..(2048)
<223> OTHER INFORMATION: Accession No. NM_145277

<400> SEQUENCE: 38

```
accgtcaact cagtagccac ctccctccct gctcagctgt ccagtactct ggccagccat     60
atactccccc ttccccccat accaaacctt ctctggttcc ctgacctcag tgagacagca    120
gccggcctgg ggacctgggg gagacacgga ggaccccctg gctggagctg acccacagag    180
tagggaatca tggctggaga attggatagc agagtaatgt ttgacctctg gaaacactca    240
ttctcaatgc aagatcctcc gctgcaatgc tgagtacgta tcgtccactc tgagccttag    300
aggtgggggt tcatcaggag cacttcgagg aggaggagga ggaggccggg gtggaggggt    360
gggctctggc ggcctctgtc gagccctccg ctcctatgcg ctctgcactc ggcgcaccgc    420
ccgcacctgc cgcggggacc tcgccttcca ttcggcggta catggcatcg aagacctgat    480
gatccagcac aactgctccc gccagggccc tacagcccct cccccgcccc ggggccccgc    540
ccttccaggc gcgggctccg gcctccctgc cccggaccct tgtgactatg aaggccggtt    600
ttcccggctg catggtcgtc ccccggggtt cttgcattgc gcttccttcg gggaccccca    660
tgtgcgcagc ttccaccatc actttcacac atgccgtgtc caaggagctt ggcctctact    720
ggataatgac ttcctctttg tccaagccac cagctccccc atggcgttgg gggccaacgc    780
taccgccacc cggaagctca ccatcatatt taagaacatg caggaatgca ttgatcagaa    840
ggtgtatcag gctgaggtgg ataatcttcc tgtagccttt gaagatggtt ctatcaatgg    900
aggtgaccga cctgggggat ccagtttgtc gattcaaact gctaaccctg ggaaccatgt    960
```

```
ggagatccaa gctgcctaca ttggcacaac tataatcatt cggcagacag ctgggcagct   1020

ctccttctcc atcaaggtag cagaggatgt ggccatggcc ttctcagctg aacaggacct   1080

gcagctctgt gttggggggt gccctccaag tcagcgactc tctcgatcag agcgcaatcg   1140

tcggggagct ataaccattg atactgccag acggctgtgc aaggaagggc ttccagtgga   1200

agatgcttac ttccattcct gtgtctttga tgttttaatt tctggtgatc ccaactttac   1260

cgtggcagct caggcagcac tggaggatgc ccgagccttc ctgccagact tagagaagct   1320

gcatctcttc ccctcagatg ctggggttcc tctttcctca gcaaccctct tagctccact   1380

cctttctggg ctctttgttc tgtggctttg cattcagtaa ggggaccatc agtcccatta   1440

ctagtttgga aatgatttgg agatacagat tggcatagaa gaatgtaaag aatcattaaa   1500

ggaagcaggg cctaggagac acgtgaaaca atgacattat ccagagtcag atgaggctgc   1560

agtccagggt tgaaattatc acagaataag gattctgggc aaggttactg cattccggat   1620

ctctgtgggg ctcttcacca atttttccag cctcatttat agtaaacaaa ttgttctaat   1680

ccatttactg cagatttcac ccttataagt ttagaggtca tgaaggtttt aatgatcagt   1740

aaagatttaa gggttgagat ttttaagagg caagagctga aagcagaaga catgatcatt   1800

agccataaga aactcaaagg aggaagacat aattagggaa agaagtctat ttgatgaata   1860

tgtgtgtgta aggtatgttc tgctttcttg attcaaaaat gaagcaggca ttgtctagct   1920

cttaggtgaa gggagtctct gcttttgaag aatggcacag gtaggacaga agtatcatcc   1980

ctacccccta actaatctgt tattaaagct acaaattctt cacaccatca aaaaaaaaaa   2040

aaaaaaaa                                                            2048
```

```
<210> SEQ ID NO 39
<211> LENGTH: 1901
<212> TYPE: DNA
<213> ORGANISM: Homo sapiens
<220> FEATURE:
<221> NAME/KEY: gene
<222> LOCATION: (1)..(1901)
<223> OTHER INFORMATION: Accession No. BC085604

<400> SEQUENCE: 39

ggaggacccc ctggctggag ctgacccaca gagtagggaa tcatggctgg agaattggat     60

agcagagtaa tgtttgacct ctggaaacac tcattctcaa tgcaagatcc tccgctgcaa    120

tgctgagtac gtatcgtcca ctctgagcct tagaggtggg ggttcatcag gagcacttcg    180

aggaggagga ggaggaggcc ggggtggagg ggtgggctct ggcggcctct gtcgagccct    240

ccgctcctat gcgctctgca ctcggcgcac cgcccgcacc tgccgcgggg acctcgcctt    300

ccattcggcg gtacatggca tcgaagacct gatgatccag cacaactgct cccgccaggg    360

ccctacagcc cctcccccgc cccggggccc cgcccttcca ggcgcgggct ccggcctccc    420

tgccccggac ccttgtgact atgaaggccg gttttcccgg ctgcatggtc gtcccccggg    480

gttcttgcat tgcgcttcct tcggggaccc ccatgtgcgc agcttccacc atcactttca    540

cacatgccgt gtccaaggag cttggcctct actggataat gacttcctct ttgtccaagc    600

caccagctcc cccatggcgt tgggggccaa cgctaccgcc acccggaagc tcaccatcat    660

atttaagaac atgcaggaat gcattgatca gaaggtgtat caggctgagg tggataatct    720

tcctgtagcc tttgaagatg gttctatcaa tggaggtgac cgacctgggg gatccagttt    780

gtcgattcaa actgctaacc ctgggaacca tgtggagatc caagctgcct acattggcac    840

aactataatc attcggcaga cagctgggca gctctccttc tccatcaagg tagcagagga    900
```

```
tgtggccatg gccttctcag ctgaacagga cctgcagctc tgtgttgggg ggtgccctcc    960

aagtcagcga ctctctcgat cagagcgcaa tcgtcgggga gctataacca ttgatactgc   1020

cagacggctg tgcaaggaag ggcttccagt ggaagatgct tacttccatt cctgtgtctt   1080

tgatgtttta atttctggtg atcccaactt taccgtggca gctcaggcag cactggagga   1140

tgcccgagcc ttcctgccag acttagagaa gctgcatctc ttcccctcag atgctggggt   1200

tcctctttcc tcagcaaccc tcttagctcc actcctttct gggctctttg ttctgtggct   1260

ttgcattcag taaggggacc atcagtccca ttactagttt ggaaatgatt tggagataca   1320

gattggcata gaagaatgta aagaatcatt aaaggaagca gggcctagga gacacgtgaa   1380

acaatgacat tatccagagt cagatgaggc tgcagtccag ggttgaaatt atcacagaat   1440

aaggattctg ggcaaggtta ctgcattccg gatctctgtg ggctcttca ccaatttttc   1500

cagcctcatt tatagtaaac aaattgttct aatccattta ctgcagattt caccccttata   1560

agtttagagg tcatgaaggt tttaatgatc agtaaagatt taagggttga gatttttaag   1620

aggcaagagc tgaaagcaga agacatgatc attagccata agaaactcaa aggaggaaga   1680

cataattagg gaaagaagtc tatttgatga atatgtgtgt gtaaggtatg ttctgctttc   1740

ttgattcaaa aatgaagcag gcattgtcta gctcttaggt gaagggagtc tctgcttttg   1800

aagaatggca caggtaggac agaagtatca tccctacccc ctaactaatc tgttattaaa   1860

gctacaaatt cttcacacca tcaaaaaaaa aaaaaaaaaa a                       1901
```

<210> SEQ ID NO 40
<211> LENGTH: 2024
<212> TYPE: DNA
<213> ORGANISM: Mus musculus
<220> FEATURE:
<221> NAME/KEY: gene
<222> LOCATION: (1)..(2024)
<223> OTHER INFORMATION: Accession No. AJ557515

<400> SEQUENCE: 40

```
ggctctctga cctgagtgag actgcagcca ttccggggca atcatggaga aagagatggg     60

ggaccccctg gctggagcag accaacagaa taggcaacta tggctcgaga acccagtatc    120

agagtaatgc ttgacctcgg gaaacatcac agaagtaccc agagaaattc actaggtagg    180

aggctcatca tctgggaaga accggtgcct ggggggacct ggctggatag gtatgggcca    240

gtcccctagt ccccggtccc cccacggcag ccctccaact ctaagcaccc tcactctcct    300

gctgctcctc tgtggacagg ctcactccca gtgcaagatc ctccgctgca atgccgagta    360

tgtctcgtcc actctgagtc ttcggggagg tggctcaccg gacacgccgc gtggaggcgg    420

ccgtggtggg ctggcctcag gtggcttgtg tcgcgccctg cgctcctacg ctctctgcac    480

gcggcgcacg gcccgcacct gccgcgggga ccttgctttc cactctgcgg tgcatggcat    540

agaggacctg atgatccagc acaactgctc acgccagggt cccacggccc cgcccccggc    600

ccggggcccc gccctgcccg gggccgggcc agcgcccctg accccagatc cctgtgacta    660

tgaggcccgg ttttccaggc tgcacggtcg agccccgggc ttcttgcatt gcgcatcctt    720

tggagatccc catgtgcgca gtttccacaa ccaatttcac acatgccgtg tccaaggagc    780

ttggcccttg ctagataacg acttcctctt tgtccaggcc accagctccc cggtttcgtc    840

gggagccaac gctaccacca tccggaagat cactatcata tttaaaaaca tgcaggaatg    900

cattgaccag aaagtctacc aggctgaggt ggacaatctt cctgcagcct ttgaagatgg    960
```

-continued

```
ttctatcaat gggggcgacc gacctggggg ctcgagtttg tccattcaaa ctgctaacct   1020

tgggagtcac gtggagattc gagctgccta cattggaaca actatcatca ttcgacagac   1080

agctgggcag ctctccttct ccatcagggt agcagaggat gtggcgcggg ccttctccgc   1140

agagcaggac ctacagctgt gtgttggggg atgccctccg agccagcgac tctctcgctc   1200

agagcgcaac cgccgtgggg ctatagccat agatactgcc agaaggctgt gtaaggaagg   1260

gcttccggtt gaagatgcct acttccaatc ctgcgtcttt gatgtttcag tctccggtga   1320

ccccaacttt actgtggcag ctcagacagc tctggacgat gcccgaatct tcttgacgga   1380

tttagagaac ttacatctct ttccctcaga tgcggggcct cccctctctc ctgccatctg   1440

cctagtcccg cttctttcgg ccctctttgt tctgtggctt tgcttcagta agtaggccag   1500

caacccatga ctggtttgga aacgatttga ggatagaggt tggtgtgaga aaccacaaag   1560

atgtgccaaa ggaaacagcg gggacaggag acaacactta ctcaatcaga tgaggttgca   1620

gtccagggct gaaatgaccc tagaataaag attctgggcc agggttttgc actccagacc   1680

ttggtgtggg ctattcacca tggatttccc agttagtgat ttcccacttg taatgaaatt   1740

ccactctcca tacacctgat accactccta caagcctaga gattgtgaga gtgctaatga   1800

ccagtgaaac attaaaggac tgagatatcg taaaggcaaa aacatgattc tctttgagaa   1860

agtcaaaaga ggagaagcta attaggaaaa gcttttggtt cagaaacgaa gtgggcattg   1920

tctggcagag gaagtcagct tttggagact ggcaccaact cagaaacggg catttccatc   1980

ccttcctaat ctgttattaa agcgattagt tctcaaaaaa aaaa                    2024
```

<210> SEQ ID NO 41
<211> LENGTH: 430
<212> TYPE: DNA
<213> ORGANISM: Homo sapiens
<220> FEATURE:
<221> NAME/KEY: gene
<222> LOCATION: (1)..(430)
<223> OTHER INFORMATION: Accession No. NM_021175

<400> SEQUENCE: 41

```
gactgtcact cggtcccaga caccagagca agctcaagac ccagcagtgg gacagccaga     60

cagacggcac gatggcactg agctcccaga tctgggccgc ttgcctcctg ctcctcctcc    120

tcctcgccag cctgaccagt ggctctgttt tcccacaaca gacgggacaa cttgcagagc    180

tgcaacccca ggacagagct ggagccaggg ccagctggat gcccatgttc cagaggcgaa    240

ggaggcgaga cacccacttc cccatctgca ttttctgctg cggctgctgt catcgatcaa    300

agtgtgggat gtgctgcaag acgtagaacc tacctgccct gcccccgtcc cctcccttcc    360

ttatttattc ctgctgcccc agaacatagg tcttggaata aaatggctgg ttcttttgtt    420

ttccaaaaaa                                                           430
```

<210> SEQ ID NO 42
<211> LENGTH: 433
<212> TYPE: DNA
<213> ORGANISM: Homo sapiens
<220> FEATURE:
<221> NAME/KEY: gene
<222> LOCATION: (1)..(433)
<223> OTHER INFORMATION: Accession No. BC020612

<400> SEQUENCE: 42

```
accagagcaa gctcaagacc cagcagtggg acagccagac agacggcacg atggcactga     60

gctcccagat ctgggccgct tgcctcctgc tcctcctcct cctcgccagc ctgaccagtg    120
```

-continued

```
gctctgtttt cccacaacag acgggacaac ttgcagagct gcaaccccag gacagagctg    180

gagccagggc cagctggatg cccatgttcc agaggcgaag gaggcgagac acccacttcc    240

ccatctgcat tttctgctgc ggctgctgtc atcgatcaaa gtgtgggatg tgctgcaaga    300

cgtagaacct acctgccctg cccccgtccc ctcccttcct tatttattcc tgctgcccca    360

gaacataggt cttggaataa aatggctggt tcttttgttt tccaaaaaaa aaaaaaaaaa    420

aaaaaaaaaa aaa                                                       433
```

<210> SEQ ID NO 43
<211> LENGTH: 410
<212> TYPE: DNA
<213> ORGANISM: Mus musculus
<220> FEATURE:
<221> NAME/KEY: gene
<222> LOCATION: (1)..(410)
<223> OTHER INFORMATION: Accession No. NM_032541

<400> SEQUENCE: 43

```
agtccttaga ctgcacagca gaacagaagg catgatggca ctcagcactc ggacccaggc     60

tgcctgtctc ctgcttctcc tccttgccag cctgagcagc accacctatc tccatcaaca    120

gatgagacag actacagagc tgcagccttt gcacggggaa gaaagcaggg cagacattgc    180

gataccaatg cagaagagaa ggaagagaga caccaacttc cccatctgca tcttctgctg    240

taaatgctgt aacaattccc agtgtggtat ctgttgcaaa acatagccta gagccacatc    300

ctgacctctc tacacccctg cagcccctca accccattat ttattcctgc cctccccacc    360

aatgaccttg aaataaagac gattttattt tcaaaaaaaa aaaaaaaaaa               410
```

<210> SEQ ID NO 44
<211> LENGTH: 419
<212> TYPE: DNA
<213> ORGANISM: Mus musculus
<220> FEATURE:
<221> NAME/KEY: gene
<222> LOCATION: (1)..(419)
<223> OTHER INFORMATION: Accession No. EST W12193

<400> SEQUENCE: 44

```
cacaagtcct tagactgcac agcagaacag aaggcatgat ggcactcagc actcggaccc     60

aggctgcctg tctcctgctt ctcctccttg ccagcctgag cagcaccacc tatctccatc    120

aacagatgag acagactaca gagctgcagc ctttgcacgg ggaagaaagc agggcagaca    180

ttgcgatacc aatgcagaag agaaggaaga gagacaccaa cttccccatc tgcatcttct    240

gctgtaaatg ctgtaacaat tcccagtgtg gtatctgttg caaaacatag cctagagcca    300

catcctgacc tctctacacc cctgcagccc ctcaacccca ttatttattc ctgccctccc    360

caccaatgac cttgaaataa agacgatttt attttcaaaa agaaaaaaaa aaaacatga     419
```

<210> SEQ ID NO 45
<211> LENGTH: 3150
<212> TYPE: DNA
<213> ORGANISM: Homo sapiens
<220> FEATURE:
<221> NAME/KEY: gene
<222> LOCATION: (1)..(3150)
<223> OTHER INFORMATION: Accession No. NM_001200

<400> SEQUENCE: 45

```
ccacaaaggg cacttggccc cagggctagg agagcgaggg gagagcacag ccacccgcct     60
```

```
cggcggcccg ggactcggct cgactcgccg gagaatgcgc ccgaggacga cggggcgcca    120
gagccgcggt gctttcaact ggcgagcgcg aatgggggtg cactggagta aggcagagtg    180
atgcgggggg gcaactcgcc tggcaccgag atcgccgccg tgcccttccc tggacccggc    240
gtcgcccagg atggctgccc cgagccatgg gccgcggcgg agctagcgcg gagcgcccga    300
ccctcgaccc ccgagtcccg gagccggccc cgcgcggggc cacgcgtccc tcgggcgctg    360
gttcctaagg aggacgacag caccagcttc tcctttctcc cttcccttcc ctgccccgca    420
ctcctccccc tgctcgctgt tgttgtgtgt cagcacttgg ctggggactt cttgaacttg    480
cagggagaat aacttgcgca ccccactttg cgccggtgcc tttgccccag cggagcctgc    540
ttcgccatct ccgagcccca ccgcccctcc actcctcggc cttgcccgac actgagacgc    600
tgttcccagc gtgaaaagag agactgcgcg gccggcaccc gggagaagga ggaggcaaag    660
aaaaggaacg gacattcggt ccttgcgcca ggtcctttga ccagagtttt tccatgtgga    720
cgctctttca atggacgtgt ccccgcgtgc ttcttagacg gactgcggtc tcctaaaggt    780
cgaccatggt ggccgggacc cgctgtcttc tagcgttgct gcttccccag gtcctcctgg    840
gcggcgcggc tggcctcgtt ccggagctgg gccgcaggaa gttcgcggcg gcgtcgtcgg    900
gccgcccctc atcccagccc tctgacgagg tcctgagcga gttcgagttg cggctgctca    960
gcatgttcgg cctgaaacag agacccaccc ccagcaggga cgccgtggtg ccccccctaca   1020
tgctagacct gtatcgcagg cactcaggtc agccgggctc acccgcccca gaccaccggt   1080
tggagagggc agccagccga gccaacactg tgcgcagctt ccaccatgaa gaatctttgg   1140
aagaactacc agaaacgagt gggaaaacaa cccggagatt cttctttaat ttaagttcta   1200
tccccacgga ggagtttatc acctcagcag agcttcaggt tttccgagaa cagatgcaag   1260
atgctttagg aaacaatagc agtttccatc accgaattaa tatttatgaa atcataaaac   1320
ctgcaacagc caactcgaaa ttccccgtga ccagactttt ggacaccagg ttggtgaatc   1380
agaatgcaag caggtgggaa agttttgatg tcacccccgc tgtgatgcgg tggactgcac   1440
agggacacgc caaccatgga ttcgtggtgg aagtggccca cttggaggag aaacaaggtg   1500
tctccaagag acatgttagg ataagcaggt ctttgcacca agatgaacac agctggtcac   1560
agataaggcc attgctagta acttttggcc atgatggaaa agggcatcct ctccacaaaa   1620
gagaaaaacg tcaagccaaa cacaaacagc ggaaacgcct taagtccagc tgtaagagac   1680
accctttgta cgtggacttc agtgacgtgg ggtggaatga ctggattgtg gctccccccgg   1740
ggtatcacgc cttttactgc cacggagaat gcccttttcc tctggctgat catctgaact   1800
ccactaatca tgccattgtt cagacgttgg tcaactctgt taactctaag attcctaagg   1860
catgctgtgt cccgacagaa ctcagtgcta tctcgatgct gtaccttgac gagaatgaaa   1920
aggttgtatt aaagaactat caggacatgg ttgtggaggg ttgtgggtgt cgctagtaca   1980
gcaaaattaa atacataaat atatatatat atatatattt tagaaaaaag aaaaaaacaa   2040
acaaacaaaa aaaccccacc ccagttgaca ctttaatatt tcccaatgaa gactttattt   2100
atggaatgga atggaaaaaa aaacagctat tttgaaaata tatttatatc tacgaaaaga   2160
agttgggaaa acaaatattt taatcagaga attattcctt aaagatttaa aatgtattta   2220
gttgtacatt ttatatgggt tcaaccccag cacatgaagt ataatggtca gatttatttt   2280
gtatttattt actattataa ccacttttta ggaaaaaaat agctaatttg tatttatatg   2340
taatcaaaag aagtatcggg tttgtacata attttccaaa aattgtagtt gttttcagtt   2400
gtgtgtattt aagatgaaaa gtctacatgg aaggttactc tggcaaagtg cttagcacgt   2460
```

-continued

```
ttgctttttt gcagtgctac tgttgagttc acaagttcaa gtccagaaaa aaaaagtgga   2520

taatccactc tgctgacttt caagattatt atattattca attctcagga atgttgcaga   2580

gtgattgtcc aatccatgag aatttacatc cttattaggt ggaatatttg gataagaacc   2640

agacattgct gatctattat agaaactctc ctcctgcccc ttaatttaca gaaagaataa   2700

agcaggatcc atagaaataa ttaggaaaac gatgaacctg caggaaagtg aatgatggtt   2760

tgttgttctt ctttcctaaa ttagtgatcc cttcaaaggg gctgatctgg ccaaagtatt   2820

caataaaacg taagatttct tcattattga tattgtggtc atatatattt aaaattgata   2880

tctcgtggcc ctcatcaagg gttggaaatt tatttgtgtt ttacctttac ctcatctgag   2940

agctctttat tctccaaaga acccagtttt ctaacttttt gcccaacacg cagcaaaatt   3000

atgcacatcg tgttttctgc ccaccctctg ttctctgacc tatcagcttg cttttctttc   3060

caaggttgtg tgtttgaaca catttctcca aatgttaaac ctatttcaga taataaatat   3120

caaatctctg gcatttcatt ctataaagtc                                     3150
```

```
<210> SEQ ID NO 46
<211> LENGTH: 2041
<212> TYPE: DNA
<213> ORGANISM: Homo sapiens
<220> FEATURE:
<221> NAME/KEY: gene
<222> LOCATION: (1)..(2041)
<223> OTHER INFORMATION: Accession No. BC069214

<400> SEQUENCE: 46

ccacaaaggg cacttggccc cagggctagg agagcgaggg gagagcacag ccacccgcct     60

cggcggcccg ggactcggct cgactcgccg gagaatgcgc ccgaggacga cggggcgcca    120

gagccgcggt gctttcaact ggcgagcgcg aatgggggtg cactggagta aggcagagtg    180

atgcgggggg gcaactcgcc tggcaccgag atcgccgccg tgcccttccc tggacccggc    240

gtcgcccagg atggctgccc cgagccatgg gccgcggcgg agctagcgcg gagcgcccga    300

ccctcgaccc ccgagtcccg gagccggccc cgcgcggggc cacgcgtccc tcgggcgctg    360

gttcctaagg aggacgacag caccagcttc tcctttctcc cttcccttcc ctgccccgca    420

ctcctccccc tgctcgctgt tgttgtgtgt cagcacttgg ctggggactt cttgaacttg    480

cagggagaat aacttgcgca ccccactttg cgccggtgcc tttgccccag cggagcctgc    540

ttcgccatct ccgagcccca ccgcccctcc actcctcggc cttgcccgac actgagacgc    600

tgttcccagc gtgaaaagag agactgcgcg gccggcaccc gggagaagga ggaggcaaag    660

aaaaggaacg gacattcggt ccttgcgcca ggtcctttga ccagagtttt tccatgtgga    720

cgctctttca atggacgtgt ccccgcgtgc ttcttagacg gactgcggtc tcctaaaggt    780

cgaccatggt ggccgggacc cgctgtcttc tagcgttgct gcttccccag gtcctcctgg    840

gcggcgcggc tggcctcgtt ccggagctgg gccgcaggaa gttcgcggcg gcgtcgtcgg    900

gccgcccctc atcccagccc tctgacgagg tcctgagcga gttcgagttg cggctgctca    960

gcatgttcgg cctgaaacag agacccaccc ccagcaggga cgccgtggtg ccccccctaca   1020

tgctagacct gtatcgcagg cactcgggtc agccgggctc acccgcccca gaccaccggt   1080

tggagagggc agccagccga gccaacactg tgcgcagctt ccaccatgaa gaatctttgg   1140

aagaactacc agaaacgagt gggaaaacaa cccggagatt cttctttaat ttaagttcta   1200

tccccacgga ggagtttatc acctcagcag agcttcaggt tttccgagaa cagatgcaag   1260
```

-continued

```
atgctttagg aaacaatagc agtttccatc accgaattaa tatttatgaa atcataaaac   1320

ctgcaacagc caactcgaaa ttccccgtga ccagtctttt ggacaccagg ttggtgaatc   1380

agaatgcaag caggtgggaa agttttgatg tcacccccgc tgtgatgcgg tggactgcac   1440

agggacacgc caaccatgga ttcgtggtgg aagtggccca cttggaggag aaacaaggtg   1500

tctccaagag acatgttagg ataagcaggt ctttgcacca agatgaacac agctggtcac   1560

agataaggcc attgctagta acttttggcc atgatggaaa agggcatcct ctccacaaaa   1620

gagaaaaacg tcaagccaaa cacaaacagc ggaaacgcct taagtccagc tgtaagagac   1680

accctttgta cgtggacttc agtgacgtgg ggtggaatga ctggattgtg gctcccccgg   1740

ggtatcacgc cttttactgc cacggagaat gccctttttcc tctggctgat catctgaact   1800

ccactaatca tgccattgtt cagacgttgg tcaactctgt taactctaag attcctaagg   1860

catgctgtgt cccgacagaa ctcagtgcta tctcgatgct gtaccttgac gagaatgaaa   1920

aggttgtatt aaagaactat caggacatgg ttgtggaggg ttgtgggtgt cgctagtaca   1980

gcaaaattaa atacataaat atatatatat atatatattt tagaaaaaaa aaaaaaaaaa   2040

a                                                                   2041
```

<210> SEQ ID NO 47
<211> LENGTH: 1957
<212> TYPE: DNA
<213> ORGANISM: Homo sapiens
<220> FEATURE:
<221> NAME/KEY: gene
<222> LOCATION: (1)..(1957)
<223> OTHER INFORMATION: Accession No. NM_001202

<400> SEQUENCE: 47

```
aagaggagga aggaagatgc gagaaggcag aggaggaggg agggagggaa ggagcgcgga     60

gcccggcccg gaagctaggt gagtgtggca tccgagctga gggacgcgag cctgagacgc    120

cgctgctgct ccggctgagt atctagcttg tctccccgat gggattcccg tccaagctat    180

ctcgagcctg cagcgccaca gtccccggcc ctcgcccagg ttcactgcaa ccgttcagag    240

gtccccagga gctgctgctg gcgagcccgc tactgcaggg acctatggag ccattccgta    300

gtgccatccc gagcaacgca ctgctgcagc ttccctgagc ctttccagca agtttgttca    360

agattggctg tcaagaatca tggactgtta ttatatgcct tgttttctgt caagacacca    420

tgattcctgg taaccgaatg ctgatggtcg ttttattatg ccaagtcctg ctaggaggcg    480

cgagccatgc tagtttgata cctgagacgg ggaagaaaaa agtcgccgag attcagggcc    540

acgcgggagg acgccgctca gggcagagcc atgagctcct gcgggacttc gaggcgacac    600

ttctgcagat gtttgggctg cgccgccgcc cgcagcctag caagagtgcc gtcattccgg    660

actacatgcg ggatctttac cggcttcagt ctggggagga ggaggaagag cagatccaca    720

gcactggtct tgagtatcct gagcgcccgg ccagccgggc caacaccgtg aggagcttcc    780

accacgaaga acatctggag aacatcccag ggaccagtga aaactctgct tttcgtttcc    840

tctttaacct cagcagcatc cctgagaacg aggtgatctc ctctgcagag cttcggctct    900

tccgggagca ggtggaccag ggccctgatt gggaaagggg cttccaccgt ataaacattt    960

atgaggttat gaagcccccca gcagaagtgg tgcctgggca cctcatcaca cgactactgg   1020

acacgagact ggtccaccac aatgtgacac ggtgggaaac ttttgatgtg agccctgcgg   1080

tccttcgctg gacccgggag aagcagccaa actatgggct agccattgag gtgactcacc   1140

tccatcagac tcggacccac cagggccagc atgtcaggat tagccgatcg ttacctcaag   1200
```

-continued

```
ggagtgggaa ttgggcccag ctccggcccc tcctggtcac ctttggccat gatggccggg   1260
gccatgcctt gacccgacgc cggagggcca agcgtagccc taagcatcac tcacagcggg   1320
ccaggaagaa gaataagaac tgccggcgcc actcgctcta tgtggacttc agcgatgtgg   1380
gctggaatga ctggattgtg gccccaccag gctaccaggc cttctactgc catggggact   1440
gcccctttcc actggctgac cacctcaact caaccaacca tgccattgtg cagaccctgg   1500
tcaattctgt caattccagt atccccaaag cctgttgtgt gcccactgaa ctgagtgcca   1560
tctccatgct gtacctggat gagtatgata aggtggtact gaaaaattat caggagatgg   1620
tagtagaggg atgtgggtgc cgctgagatc aggcagtcct tgaggataga cagatataca   1680
caccacacac acacaccaca tacaccacac acacacgttc ccatccactc acccacacac   1740
tacacagact gcttccttat agctggactt ttatttaaaa aaaaaaaaaa aaaaggaaaa   1800
aatccctaaa cattcacctt gaccttattt atgactttac gtgcaaatgt tttgaccata   1860
ttgatcatat attttgacaa aatatattta taactacgta ttaaaagaaa aaaataaaat   1920
gagtcattat tttaaaggta aaaaaaaaaa aaaaaaa                            1957
```

<210> SEQ ID NO 48
<211> LENGTH: 1573
<212> TYPE: DNA
<213> ORGANISM: Homo sapiens
<220> FEATURE:
<221> NAME/KEY: gene
<222> LOCATION: (1)..(1573)
<223> OTHER INFORMATION: Accession No. BC020546

<400> SEQUENCE: 48

```
tcgacccacg cgtccgggca gaggaggagg gagggaggga aggagcgcgg agcccggccc     60
ggaagctagg agccattccg tagtgccatc ccgagcaacg cactgctgca gcttccctga    120
gcctttccag caagtttgtt caagattggc tgtcaagaat catggactgt tattatatgc    180
cttgttttct gtcaagacac catgattcct ggtaaccgaa tgctgatggt cgttttatta    240
tgccaagtcc tgctaggagg cgcgagccat gctagtttga tacctgagac ggggaagaaa    300
aaagtcgccg agattcaggg ccacgcggga ggacgccgct cagggcagag ccatgagctc    360
ctgcgggact tcgaggcgac acttctgcag atgtttgggc tgcgccgccg cccgcagcct    420
agcaagagtg ccgtcattcc ggactacatg cgggatcttt accggcttca gtctggggag    480
gaggaggaag agcagatcca cagcactggt cttgagtatc ctgagcgccc ggccagccgg    540
gccaacaccg tgaggagctt ccaccacgaa gaacatctgg agaacatccc agggaccagt    600
gaaaactctg cttttcgttt cctctttaac ctcagcagca tccctgagaa cgaggcgatc    660
tcctctgcag agcttcggct cttccgggag caggtggacc agggccctga ttgggaaagg    720
ggcttccacc gtataaacat ttatgaggtt atgaagcccc cagcagaagt ggtgcctggg    780
cacctcatca cacgactact ggacacgaga ctggtccacc acaatgtgac acggtgggaa    840
acttttgatg tgagccctgc ggtccttcgc tggacccggg agaagcagcc aaactatggg    900
ctagccattg aggtgactca cctccatcag actcggaccc accagggcca gcatgtcagg    960
attagccgat cgttacctca agggagtggg aattgggccc agctccggcc cctcctggtc   1020
acctttggcc atgatggccg gggccatgcc ttgacccgac gccggagggc caagcgtagc   1080
cctaagcatc actcacagcg ggccaggaag aagaataaga actgccggcg ccactcgctc   1140
tatgtggact tcagcgatgt gggctggaat gactggattg tggccccacc aggctaccag   1200
```

-continued

```
gccttctact gccatgggga ctgccccttt ccactggctg accacctcaa ctcaaccaac   1260

catgccattg tgcagaccct ggtcaattct gtcaattcca gtatccccaa agcctgttgt   1320

gtgcccactg aactgagtgc catctccatg ctgtacctgg atgagtatga taaggtggta   1380

ctgaaaaatt atcaggagat ggtagtagag ggatgtgggt gccgctgaga tcaggcagtc   1440

cttgaggata gacagatata cacaccacac acacacacca catacaccac acacacacgt   1500

tcccatccac tcacccacac actacacaga ctgcttcctt atagctggac ttttatttaa   1560

aaaaaaaaaa aaa                                                      1573
```

<210> SEQ ID NO 49
<211> LENGTH: 1852
<212> TYPE: DNA
<213> ORGANISM: Homo sapiens
<220> FEATURE:
<221> NAME/KEY: gene
<222> LOCATION: (1)..(1852)
<223> OTHER INFORMATION: Accession No. NM_001101

<400> SEQUENCE: 49

```
accgccgaga ccgcgtccgc cccgcgagca cagagcctcg cctttgccga tccgccgccc     60

gtccacaccc gccgccagct caccatggat gatgatatcg ccgcgctcgt cgtcgacaac    120

ggctccggca tgtgcaaggc cggcttcgcg ggcgacgatg ccccccgggc cgtcttcccc    180

tccatcgtgg ggcgccccag gcaccagggc gtgatggtgg gcatgggtca gaaggattcc    240

tatgtgggcg acgaggccca gagcaagaga ggcatcctca ccctgaagta ccccatcgag    300

cacggcatcg tcaccaactg ggacgacatg gagaaaatct ggcaccacac cttctacaat    360

gagctgcgtg tggctcccga ggagcacccc gtgctgctga ccgaggcccc cctgaacccc    420

aaggccaacc gcgagaagat gacccagatc atgtttgaga ccttcaacac cccagccatg    480

tacgttgcta tccaggctgt gctatccctg tacgcctctg gccgtaccac tggcatcgtg    540

atggactccg gtgacggggt cacccacact gtgcccatct acgaggggta tgccctcccc    600

catgccatcc tgcgtctgga cctggctggc cgggacctga ctgactacct catgaagatc    660

ctcaccgagc gcggctacag cttcaccacc acggccgagc gggaaatcgt gcgtgacatt    720

aaggagaagc tgtgctacgt cgccctggac ttcgagcaag agatggccac ggctgcttcc    780

agctcctccc tggagaagag ctacgagctg cctgacggcc aggtcatcac cattggcaat    840

gagcggttcc gctgccctga ggcactcttc cagccttcct tcctgggcat ggagtcctgt    900

ggcatccacg aaactacctt caactccatc atgaagtgtg acgtggacat ccgcaaagac    960

ctgtacgcca acacagtgct gtctggcggc accaccatgt accctggcat tgccgacagg   1020

atgcagaagg agatcactgc cctggcaccc agcacaatga agatcaagat cattgctcct   1080

cctgagcgca agtactccgt gtggatcggc ggctccatcc tggcctcgct gtccaccttc   1140

cagcagatgt ggatcagcaa gcaggagtat gacgagtccg gcccctccat cgtccaccgc   1200

aaatgcttct aggcggacta tgacttagtt gcgttacacc ctttcttgac aaaacctaac   1260

ttgcgcagaa aacaagatga gattggcatg gctttatttg tttttttgt tttgttttgg   1320

ttttttttt tttttggct tgactcagga tttaaaaact ggaacggtga aggtgacagc   1380

agtcggttgg agcgagcatc ccccaaagtt cacaatgtgg ccgaggactt tgattgcaca   1440

ttgttgtttt tttaatagtc attccaaata tgagatgcgt tgttacagga agtcccttgc   1500

catcctaaaa gccaccccac ttctctctaa ggagaatggc ccagtcctct cccaagtcca   1560

cacaggggag gtgatagcat tgctttcgtg taaattatgt aatgcaaaat ttttttaatc   1620
```

-continued ttcgccttaa tactttttta ttttgtttta ttttgaatga tgagccttcg tgccccccct 1680
tccccctttt ttgtccccca acttgagatg tatgaaggct tttggtctcc ctgggagtgg 1740
gtggaggcag ccagggctta cctgtacact gacttgagac cagttgaata aaagtgcaca 1800
ccttaaaaat gaaaaaaaaa aaaaaaaaaa aaaaaaaaaa aaaaaaaaaa aa 1852

<210> SEQ ID NO 50
<211> LENGTH: 1805
<212> TYPE: DNA
<213> ORGANISM: Homo sapiens
<220> FEATURE:
<221> NAME/KEY: gene
<222> LOCATION: (1)..(1805)
<223> OTHER INFORMATION: Accession No. BC001301

<400> SEQUENCE: 50
cgccccgcga gcacagagcc tcgcctttgc cgatccgccg cccgtccaca cccgccgcca 60
gctcaccatg gatgatgata tcgccgcgct cgtcgtcgac aacggctccg gcatgtgcaa 120
ggccggcttc gcgggcgacg atgccccccg ggccgtcttc ccctccatcg tggggcgccc 180
caggcaccag ggcgtgatgg tgggcatggg tcagaaggat tcctatgtgg gcgacgaggc 240
ccagagcaag agaggcatcc tcaccctgaa gtaccccatc gagcacggca tcgtcaccaa 300
ctgggacgac atggagaaaa tctggcacca caccttctac aatgagctgc gtgtggctcc 360
cgaggagcac cccgtgctgc tgaccgaggc ccccctgaac cccaaggcca accgcgagaa 420
gatgacccag atcatgtttg agaccttcaa caccccagcc atgtacgttg ctatccaggc 480
tgtgctatcc ctgtacgcct ctggccgtac cactggcatc gtgatggact ccggtgacgg 540
ggtcacccac actgtgccca tctacgaggg gtatgccctc ccccatgcca tcctgcgtct 600
ggacctggct ggccgggacc tgactgacta cctcatgaag atcctcaccg agcgcggcta 660
cagcttcacc accacggccg agcgggaaat cgtgcgtgac attaaggaga agctgtgcta 720
cgtcgccctg gacttcgagc aagagatggc cacggctgct tccagctcct ccctggagaa 780
gagctacgag ctgcctgacg gccaggtcat caccattggc aatgagcggt tccgctgccc 840
tgaggcactc ttccagcctt ccttcctggg catggagtcc tgtggcatcc acgaaactac 900
cttcaactcc atcatgaagt gtgacgtgga catccgcaaa gacctgtacg ccaacacagt 960
gctgtctggc ggcaccacca tgtaccctgg cattgccgac aggatgcaga aggagatcac 1020
tgccctggca cccagcacaa tgaagatcaa gatcattgct cctcctgagc gcaagtactc 1080
cgtgtggatc ggcggctcca tcctggcctc gctgtccacc ttccagcaga tgtggatcag 1140
caagcaggag tatgacgagt ccggcccctc catcgtccac cgcaaatgct tctaggcgga 1200
ctatgactta gttgcgttac accctttctt gacaaaacct aacttgcgca gaaaacaaga 1260
tgagattggc atggctttat ttgttttttt tgttttgttt tggttttttt tttttttttg 1320
gcttgactca ggatttaaaa actggaacgg tgaaggtgac agcagtcggt tggagcgagc 1380
atcccccaaa gttcacaatg tggccgagga ctttgattgc acattgttgt ttttttaata 1440
gtcattccaa atatgagatg cgttgttaca ggaagtccct tgccatccta aaagccaccc 1500
cacttctctc taaggagaat ggcccagtcc tctcccaagt ccacacaggg gaggtgatag 1560
cattgctttc gtgtaaatta tgtaatgcaa aattttttta atcttcgcct taatactttt 1620
ttattttgtt ttattttgaa tgatgagcct tcgtgccccc ccttccccct tttttgtccc 1680
ccaacttgag atgtatgaag gcttttggtc tccctgggag tgggtggagg cagccagggc 1740

```
ttacctgtac actgacttga gaccagttga ataaaagtgc acaccttaaa aaaaaaaaaa    1800

aaaaa                                                                1805

<210> SEQ ID NO 51
<211> LENGTH: 402
<212> TYPE: DNA
<213> ORGANISM: Homo sapiens
<220> FEATURE:
<221> NAME/KEY: promoter
<222> LOCATION: (1)..(402)
<223> OTHER INFORMATION: Human hepcidin promoter

<400> SEQUENCE: 51

gctcatcaaa ctgcttaacc gctgaagcaa aaggggggaac ttttttcccg atcagcagaa     60

tgacatcgtg atggggaaag ggctccccag atggctggtg agcagtgtgt gtctgtgacc    120

ccgtctgccc caccccctga acacacctct gccggctgag ggtgacacaa ccctgttccc    180

tgtcgctctg ttcccgctta tctctcccgc cttttcggcg ccaccacctt cttggaaatg    240

agacagagca aaggggaggg ggctcagacc accgcctccc ctggcaggcc ccataaaagc    300

gactgtcact cggtcccaga caccagagca agctcaagac ccagcagtgg gacagccaga    360

cagacggcac gatggcactg agctcccaga tctgggccgc tt                       402

<210> SEQ ID NO 52
<211> LENGTH: 402
<212> TYPE: DNA
<213> ORGANISM: Pan troglodytes
<220> FEATURE:
<221> NAME/KEY: promoter
<222> LOCATION: (1)..(402)
<223> OTHER INFORMATION: Chimpanzee Hepcidin promoter

<400> SEQUENCE: 52

gctcatcaaa ctgcttaacc gctgaagcaa aaggggggaac ttttttcccg atcagcagaa     60

tgacatcgtg atggggaaag ggctccccag atggctggcg agcagtgtgt gtctgtgacc    120

ccgtctgccc caccccctga acacacctct gccggctgag ggtgacacaa ccctgttccc    180

tgtcgctctg ttcccgctta tctctcccgc cttttcggcg ccaccacctt cttggaaatg    240

agacagagca aaggggaggg ggctcagacc accgcctccc ctggcaggcc ccataaaagc    300

gactgtcact cggtccgaga caccagagca agctcaagac ccagcagtgg gacagccaga    360

cagacggcac gatggcactg agctcccaga tctgggccgc tt                       402

<210> SEQ ID NO 53
<211> LENGTH: 413
<212> TYPE: DNA
<213> ORGANISM: Canis familiaris
<220> FEATURE:
<221> NAME/KEY: promoter
<222> LOCATION: (1)..(413)
<223> OTHER INFORMATION: Dog Hepcidin promoter

<400> SEQUENCE: 53

gctcatcgac ctgttcgact cttggggcaa aggagggact tttattttcc gccgtcaaca     60

gatgatgcca tgtcagggaa agtgtttccc aggtggctgg ctagaggcgt gtgtctgtgt    120

gtgtctgtgg ccccgtctgc cccaccccct ggacacacct ctgctggcta agggtgacat    180

aacactgttc cctgtcactc tgttcccgct tatctcccgt cttgtcggcg ccaccacctt    240

cttggaaatg agttaggaca aaggggaggg ggctcagcac ccccgcctcc cccagaagga    300

cccataaaag caaccgaatc ggggccccag acaccacagc aagtctgaaa cctgacagca    360
```

ggacagccag acggacggca caatggccct gagcacgcgg atccaggctg cct 413

<210> SEQ ID NO 54
<211> LENGTH: 366
<212> TYPE: DNA
<213> ORGANISM: Rattus rattus
<220> FEATURE:
<221> NAME/KEY: promoter
<222> LOCATION: (1)..(366)
<223> OTHER INFORMATION: Rat Hepcidin promoter

<400> SEQUENCE: 54
agtcaccaat caatgtttag ggtaaaagag ggggattttt ctgagagcca tggggtgaca 60
tcacaggtgg ctggctggag gcttgttgtc catggctctg ccccaccttc tgaatgcacc 120
tctgctggct gagagtgaca taaccctgtc ccctgtcact ctgttcccgc ttatctctcc 180
cgcctgtttg gcgccactat cttcttggaa atgagtcagg gcaaaaggga gggggctcag 240
gtgaccctcc tcccactggt cccataaaaa ggactgggac tggctcctag acaccagctc 300
aagtccttgg actacactgc aggacagaag gcaagatggc actaagcact cggatccagg 360
ctgcct 366

<210> SEQ ID NO 55
<211> LENGTH: 382
<212> TYPE: DNA
<213> ORGANISM: Mus musculus
<220> FEATURE:
<221> NAME/KEY: promoter
<222> LOCATION: (1)..(382)
<223> OTHER INFORMATION: Mouse Hepcidin promoter

<400> SEQUENCE: 55
actcaccaat ccaatcactg tttaggggaa agaaggggaa tttttctgag agccacagtg 60
tgacatcaca ggtggctggc tgcaggcttg tgtccctggt tctgtctgcc ccaccctctg 120
gatgcacctc tgctggctgt aggtgacaca accctgtccc ctgtcactgt tcccgcttat 180
ctctcccgcc tgtttggcgc cactattttc ttggaaatga gtcagagcaa aatgggggtg 240
ggtgaggcgc aggtgaccct cccctaccac tagtcccata aaaaggactg ggactgctcc 300
tagacagcca ccacacaagt ccttagactg cacagcagaa cagaaggcat gatggcactc 360
agcactcgga cccaggctgc ct 382

<210> SEQ ID NO 56
<211> LENGTH: 454
<212> TYPE: PRT
<213> ORGANISM: Mus musculus
<220> FEATURE:
<221> NAME/KEY: mat_peptide
<222> LOCATION: (1)..(454)
<223> OTHER INFORMATION: mDL-2

<400> SEQUENCE: 56

Met Gln Pro Pro Arg Glu Arg Leu Val Val Thr Gly Arg Ala Gly Trp
1 5 10 15

Met Gly Met Gly Arg Gly Ala Gly Arg Ser Ala Leu Gly Leu Trp Pro
20 25 30

Thr Leu Ala Phe Leu Leu Cys Ser Phe Pro Ala Ala Ile Ser Pro Cys
35 40 45

Lys Ile Leu Lys Cys Asn Ser Glu Phe Trp Ser Ala Thr Ser Ser Gly
50 55 60

Ser His Ala Pro Ala Ser Asp Asp Val Pro Glu Phe Cys Ala Ala Leu
65 70 75 80

Arg Thr Tyr Ala Leu Cys Thr Arg Arg Thr Ala Arg Thr Cys Arg Gly
85 90 95

Asp Leu Ala Tyr His Ser Ala Val His Gly Ile Glu Asp Leu Met Ser
100 105 110

Gln His Asn Cys Ser Lys Asp Gly Pro Thr Ser Gln Pro Arg Val Arg
115 120 125

Thr Leu Pro Pro Ala Gly Asp Ser Gln Glu Arg Ser Asp Ser Pro Glu
130 135 140

Ile Cys His Tyr Glu Lys Ser Phe His Lys His Ser Ala Ala Pro Asn
145 150 155 160

Tyr Thr His Cys Gly Leu Phe Gly Asp Pro His Leu Arg Thr Phe Thr
165 170 175

Asp His Phe Gln Thr Cys Lys Val Gln Gly Ala Trp Pro Leu Ile Asp
180 185 190

Asn Asn Tyr Leu Asn Val Gln Val Thr Asn Thr Pro Val Leu Pro Gly
195 200 205

Ser Ala Ala Thr Ala Thr Ser Lys Leu Thr Ile Ile Phe Lys Asn Phe
210 215 220

Gln Glu Cys Val Asp Gln Lys Val Tyr Gln Ala Glu Met Asp Glu Leu
225 230 235 240

Pro Ser Ala Phe Ala Asp Gly Ser Lys Asn Gly Gly Asp Lys His Gly
245 250 255

Ala Asn Ser Leu Lys Ile Thr Glu Lys Val Ser Gly Gln His Val Glu
260 265 270

Ile Gln Ala Lys Tyr Ile Gly Thr Thr Ile Val Val Arg Gln Val Gly
275 280 285

Arg Tyr Leu Thr Phe Ala Val Arg Met Pro Glu Glu Val Val Asn Ala
290 295 300

Val Glu Asp Arg Asp Ser Gln Gly Leu Tyr Leu Cys Leu Arg Gly Cys
305 310 315 320

Pro Leu Asn Gln Gln Ile Asp Phe Gln Ala Phe Arg Ala Asn Ala Glu
325 330 335

Ser Pro Arg Arg Pro Ala Ala Ala Ser Pro Ser Pro Val Val Pro Glu
340 345 350

Thr Phe Pro Tyr Glu Thr Ala Val Ala Lys Cys Lys Glu Lys Leu Pro
355 360 365

Val Glu Asp Leu Tyr Tyr Gln Ala Cys Val Phe Asp Leu Leu Thr Thr
370 375 380

Gly Asp Val Asn Phe Thr Leu Ala Ala Tyr Tyr Ala Leu Glu Asp Gly
385 390 395 400

Lys Met Leu His Ser Asn Lys Asp Lys Leu His Leu Phe Glu Arg Thr
405 410 415

Arg Glu Leu Pro Gly Ala Val Ala Ala Ala Ala Ala Ala Ala Thr Thr
420 425 430

Phe Pro Leu Ala Pro Gln Ile Leu Leu Gly Thr Ile Pro Leu Leu Val
435 440 445

Leu Leu Pro Val Leu Trp
450

<210> SEQ ID NO 57
<211> LENGTH: 436
<212> TYPE: PRT

<213> ORGANISM: Mus musculus
<220> FEATURE:
<221> NAME/KEY: mat_peptide
<222> LOCATION: (1)..(436)
<223> OTHER INFORMATION: m-DRAGON (mRGMb)

<400> SEQUENCE: 57

```
Met Gly Val Arg Ala Ala Pro Ser Cys Ala Ala Ala Pro Ala Ala Ala
1               5                   10                  15

Gly Ala Glu Gln Ser Arg Arg Pro Gly Leu Trp Pro Pro Ser Pro Pro
            20                  25                  30

Pro Pro Leu Leu Leu Leu Leu Leu Leu Ser Leu Gly Leu Leu His Ala
        35                  40                  45

Gly Asp Cys Gln Gln Pro Thr Gln Cys Arg Ile Gln Lys Cys Thr Thr
    50                  55                  60

Asp Phe Val Ala Leu Thr Ala His Leu Asn Ser Ala Ala Asp Gly Phe
65                  70                  75                  80

Asp Ser Glu Phe Cys Lys Ala Leu Arg Ala Tyr Ala Gly Cys Thr Gln
                85                  90                  95

Arg Thr Ser Lys Ala Cys Arg Gly Asn Leu Val Tyr His Ser Ala Val
            100                 105                 110

Leu Gly Ile Ser Asp Leu Met Ser Gln Arg Asn Cys Ser Lys Asp Gly
        115                 120                 125

Pro Thr Ser Ser Thr Asn Pro Glu Val Thr His Asp Pro Cys Asn Tyr
    130                 135                 140

His Ser His Gly Gly Val Arg Glu His Gly Gly Gly Asp Gln Arg Pro
145                 150                 155                 160

Pro Asn Tyr Leu Phe Cys Gly Leu Phe Gly Asp Pro His Leu Arg Thr
                165                 170                 175

Phe Lys Asp His Phe Gln Thr Cys Lys Val Glu Gly Ala Trp Pro Leu
            180                 185                 190

Ile Asp Asn Asn Tyr Leu Ser Val Gln Val Thr Asn Val Pro Val Val
        195                 200                 205

Pro Gly Ser Ser Ala Thr Ala Thr Asn Lys Val Thr Ile Ile Phe Lys
    210                 215                 220

Ala Gln His Glu Cys Thr Asp Gln Lys Val Tyr Gln Ala Val Thr Asp
225                 230                 235                 240

Asp Leu Pro Ala Ala Phe Val Asp Gly Thr Thr Ser Gly Gly Asp Gly
                245                 250                 255

Asp Val Lys Ser Leu His Ile Val Glu Lys Glu Ser Gly Arg Tyr Val
            260                 265                 270

Glu Met His Ala Arg Tyr Ile Gly Thr Thr Val Phe Val Arg Gln Leu
        275                 280                 285

Gly Arg Tyr Leu Thr Leu Ala Ile Arg Met Pro Glu Asp Leu Ala Met
    290                 295                 300

Ser Tyr Glu Glu Ser Gln Asp Leu Gln Leu Cys Val Asn Gly Cys Pro
305                 310                 315                 320

Met Ser Glu Cys Ile Asp Asp Gly Gln Gly Gln Val Ser Ala Ile Leu
                325                 330                 335

Gly His Ser Leu Pro His Thr Thr Ser Val Gln Ala Trp Pro Gly Tyr
            340                 345                 350

Thr Leu Glu Thr Ala Ser Thr Gln Cys His Glu Lys Met Pro Val Lys
        355                 360                 365

Asp Ile Tyr Phe Gln Ser Cys Val Phe Asp Leu Leu Thr Thr Gly Asp
    370                 375                 380
```

```
Ala Asn Phe Thr Ala Ala Ala His Ser Ala Leu Glu Asp Val Glu Ala
385                 390                 395                 400

Leu His Pro Arg Lys Glu Arg Trp His Ile Phe Pro Ser Ser Cys Gly
                405                 410                 415

Gly Cys Arg Asp Leu Pro Val Gly Leu Gly Leu Thr Cys Leu Ile Leu
            420                 425                 430

Ile Met Phe Leu
        435


<210> SEQ ID NO 58
<211> LENGTH: 420
<212> TYPE: PRT
<213> ORGANISM: Mus musculus
<220> FEATURE:
<221> NAME/KEY: mat_peptide
<222> LOCATION: (1)..(420)
<223> OTHER INFORMATION: mDL-1

<400> SEQUENCE: 58

Met Gly Gln Ser Pro Ser Pro Arg Ser Pro His Gly Ser Pro Pro Thr
1               5                   10                  15

Leu Ser Thr Leu Thr Leu Leu Leu Leu Leu Cys Gly Gln Ala His Ser
            20                  25                  30

Gln Cys Lys Ile Leu Arg Cys Asn Ala Glu Tyr Val Ser Ser Thr Leu
        35                  40                  45

His Leu Arg Gly Gly Gly Ser Pro Asp Thr Pro Arg Gly Gly Gly Arg
    50                  55                  60

Gly Gly Leu Ala Ser Gly Gly Leu Cys Arg Ala Leu Arg Ser Tyr Ala
65                  70                  75                  80

Leu Cys Thr Arg Arg Thr Ala Arg Thr Cys Arg Gly Asp Leu Ala Phe
                85                  90                  95

His Ser Ala Val His Gly Ile Glu Asp Leu Met Ile Gln His Asn Cys
            100                 105                 110

Ser Arg Gln Gly Pro Thr Ala Pro Pro Pro Ala Arg Gly Pro Ala Leu
        115                 120                 125

Pro Gly Ala Gly Pro Ala Pro Leu Thr Pro Asp Pro Cys Asp Tyr Glu
    130                 135                 140

Ala Arg Phe Ser Arg Leu His Gly Arg Ala Pro Gly Phe Leu His Cys
145                 150                 155                 160

Ala Ser Phe Gly Asp Pro His Val Arg Ser Phe His Asn Gln Phe His
                165                 170                 175

Thr Cys Arg Val Gln Gly Ala Trp Pro Leu Leu Asp Asn Asp Phe Leu
            180                 185                 190

Phe Val Gln Ala Thr Ser Ser Pro Val Ser Ser Gly Ala Asn Ala Thr
        195                 200                 205

Thr Ile Arg Lys Ile Thr Ile Ile Phe Lys Asn Met Gln Glu Cys Ile
    210                 215                 220

Asp Gln Lys Val Tyr Gln Ala Glu Val Asp Asn Leu Pro Ala Ala Phe
225                 230                 235                 240

Glu Asp Gly Ser Ile Asn Gly Gly Asp Arg Pro Gly Gly Ser Ser Leu
                245                 250                 255

Ser Ile Gln Thr Ala Asn Leu Gly Ser His Val Glu Ile Arg Ala Ala
            260                 265                 270

Tyr Ile Gly Thr Thr Ile Ile Ile Arg Gln Thr Ala Gly Gln Leu Ser
        275                 280                 285
```

-continued

```
Phe Ser Ile Arg Val Ala Glu Asp Val Ala Arg Ala Phe Ser Ala Glu
    290                 295                 300

Gln Asp Leu Gln Leu Cys Val Gly Gly Cys Pro Pro Ser Gln Arg Leu
305                 310                 315                 320

Ser Arg Ser Glu Arg Asn Arg Arg Gly Ala Ile Ala Ile Asp Thr Ala
                325                 330                 335

Arg Arg Leu Cys Lys Glu Gly Leu Pro Val Glu Asp Ala Tyr Phe Gln
            340                 345                 350

Ser Cys Val Phe Asp Val Ser Val Ser Gly Asp Pro Asn Phe Thr Val
        355                 360                 365

Ala Ala Gln Thr Ala Leu Asp Asp Ala Arg Ile Phe Leu Thr Asp Leu
    370                 375                 380

Glu Asn Leu His Leu Phe Pro Ser Asp Ala Gly Pro Pro Leu Ser Pro
385                 390                 395                 400

Ala Ile Cys Leu Val Pro Leu Leu Ser Ala Leu Phe Val Leu Trp Leu
                405                 410                 415

Cys Phe Ser Lys
            420


<210> SEQ ID NO 59
<211> LENGTH: 426
<212> TYPE: PRT
<213> ORGANISM: Homo sapiens

<400> SEQUENCE: 59

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Leu Cys Gly His
            20                  25                  30

Ala His Ser Gln Cys Lys Ile Leu Arg Cys Asn Ala Glu Tyr Val Ser
        35                  40                  45

Ser Thr Leu Ser Leu Arg Gly Gly Gly Ser Ser Gly Ala Leu Arg Gly
    50                  55                  60

Gly Gly Gly Gly Gly Arg Gly Gly Gly Val Gly Ser Gly Gly Leu Cys
65                  70                  75                  80

Arg Ala Leu Arg Ser Tyr Ala Leu Cys Thr Arg Arg Thr Ala Arg Thr
                85                  90                  95

Cys Arg Gly Asp Leu Ala Phe His Ser Ala Val His Gly Ile Glu Asp
            100                 105                 110

Leu Met Ile Gln His Asn Cys Ser Arg Gln Gly Pro Thr Ala Pro Pro
        115                 120                 125

Pro Pro Arg Gly Pro Ala Leu Pro Gly Ala Gly Ser Gly Leu Pro Ala
    130                 135                 140

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
            180                 185                 190

Leu Leu Asp Asn Asp Phe Leu Phe Val Gln Ala Thr Ser Ser Pro Met
        195                 200                 205

Ala Leu Gly Ala Asn Ala Thr Ala Thr Arg Lys Leu Thr Ile Ile Phe
    210                 215                 220

Lys Asn Met Gln Glu Cys Ile Asp Gln Lys Val Tyr Gln Ala Glu Val
225                 230                 235                 240
```

```
Asp Asn Leu Pro Val Ala Phe Glu Asp Gly Ser Ile Asn Gly Gly Asp
                245                 250                 255

Arg Pro Gly Gly Ser Ser Leu Ser Ile Gln Thr Ala Asn Pro Gly Asn
            260                 265                 270

His Val Glu Ile Gln Ala Ala Tyr Ile Gly Thr Thr Ile Ile Ile Arg
        275                 280                 285

Gln Thr Ala Gly Gln Leu Ser Phe Ser Ile Lys Val Ala Glu Asp Val
    290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg Gly
                325                 330                 335

Ala Ile Thr Ile Asp Thr Ala Arg Arg Leu Cys Lys Glu Gly Leu Pro
            340                 345                 350

Val Glu Asp Ala Tyr Phe His Ser Cys Val Phe Asp Val Leu Ile Ser
        355                 360                 365

Gly Asp Pro Asn Phe Thr Val Ala Ala Gln Ala Ala Leu Glu Asp Ala
    370                 375                 380

Arg Ala Phe Leu Pro Asp Leu Glu Lys Leu His Leu Phe Pro Ser Asp
385                 390                 395                 400

Ala Gly Val Pro Leu Ser Ser Ala Thr Leu Leu Ala Pro Leu Leu Ser
                405                 410                 415

Gly Leu Phe Val Leu Trp Leu Cys Ile Gln
            420                 425
```

<210> SEQ ID NO 60
<211> LENGTH: 420
<212> TYPE: PRT
<213> ORGANISM: Mus musculus

<400> SEQUENCE: 60

```
Met Gly Gln Ser Pro Ser Pro Arg Ser Pro His Gly Ser Pro Pro Thr
1               5                   10                  15

Leu Ser Thr Leu Thr Leu Leu Leu Leu Leu Cys Gly Gln Ala His Ser
            20                  25                  30

Gln Cys Lys Ile Leu Arg Cys Asn Ala Glu Tyr Val Ser Ser Thr Leu
        35                  40                  45

Ser Leu Arg Gly Gly Gly Ser Pro Asp Thr Pro Arg Gly Gly Gly Arg
    50                  55                  60

Gly Gly Leu Ala Ser Gly Gly Leu Cys Arg Ala Leu Arg Ser Tyr Ala
65                  70                  75                  80

Leu Cys Thr Arg Arg Thr Ala Arg Thr Cys Arg Gly Asp Leu Ala Phe
                85                  90                  95

His Ser Ala Val His Gly Ile Glu Asp Leu Met Ile Gln His Asn Cys
            100                 105                 110

Ser Arg Gln Gly Pro Thr Ala Pro Pro Pro Ala Arg Gly Pro Ala Leu
        115                 120                 125

Pro Gly Ala Gly Pro Ala Pro Leu Thr Pro Asp Pro Cys Asp Tyr Glu
    130                 135                 140

Ala Arg Phe Ser Arg Leu His Gly Arg Ala Pro Gly Phe Leu His Cys
145                 150                 155                 160

Ala Ser Phe Gly Asp Pro His Val Arg Ser Phe His Asn Gln Phe His
                165                 170                 175

Thr Cys Arg Val Gln Gly Ala Trp Pro Leu Leu Asp Asn Asp Phe Leu
```

```
            180                 185                 190

Phe Val Gln Ala Thr Ser Ser Pro Val Ser Ser Gly Ala Asn Ala Thr
        195                 200                 205

Thr Ile Arg Lys Ile Thr Ile Ile Phe Lys Asn Met Gln Glu Cys Ile
    210                 215                 220

Asp Gln Lys Val Tyr Gln Ala Glu Val Asp Asn Leu Pro Ala Ala Phe
225                 230                 235                 240

Glu Asp Gly Ser Ile Asn Gly Gly Asp Arg Pro Gly Gly Ser Ser Leu
                245                 250                 255

Ser Ile Gln Thr Ala Asn Leu Gly Ser His Val Glu Ile Arg Ala Ala
            260                 265                 270

Tyr Ile Gly Thr Thr Ile Ile Ile Arg Gln Thr Ala Gly Gln Leu Ser
        275                 280                 285

Phe Ser Ile Arg Val Ala Glu Asp Val Ala Arg Ala Phe Ser Ala Glu
    290                 295                 300

Gln Asp Leu Gln Leu Cys Val Gly Gly Cys Pro Pro Ser Gln Arg Leu
305                 310                 315                 320

Ser Arg Ser Glu Arg Asn Arg Arg Gly Ala Ile Ala Ile Asp Thr Ala
                325                 330                 335

Arg Arg Leu Cys Lys Glu Gly Leu Pro Val Glu Asp Ala Tyr Phe Gln
            340                 345                 350

Ser Cys Val Phe Asp Val Ser Val Ser Gly Asp Pro Asn Phe Thr Val
        355                 360                 365

Ala Ala Gln Thr Ala Leu Asp Asp Ala Arg Ile Phe Leu Thr Asp Leu
    370                 375                 380

Glu Asn Leu His Leu Phe Pro Ser Asp Ala Gly Pro Pro Leu Ser Pro
385                 390                 395                 400

Ala Ile Cys Leu Val Pro Leu Leu Ser Ala Leu Phe Val Leu Trp Leu
                405                 410                 415

Cys Phe Ser Lys
            420


<210> SEQ ID NO 61
<211> LENGTH: 426
<212> TYPE: PRT
<213> ORGANISM: Homo sapiens

<400> SEQUENCE: 61

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Leu Cys Gly His
            20                  25                  30

Ala His Ser Gln Cys Lys Ile Leu Arg Cys Asn Ala Glu Tyr Val Ser
        35                  40                  45

Ser Thr Leu Ser Leu Arg Gly Gly Gly Ser Ser Gly Ala Leu Arg Gly
    50                  55                  60

Gly Gly Gly Gly Gly Arg Gly Gly Gly Val Gly Ser Gly Gly Leu Cys
65                  70                  75                  80

Arg Ala Leu Arg Ser Tyr Ala Leu Cys Thr Arg Arg Thr Ala Arg Thr
                85                  90                  95

Cys Arg Gly Asp Leu Ala Phe His Ser Ala Val His Gly Ile Glu Asp
            100                 105                 110

Leu Met Ile Gln His Asn Cys Ser Arg Gln Gly Pro Thr Ala Pro Pro
        115                 120                 125
```

-continued

```
Pro Pro Arg Gly Pro Ala Leu Pro Gly Ala Gly Ser Gly Leu Pro Ala
    130                 135                 140

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
            180                 185                 190

Leu Leu Asp Asn Asp Phe Leu Phe Val Gln Ala Thr Ser Ser Pro Met
        195                 200                 205

Ala Leu Gly Ala Asn Ala Thr Ala Thr Arg Lys Leu Thr Ile Ile Phe
    210                 215                 220

Lys Asn Met Gln Glu Cys Ile Asp Gln Lys Val Tyr Gln Ala Glu Val
225                 230                 235                 240

Asp Asn Leu Pro Val Ala Phe Glu Asp Gly Ser Ile Asn Gly Gly Asp
                245                 250                 255

Arg Pro Gly Gly Ser Ser Leu Ser Ile Gln Thr Ala Asn Pro Gly Asn
            260                 265                 270

His Val Glu Ile Gln Ala Ala Tyr Ile Gly Thr Thr Ile Ile Ile Arg
        275                 280                 285

Gln Thr Ala Gly Gln Leu Ser Phe Ser Ile Lys Val Ala Glu Asp Val
    290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg Gly
                325                 330                 335

Ala Ile Thr Ile Asp Thr Ala Arg Arg Leu Cys Lys Glu Gly Leu Pro
            340                 345                 350

Val Glu Asp Ala Tyr Phe His Ser Cys Val Phe Asp Val Leu Ile Ser
        355                 360                 365

Gly Asp Pro Asn Phe Thr Val Ala Ala Gln Ala Ala Leu Glu Asp Ala
    370                 375                 380

Arg Ala Phe Leu Pro Asp Leu Glu Lys Leu His Leu Phe Pro Ser Asp
385                 390                 395                 400

Ala Gly Val Pro Leu Ser Ser Ala Thr Leu Leu Ala Pro Leu Leu Ser
                405                 410                 415

Gly Leu Phe Val Leu Trp Leu Cys Ile Gln
            420                 425
```

<210> SEQ ID NO 62
<211> LENGTH: 464
<212> TYPE: PRT
<213> ORGANISM: Mus musculus

<400> SEQUENCE: 62

```
Met Gln Pro Pro Arg Glu Arg Leu Val Val Thr Gly Arg Ala Gly Trp
1               5                   10                  15

Met Gly Met Gly Arg Gly Ala Gly Arg Ser Ala Leu Gly Leu Trp Pro
            20                  25                  30

Thr Leu Ala Phe Leu Leu Cys Ser Phe Pro Ala Ala Ile Ser Pro Cys
        35                  40                  45

Lys Ile Leu Lys Cys Asn Ser Glu Phe Trp Ser Ala Thr Ser Ser Gly
    50                  55                  60

Ser His Ala Pro Ala Ser Asp Asp Val Pro Glu Phe Cys Ala Ala Leu
65                  70                  75                  80
```

```
Arg Thr Tyr Ala Leu Cys Thr Arg Arg Thr Ala Arg Thr Cys Arg Gly
                85                  90                  95

Asp Leu Ala Tyr His Ser Ala Val His Gly Ile Glu Asp Leu Met Ser
            100                 105                 110

Gln His Asn Cys Ser Lys Asp Gly Pro Thr Ser Gln Pro Arg Val Arg
        115                 120                 125

Thr Leu Pro Pro Ala Gly Asp Ser Gln Glu Arg Ser Asp Ser Pro Glu
    130                 135                 140

Ile Cys His Tyr Glu Lys Ser Phe His Lys His Ser Ala Ala Pro Asn
145                 150                 155                 160

Tyr Thr His Cys Gly Leu Phe Gly Asp Pro His Leu Arg Thr Phe Thr
                165                 170                 175

Asp His Phe Gln Thr Cys Lys Val Gln Gly Ala Trp Pro Leu Ile Asp
            180                 185                 190

Asn Asn Tyr Leu Asn Val Gln Val Thr Asn Thr Pro Val Leu Pro Gly
        195                 200                 205

Ser Ala Ala Thr Ala Thr Ser Lys Thr Leu Ala Thr Val Leu Gly Pro
    210                 215                 220

Met Gln Leu Thr Ile Ile Phe Lys Asn Phe Gln Glu Cys Val Asp Gln
225                 230                 235                 240

Lys Val Tyr Gln Ala Glu Met Asp Glu Leu Pro Ser Ala Phe Ala Asp
                245                 250                 255

Gly Ser Lys Asn Gly Gly Asp Lys His Gly Ala Asn Ser Leu Lys Ile
            260                 265                 270

Thr Glu Lys Val Ser Gly Gln His Val Glu Ile Gln Ala Lys Tyr Ile
        275                 280                 285

Gly Thr Thr Ile Val Val Arg Gln Val Gly Arg Tyr Leu Thr Phe Ala
    290                 295                 300

Val Arg Met Pro Glu Glu Val Val Asn Ala Val Glu Asp Arg Asp Ser
305                 310                 315                 320

Gln Gly Leu Tyr Leu Cys Leu Arg Gly Cys Pro Leu Asn Gln Gln Ile
                325                 330                 335

Asp Phe Gln Ala Phe Arg Ala Asn Ala Glu Ser Pro Arg Arg Pro Ala
            340                 345                 350

Ala Ala Ser Pro Ser Pro Val Val Pro Glu Thr Phe Pro Tyr Glu Thr
        355                 360                 365

Ala Val Ala Lys Cys Lys Glu Lys Leu Pro Val Glu Asp Leu Tyr Tyr
    370                 375                 380

Gln Ala Cys Val Phe Asp Leu Leu Thr Thr Gly Asp Val Asn Phe Thr
385                 390                 395                 400

Leu Ala Ala Tyr Tyr Ala Leu Glu Asp Gly Lys Met Leu His Ser Asn
                405                 410                 415

Lys Asp Lys Leu His Leu Phe Glu Arg Thr Arg Glu Leu Pro Gly Ala
            420                 425                 430

Val Ala Ala Ala Ala Ala Ala Ala Thr Thr Phe Pro Leu Ala Pro Gln
        435                 440                 445

Ile Leu Leu Gly Thr Ile Pro Leu Leu Val Leu Leu Pro Val Leu Trp
    450                 455                 460
```

<210> SEQ ID NO 63
<211> LENGTH: 450
<212> TYPE: PRT
<213> ORGANISM: Mus musculus -continued

<400> SEQUENCE: 63

```
Met Gln Pro Pro Arg Glu Arg Leu Val Val Thr Gly Arg Ala Gly Trp
1               5                   10                  15

Met Gly Met Gly Arg Gly Ala Gly Arg Ser Ala Leu Gly Phe Trp Pro
            20                  25                  30

Thr Leu Ala Phe Leu Leu Cys Ser Phe Pro Ala Ala Thr Ser Pro Cys
        35                  40                  45

Lys Ile Leu Lys Cys Asn Ser Glu Phe Trp Ser Ala Thr Ser Gly Ser
    50                  55                  60

His Ala Pro Ala Ser Asp Asp Thr Pro Glu Phe Cys Ala Ala Leu Arg
65                  70                  75                  80

Ser Tyr Ala Leu Cys Thr Arg Arg Thr Ala Arg Thr Cys Arg Gly Asp
                85                  90                  95

Leu Ala Tyr His Ser Ala Val His Gly Ile Glu Asp Leu Met Ser Gln
            100                 105                 110

His Asn Cys Ser Lys Asp Gly Pro Thr Ser Gln Pro Arg Leu Arg Thr
        115                 120                 125

Leu Pro Pro Ala Gly Asp Ser Gln Glu Arg Ser Asp Ser Pro Glu Ile
    130                 135                 140

Cys His Tyr Glu Lys Ser Phe His Lys His Ser Ala Thr Pro Asn Tyr
145                 150                 155                 160

Thr His Cys Gly Leu Phe Gly Asp Pro His Leu Arg Thr Phe Thr Asp
                165                 170                 175

Arg Phe Gln Thr Cys Lys Val Gln Gly Ala Trp Pro Leu Ile Asp Asn
            180                 185                 190

Asn Tyr Leu Asn Val Gln Val Thr Asn Thr Pro Val Leu Pro Gly Ser
        195                 200                 205

Ala Ala Thr Ala Thr Ser Lys Leu Thr Ile Ile Phe Lys Asn Phe Gln
    210                 215                 220

Glu Cys Val Asp Gln Lys Val Tyr Gln Ala Glu Met Asp Glu Leu Pro
225                 230                 235                 240

Ala Ala Phe Val Asp Gly Ser Lys Asn Gly Gly Asp Lys His Gly Ala
                245                 250                 255

Asn Ser Leu Lys Ile Thr Glu Lys Val Ser Gly Gln His Val Glu Ile
            260                 265                 270

Gln Ala Lys Tyr Ile Gly Thr Thr Ile Val Val Arg Gln Val Gly Arg
        275                 280                 285

Tyr Leu Thr Phe Ala Val Arg Met Pro Glu Glu Val Val Asn Ala Val
    290                 295                 300

Glu Asp Trp Asp Ser Gln Gly Leu Tyr Leu Cys Leu Arg Gly Cys Pro
305                 310                 315                 320

Leu Asn Gln Gln Ile Asp Phe Gln Ala Phe His Thr Asn Ala Glu Gly
                325                 330                 335

Thr Gly Ala Arg Arg Leu Ala Ala Ala Ser Pro Ala Pro Thr Ala Pro
            340                 345                 350

Glu Thr Phe Pro Tyr Glu Thr Ala Val Ala Lys Cys Lys Glu Lys Leu
        355                 360                 365

Pro Val Glu Asp Leu Tyr Tyr Gln Ala Cys Val Phe Asp Leu Leu Thr
    370                 375                 380

Thr Gly Asp Val Asn Phe Thr Leu Ala Ala Tyr Tyr Ala Leu Glu Asp
385                 390                 395                 400

Val Lys Met Leu His Ser Asn Lys Asp Lys Leu His Leu Tyr Glu Arg
                405                 410                 415
```

```
Thr Arg Asp Leu Pro Gly Arg Ala Ala Ala Gly Leu Pro Leu Ala Pro
            420                 425                 430

Arg Pro Leu Leu Gly Ala Leu Val Pro Leu Leu Ala Leu Leu Pro Val
        435                 440                 445

Phe Cys
    450


<210> SEQ ID NO 64
<211> LENGTH: 433
<212> TYPE: PRT
<213> ORGANISM: Danio rerio

<400> SEQUENCE: 64

Met Val Met Gly Lys Gly Ala Gly Pro Ser Ala Leu Gln Val Cys Gln
1               5                   10                  15

Phe Leu Ala Leu Phe Leu Ser Leu Phe Pro Ala Ala Thr Leu Gln Cys
            20                  25                  30

Lys Ile Leu Lys Cys Asn Ser Glu Phe Trp Ala Ser Thr Ser Asn Ser
        35                  40                  45

Gly Pro Glu Glu Glu Phe Cys Thr Ala Leu Arg Ala Tyr Asn Ser Cys
    50                  55                  60

Val Arg Arg Thr Ala Arg Thr Cys Arg Gly Asp Leu Ala Tyr His Ser
65                  70                  75                  80

Ala Gln His Gly Ile Glu Asp Leu Met Ser Gln His Asn Cys Ser Lys
                85                  90                  95

Glu Gly Pro Thr Thr Gln Pro Arg Ala Arg Thr Val Pro Pro Pro Val
            100                 105                 110

Leu Ser Pro Pro Gln Thr Asp Ile His Ile Pro Ser Asp Glu Pro Glu
        115                 120                 125

Val Cys His Tyr Glu Arg Ser Leu Pro Arg Asn Ala Ala Pro Pro Asn
    130                 135                 140

Tyr Thr His Cys Gly Phe Phe Gly Asp Pro His Leu Arg Thr Phe Asn
145                 150                 155                 160

Asp Asp Phe Gln Thr Cys Lys Val Glu Gly Ala Trp Pro Leu Ile His
                165                 170                 175

Asn Lys Tyr Leu Ser Val Gln Val Thr Asn Thr Pro Val Val Val Gly
            180                 185                 190

Ser Ser Ala Thr Ala Thr Ser Lys Leu Thr Ile Ile Phe Asn Ser Phe
        195                 200                 205

Gln Glu Cys Val Asp Gln Lys Thr Tyr Arg Ala Glu Thr Glu Asp Leu
    210                 215                 220

Pro Ala Ala Phe Ile Asp Gly Ser Lys Asn Gly Gly Glu Gly His Gly
225                 230                 235                 240

Ala Asn Thr Leu Arg Val Val Glu Lys Val Pro Gly Gln His Val Glu
                245                 250                 255

Ile Gln Ala Arg Tyr Ile Gly Thr Thr Ile Val Val Arg Lys Val Gly
            260                 265                 270

His Tyr Leu Thr Phe Ala Val Arg Met Pro Glu Glu Val Val Asn Ser
        275                 280                 285

Val Glu Asp Gln Asp Asn Gln Asp Leu Tyr Leu Cys Leu His Gly Cys
    290                 295                 300

Pro Ala Asn Gln Arg Ile Asp Phe Arg Thr Phe Lys Ala Arg Ala Ala
305                 310                 315                 320
```

```
Glu Ser His Gly Val Gly Arg Gly Arg Pro Gly Asn Pro Ser Tyr Gly
                325                 330                 335

Phe Thr Tyr Gln Ser Ala Met Ala Lys Cys Lys Glu Arg Leu Pro Val
            340                 345                 350

Glu Asp Leu Tyr Phe Gln Ser Cys Val Phe Asp Leu Leu Ser Ser Gly
        355                 360                 365

Asp Ile Asn Phe Thr Leu Ala Ala Tyr Tyr Ala Phe Glu Asp Val Lys
    370                 375                 380

Met Leu His Ser Asn Lys Asn Lys Tyr His Leu Phe Glu Lys Asp Thr
385                 390                 395                 400

Ile Phe Asn Ser Ala Ser Arg Lys Leu Ala Phe Ser Ile Leu Ile Phe
                405                 410                 415

Ile Ser Phe Val Ile Val Gln Leu Trp Ile Asp Ser Cys Ser Ile Cys
            420                 425                 430

Leu
```

<210> SEQ ID NO 65
<211> LENGTH: 21
<212> TYPE: DNA
<213> ORGANISM: Artificial Sequence
<220> FEATURE:
<223> OTHER INFORMATION: BMP2 siRNA RNA/DNA

<400> SEQUENCE: 65
gguuuuccga gaacagaugt t 21

<210> SEQ ID NO 66

<400> SEQUENCE: 66

000

<210> SEQ ID NO 67
<211> LENGTH: 21
<212> TYPE: DNA
<213> ORGANISM: Artificial Sequence
<220> FEATURE:
<223> OTHER INFORMATION: BMP4 siRNA RNA/DNA

<400> SEQUENCE: 67
gggaccagug aaaacucugt t 21

<210> SEQ ID NO 68
<211> LENGTH: 21
<212> TYPE: DNA
<213> ORGANISM: Artificial Sequence
<220> FEATURE:
<223> OTHER INFORMATION: BMP6 siRNA RNA/DNA

<400> SEQUENCE: 68
gcgacaccac aaagaguuct t 21

<210> SEQ ID NO 69
<211> LENGTH: 21
<212> TYPE: DNA
<213> ORGANISM: Artificial Sequence
<220> FEATURE:
<223> OTHER INFORMATION: BMP7 siRNA RNA/DNA

<400> SEQUENCE: 69
ggcaaaaccu agcaggaaat t 21